United States Patent
Pan et al.

(10) Patent No.: US 11,459,329 B2
(45) Date of Patent: Oct. 4, 2022

(54) IMIDAZOPYRIDAZINE AND IMIDAZOPYRIDINE COMPOUNDS AND USES THEREOF

(71) Applicant: Incyte Corporation, Wilmington, DE (US)

(72) Inventors: Jun Pan, Media, PA (US); Jeremy Roach, Philadelphia, PA (US); Song Mei, Wilmington, DE (US); Chunhong He, Boothwyn, PA (US); Liangxing Wu, Wilmington, DE (US); Wenqing Yao, Chadds Ford, PA (US)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 16/720,935

(22) Filed: Dec. 19, 2019

(65) Prior Publication Data

US 2020/0199131 A1   Jun. 25, 2020

Related U.S. Application Data

(60) Provisional application No. 62/935,891, filed on Nov. 15, 2019, provisional application No. 62/782,994, filed on Dec. 20, 2018.

(51) Int. Cl.
*C07D 487/04*   (2006.01)
*C07D 519/00*   (2006.01)
*A61K 31/519*   (2006.01)

(52) U.S. Cl.
CPC ......... *C07D 487/04* (2013.01); *C07D 519/00* (2013.01); *A61K 31/519* (2013.01)

(58) Field of Classification Search
CPC .................................................... C07D 487/04
USPC ....................................................... 544/236
See application file for complete search history.

(56) References Cited

U.S. PATENT DOCUMENTS

| | | | | |
|---|---|---|---|---|
| 8,367,662 | B2 * | 2/2013 | Shaw ...................... | A61P 11/00 514/233.2 |
| 8,987,273 | B2 * | 3/2015 | Rehwinkel .............. | A61P 43/00 514/252.06 |
| 9,682,983 | B2 * | 6/2017 | Alimardanov .......... | A61P 31/10 |
| 2017/0107216 | A1 | 4/2017 | Wu et al. | |
| 2017/0145025 | A1 | 5/2017 | Li et al. | |
| 2017/0174671 | A1 | 6/2017 | Wu et al. | |
| 2017/0174679 | A1 | 6/2017 | Lajkiewicz et al. | |
| 2017/0320875 | A1 | 11/2017 | Li et al. | |
| 2017/0342060 | A1 | 11/2017 | Lu et al. | |
| 2017/0362253 | A1 | 12/2017 | Xiao et al. | |
| 2018/0016260 | A1 | 1/2018 | Yu et al. | |
| 2018/0057486 | A1 | 3/2018 | Wu et al. | |
| 2018/0177784 | A1 | 6/2018 | Wu et al. | |
| 2018/0177870 | A1 | 6/2018 | Liu et al. | |
| 2018/0179179 | A1 | 6/2018 | Wu et al. | |
| 2018/0179197 | A1 | 6/2018 | Wu et al. | |
| 2018/0179201 | A1 | 6/2018 | Wu et al. | |
| 2018/0179202 | A1 | 6/2018 | Wu et al. | |

FOREIGN PATENT DOCUMENTS

| | | |
|---|---|---|
| WO | WO 2002/000196 | 1/2002 |
| WO | WO 2009/013335 | 1/2009 |
| WO | WO 2009/050183 | 4/2009 |
| WO | WO 2014/160203 | 10/2014 |
| WO | WO 2018/053126 | 3/2018 |
| WO | WO 2018/136634 | 7/2018 |
| WO | WO 2018/165569 | 9/2018 |
| WO | WO 2020/132197 | 6/2020 |

OTHER PUBLICATIONS

Venkatesh, J. Pharm. Sci. 89, 145-154 (2000).*
J. G. Cannon, Chapter Nineteen in Burger's Medicinal Chemistry and Drug Discovery, Fifth Edition, vol. I: Principles and Practice, Wiley-Interscience 1995, pp. 783-802, 784.*
Dorwald (Side Reactions in Organic Synthesis, 2005, Wiley: VCH, Weinheim p. IX of Preface p. 1-15).*
Andriopoulos et al., "BMP6 is a key endogenous regulator of hepcidin expression and iron metabolism," Nature Genetics, 2009, 41(4):482-487.
Asshoff et al., "Momelotinib inhibits ACVR1/ALK2, decreases hepcidin production, and ameliorates anemia of chronic disease in rodents," Blood, 2017, 129(13):1823-1830.
Atzrodt et al., "The Renaissance of H/D" Angew Chem Int Ed., 2007, 46(41):7744-7765.
Berge et al., "Pharmaceutical salts," J Pharm Sci., 1977, 66(1):1-19.
Blobe et al., "Role of transforming growth factor beta in human disease," New England Journal of Medicine, 2000, 342(18):1350-1358.
Blom et al., "Preparative LC-MS Purification: Improved Compound Specific Method Optimization," J Combi Chem., 2004, 6:874-883.
Blom et al., "Optimizing Preparative LC-MS Configurations and Methods for Parallel Synthesis Purification," J Combi Chem., 2003, 5(5):670-683.
Blom., "Two-Pump At Column Dilution Configuration for Preparative LC-MS," J Combi Chem., 2002, 4(4):295-301.

(Continued)

*Primary Examiner* — Nizal S Chandrakumar
(74) *Attorney, Agent, or Firm* — Fish & Richardson P.C.

(57) ABSTRACT

Disclosed are compounds of Formula (I), methods of using the compounds for inhibiting ALK2 activity and pharmaceutical compositions comprising such compounds. The compounds are useful in treating, preventing or ameliorating diseases or disorders associated with ALK2 activity such as cancer.

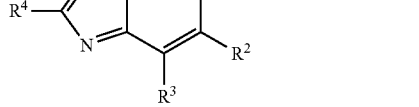

61 Claims, No Drawings

(56) References Cited

OTHER PUBLICATIONS

Buczkowicz et al., "Genomic analysis of diffuse intrinsic pontine gliomas identifies three molecular subgroups and recurrent activating ACVR1 mutations," Nature Genetics, 2014, 46(5):451-456.
Fukuda et al., "A unique mutation of ALK2, G356D, found in a patient with fibrodysplasia ossificans progressiva is a moderately activated BMP type I receptor," Biochemical and Biophysical Research Communications, 2008, 377(3):905-909.
Fukuda et al., "Constitutively activated ALK2 and increased SMAD1/5 cooperatively induce bone morphogenetic protein signaling in fibrodysplasia ossificans progressiva," Journal of Biological Chemistry, 2009, 284(11):7149-7156.
Gennaro, "Performulation," Remington's Pharmaceutical Sciences, 17$^{th}$ Ed., Mack Publishing Company, Easton, 1985, chapter 76, pp. 1409-1418.
Greene and Wuts, "Protective Groups in Organic Synthesis," 3rd. Ed., Wiley & Sons Inc., New York, 1999, 799 pages.
International Search Report in International Application No. PCT/US2019/067403, dated Mar. 30, 2020, 13 pages.
Kerekes et al., "Aurora kinase inhibitors based on the imidazo[1,2-a]pyrazine core: fluorine and deuterium incorporation improve oral absorption and exposure," J Med Chem., 2011, 54(1):201-210.
Kinzel et al., "A New Palladium Precatalyst Allows for the Fast Suzuki—Miyaura Coupling Reactions of Unstable Polyfluorophenyl and 2-Heteroaryl Boronic Acids," J Am Chem Soc., 2010, 132(40):14073-14075.
Massague et al., "TGFbeta signaling in growth control, cancer, and heritable disorders," Cell, 2000, 103(2):295-309.
Pardanani et al., "Associations and prognostic interactions between circulating levels of hepcidin, ferritin and inflammatory cytokines in primary myelofibrosis," American Journal of Hematology, 2013, 88(4):312-316.
Ross et al., "Molecular mechanism of hepcidin-mediated ferroportin internalization requires ferroportin lysines, not tyrosines or JAK-STAT" Cell Metabolism, 2012, 15:905-917.
Shen et al., "The fibrodysplasia ossificans progressiva R206H ACVR1 mutation activates BMP-independent chondrogenesis and zebrafish embryo ventralization," Journal of Clinical Investigation, 2009, 119(11):3462-3472.
Steinbicker et al., "Inhibition of bone morphogenetic protein signaling attenuates anemia associated with inflammation," Blood, 2011, 117(18):4915-4923.
Steinbicker et al., "Perturbation of hepcidin expression by BMP type I receptor deletion induces iron overload in mice," Blood, 2011, 118(15):4224-4230.
Taylor et al., "ACVR1 mutations in DIPG: lessons learned from FOP," Cancer Research, 2014, 74(17):4565-4570.
Taylor et al., "Recurrent activating ACVR1 mutations in diffuse intrinsic pontine glioma," Nature Genetics, 2014, 46(5):457-461.
Tefferi et al., "One thousand patients with primary myelofibrosis: the mayo clinic experience," Mayo Clinic Proceedings, 2012, 87(1):25-33.
Theurl et al., "Pathways for the regulation of hepcidin expression in anemia of chronic disease and iron deficiency anemia in vivo," Haematologica, 2011, 96(12):1761-1769.
Van Dinther et al., "ALK2 R206H mutation linked to fibrodysplasia ossificans progressiva confers constitutive activity to the BMP type I receptor and sensitizes mesenchymal cells to BMP-induced osteoblast differentiation and bone formation," Journal of Bone and Mineral Research, 2010, 25(6):1208-1215.
Weiss et al., "Anemia of chronic disease," New England Journal of Medicine, 2005, 352(10):1011-1023.
Wolfe et al., "An Ammonia Equivalent for the Palladium-Catalyzed Amination of Aryl Halides and Triflates," Tetrahedron Lett., Sep. 8, 1997, 38(36):6367-6370.
Xu et al., "Design, synthesis and biological evaluation of deuterated nintedanib for improving pharmacokinetic properties," J Label Compd Radiopharm., 2015, 58(7):308-312.
Yu et al., "BMP type I receptor inhibition reduces heterotopic [corrected] ossification," Nature Medicine, 2008, 14:1363-1369.
Zhao et al., "Iron regulation by hepcidin," Journal of Clinical Investigation, 2013, 123(6):2337-2343.
International Preliminary Report on Patentability in International Application No. PCT/US2019/067403, dated Jun. 16, 2021, 7 pages.
Hopkins, "Inhibitors of the bone morphogenetic protein (BMP) signaling pathway: a patent review (2008-2015)," Expert Opin Ther Pat., Aug. 4, 2016, 26(10):1115-1128.
International Search Report and Written Opinion in International Application No. PCT/US2021/036839, dated Aug. 20, 2021, 15 pages.
Ecuador Opposition in Ecuador Application No. SENADI-2021-44843, dated Jul. 2022, 19 pages.
Manuel Pachon and Zoraida Sanchez Avila, "The Court of Justive of the Andean Community," Gustavo Ibanex Legal Editions, Bogota, dated May 20, 1998, Process 12-IP-98, Retrieved from URL <http://intranet.comunidadandina.org/Documentos/Procesos/12-ip-98.doc>, 32 pages.
Gaceta Oficial, "Court of Justive of the Andean Community," Oct. 12, 2001, retrieved from URL <http://intranet.comunidadandina.org/documentos/Gacetas/gace722.pdf>, 2 pages.
Pinzon, "Morality, Ethics and Bio-Ethics as Social Limits for the Protections of Inventions Through Patents," Frónesis, Dec. 2006, [retrieved on Dec. 7, 2011] retrieved from URL <http://www.scielo.org.ve/scielo.php?pid=S1315-62682006000300002&script=sci_arttext> 13(3):9-31 (English Abstract Only).
Negre, "New Galencila Formas de Administration," Formacion Continuada, Jan. 2002, vol. 3.2, pp. 28-65 English Translation.
Wikipedia.com, "Medication," last updated Jul. 21, 2022, retrieved from URL <http://es.wikipedia.org/wiki/Forma_gal%C3%A9nica>, 44 pages.
Nies and Spielberg et al., "Principles of Therapeutics," Goodman & Gilman, 1996, 9th Edition, Chapter 3, page 47.
No Author, Process No. 151-IP-2005, "Crystal Acid [R-(R*,R*)]-2-(4-Fluorophenyl)-B Δ-Dihydroxy-5-(1-Methylethyl)-3-Phenyl-4[(Fenilamino)Carbonyl]-1H-Pyrrole-1-Heptanoic. Calcium Salt (2:1)," Expediente: N° 2003-00255, Nov. 15, 2005, 52 pages.

\* cited by examiner

IMIDAZOPYRIDAZINE AND IMIDAZOPYRIDINE COMPOUNDS AND USES THEREOF

FIELD OF THE INVENTION

The disclosure provides compounds as well as their compositions and methods of use. The compounds modulate activin receptor-like kinase-2 (ALK2) activity and are useful in the treatment of various diseases including cancer.

BACKGROUND OF THE INVENTION

Bone morphogenetic protein (BMP) signaling belongs to the transforming growth factor beta (TGF-β) superfamily and TGF-β signaling ligands include more than 25 different ligands: TGF-β growth and differentiation factors, BMPs and Activins. The binding of BMP ligands leads to the assembly of tetrameric receptor complexes composed of two constitutively-active type II receptor serine/threonine kinases (BMPRII, ACTRIIA, or ACTRIIB) and activate two type I receptor serine/threonine kinases (ALK1, ALK2, ALK3, or ALK6). Furthermore, the activated type I receptors phosphorylate BMP receptor responsive SMAD proteins 1/5/8 and the activated SMAD1/5/8 associated with co-SMAD4 translocate to the nucleus to regulate gene transcription. (Ross, S. L., et al. Cell Metabolism 2012, 15, 905-917; Blobe, G. C., et al. New England Journal of Medicine 2000, 342, 1350-1358).

BMPR kinase activin A receptor, type I (ACVR1) is also called activin receptor-like kinase-2 (ALK2). It is composed of a ligand-binding extracellular domain and a cytoplasmic domain with serine/threonine specificity. ALK2 has been reported to mediate multiple human diseases (Massague, J., et al. Cell 2000, 103, 295-309; Taylor, K R., et al. Cancer Research 2014, 74, 4565-4570). ALK2 and ALK3 have been shown to play an essential role in regulating the hepcidin levels and affecting the anemia of chronic disease (Andriopoulos, B., et al. Nature Genetics 2009 41, 482-487; Steinbicker, A. U., et al. Blood 2011, 118, 4224-4230; Steinbicker, A. U., et al. Blood 2011, 117, 4915-4923). Hepcidin is a small peptide hormone primarily synthesized in hepatocytes and reduces both duodenal iron absorption and iron export from monocytes/macrophages by binding to and inducing the internalization and degradation of the iron exporter ferroportin (FPN1) (Theurl, I. et al. Haematologica 2011, 96, 1761-1769; Zhao, N., et al. Journal of Clinical Investigation 2013, 123, 2337-2343). The elevated serum hepcidin levels enhance storage of iron within the reticuloendothelial system and result in reduced iron availability and iron restricted erythropoiesis. Inappropriately increased hepcidin expression causes severe functional iron deficiency anemia in humans and is central to the pathophysiology of anemia of chronic disease (ACD) (Weiss, G. et al. New England Journal of Medicine 2005, 352, 1011-1023). Accordingly, there is a need for new compounds that modulate ALK2 activity.

SUMMARY

The present disclosure provides, inter alia, a compound of Formula I:

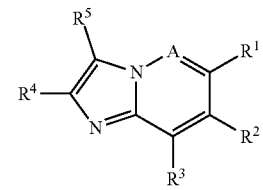

I or a pharmaceutically acceptable salt thereof, wherein constituent variables are defined herein.

The present disclosure further provides a pharmaceutical composition comprising a compound of the disclosure, or a pharmaceutically acceptable salt thereof, and at least one pharmaceutically acceptable carrier or excipient.

The present disclosure further provides methods of inhibiting ALK2 activity, which comprises administering to patient a compound of the disclosure, or a pharmaceutically acceptable salt thereof.

The present disclosure further provides methods of treating a disease or disorder in a patient comprising administering to the patient a therapeutically effective amount of a compound of the disclosure, or a pharmaceutically acceptable salt thereof.

The present disclosure further provides use of a compound of Formula (I), or a pharmaceutically acceptable salt thereof, for the preparation of a medicament for use in any of the methods described herein.

DETAILED DESCRIPTION

Compounds

The present disclosure provides a compound of Formula I:

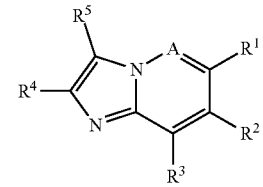

I or a pharmaceutically acceptable salt thereof, wherein:
$R^1$ is selected from $Cy^1$, $C_{1-6}$ alkyl, $C_{2-6}$ alkenyl, $C_{2-6}$ alkynyl, $C_{1-6}$ haloalkyl, halo, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NOR^a)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein said $C_{1-6}$ alkyl, $C_{2-6}$ alkenyl and $C_{2-6}$ alkynyl are each optionally substituted with 1, 2, 3, or 4 substituents independently selected from $R^{10}$;

$Cy^1$ is selected from $C_{3-14}$ cycloalkyl, 4-14 membered heterocycloalkyl, $C_{6-10}$ aryl and 5-10 membered heteroaryl; wherein the 4-14 membered heterocycloalkyl and 5-10 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl and 4-14 membered heterocycloalkyl is optionally substituted by oxo to form a carbonyl group; and wherein the $C_{3-14}$ cycloalkyl, 4-14 membered heterocycloalkyl, $C_{6-10}$ aryl and 5-10 membered heteroaryl are each optionally substituted with 1, 2, 3 or 4 substituents independently selected from $R^{10}$;

$R^2$ is selected from $C_{6-10}$ aryl and 5-10 membered heteroaryl; wherein the 5-10 membered heteroaryl has at least one ring-forming carbon atom and 1, 2, 3, or 4 ring-forming heteroatoms independently selected from N, O, and S; wherein the N and S are optionally oxidized; wherein a ring-forming carbon atom of the 5-10 membered heteroaryl is optionally substituted by oxo to form a carbonyl group; and wherein the $C_{6-10}$ aryl and 5-10 membered heteroaryl are each optionally substituted with 1, 2, 3, 4 or 5 substituents independently selected from $R^{20}$;

or two adjacent $R^{20}$ substituents on $R^2$, taken together with the atoms to which they are attached, form a fused 4-, 5-, 6- or 7-membered heterocycloalkyl ring, or a fused $C_{3-7}$ cycloalkyl ring; wherein the fused 4-, 5-, 6- or 7-membered heterocycloalkyl ring each has at least one ring-forming carbon atom and 1, 2, 3, or 4 ring-forming heteroatoms independently selected from N, O, and S; wherein a ring-forming carbon atom of each fused 4-, 5-, 6- or 7-membered heterocycloalkyl ring is optionally substituted by oxo to form a carbonyl group; and wherein the fused 4-, 5-, 6- or 7-membered heterocycloalkyl ring and fused $C_{3-7}$ cycloalkyl ring are each optionally substituted with 1, 2, 3 or 4 substituents independently selected from $R^{21}$;

$R^3$ is selected from H, D, halo, CN, $C_{1-6}$ alkyl, $OR^{a7}$ and $NR^{c7}R^{d7}$; wherein the $C_{1-6}$ alkyl is optionally substituted with 1, 2, or 3 substituents independently selected from $R^g$;

$R^4$ is selected from H, D, halo, CN, $C_{1-6}$ alkyl, $OR^{a8}$ and $NR^{c8}R^{d8}$; wherein the $C_{1-6}$ alkyl is optionally substituted with 1, 2, or 3 substituents independently selected from $R^g$;

$R^5$ is selected from $C_{6-10}$ aryl and 5-10 membered heteroaryl; wherein the 5-10 membered heteroaryl has at least one ring-forming carbon atom and 1, 2, 3, or 4 ring-forming heteroatoms independently selected from N, O, and S; wherein the N and S are optionally oxidized; wherein a ring-forming carbon atom of the 5-10 membered heteroaryl is optionally substituted by oxo to form a carbonyl group; and wherein the $C_{6-10}$ aryl and 5-10 membered heteroaryl are each optionally substituted with 1, 2, 3, 4 or 5 substituents independently selected from $R^{50}$;

or two adjacent $R^{50}$ substituents on $R^5$, taken together with the atoms to which they are attached, form a fused 4-, 5-, 6- or 7-membered heterocycloalkyl ring, or a fused $C_{3-7}$ cycloalkyl ring; wherein the fused 4-, 5-, 6- or 7-membered heterocycloalkyl ring each has at least one ring-forming carbon atom and 1, 2, 3, or 4 ring-forming heteroatoms independently selected from N, O, and S; wherein a ring-forming carbon atom of each fused 4-, 5-, 6- or 7-membered heterocycloalkyl ring is optionally substituted by oxo to form a carbonyl group; and wherein the fused 4-, 5-, 6- or 7-membered heterocycloalkyl ring and fused $C_{3-7}$ cycloalkyl ring are each optionally substituted with 1, 2, 3 or 4 substituents independently selected from $R^{51}$;

A is N or $CR^A$;

$R^A$ is selected from H, D, $C_{1-6}$ alkyl, $C_{2-6}$ alkenyl, $C_{2-6}$ alkynyl, $C_{1-6}$ haloalkyl, halo, CN, $NO_2$, $OR^{a12}$, $SR^{a12}$, $C(O)R^{b12}$, $C(O)NR^{c12}R^{d12}$, $C(O)OR^{a12}$, $OC(O)R^{b12}$, $OC(O)NR^{c12}R^{d12}$ $NR^{c12}R^{d12}$, $NR^{c12}C(O)R^{b12}$, $NR^{c12}C(O)OR^{a12}$, $NR^{c12}C(O)NR^{c12}R^{d12}$, $NR^{c12}S(O)R^{b12}$, $NR^{c12}S(O)_2R^{b12}$, $NR^{c12}S(O)_2NR^{c12}R^{d12}$, $S(O)R^{b12}$, $S(O)NR^{c12}R^{d12}$, $S(O)_2R^{b12}$ and $S(O)_2NR^{c12}R^{d12}$; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{10}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NOR^{a1})R^{b1}$, $C(=NR^{e1})NR^{c1}R^{d1}$, $NR^{c1}C(=NR^{e1})NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{11}$;

or two $R^{10}$ substituents taken together with the carbon atom to which they are attached form a spiro 4-7-membered heterocycloalkyl ring, or a spiro $C_{3-6}$ cycloalkyl ring; wherein each spiro 4-7-membered heterocycloalkyl ring has at least one ring-forming carbon atom and 1, 2 or 3, ring-forming heteroatoms independently selected from N, O, and S; wherein a ring-forming carbon atom of each spiro 4-7-membered heterocycloalkyl ring is optionally substituted by oxo to form a carbonyl group; and wherein the spiro 4-7-membered heterocycloalkyl ring and spiro $C_{3-6}$ cycloalkyl ring are each optionally substituted with 1, 2, 3 or 4 substituents independently selected from $R^{11}$;

each $R^{11}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a3}$, $SR^{a3}$, $C(O)R^{b3}$, $C(O)NR^{c3}R^{d3}$, $C(O)OR^{a3}$, $NR^{c3}R^{d3}$, $NR^{c3}C(O)R^{b3}$, $NR^{c3}C(O)OR^{a3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{12}$;

each $R^{12}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, $C_{6-10}$ aryl, 5-10 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a5}$, $SR^{a5}$, $C(O)R^{b5}$, $C(O)NR^{c5}R^{d5}$, $C(O)OR^{a5}$, $NR^{c5}R^{d5}$, $NR^{c5}C(O)R^{b5}$, $NR^{c5}C(O)OR^{a5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$; wherein said $C_{1-6}$ alkyl, $C_{2-6}$ alkenyl, $C_{2-6}$ alkynyl, $C_{3-6}$ cycloalkyl, $C_{6-10}$ aryl, 5-10 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, $C_{6-10}$ aryl-$C_{1-3}$ alkylene, and 5-10 membered heteroaryl-$C_{1-3}$ alkylene are each optionally substituted with 1, 2, 3, or 4 substituents independently selected from $R^g$;

each $R^{20}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NOR^{a2})R^{b2}$, $C(=NR^{e2})NR^{c2}R^{d2}$, $NR^{c2}C(=NR^{e2})NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$; wherein a ring-forming carbon atom of the 4-10 membered heterocycloalkyl is optionally substituted by oxo to form a carbonyl group; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{21}$;

each $R^{21}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a4}$, $SR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $NR^{c4}C(O)OR^{a4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{22}$;

each $R^{22}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, 5-6 membered heteroaryl-$C_{1-3}$ alkylene, halo, D, CN, $OR^{a6}$, $SR^{a6}$, $C(O)R^{b6}$, $C(O)NR^{c6}R^{d6}$, $C(O)OR^{a6}$, $NR^{c6}R^{d6}$, $NR^{c6}C(O)R^{b6}$, $NR^{c6}C(O)OR^{a6}$, $NR^{c6}S(O)R^{b6}$, $NR^{c6}S(O)_2R^{b6}$, $NR^{c6}S(O)_2NR^{c6}R^{d6}$, $S(O)R^{b6}$, $S(O)NR^{c6}R^{d6}$, $S(O)_2R^{b6}$, and $S(O)_2NR^{c6}R^{d6}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene are each optionally substituted with 1, 2, 3, or 4 substituents independently selected from $R^g$;

each $R^{50}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a9}$, $SR^{a9}$, $C(O)R^{b9}$, $C(O)NR^{c9}R^{d9}$, $C(O)OR^{a9}$, $OC(O)R^{b9}$, $OC(O)NR^{c9}R^{d9}$, $NR^{c9}R^{d9}$, $NR^{c9}C(O)R^{b9}$, $NR^{c9}C(O)OR^{a9}$, $NR^{c9}C(O)NR^{c9}R^{d9}$, $C(=NR^{e9})R^{b9}$, $C(=NOR^{a9})R^{b9}$, $C(=NR^{e9})NR^{c9}R^{d9}$, $NR^{c9}C(=NR^{e9})NR^{c9}R^{d9}$, $NR^{c9}S(O)R^{b9}$, $NR^{c9}S(O)_2R^{b9}$, $NR^{c9}S(O)_2NR^{c9}R^{d9}$, $S(O)R^{b9}$, $S(O)NR^{c9}R^{d9}$, $S(O)_2R^{b9}$, and $S(O)_2NR^{c9}R^{d9}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{51}$;

each $R^{51}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a10}$, $SR^{a10}$, $C(O)R^{b10}$, $C(O)NR^{c10}R^{d10}$, $C(O)OR^{a10}$, $NR^{c10}R^{d10}$, $NR^{c10}C(O)R^{b10}$, $NR^{c10}C(O)OR^{a10}$, $NR^{c10}S(O)R^{b10}$, $NR^{c10}S(O)_2R^{b10}$, $NR^{c10}S(O)_2NR^{c10}R^{d10}$, $S(O)R^{b10}$, $S(O)NR^{c10}R^{d10}$, $S(O)_2R^{b10}$, and $S(O)_2NR^{c10}R^{d10}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{52}$;

each $R^{52}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, 5-6 membered heteroaryl-$C_{1-3}$ alkylene, halo, D, CN, $OR^{a11}$, $SR^{a11}$, $C(O)R^{b11}$, $C(O)NR^{c11}R^{d11}$, $C(O)OR^{a11}$, $NR^{c11}R^{d11}$, $NR^{c11}C(O)R^{b11}$, $NR^{c11}C(O)OR^{a11}$, $NR^{c11}S(O)R^{b11}$, $NR^{c11}S(O)_2R^{b11}$, $NR^{c11}S(O)_2NR^{c11}R^{d11}$, $S(O)R^{b11}$, $S(O)NR^{c11}R^{d11}$, $S(O)_2R^{b11}$, and $S(O)_2NR^{c11}R^{d11}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene are each optionally substituted with 1, 2, 3, or 4 substituents independently selected from $R^g$;

each $R^a$, $R^c$, and $R^d$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene are each optionally substituted with 1, 2, 3, or 4 substituents independently selected from $R^{10}$;

or any $R^c$ and $R^d$ attached to the same N atom, together with the N atom to which they are attached, form a 4-10 membered heterocycloalkyl group optionally substituted with 1, 2, 3 or 4 substituents independently selected from $R^{10}$;

each $R^b$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene are each optionally substituted with 1, 2, 3, or 4 substituents independently selected from $R^{10}$;

each $R^e$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{a1}$, $R^{c1}$ and $R^{d1}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene are each optionally substituted with 1, 2, 3, or 4 substituents independently selected from $R^{11}$;

or any $R^{c1}$ and $R^{d1}$ attached to the same N atom, together with the N atom to which they are attached, form a 4-10 membered heterocycloalkyl group optionally substituted with 1, 2, 3 or 4 substituents independently selected from $R^{11}$;

each $R^{b1}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene are each optionally substituted with 1, 2, 3, or 4 substituents independently selected from $R^{11}$;

each $R^{e1}$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{a2}$, $R^{c2}$ and $R^{d2}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene are each optionally substituted with 1, 2, 3, or 4 substituents independently selected from $R^{21}$;

or any $R^{c2}$ and $R^{d2}$ attached to the same N atom, together with the N atom to which they are attached, form a 4-10 membered heterocycloalkyl group optionally substituted with 1, 2, 3 or 4 substituents independently selected from $R^{21}$;

each $R^{b2}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene are each optionally substituted with 1, 2, 3, or 4 substituents independently selected from $R^{21}$;

each $R^{e2}$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{a3}$, $R^{c3}$ and $R^{d3}$ is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene; wherein said $C_{1-6}$ alkyl $C_{2-6}$ alkenyl, $C_{2-6}$ alkynyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene are each optionally substituted with 1, 2, 3, or 4 substituents independently selected from $R^{12}$;

or any $R^{c3}$ and $R^{d3}$ attached to the same N atom, together with the N atom to which they are attached, form a 4-, 5-, 6- or 7-membered heterocycloalkyl group optionally substituted with 1, 2 or 3 substituents independently selected from $R^{12}$;

each $R^{b3}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene; wherein said $C_{1-6}$ alkyl $C_{2-6}$ alkenyl, $C_{2-6}$ alkynyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene are each optionally substituted with 1, 2, 3, or 4 substituents independently selected from $R^{12}$;

each $R^{a4}$, $R^{c4}$ and $R^{d4}$ is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene; wherein said $C_{1-6}$ alkyl $C_{2-6}$ alkenyl, $C_{2-6}$ alkynyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene are each optionally substituted with 1, 2, 3, or 4 substituents independently selected from $R^{22}$;

or any $R^{c4}$ and $R^{d4}$ attached to the same N atom, together with the N atom to which they are attached, form a 4-, 5-, 6- or 7-membered heterocycloalkyl group optionally substituted with 1, 2 or 3 substituents independently selected from $R^{22}$;

each $R^{b4}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene; wherein said $C_{1-6}$ alkyl $C_{2-6}$ alkenyl, $C_{2-6}$ alkynyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene are each optionally substituted with 1, 2, 3, or 4 substituents independently selected from $R^{22}$;

each $R^{a5}$, $R^{c5}$ and $R^{d5}$ is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

or any $R^{c5}$ and $R^{d5}$ attached to the same N atom, together with the N atom to which they are attached, form a 4-, 5-, 6- or 7-membered heterocycloalkyl group optionally substituted with 1, 2 or 3 substituents independently selected from $R^g$;

each $R^{b5}$ is independently selected from $C_{1-6}$ alkyl, $C_{2-6}$ alkenyl, $C_{2-6}$ alkynyl and $C_{1-6}$ haloalkyl; wherein said $C_{1-6}$ alkyl $C_{2-6}$ alkenyl and $C_{2-6}$ alkynyl are each optionally substituted with 1, 2, 3, or 4 substituents independently selected from $R^g$;

each $R^{a6}$, $R^{c6}$ and $R^{d6}$ is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

or any $R^{c6}$ and $R^{d6}$ attached to the same N atom, together with the N atom to which they are attached, form a 4-, 5-, 6- or 7-membered heterocycloalkyl group optionally substituted with 1, 2 or 3 substituents independently selected from $R^g$;

each $R^{b6}$ is independently selected from $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{a7}$, $R^{c7}$ and $R^{d7}$ is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{a8}$, $R^{c8}$ and $R^{d8}$ is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{a9}$, $R^{c9}$ and $R^{d9}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene are each optionally substituted with 1, 2, 3, or 4 substituents independently selected from $R^{51}$;

or any $R^{c9}$ and $R^{d9}$ attached to the same N atom, together with the N atom to which they are attached, form a 4-10 membered heterocycloalkyl group optionally substituted with 1, 2, 3 or 4 substituents independently selected from $R^{51}$;

each $R^{b9}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene are each optionally substituted with 1, 2, 3, or 4 substituents independently selected from $R^{51}$;

each $R^{e9}$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{a10}$, $R^{c10}$ and $R^{d10}$ is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene; wherein said $C_{1-6}$ alkyl $C_{2-6}$ alkenyl, $C_{2-6}$ alkynyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene are each optionally substituted with 1, 2, 3, or 4 substituents independently selected from $R^{52}$;

or any $R^{c10}$ and $R^{d10}$ attached to the same N atom, together with the N atom to which they are attached, form a 4-, 5-, 6- or 7-membered heterocycloalkyl group optionally substituted with 1, 2 or 3 substituents independently selected from $R^{52}$;

each $R^{b10}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene; wherein said $C_{1-6}$ alkyl $C_{2-6}$ alkenyl, $C_{2-6}$ alkynyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene are each optionally substituted with 1, 2, 3, or 4 substituents independently selected from $R^{52}$;

each $R^{a11}$, $R^{c11}$ and $R^{d11}$ is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

or any $R^{c11}$ and $R^{d11}$ attached to the same N atom, together with the N atom to which they are attached, form a 4-, 5-, 6- or 7-membered heterocycloalkyl group optionally substituted with 1, 2 or 3 substituents independently selected from $R^g$;

each $R^{b11}$ is independently selected from $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{a12}$, $R^{c12}$, and $R^{d12}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl- $C_{1-3}$ alkylene; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene are each optionally substituted with 1, 2, 3, or 4 substituents independently selected from $R^g$;

or any $R^{c12}$ and $R^{d12}$ attached to the same N atom, together with the N atom to which they are attached, form a 4-10 membered heterocycloalkyl group optionally substituted with 1, 2, 3 or 4 substituents independently selected from $R^g$;

each $R^{b12}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene are each optionally substituted with 1, 2, 3, or 4 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-6}$ haloalkyl, $C_{3-6}$ cycloalkyl, $C_{3-6}$ cycloalkyl-$C_{1-2}$ alkylene, $C_{1-6}$ alkoxy, $C_{1-6}$ haloalkoxy, $C_{1-3}$ alkoxy-$C_{1-3}$ alkyl, $C_{1-3}$ alkoxy-$C_{1-3}$ alkoxy, HO—$C_{1-3}$ alkoxy, HO—$C_{1-3}$ alkyl, cyano-$C_{1-3}$ alkyl, $H_2N$—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

provided that:

1) when $Cy^1$ is $C_{6-10}$ aryl, then $R^{10}$ is other than substituted cyclobutyl; and 2) a compound of Formula I is other than 3-(2-benzofuranyl)-6-chloro-7-phenyl-imidazo[1,2-b]pyridazine and 3-(2-benzofuranyl)-6-[3-(methylsulfonyl)propoxy]-7-phenyl-imidazo[1,2-b]pyridazine.

In some embodiments, the compound of Formula I is a compound wherein:

$R^1$ is selected from $Cy^1$, $C_{1-6}$ alkyl, $C_{2-6}$ alkenyl, $C_{2-6}$ alkynyl, $C_{1-6}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NOR^a)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein said $C_{1-6}$ alkyl, $C_{2-6}$ alkenyl and $C_{2-6}$ alkynyl are each optionally substituted with 1, 2, 3, or 4 substituents independently selected from $R^{10}$;

$Cy^1$ is selected from $C_{3-14}$ cycloalkyl, 4-14 membered heterocycloalkyl, $C_{6-10}$ aryl and 5-10 membered heteroaryl; wherein the 4-14 membered heterocycloalkyl and 5-10 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl and 4-14 membered heterocycloalkyl is optionally substituted by oxo to form a carbonyl group; and wherein the $C_{3-14}$ cycloalkyl, 4-14 membered heterocycloalkyl, $C_{6-10}$ aryl and 5-10 membered heteroaryl are each optionally substituted with 1, 2, 3 or 4 substituents independently selected from $R^{10}$;

$R^2$ is selected from $C_{6-10}$ aryl and 5-10 membered heteroaryl; wherein the 5-10 membered heteroaryl has at least one ring-forming carbon atom and 1, 2, 3, or 4 ring-forming heteroatoms independently selected from N, O, and S; wherein the N and S are optionally oxidized; wherein a ring-forming carbon atom of the 5-10 membered heteroaryl is optionally substituted by oxo to form a carbonyl group; and wherein the $C_{6-10}$ aryl and 5-10 membered heteroaryl are each optionally substituted with 1, 2, 3, 4 or 5 substituents independently selected from $R^{20}$;

or two adjacent $R^{20}$ substituents on $R^2$, taken together with the atoms to which they are attached, form a fused 4-, 5-, 6- or 7-membered heterocycloalkyl ring, or a fused $C_{3-7}$ cycloalkyl ring; wherein the fused 4-, 5-, 6- or 7-membered heterocycloalkyl ring each has at least one ring-forming carbon atom and 1, 2, 3, or 4 ring-forming heteroatoms independently selected from N, O, and S; wherein a ring-forming carbon atom of each fused 4-, 5-, 6- or 7-membered heterocycloalkyl ring is optionally substituted by oxo to form a carbonyl group; and wherein the fused 4-, 5-, 6- or 7-membered heterocycloalkyl ring and fused $C_{3-7}$ cycloalkyl ring are each optionally substituted with 1, 2, 3 or 4 substituents independently selected from $R^{21}$;

$R^3$ is selected from H, D, halo, CN, $C_{1-6}$ alkyl, $OR^{a7}$ and $NR^{c7}R^{d7}$; wherein the $C_{1-6}$ alkyl is optionally substituted with 1, 2, or 3 substituents independently selected from $R^g$;

$R^4$ is selected from H, D, halo, CN, $C_{1-6}$ alkyl, $OR^{a8}$ and $NR^{c8}R^{d8}$; wherein the $C_{1-6}$ alkyl is optionally substituted with 1, 2, or 3 substituents independently selected from $R^g$;

$R^5$ is selected from $C_{6-10}$ aryl and 5-10 membered heteroaryl; wherein the 5-10 membered heteroaryl has at least one ring-forming carbon atom and 1, 2, 3, or 4 ring-forming heteroatoms independently selected from N, O, and S; wherein the N and S are optionally oxidized; wherein a ring-forming carbon atom of the 5-10 membered heteroaryl is optionally substituted by oxo to form a carbonyl group; and wherein the $C_{6-10}$ aryl and 5-10 membered heteroaryl are each optionally substituted with 1, 2, 3, 4 or 5 substituents independently selected from $R^{50}$;

or two adjacent $R^{50}$ substituents on $R^5$, taken together with the atoms to which they are attached, form a fused 4-, 5-, 6- or 7-membered heterocycloalkyl ring, or a fused $C_{3-7}$ cycloalkyl ring; wherein the fused 4-, 5-, 6- or 7-membered heterocycloalkyl ring each has at least one ring-forming carbon atom and 1, 2, 3, or 4 ring-forming heteroatoms independently selected from N, O, and S; wherein a ring-forming carbon atom of each fused 4-, 5-, 6- or 7-membered heterocycloalkyl ring is optionally substituted by oxo to form a carbonyl group; and wherein the fused 4-, 5-, 6- or 7-membered heterocycloalkyl ring and fused $C_{3-7}$ cycloalkyl ring are each optionally substituted with 1, 2, 3 or 4 substituents independently selected from $R^{51}$;

A is N or $CR^4$;

$R^4$ is selected from H, D, $C_{1-6}$ alkyl, $C_{2-6}$ alkenyl, $C_{2-6}$ alkynyl, $C_{1-6}$ haloalkyl, halo, CN, $NO_2$, $OR^{a12}$, $SR^{a12}$, $C(O)R^{b12}$, $C(O)NR^{c12}R^{d12}$, $C(O)OR^{a12}$, $OC(O)R^{b12}$, $OC(O)NR^{c12}R^{d12}$ $NR^{c12}R^{d12}$, $NR^{c12}C(O)R^{b12}$, $NR^{c12}C(O)OR^{a12}$, $NR^{c12}C(O)NR^{c12}R^{d12}$, $NR^{c12}S(O)R^{b12}$, $NR^{c12}S(O)_2R^{b12}$, $NR^{c12}S(O)_2NR^{c12}R^{d12}$, $S(O)R^{b12}$, $S(O)NR^{c12}R^{d12}$, $S(O)_2R^{b12}$ and $S(O)_2NR^{c12}R^{d12}$; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{10}$ is independently selected from $C_{1-6}$ alkyl, $C_{2-6}$ alkenyl, $C_{2-6}$ alkynyl, $C_{1-6}$ haloalkyl, $C_{5-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NOR^{a1})R^{b1}$, $C(=NR^{e1})NR^{c1}R^{d1}$, $NR^{c1}C(=NR^{e1})NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, and $S(O)_2NR^{c1}R^{d1}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{11}$;

or two $R^{10}$ substituents taken together with the carbon atom to which they are attached form a spiro 4-7-membered heterocycloalkyl ring, or a spiro $C_{3-6}$ cycloalkyl ring; wherein each spiro 4-7-membered heterocycloalkyl ring has at least one ring-forming carbon atom and 1, 2 or 3, ring-forming heteroatoms independently selected from N, O, and S; wherein a ring-forming carbon atom of each spiro 4-7-membered heterocycloalkyl ring is optionally substituted by oxo to form a carbonyl group; and wherein the spiro 4-7-membered heterocycloalkyl ring and spiro $C_{3-6}$ cycloalkyl ring are each optionally substituted with 1, 2, 3 or 4 substituents independently selected from $R^{11}$;

each $R^{11}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a3}$, $SR^{a3}$, $C(O)R^{b3}$, $C(O)NR^{c3}R^{d3}$, $C(O)OR^{a3}$, $NR^{c3}R^{d3}$, $NR^{c3}C(O)R^{b3}$, $NR^{c3}C(O)OR^{a3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{12}$;

each $R^{12}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, $C_{6-10}$ aryl, 5-10 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a5}$, $SR^{a5}$, $C(O)R^{b5}$, $C(O)NR^{c5}R^{d5}$, $C(O)OR^{a5}$, $NR^{c5}R^{d5}$, $NR^{c5}C(O)R^{b5}$, $NR^{c5}C(O)OR^{a5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$; wherein said $C_{1-6}$ alkyl, $C_{2-6}$ alkenyl, $C_{2-6}$ alkynyl, $C_{3-6}$ cycloalkyl, $C_{6-10}$ aryl, 5-10 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, $C_{6-10}$ aryl-$C_{1-3}$ alkylene, and 5-10 membered heteroaryl-$C_{1-3}$ alkylene are each optionally substituted with 1, 2, 3, or 4 substituents independently selected from $R^g$;

each $R^{20}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NOR^{a2})R^{b2}$, $C(=NR^{e2})NR^{c2}R^{d2}$, $NR^{c2}C(=NR^{e2})NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$; wherein a ring-forming carbon atom of the 4-10 membered heterocycloalkyl is optionally substituted by oxo to form a carbonyl group; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{21}$;

each $R^{21}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a4}$, $SR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $NR^{c4}C(O)OR^{a4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{22}$;

each $R^{22}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, 5-6 membered heteroaryl-$C_{1-3}$ alkylene, halo, D, CN, $OR^{a6}$, $SR^{a6}$, $C(O)R^{b6}$, $C(O)NR^{c6}R^{d6}$, $C(O)OR^{a6}$, $NR^{c6}R^{d6}$, $NR^{c6}C(O)R^{b6}$, $NR^{c6}C(O)OR^{a6}$, $NR^{c6}S(O)R^{b6}$, $NR^{c6}S(O)_2R^{b6}$, $NR^{c6}S(O)_2NR^{c6}R^{d6}$, $S(O)R^{b6}$, $S(O)NR^{c6}R^{d6}$, $S(O)_2R^{b6}$, and $S(O)_2NR^{c6}R^{d6}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene are each optionally substituted with 1, 2, 3, or 4 substituents independently selected from $R^g$;

each $R^{50}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a9}$, $SR^{a9}$, $C(O)R^{b9}$, $C(O)NR^{c9}R^{d9}$, $C(O)OR^{a9}$, $OC(O)R^{b9}$, $OC(O)NR^{c9}R^{d9}$, $NR^{c9}R^{d9}$, $NR^{c9}C(O)R^{b9}$, $NR^{c9}C(O)OR^{a9}$, $NR^{c9}C(O)NR^{c9}R^{d9}$, $C(=NR^{e9})R^{b9}$, $C(=NOR^{a9})R^{b9}$, $C(=NR^{e9})NR^{c9}R^{d9}$, $NR^{c9}C(=NR^{e9})NR^{c9}R^{d9}$, $NR^{c9}S(O)R^{b9}$, $NR^{c9}S(O)_2R^{b9}$, $NR^{c9}S(O)_2NR^{c9}R^{d9}$, $S(O)R^{b9}$, $S(O)NR^{c9}R^{d9}$, $S(O)_2R^{b9}$, and $S(O)_2NR^{c9}R^{d9}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{51}$;

each $R^{51}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a10}$, $SR^{a10}$, $C(O)R^{b10}$, $C(O)NR^{c1}R^{d1}$, $C(O)OR^{a10}$, $NR^{c10}R^{d10}$, $NR^{c10}C(O)R^{b10}$, $NR^{c10}C(O)OR^{a10}$, $NR^{c10}S(O)R^{b10}$, $NR^{c10}S(O)_2R^{b10}$, $NR^{c10}S(O)_2NR^{c10}R^{d10}$, $S(O)R^{b10}$, $S(O)NR^{c10}R^{d10}$, $S(O)_2R^{b10}$, and $S(O)_2NR^{c10}R^{d10}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{52}$;

each $R^{52}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, 5-6 membered heteroaryl-$C_{1-3}$ alkylene, halo, D, CN, $OR^{a11}$, $SR^{a11}$, $C(O)R^{b11}$; $C(O)NR^{c11}R^{d11}$, $C(O)OR^{a11}$, $NR^{c11}R^{d11}$, $NR^{c11}C(O)R^{b11}$, $NR^{c11}C(O)OR^{a11}$, $NR^{c11}S(O)R^{b11}$, $NR^{c11}S(O)_2R^{b11}$, $NR^{c11}S(O)_2NR^{c11}R^{d11}$, $S(O)R^{b11}$, $S(O)NR^{c11}R^{d11}$, $S(O)_2R^{b11}$, and $S(O)_2NR^{c11}R^{d11}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene are each optionally substituted with 1, 2, 3, or 4 substituents independently selected from $R^g$;

each $R^a$, $R^c$, and $R^d$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene are each optionally substituted with 1, 2, 3, or 4 substituents independently selected from $R^{10}$;

or any $R^c$ and $R^d$ attached to the same N atom, together with the N atom to which they are attached, form a 4-10 membered heterocycloalkyl group optionally substituted with 1, 2, 3 or 4 substituents independently selected from $R^{10}$;

each $R^b$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene are each optionally substituted with 1, 2, 3, or 4 substituents independently selected from $R^{10}$;

each $R^e$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{a1}$, $R^{c1}$ and $R^{d1}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene are each optionally substituted with 1, 2, 3, or 4 substituents independently selected from $R^{11}$;

or any $R^{c1}$ and $R^{d1}$ attached to the same N atom, together with the N atom to which they are attached, form a 4-10 membered heterocycloalkyl group optionally substituted with 1, 2, 3 or 4 substituents independently selected from $R^{11}$;

each $R^{b1}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene are each optionally substituted with 1, 2, 3, or 4 substituents independently selected from $R^{11}$; each $R^{e1}$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{a2}$, $R^{c2}$ and $R^{d2}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene are each optionally substituted with 1, 2, 3, or 4 substituents independently selected from $R^{21}$;

or any $R^{c2}$ and $R^{d2}$ attached to the same N atom, together with the N atom to which they are attached, form a 4-10 membered heterocycloalkyl group optionally substituted with 1, 2, 3 or 4 substituents independently selected from $R^{21}$;

each $R^{b2}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene are each optionally substituted with 1, 2, 3, or 4 substituents independently selected from $R^{21}$;

each $R^{e2}$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{a3}$, $R^{c3}$ and $R^{d3}$ is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene; wherein said $C_{1-6}$ alkyl $C_{2-6}$ alkenyl, $C_{2-6}$ alkynyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene are each optionally substituted with 1, 2, 3, or 4 substituents independently selected from $R^{12}$;

or any $R^{c3}$ and $R^{d3}$ attached to the same N atom, together with the N atom to which they are attached, form a 4-, 5-, 6- or 7-membered heterocycloalkyl group optionally substituted with 1, 2 or 3 substituents independently selected from $R^{12}$;

each $R^{b3}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene; wherein said $C_{1-6}$ alkyl $C_{2-6}$ alkenyl, $C_{2-6}$ alkynyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene are each optionally substituted with 1, 2, 3, or 4 substituents independently selected from $R^{12}$;

each $R^{a4}$, $R^{c4}$ and $R^{d4}$ is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene; wherein said $C_{1-6}$ alkyl $C_{2-6}$ alkenyl, $C_{2-6}$ alkynyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene are each optionally substituted with 1, 2, 3, or 4 substituents independently selected from $R^{22}$;

or any $R^{c4}$ and $R^{d4}$ attached to the same N atom, together with the N atom to which they are attached, form a 4-, 5-, 6- or 7-membered heterocycloalkyl group optionally substituted with 1, 2 or 3 substituents independently selected from $R^{22}$;

each $R^{b4}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene; wherein said $C_{1-6}$ alkyl $C_{2-6}$ alkenyl, $C_{2-6}$ alkynyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene are each optionally substituted with 1, 2, 3, or 4 substituents independently selected from $R^{22}$;

each $R^{a5}$, $R^{c5}$ and $R^{d5}$ is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

or any $R^{c5}$ and $R^{d5}$ attached to the same N atom, together with the N atom to which they are attached, form a 4-, 5-, 6- or 7-membered heterocycloalkyl group optionally substituted with 1, 2 or 3 substituents independently selected from $R^g$;

each $R^{b5}$ is independently selected from $C_{1-6}$ alkyl, $C_{2-6}$ alkenyl, $C_{2-6}$ alkynyl and $C_{1-6}$ haloalkyl; wherein said $C_{1-6}$ alkyl $C_{2-6}$ alkenyl and $C_{2-6}$ alkynyl are each optionally substituted with 1, 2, 3, or 4 substituents independently selected from $R^g$;

each $R^{a6}$, $R^{c6}$ and $R^{d6}$ is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

or any $R^{c6}$ and $R^{d6}$ attached to the same N atom, together with the N atom to which they are attached, form a 4-, 5-, 6- or 7-membered heterocycloalkyl group optionally substituted with 1, 2 or 3 substituents independently selected from $R^g$;

each $R^{b6}$ is independently selected from $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{a7}$, $R^{c7}$ and $R^{d7}$ is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{a8}$, $R^{c8}$ and $R^{d8}$ is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{a9}$, $R^{c9}$ and $R^{d9}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene are each optionally substituted with 1, 2, 3, or 4 substituents independently selected from $R^{51}$;

or any $R^{c9}$ and $R^{d9}$ attached to the same N atom, together with the N atom to which they are attached, form a 4-10 membered heterocycloalkyl group optionally substituted with 1, 2, 3 or 4 substituents independently selected from $R^{51}$;

each $R^{b9}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene are each optionally substituted with 1, 2, 3, or 4 substituents independently selected from $R^{51}$;

each $R^{e9}$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{a10}$, $R^{c10}$ and $R^{d10}$ is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene; wherein said $C_{1-6}$ alkyl $C_{2-6}$ alkenyl, $C_{2-6}$ alkynyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene are each optionally substituted with 1, 2, 3, or 4 substituents independently selected from $R^{52}$;

or any $R^{c10}$ and $R^{d10}$ attached to the same N atom, together with the N atom to which they are attached, form a 4-, 5-, 6- or 7-membered heterocycloalkyl group optionally substituted with 1, 2 or 3 substituents independently selected from $R^{52}$;

each $R^{b10}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene; wherein said $C_{1-6}$ alkyl $C_{2-6}$ alkenyl, $C_{2-6}$ alkynyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene are each optionally substituted with 1, 2, 3, or 4 substituents independently selected from $R^{52}$;

each $R^{a11}$, $R^{c11}$ and $R^{d11}$ is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

or any $R^{c11}$ and $R^{d11}$ attached to the same N atom, together with the N atom to which they are attached, form a 4-, 5-, 6- or 7-membered heterocycloalkyl group optionally substituted with 1, 2 or 3 substituents independently selected from $R^g$;

each $R^{b11}$ is independently selected from $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{a12}$, $R^{c12}$, and $R^{d12}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene are each optionally substituted with 1, 2, 3, or 4 substituents independently selected from $R^g$;

or any $R^{c12}$ and $R^{d12}$ attached to the same N atom, together with the N atom to which they are attached, form a 4-10 membered heterocycloalkyl group optionally substituted with 1, 2, 3 or 4 substituents independently selected from $R^g$;

each $R^{b12}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene are each optionally substituted with 1, 2, 3, or 4 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-6}$ haloalkyl, $C_{3-6}$ cycloalkyl, $C_{3-6}$ cycloalkyl-$C_{1-2}$ alkylene, $C_{1-6}$ alkoxy, $C_{1-6}$ haloalkoxy, $C_{1-3}$ alkoxy-$C_{1-3}$ alkyl, $C_{1-3}$ alkoxy-$C_{1-3}$ alkoxy, HO—$C_{1-3}$ alkoxy, HO—$C_{1-3}$ alkyl, cyano-$C_{1-3}$ alkyl, $H_2N$—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, the compound of Formula I is a compound wherein:

$R^1$ is selected from $C_{1-6}$ alkyl, $C_{2-6}$ alkenyl, $C_{2-6}$ alkynyl, $C_{1-6}$ haloalkyl, CN, $C(O)R^b$, $C(O)NR^cR^d$, $C(O)OR^a$, $C(=NR^e)R^b$, $C(=NOR^a)R^b$, and $C(=NR^e)NR^cR^d$, wherein said $C_{1-6}$ alkyl, $C_{2-6}$ alkenyl and $C_{2-6}$ alkynyl are each optionally substituted with 1, 2, 3, or 4 substituents independently selected from $R^{10}$;

$R^2$ is selected from $C_{6-10}$ aryl and 5-10 membered heteroaryl; wherein the 5-10 membered heteroaryl has at least one ring-forming carbon atom and 1, 2, 3, or 4 ring-forming heteroatoms independently selected from N, O, and S; wherein the N and S are optionally oxidized; wherein a ring-forming carbon atom of the 5-10 membered heteroaryl is optionally substituted by oxo to form a carbonyl group; and wherein the $C_{6-10}$ aryl and 5-10 membered heteroaryl are each optionally substituted with 1, 2, 3, 4 or 5 substituents independently selected from $R^{20}$;

or two adjacent $R^{20}$ substituents on $R^2$, taken together with the atoms to which they are attached, form a fused 4-, 5-, 6- or 7-membered heterocycloalkyl ring, or a fused $C_{3-7}$ cycloalkyl ring; wherein the fused 4-, 5-, 6- or 7-membered heterocycloalkyl ring each has at least one ring-forming carbon atom and 1, 2, 3, or 4 ring-forming heteroatoms independently selected from N, O, and S; wherein a ring-forming carbon atom of each fused 4-, 5-, 6- or 7-membered heterocycloalkyl ring is optionally substituted by oxo to form a carbonyl group; and wherein the fused 4-, 5-, 6- or 7-membered heterocycloalkyl ring and fused $C_{3-7}$ cycloalkyl ring are each optionally substituted with 1, 2, 3 or 4 substituents independently selected from $R^{21}$;

$R^3$ is selected from H, D, halo, CN, $C_{1-6}$ alkyl, $OR^{a7}$ and $NR^{c7}R^{d7}$; wherein the $C_{1-6}$ alkyl is optionally substituted with 1, 2, or 3 substituents independently selected from $R^g$;

$R^4$ is selected from H, D, halo, CN, $C_{1-6}$ alkyl, $OR^{a8}$ and $NR^{c8}R^{d8}$; wherein the $C_{1-6}$ alkyl is optionally substituted with 1, 2, or 3 substituents independently selected from $R^g$;

$R^5$ is selected from $C_{6-10}$ aryl and 5-10 membered heteroaryl; wherein the 5-10 membered heteroaryl has at least one ring-forming carbon atom and 1, 2, 3, or 4 ring-forming heteroatoms independently selected from N, O, and S; wherein the N and S are optionally oxidized; wherein a ring-forming carbon atom of the 5-10 membered heteroaryl is optionally substituted by oxo to form a carbonyl group; and wherein the $C_{6-10}$ aryl and 5-10 membered heteroaryl are each optionally substituted with 1, 2, 3, 4 or 5 substituents independently selected from $R^{50}$;

or two adjacent $R^{50}$ substituents on $R^5$, taken together with the atoms to which they are attached, form a fused 4-, 5-, 6- or 7-membered heterocycloalkyl ring, or a fused $C_{3-7}$ cycloalkyl ring; wherein the fused 4-, 5-, 6- or 7-membered heterocycloalkyl ring each has at least one ring-forming carbon atom and 1, 2, 3, or 4 ring-forming heteroatoms independently selected from N, O, and S; wherein a ring-forming carbon atom of each fused 4-, 5-, 6- or 7-membered heterocycloalkyl ring is optionally substituted by oxo to form a carbonyl group; and wherein the fused 4-, 5-, 6- or 7-membered heterocycloalkyl ring and fused $C_{3-7}$ cycloalkyl ring are each optionally substituted with 1, 2, 3 or 4 substituents independently selected from $R^{51}$;

A is N or $CR^A$;

$R^A$ is selected from H, D, $C_{1-6}$ alkyl, $C_{2-6}$ alkenyl, $C_{2-6}$ alkynyl, $C_{1-6}$ haloalkyl, halo, CN, $NO_2$, $OR^{a12}$, $SR^{a12}$, $C(O)R^{b12}$, $C(O)NR^{c12}R^{d12}$, $C(O)OR^{a12}$, $OC(O)R^{b12}$, $OC(O)NR^{c12}R^{d12}$, $NR^{c12}R^{d12}$, $NR^{c12}C(O)R^{b12}$, $NR^{c12}C(O)OR^{a12}$, $NR^{c12}C(O)NR^{c12}R^{d12}$, $NR^{c12}S(O)R^{b12}$, $NR^{c12}S(O)_2R^{b12}$, $NR^{c12}S(O)_2NR^{c12}R^{d12}$, $S(O)R^{b12}$, $S(O)NR^{c12}R^{d12}$, $S(O)_2R^{b12}$ and $S(O)_2NR^{c12}R^{d12}$; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{10}$ is independently selected from $C_{1-6}$ alkyl, $C_{2-6}$ alkenyl, $C_{2-6}$ alkynyl, $C_{1-6}$ haloalkyl, $C_{5-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NOR^{a1})R^{b1}$, $C(=NR^{e1})NR^{c1}R^{d1}$, $NR^{c1}C(=NR^{e1})NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, and $S(O)_2NR^{c1}R^{d1}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{11}$;

or two $R^{10}$ substituents taken together with the carbon atom to which they are attached form a spiro 4-7-membered heterocycloalkyl ring, or a spiro $C_{3-6}$ cycloalkyl ring; wherein each spiro 4-7-membered heterocycloalkyl ring has at least one ring-forming carbon atom and 1, 2 or 3, ring-forming heteroatoms independently selected from N, O, and S; wherein a ring-forming carbon atom of each spiro 4-7-membered heterocycloalkyl ring is optionally substituted by oxo to form a carbonyl group; and wherein the spiro 4-7-membered heterocycloalkyl ring and spiro $C_{3-6}$ cycloalkyl ring are each optionally substituted with 1, 2, 3 or 4 substituents independently selected from $R^{11}$;

each $R^{11}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a3}$, $SR^{a3}$, $C(O)R^{b3}$, $C(O)NR^{c3}R^{d3}$, $C(O)OR^{a3}$, $NR^{c3}R^{d3}$, $NR^{c3}C(O)R^{b3}$, $NR^{c3}C(O)OR^{a3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{12}$;

each $R^{12}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, $C_{6-10}$ aryl, 5-10 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a5}$, $SR^{a5}$, $C(O)R^{b5}$, $C(O)NR^{c5}R^{d5}$, $C(O)OR^{a5}$, $NR^{c5}R^{d5}$, $NR^{c5}C(O)R^{b5}$, $NR^{c5}C(O)OR^{a5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$; wherein said $C_{1-6}$ alkyl, $C_{2-6}$ alkenyl, $C_{2-6}$ alkynyl, $C_{3-6}$ cycloalkyl, $C_{6-10}$ aryl, 5-10 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, $C_{6-10}$ aryl-$C_{1-3}$ alkylene, and 5-10 membered heteroaryl-$C_{1-3}$ alkylene are each optionally substituted with 1, 2, 3, or 4 substituents independently selected from $R^g$;

each $R^{20}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NOR^{a2})R^{b2}$, $C(=NR^{e2})NR^{c2}R^{d2}$, $NR^{c2}C(=NR^{e2})NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$; wherein a ring-forming carbon atom of the 4-10 membered heterocycloalkyl is optionally substituted by oxo to form a carbonyl group; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{21}$;

each $R^{21}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a4}$, $SR^{a4}$, $C(O)R^{b4}$, $C(O)NR^{c4}R^{d4}$, $C(O)OR^{a4}$, $NR^{c4}R^{d4}$, $NR^{c4}C$ (O)R$^{b4}$, NR$^{c4}$C(O)OR$^{a4}$, NR$^{c4}$S(O)R$^{b4}$, NR$^{c4}$S(O)$_2$R$^{b4}$, NR$^{c4}$S(O)$_2$NR$^{c4}$R$^{d4}$, S(O)R$^{b4}$, S(O)NR$^{c4}$R$^{d4}$, S(O)$_2$R$^{b4}$, and S(O)$_2$NR$^{c4}$R$^{d4}$; wherein said C$_{1-6}$ alkyl, C$_{2-6}$ alkenyl, C$_{2-6}$ alkynyl, C$_{3-10}$ cycloalkyl, 4-10 membered heterocycloalkyl, C$_{6-10}$ aryl, 5-10 membered heteroaryl, C$_{3-10}$ cycloalkyl-C$_{1-3}$ alkylene, 4-10 membered heterocycloalkyl-C$_{1-3}$ alkylene, C$_{6-10}$ aryl-C$_{1-3}$ alkylene and 5-10 membered heteroaryl-C$_{1-3}$ alkylene are each optionally substituted with 1, 2, 3, or 4 substituents independently selected from R$^{22}$;

each R$^{22}$ is independently selected from C$_{1-6}$ alkyl, C$_{2-6}$ alkenyl, C$_{2-6}$ alkynyl, C$_{1-6}$ haloalkyl, C$_{3-6}$ cycloalkyl, phenyl, 5-6 membered heteroaryl, 4-7 membered heterocycloalkyl, C$_{3-6}$ cycloalkyl-C$_{1-3}$ alkylene, 4-7 membered heterocycloalkyl-C$_{1-3}$ alkylene, phenyl-C$_{1-3}$ alkylene, 5-6 membered heteroaryl-C$_{1-3}$ alkylene, halo, D, CN, OR$^{a6}$, SR$^{a6}$, C(O)R$^{b6}$, C(O)NR$^{c6}$R$^{d6}$, C(O)OR$^{a6}$, NR$^{c6}$R$^{d6}$, NR$^{c6}$C(O)R$^{b6}$, NR$^{c6}$C(O)OR$^{a6}$, NR$^{c6}$S(O)R$^{b6}$, NR$^{c6}$S(O)$_2$R$^{b6}$, NR$^{c6}$S(O)$_2$NR$^{c6}$R$^{d6}$, S(O)R$^{b6}$, S(O)NR$^{c6}$R$^{d6}$, S(O)$_2$R$^{b6}$, and S(O)$_2$NR$^{c6}$R$^{d6}$; wherein said C$_{1-6}$ alkyl, C$_{2-6}$ alkenyl, C$_{2-6}$ alkynyl, C$_{3-6}$ cycloalkyl, phenyl, 5-6 membered heteroaryl, 4-7 membered heterocycloalkyl, C$_{3-6}$ cycloalkyl-C$_{1-3}$ alkylene, 4-7 membered heterocycloalkyl-C$_{1-3}$ alkylene, phenyl-C$_{1-3}$ alkylene, and 5-6 membered heteroaryl-C$_{1-3}$ alkylene are each optionally substituted with 1, 2, 3, or 4 substituents independently selected from R$^g$;

each R$^{50}$ is independently selected from C$_{1-6}$ alkyl, C$_{2-6}$ alkenyl, C$_{2-6}$ alkynyl, C$_{1-6}$ haloalkyl, C$_{3-10}$ cycloalkyl, 4-10 membered heterocycloalkyl, C$_{6-10}$ aryl, 5-10 membered heteroaryl, C$_{3-10}$ cycloalkyl-C$_{1-3}$ alkylene, 4-10 membered heterocycloalkyl-C$_{1-3}$ alkylene, C$_{6-10}$ aryl-C$_{1-3}$ alkylene, 5-10 membered heteroaryl-C$_{1-3}$ alkylene, halo, D, CN, NO$_2$, OR$^{a9}$, SR$^{a9}$, C(O)R$^{b9}$, C(O)NR$^{c9}$R$^{d9}$, C(O)OR$^{a9}$, OC(O)R$^{b9}$, OC(O)NR$^{c9}$R$^{d9}$, NR$^{c9}$R$^{d9}$, NR$^{c9}$C(O)R$^{b9}$, NR$^{c9}$C(O)OR$^{a9}$, NR$^{c9}$C(O)NR$^{c9}$R$^{d9}$, C(=NR$^{e9}$)R$^{b9}$, C(=NOR$^{a9}$)R$^{b9}$, C(=NR$^{e9}$)NR$^{c9}$R$^{d9}$, NR$^{c9}$C(=NR$^{e9}$)NR$^{c9}$R$^{d9}$, NR$^{c9}$S(O)R$^{b9}$, NR$^{c9}$S(O)$_2$R$^{b9}$, NR$^{c9}$S(O)$_2$NR$^{c9}$R$^{d9}$, S(O)R$^{b9}$, S(O)NR$^{c9}$R$^{d9}$, S(O)$_2$R$^{b9}$, and S(O)$_2$NR$^{c9}$R$^{d9}$; wherein said C$_{1-6}$ alkyl, C$_{2-6}$ alkenyl, C$_{2-6}$ alkynyl, C$_{3-10}$ cycloalkyl, 4-10 membered heterocycloalkyl, C$_{6-10}$ aryl, 5-10 membered heteroaryl, C$_{3-10}$ cycloalkyl-C$_{1-3}$ alkylene, 4-10 membered heterocycloalkyl-C$_{1-3}$ alkylene, C$_{6-10}$ aryl-C$_{1-3}$ alkylene and 5-10 membered heteroaryl-C$_{1-3}$ alkylene are each optionally substituted with 1, 2, 3, or 4 substituents independently selected from R$^{51}$;

each R$^{51}$ is independently selected from C$_{1-6}$ alkyl, C$_{2-6}$ alkenyl, C$_{2-6}$ alkynyl, C$_{1-6}$ haloalkyl, C$_{3-10}$ cycloalkyl, 4-10 membered heterocycloalkyl, C$_{6-10}$ aryl, 5-10 membered heteroaryl, C$_{3-10}$ cycloalkyl-C$_{1-3}$ alkylene, 4-10 membered heterocycloalkyl-C$_{1-3}$ alkylene, C$_{6-10}$ aryl-C$_{1-3}$ alkylene, 5-10 membered heteroaryl-C$_{1-3}$ alkylene, halo, D, CN, OR$^{a10}$, SR$^{a10}$, C(O)R$^{b10}$, C(O)NR$^{c10}$R$^{d10}$, C(O)OR$^{a10}$, NR$^{c10}$R$^{d10}$, NR$^{c10}$C(O)R$^{b10}$, NR$^{c10}$C(O)OR$^{a10}$, NR$^{c10}$S(O)R$^{b10}$, NR$^{c10}$S(O)$_2$R$^{b10}$, NR$^{c10}$S(O)$_2$NR$^{c10}$R$^{d10}$, S(O)R$^{b10}$, S(O)NR$^{c10}$R$^{d10}$, S(O)$_2$R$^{b10}$, and S(O)$_2$NR$^{c10}$R$^{d10}$; wherein said C$_{1-6}$ alkyl, C$_{2-6}$ alkenyl, C$_{2-6}$ alkynyl, C$_{3-10}$ cycloalkyl, 4-10 membered heterocycloalkyl, C$_{6-10}$ aryl, 5-10 membered heteroaryl, C$_{3-10}$ cycloalkyl-C$_{1-3}$ alkylene, 4-10 membered heterocycloalkyl-C$_{1-3}$ alkylene, C$_{6-10}$ aryl-C$_{1-3}$ alkylene and 5-10 membered heteroaryl-C$_{1-3}$ alkylene are each optionally substituted with 1, 2, 3, or 4 substituents independently selected from R$^{52}$;

each R$^{52}$ is independently selected from C$_{1-6}$ alkyl, C$_{2-6}$ alkenyl, C$_{2-6}$ alkynyl, C$_{1-6}$ haloalkyl, C$_{3-6}$ cycloalkyl, phenyl, 5-6 membered heteroaryl, 4-7 membered heterocycloalkyl, C$_{3-6}$ cycloalkyl-C$_{1-3}$ alkylene, 4-7 membered heterocycloalkyl-C$_{1-3}$ alkylene, phenyl-C$_{1-3}$ alkylene, 5-6 membered heteroaryl-C$_{1-3}$ alkylene, halo, D, CN, OR$^{a11}$, SR$^{a11}$, C(O)R$^{b11}$, C(O)NR$^{c11}$R$^{d11}$, C(O)OR$^{a11}$, NR$^{c11}$R$^{d11}$, NR$^{c11}$C(O)R$^{b11}$, NR$^{c11}$C(O)OR$^{a11}$, NR$^{c11}$S(O)R$^{b11}$, NR$^{c11}$S(O)$_2$R$^{b11}$, NR$^{c11}$S(O)$_2$NR$^{c11}$R$^{d11}$, S(O)R$^{b11}$, S(O)NR$^{c11}$R$^{d11}$, S(O)$_2$R$^{b11}$, and S(O)$_2$NR$^{c11}$R$^{d11}$; wherein said C$_{1-6}$ alkyl, C$_{2-6}$ alkenyl, C$_{2-6}$ alkynyl, C$_{3-6}$ cycloalkyl, phenyl, 5-6 membered heteroaryl, 4-7 membered heterocycloalkyl, C$_{3-6}$ cycloalkyl-C$_{1-3}$ alkylene, 4-7 membered heterocycloalkyl-C$_{1-3}$ alkylene, phenyl-C$_{1-3}$ alkylene, and 5-6 membered heteroaryl-C$_{1-3}$ alkylene are each optionally substituted with 1, 2, 3, or 4 substituents independently selected from R$^g$;

each R$^a$, R$^c$, and R$^d$ is independently selected from H, C$_{1-6}$ alkyl, C$_{2-6}$ alkenyl, C$_{2-6}$ alkynyl, C$_{1-6}$ haloalkyl, C$_{3-10}$ cycloalkyl, 4-10 membered heterocycloalkyl, C$_{6-10}$ aryl, 5-10 membered heteroaryl, C$_{3-10}$ cycloalkyl-C$_{1-3}$ alkylene, 4-10 membered heterocycloalkyl-C$_{1-3}$ alkylene, C$_{6-10}$ aryl-C$_{1-3}$ alkylene, and 5-10 membered heteroaryl-C$_{1-3}$ alkylene; wherein said C$_{1-6}$ alkyl, C$_{2-6}$ alkenyl, C$_{2-6}$ alkynyl, C$_{3-10}$ cycloalkyl, 4-10 membered heterocycloalkyl, C$_{6-10}$ aryl, 5-10 membered heteroaryl, C$_{3-10}$ cycloalkyl-C$_{1-3}$ alkylene, 4-10 membered heterocycloalkyl-C$_{1-3}$ alkylene, C$_{6-10}$ aryl-C$_{1-3}$ alkylene, and 5-10 membered heteroaryl-C$_{1-3}$ alkylene are each optionally substituted with 1, 2, 3, or 4 substituents independently selected from R$^{10}$;

or any R$^c$ and R$^d$ attached to the same N atom, together with the N atom to which they are attached, form a 4-10 membered heterocycloalkyl group optionally substituted with 1, 2, 3 or 4 substituents independently selected from R$^{10}$;

each R$^b$ is independently selected from C$_{1-6}$ alkyl, C$_{2-6}$ alkenyl, C$_{2-6}$ alkynyl, C$_{1-6}$ haloalkyl, C$_{3-10}$ cycloalkyl, 4-10 membered heterocycloalkyl, C$_{6-10}$ aryl, 5-10 membered heteroaryl, C$_{3-10}$ cycloalkyl-C$_{1-3}$ alkylene, 4-10 membered heterocycloalkyl-C$_{1-3}$ alkylene, C$_{6-10}$ aryl-C$_{1-3}$ alkylene, and 5-10 membered heteroaryl-C$_{1-3}$ alkylene; wherein said C$_{1-6}$ alkyl, C$_{2-6}$ alkenyl, C$_{2-6}$ alkynyl, C$_{3-10}$ cycloalkyl, 4-10 membered heterocycloalkyl, C$_{6-10}$ aryl, 5-10 membered heteroaryl, C$_{3-10}$ cycloalkyl-C$_{1-3}$ alkylene, 4-10 membered heterocycloalkyl-C$_{1-3}$ alkylene, C$_{6-10}$ aryl-C$_{1-3}$ alkylene, and 5-10 membered heteroaryl-C$_{1-3}$ alkylene are each optionally substituted with 1, 2, 3, or 4 substituents independently selected from R$^{10}$;

each R$^e$ is independently selected from H, CN, C$_{1-6}$ alkyl, C$_{1-6}$ haloalkyl, C$_{1-6}$ alkylthio, C$_{1-6}$ alkylsulfonyl, C$_{1-6}$ alkylcarbonyl, C$_{1-6}$ alkylaminosulfonyl, carbamyl, C$_{1-6}$ alkylcarbamyl, di(C$_{1-6}$ alkyl)carbamyl, aminosulfonyl, C$_{1-6}$ alkylaminosulfonyl and di(C$_{1-6}$ alkyl)aminosulfonyl;

each R$^{a1}$, R$^{c1}$ and R$^{d1}$ is independently selected from H, C$_{1-6}$ alkyl, C$_{2-6}$ alkenyl, C$_{2-6}$ alkynyl, C$_{1-6}$ haloalkyl, C$_{3-10}$ cycloalkyl, 4-10 membered heterocycloalkyl, C$_{6-10}$ aryl, 5-10 membered heteroaryl, C$_{3-10}$ cycloalkyl-C$_{1-3}$ alkylene, 4-10 membered heterocycloalkyl-C$_{1-3}$ alkylene, C$_{6-10}$ aryl-C$_{1-3}$ alkylene, and 5-10 membered heteroaryl-C$_{1-3}$ alkylene; wherein said C$_{1-6}$ alkyl, C$_{2-6}$ alkenyl, C$_{2-6}$ alkynyl, C$_{3-10}$ cycloalkyl, 4-10 membered heterocycloalkyl, C$_{6-10}$ aryl, 5-10 membered heteroaryl, C$_{3-10}$ cycloalkyl-C$_{1-3}$ alkylene, 4-10 membered heterocycloalkyl-C$_{1-3}$ alkylene, C$_{6-10}$ aryl-C$_{1-3}$ alkylene, and 5-10 membered heteroaryl-C$_{1-3}$ alkylene are each optionally substituted with 1, 2, 3, or 4 substituents independently selected from R$^{11}$;

or any R$^{c1}$ and R$^{d1}$ attached to the same N atom, together with the N atom to which they are attached, form a 4-10 membered heterocycloalkyl group optionally substituted with 1, 2, 3 or 4 substituents independently selected from R$^{11}$;

each R$^{b1}$ is independently selected from C$_{1-6}$ alkyl, C$_{2-6}$ alkenyl, C$_{2-6}$ alkynyl, C$_{1-6}$ haloalkyl, C$_{3-10}$ cycloalkyl, 4-10 membered heterocycloalkyl, C$_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene are each optionally substituted with 1, 2, 3, or 4 substituents independently selected from $R^{11}$;

each $R^{e1}$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{a2}$, $R^{c2}$ and $R^{d2}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene are each optionally substituted with 1, 2, 3, or 4 substituents independently selected from $R^{21}$;

or any $R^{c2}$ and $R^{d2}$ attached to the same N atom, together with the N atom to which they are attached, form a 4-10 membered heterocycloalkyl group optionally substituted with 1, 2, 3 or 4 substituents independently selected from $R^{21}$;

each $R^{b2}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene are each optionally substituted with 1, 2, 3, or 4 substituents independently selected from $R^{21}$;

each $R^{e2}$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{a3}$, $R^{c3}$ and $R^{d3}$ is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene; wherein said $C_{1-6}$ alkyl $C_{2-6}$ alkenyl, $C_{2-6}$ alkynyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene are each optionally substituted with 1, 2, 3, or 4 substituents independently selected from $R^{12}$;

or any $R^{c3}$ and $R^{d3}$ attached to the same N atom, together with the N atom to which they are attached, form a 4-, 5-, 6- or 7-membered heterocycloalkyl group optionally substituted with 1, 2 or 3 substituents independently selected from $R^{12}$;

each $R^{b3}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene; wherein said $C_{1-6}$ alkyl $C_{2-6}$ alkenyl, $C_{2-6}$ alkynyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene are each optionally substituted with 1, 2, 3, or 4 substituents independently selected from $R^{12}$;

each $R^{a4}$, $R^{c4}$ and $R^{d4}$ is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene; wherein said $C_{1-6}$ alkyl $C_{2-6}$ alkenyl, $C_{2-6}$ alkynyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene are each optionally substituted with 1, 2, 3, or 4 substituents independently selected from $R^{22}$;

or any $R^{c4}$ and $R^{d4}$ attached to the same N atom, together with the N atom to which they are attached, form a 4-, 5-, 6- or 7-membered heterocycloalkyl group optionally substituted with 1, 2 or 3 substituents independently selected from $R^{22}$;

each $R^{b4}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene; wherein said $C_{1-6}$ alkyl $C_{2-6}$ alkenyl, $C_{2-6}$ alkynyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene are each optionally substituted with 1, 2, 3, or 4 substituents independently selected from $R^{22}$;

each $R^{a5}$, $R^{c5}$ and $R^{d5}$ is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

or any $R^{c5}$ and $R^{d5}$ attached to the same N atom, together with the N atom to which they are attached, form a 4-, 5-, 6- or 7-membered heterocycloalkyl group optionally substituted with 1, 2 or 3 substituents independently selected from $R^g$;

each $R^{b5}$ is independently selected from $C_{1-6}$ alkyl, $C_{2-6}$ alkenyl, $C_{2-6}$ alkynyl and $C_{1-6}$ haloalkyl; wherein said $C_{1-6}$ alkyl $C_{2-6}$ alkenyl and $C_{2-6}$ alkynyl are each optionally substituted with 1, 2, 3, or 4 substituents independently selected from $R^g$;

each $R^{a6}$, $R^{c6}$ and $R^{d6}$ is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

or any $R^{c6}$ and $R^{d6}$ attached to the same N atom, together with the N atom to which they are attached, form a 4-, 5-, 6- or 7-membered heterocycloalkyl group optionally substituted with 1, 2 or 3 substituents independently selected from $R^g$;

each $R^{b6}$ is independently selected from $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{a7}$, $R^{c7}$ and $R^{d7}$ is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{a8}$, $R^{c8}$ and $R^{d8}$ is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{a9}$, $R^{c9}$ and $R^{d9}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene are each optionally substituted with 1, 2, 3, or 4 substituents independently selected from $R^{51}$;

or any $R^{c9}$ and $R^{d9}$ attached to the same N atom, together with the N atom to which they are attached, form a 4-10 membered heterocycloalkyl group optionally substituted with 1, 2, 3 or 4 substituents independently selected from $R^{51}$;

each $R^{b9}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene are each optionally substituted with 1, 2, 3, or 4 substituents independently selected from $R^{51}$;

each $R^{e9}$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{a10}$, $R^{c10}$ and $R^{d10}$ is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene; wherein said $C_{1-6}$ alkyl $C_{2-6}$ alkenyl, $C_{2-6}$ alkynyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene are each optionally substituted with 1, 2, 3, or 4 substituents independently selected from $R^{52}$;

or any $R^{c10}$ and $R^{d10}$ attached to the same N atom, together with the N atom to which they are attached, form a 4-, 5-, 6- or 7-membered heterocycloalkyl group optionally substituted with 1, 2 or 3 substituents independently selected from $R^{52}$;

each $R^{b10}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene; wherein said $C_{1-6}$ alkyl $C_{2-6}$ alkenyl, $C_{2-6}$ alkynyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene are each optionally substituted with 1, 2, 3, or 4 substituents independently selected from $R^{52}$;

each $R^{a11}$, $R^{c11}$ and $R^{d11}$ is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

or any $R^{c11}$ and $R^{d11}$ attached to the same N atom, together with the N atom to which they are attached, form a 4-, 5-, 6- or 7-membered heterocycloalkyl group optionally substituted with 1, 2 or 3 substituents independently selected from $R^g$;

each $R^{b11}$ is independently selected from $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{a12}$, $R^{c12}$, and $R^{d12}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene are each optionally substituted with 1, 2, 3, or 4 substituents independently selected from $R^g$;

or any $R^{c12}$ and $R^{d12}$ attached to the same N atom, together with the N atom to which they are attached, form a 4-10 membered heterocycloalkyl group optionally substituted with 1, 2, 3 or 4 substituents independently selected from $R^g$;

each $R^{b12}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene are each optionally substituted with 1, 2, 3, or 4 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-6}$ haloalkyl, $C_{3-6}$ cycloalkyl, $C_{3-6}$ cycloalkyl-$C_{1-2}$ alkylene, $C_{1-6}$ alkoxy, $C_{1-6}$ haloalkoxy, $C_{1-3}$ alkoxy-$C_{1-3}$ alkyl, $C_{1-3}$ alkoxy-$C_{1-3}$ alkoxy, HO—$C_{1-3}$ alkoxy, HO—$C_{1-3}$ alkyl, cyano-$C_{1-3}$ alkyl, $H_2N$—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl) carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, $R^1$ is selected from $Cy^1$, $C_{1-6}$ alkyl, $C_{2-6}$ alkenyl, $C_{2-6}$ alkynyl, $C_{1-6}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein said $C_{1-6}$ alkyl, $C_{2-6}$ alkenyl and $C_{2-6}$ alkynyl are each optionally substituted with 1, 2, 3, or 4 substituents independently selected from $R^{10}$.

In some embodiments, $R^1$ is selected from $Cy^1$, $C_{1-6}$ alkyl, $C_{2-6}$ alkenyl, $C_{2-6}$ alkynyl, $C_{1-6}$ haloalkyl, CN, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, and $NR^cC(O)OR^a$; wherein said $C_{1-6}$ alkyl, $C_{2-6}$ alkenyl and $C_{2-6}$ alkynyl are each optionally substituted with 1, 2, 3, or 4 substituents independently selected from $R^{10}$.

In some embodiments, $R^1$ is selected from $Cy^1$, $C_{1-6}$ alkyl, $C_{2-6}$ alkenyl, $C_{2-6}$ alkynyl, $C_{1-6}$ haloalkyl, CN, $OR^a$, $C(O)R^b$, $C(O)NR^cR^d$, $C(O)OR^a$, $OC(O)R^b$, $NR^cR^d$, and $NR^cC(O)R^b$; wherein said $C_{1-6}$ alkyl, $C_{2-6}$ alkenyl and $C_{2-6}$ alkynyl are each optionally substituted with 1, 2, 3, or 4 substituents independently selected from $R^{10}$.

In some embodiments, $R^1$ is selected from $C_{1-6}$ alkyl, $C_{2-6}$ alkenyl, $C_{2-6}$ alkynyl, $C_{1-6}$ haloalkyl, CN, $C(O)R^b$, $C(O)NR^cR^d$, $C(O)OR^a$, $C(=NR^e)R^b$, $C(=NOR^a)R^b$, and $C(=NR^e)NR^cR^d$, wherein said $C_{1-6}$ alkyl, $C_{2-6}$ alkenyl and $C_{2-6}$ alkynyl are each optionally substituted with 1, 2, 3, or 4 substituents independently selected from $R^{10}$.

In some embodiments, $R^1$ is selected from $Cy^1$, $C_{1-6}$ alkyl, $C_{2-6}$ alkenyl, $C_{2-6}$ alkynyl, $C_{1-6}$ haloalkyl, CN, $OR^a$, $C(O)R^b$, $C(O)NR^cR^d$, and $C(O)OR^a$; wherein said $C_{1-6}$ alkyl, $C_{2-6}$ alkenyl and $C_{2-6}$ alkynyl are each optionally substituted with 1, 2, 3, or 4 substituents independently selected from $R^{10}$.

In some embodiments, $R^1$ is selected from $C_{1-6}$ alkyl, $C_{2-6}$ alkenyl, $C_{2-6}$ alkynyl, $C_{1-6}$ haloalkyl, CN, $C(O)R^b$, $C(O)NR^cR^d$, and $C(O)OR^a$; wherein said $C_{1-6}$ alkyl, $C_{2-6}$ alkenyl and $C_{2-6}$ alkynyl are each optionally substituted with 1, 2, 3, or 4 substituents independently selected from $R^{10}$.

In some embodiments, $R^1$ is selected from $C_{1-6}$ alkyl, CN, $C(O)NR^cR^d$, $C(O)R^b$, and $C(O)OR^a$; wherein said $C_{1-6}$ alkyl is optionally substituted with 1, 2, 3, or 4 substituents independently selected from $R^{10}$.

In some embodiments, $R^1$ is selected from $C_{1-6}$ alkyl, CN, $C(O)NR^cR^d$, and $C(O)OR^a$; wherein said $C_{1-6}$ alkyl is optionally substituted with 1, 2, 3, or 4 substituents independently selected from $R^{10}$.

In some embodiments, $R^1$ is $C_{1-6}$ alkyl. In some embodiments, $R^1$ is methyl.

In some embodiments, $R^1$ is $C(O)OR^a$.

In some embodiments, $R^1$ is $C(O)R^b$.

In some embodiments, $R^1$ is $C(O)NR^cR^d$.

In some embodiments, $R^1$ is selected from methyl, methoxycarbonyl, carbamoyl, cyano, hydroxymethyl, methoxymethyl, N-(4-hydroxy-4-methylcyclohexyl)carbamoyl (e.g., N-((1R,4R)-(4-hydroxy-4-methylcyclohexyl) carbamoyl), and 4-ethoxycarbonyl-piperazin-1-ylcarbonyl.

In some embodiments, each $R^{10}$ is selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl, are each optionally substituted with 1, 2, 3, or 4 substituents independently selected from $R^{11}$.

In some embodiments, each $R^{10}$ is selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $OR^{a1}$, $C(O)OR^{a1}$, $NR^{c1}R^{d1}$, and $S(O)_2NR^{c1}R^{d1}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl are each optionally substituted with 1 or 2 substituents independently selected from $R^{11}$.

In some embodiments, each $R^{10}$ is selected from $C_{1-6}$ alkyl, $C_{1-6}$ haloalkyl, halo, D, CN, $OR^{a1}$, $C(O)R^{b1}$, $C(O)NR^{c1}R^{d1}$, $C(O)OR^{a1}$, $NR^{c1}R^{d1}$, and $S(O)_2NR^{c1}R^{d1}$; wherein said $C_{1-6}$ alkyl is optionally substituted with 1, 2, 3, or 4 substituents independently selected from $R^{11}$.

In some embodiments, each $R^{10}$ is selected from $C_{1-6}$ alkyl, $OR^{a1}$, and $C(O)OR^{a1}$; wherein said $C_{1-6}$ alkyl is optionally substituted with 1 or 2 substituents independently selected from $R^{11}$.

In some embodiments, each $R^{10}$ is $C_{1-6}$ alkyl; wherein said $C_{1-6}$ alkyl, is optionally substituted with 1 or 2 substituents independently selected from $R^{11}$.

In some embodiments, each $R^{10}$ is selected from $C(O)R^{b1}$, and $C(O)OR^{a1}$. In some embodiments, each $R^{10}$ is $OR^{a1}$. In some embodiments, each $R^{10}$ is $C(O)OR^{a1}$.

In some embodiments, each $R^{10}$ is selected from methyl, OH, methoxy, and ethoxycarbonyl.

In some embodiments, two of the $R^{10}$ substituents taken together with the carbon atom to which they are attached form a spiro 4-7-membered heterocycloalkyl ring; wherein each spiro 4-7-membered heterocycloalkyl ring has at least one ring-forming carbon atom and 1, 2 or 3, ring-forming heteroatoms independently selected from N, O, and S; wherein a ring-forming carbon atom of each spiro 4-7-membered heterocycloalkyl ring is optionally substituted by oxo to form a carbonyl group; and wherein the spiro 4-7-membered heterocycloalkyl ring is optionally substituted with 1, 2, 3 or 4 substituents independently selected from $R^{11}$.

In some embodiments, two of the $R^{10}$ substituents taken together with the carbon atom to which they are attached form a spiro $C_{3-6}$ cycloalkyl ring; wherein the spiro $C_{3-6}$ cycloalkyl ring is optionally substituted with 1, 2, 3 or 4 substituents independently selected from $R^{11}$.

In some embodiments, each $R^{11}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $OR^{a3}$, $SR^{a3}$, $C(O)R^{b3}$, $C(O)NR^{c3}R^{d3}$, $C(O)OR^{a3}$, $NR^{c3}R^{d3}$, and $NR^{c3}C(O)R^{b3}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl are each optionally substituted with 1 or 2 substituents independently selected from $R^{12}$.

In some embodiments, each $R^{11}$ is independently selected from $C_{1-6}$ alkyl, $C_{1-6}$ haloalkyl, halo, D, CN, $OR^{a3}$, and $NR^{c3}R^{d3}$; wherein said $C_{1-6}$ alkyl, is optionally substituted with 1 or 2 substituents independently selected from $R^{12}$.

In some embodiments, each $R^{11}$ is independently selected from $C_{1-6}$ alkyl, In some embodiments, $R^1$ is $Cy^1$.

In some embodiments, $Cy^1$ is $C_{3-14}$ cycloalkyl optionally substituted with 1, 2, 3 or 4 substituents independently selected from $R^{15}$.

In some embodiments, $Cy^1$ is 4-14 membered heterocycloalkyl having at least one ring-forming carbon atom and 1, 2, 3, or 4 ring-forming heteroatoms independently selected from N, O, and S; wherein the N and S are optionally oxidized; wherein a ring-forming carbon atom of 4-14 membered heterocycloalkyl is optionally substituted by oxo to form a carbonyl group; and wherein the 4-14 membered heterocycloalkyl is optionally substituted with 1, 2, 3 or 4 substituents independently selected from $R^5$.

In some embodiments, $Cy^1$ is $C_{6-10}$ aryl optionally substituted with 1, 2, 3 or 4 substituents independently selected from $R^{15}$.

In some embodiments, $Cy^1$ is 5-10 membered heteroaryl; wherein the 5-10 membered heteroaryl has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl is optionally substituted by oxo to form a carbonyl group; and wherein the 5-10 membered heteroaryl is optionally substituted with 1, 2, 3 or 4 substituents independently selected from $R^{10}$.

In some embodiments, $R^2$ is $C_{6-10}$ aryl, optionally substituted with 1, 2, 3, 4 or 5 substituents independently selected from $R^{20}$.

In some embodiments, $R^2$ is 5-10 membered heteroaryl; wherein the 5-10 membered heteroaryl has at least one ring-forming carbon atom and 1, 2, 3, or 4 ring-forming heteroatoms independently selected from N, O, and S; wherein the N and S are optionally oxidized; wherein a ring-forming carbon atom of the 5-10 membered heteroaryl is optionally substituted by oxo to form a carbonyl group; and wherein the 5-10 membered heteroaryl is optionally substituted with 1, 2, 3, 4 or 5 substituents independently selected from $R^{20}$.

In some embodiments, $R^2$ is selected from phenyl and 5-6 membered heteroaryl; wherein the 5-6 membered heteroaryl has at least one ring-forming carbon atom and 1, 2, 3, or 4 ring-forming heteroatoms independently selected from N, O, and S; wherein the N and S are optionally oxidized; wherein a ring-forming carbon atom of the 5-6 membered heteroaryl is optionally substituted by oxo to form a carbonyl group; and wherein the phenyl and 5-6 membered heteroaryl are each optionally substituted with 1, 2, 3, 4 or 5 substituents independently selected from $R^{20}$.

In some embodiments, $R^2$ is 5-6 membered heteroaryl; wherein the 5-6 membered heteroaryl has at least one ring-forming carbon atom and 1, 2, 3, or 4 ring-forming heteroatoms independently selected from N, O, and S; wherein the N and S are optionally oxidized; wherein a ring-forming carbon atom of the 5-6 membered heteroaryl is optionally substituted by oxo to form a carbonyl group; and wherein the 5-6 membered heteroaryl is optionally substituted with 1, 2, 3, 4 or 5 substituents independently selected from $R^{20}$.

In some embodiments, $R^2$ is phenyl, optionally substituted with 1, 2, 3, 4 or 5 substituents independently selected from $R^{20}$.

In some embodiments, $R^2$ is phenyl, optionally substituted with 1 or 2 substituents independently selected from $R^{20}$.

In some embodiments, $R^2$ is phenyl, substituted at the para position with $R^{20}$.

In some embodiments, $R^2$ is phenyl, substituted at the meta position with $R^{20}$.

In some embodiments, $R^2$ is phenyl, substituted at the ortho position with $R^{20}$.

In some embodiments, $R^2$ is pyrazole, optionally substituted with 1, 2, 3, or 4 substituents independently selected from $R^{20}$.

In some embodiments, $R^2$ is pyrazole, optionally substituted with 1 or 2 substituents independently selected from $R^{20}$.

In some embodiments, $R^2$ is selected from phenyl and pyrazolyl; wherein the phenyl and pyrazolyl are each optionally substituted with 1 or 2 substituents independently selected from $R^{20}$.

In some embodiments, each $R^{20}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl, are each optionally substituted with 1, 2, 3, or 4 substituents independently selected from $R^{21}$.

In some embodiments, each $R^{20}$ is independently selected from $C_{1-6}$ alkyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $OR^{a2}$, $C(O)R^{b2}$, $C(O)NR^{c2}R^{d2}$, $C(O)OR^{a2}$, $NR^{c2}R^{d2}$, $S(O)_2R^{b2}$, and $S(O)_2NR^{c2}R^{d2}$; wherein a ring-forming carbon atom of the 4-10 membered heterocycloalkyl is optionally substituted by oxo to form a carbonyl group; wherein said $C_{1-6}$ alkyl, $C_{3-10}$ cycloalkyl, 4-10 membered heterocycloalkyl, $C_{6-10}$ aryl, and 5-10 membered heteroaryl, are each optionally substituted with 1, 2, 3, or 4 substituents independently selected from $R^{21}$.

In some embodiments, each $R^{20}$ is independently selected from $C_{1-6}$ alkyl, $C_{3-10}$ cycloalkyl, 4-10 membered heterocycloalkyl, halo, $NR^{c2}R^{d2}$, and $C(O)NR^{c2}R^{d2}$, wherein a ring-forming carbon atom of the 4-10 membered heterocycloalkyl is optionally substituted by oxo to form a carbonyl group; wherein said $C_{1-6}$ alkyl, $C_{3-10}$ cycloalkyl, and 4-10 membered heterocycloalkyl, are each optionally substituted with 1, 2, 3, or 4 substituents independently selected from $R^{21}$.

In some embodiments, each $R^{20}$ is independently selected from $C_{1-6}$ alkyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a2}$, $C(O)R^{b2}$, $C(O)NR^{c2}R^{d2}$, $C(O)OR^{a2}$, $NR^{c2}R^{d2}$, $S(O)_2R^{b2}$, and $S(O)_2NR^{c2}R^{d2}$; wherein a ring-forming carbon atom of the 4-10 membered heterocycloalkyl is optionally substituted by oxo to form a carbonyl group; wherein said $C_{1-6}$ alkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene are each optionally substituted with 1, 2, 3, or 4 substituents independently selected from $R^{21}$.

In some embodiments, each $R^{20}$ is independently selected from $C_{1-6}$ alkyl, $C_{3-10}$ cycloalkyl, 4-10 membered heterocycloalkyl, 4-10 membered heterocycloalkyl-$C_{1-3}$ alkylene, halo, $NR^{c2}R^{d2}$, and $C(O)NR^{c2}R^{d2}$, wherein a ring-forming carbon atom of the 4-10 membered heterocycloalkyl is optionally substituted by oxo to form a carbonyl group; wherein said $C_{1-6}$ alkyl, $C_{3-10}$ cycloalkyl, 4-10 membered heterocycloalkyl and 4-10 membered heterocycloalkyl-$C_{1-3}$ alkylene are each optionally substituted with 1, 2, 3, or 4 substituents independently selected from $R^{21}$.

In some embodiments, each $R^{20}$ is independently selected from $C_{1-6}$ alkyl, $C_{1-6}$ haloalkyl, $C_{3-6}$ cycloalkyl, 4-6 membered heterocycloalkyl, phenyl, 5-6 membered heteroaryl, $C_{3-6}$ cycloalkyl-$C_{1-3}$ alkylene, 4-6 membered heterocycloalkyl-$C_{1-3}$ alkylene, phenyl-$C_{1-3}$ alkylene, 5-6 membered heteroaryl-$C_{1-3}$ alkylene, halo, D, CN, $OR^{a2}$, $C(O)R^{b2}$, $C(O)NR^{c2}R^{d2}$, $C(O)OR^{a2}$, $NR^{c2}R^{d2}$, $S(O)_2R^{b2}$, and $S(O)_2NR^{c2}R^{d2}$; wherein a ring-forming carbon atom of the 4-6 membered heterocycloalkyl is optionally substituted by oxo to form a carbonyl group; wherein said $C_{1-6}$ alkyl, $C_{3-6}$ cycloalkyl, 4-6 membered heterocycloalkyl, phenyl, 5-6 membered heteroaryl, $C_{3-6}$ cycloalkyl-$C_{1-3}$ alkylene, 4-6 membered heterocycloalkyl-$C_{1-3}$ alkylene, phenyl-$C_{1-3}$ alkylene, and 5-6 membered heteroaryl-$C_{1-3}$ alkylene are each optionally substituted with 1, 2, 3, or 4 substituents independently selected from $R^{21}$.

In some embodiments, each $R^{20}$ is independently selected from $C_{1-6}$ alkyl, $C_{3-6}$ cycloalkyl, 4-6 membered heterocycloalkyl, 4-6 membered heterocycloalkyl-$C_{1-3}$ alkylene, halo, $NR^{c2}R^{d2}$, and $C(O)NR^{c2}R^{d2}$, wherein a ring-forming carbon atom of the 4-6 membered heterocycloalkyl is optionally substituted by oxo to form a carbonyl group; wherein said $C_{1-6}$ alkyl, $C_{3-6}$ cycloalkyl, 4-6 membered heterocycloalkyl and 4-6 membered heterocycloalkyl-$C_{1-3}$ alkylene are each optionally substituted with 1, 2, 3, or 4 substituents independently selected from $R^{21}$.

In some embodiments, $R^{20}$ is $C_{1-6}$ alkyl, optionally substituted with 1, 2, 3, or 4 substituents independently selected from $R^{21}$.

In some embodiments, $R^{20}$ is $C_{3-10}$ cycloalkyl, optionally substituted with 1, 2, 3, or 4 substituents independently selected from $R^{21}$.

In some embodiments, $R^{20}$ is $C_{3-6}$ cycloalkyl, optionally substituted with 1, 2, 3, or 4 substituents independently selected from $R^{21}$.

In some embodiments, $R^{20}$ is 4-10 membered heterocycloalkyl, optionally substituted with 1, 2, 3, or 4 substituents independently selected from $R^{21}$, and wherein a ring-forming carbon atom of the 4-10 membered heterocycloalkyl is optionally substituted by oxo to form a carbonyl group.

In some embodiments, $R^{20}$ is 4-6 membered heterocycloalkyl, optionally substituted with 1, 2, 3, or 4 substituents independently selected from $R^{21}$, and wherein a ring-forming carbon atom of the 4-10 membered heterocycloalkyl is optionally substituted by oxo to form a carbonyl group.

In some embodiments, $R^{20}$ is 4-10 membered heterocycloalkyl-$C_{1-3}$ alkylene, optionally substituted with 1, 2, 3, or 4 substituents independently selected from $R^{21}$, and wherein a ring-forming carbon atom of the 4-10 membered heterocycloalkyl-$C_{1-3}$ alkylene is optionally substituted by oxo to form a carbonyl group.

In some embodiments, $R^{20}$ is 4-6 membered heterocycloalkyl-$C_{1-3}$ alkylene, optionally substituted with 1, 2, 3, or 4 substituents independently selected from $R^{21}$, and wherein a ring-forming carbon atom of the 4-6 membered heterocycloalkyl-$C_{1-3}$ alkylene is optionally substituted by oxo to form a carbonyl group.

In some embodiments, $R^{20}$ is halo.

In some embodiments, $R^{20}$ is $NR^{c2}R^{d2}$.

In some embodiments, $R^{20}$ is $C(O)NR^{c2}R^{d2}$.

In some embodiments, $R^{20}$ is selected from fluoro, piperazin-1-yl, 4-(2-hydroxyethyl)piperazin-1-yl, 4-methyl-2-oxopiperazin-1-yl, piperazin-1-ylcarbonyl, 4-methylpiperazin-1-ylcarbonyl, (2-methylpyrrolidin-1-yl)methyl (e.g., (2-(R)-methylpyrrolidin-1-yl)methyl), tetrahydro-2H-pyran-4-yl, 4-hydroxycyclohexyl, and piperidin-4-ylmethyl.

In some embodiments, $R^{20}$ is selected from fluoro, piperazinyl, (2-hydroxyethyl)piperazinyl, methyloxopiperazinyl, methylpiperazinyl, piperazinecarbonyl, methylpiperazinecarbonyl, (methylpyrrolidinyl)methyl, piperidinyl, tetrahydropyranyl, hydroxycyclohexyl, piperidinylmethyl, hydroxypiperidinylmethyl, azetidinylmethyl, difluoroazetidinylmethyl, methyl, ethyl, isopropyl, dimethylcarbamoyl, morpholinomethyl, methylmorpholinomethyl, hydroxymethylmorpholinomethyl, pyrrolidinylmethyl, hydroxymethylpyrrolidinylmethyl, and (dimethylamino)methyl.

In some embodiments, $R^{20}$ is selected from fluoro, piperazin-1-yl, 4-(2-hydroxyethyl)piperazin-1-yl, 4-methyl-2-oxopiperazin-1-yl, 4-methylpiperazin-1-yl, piperazin-1-ylcarbonyl, 4-methylpiperazin-1-ylcarbonyl, (2-methylpyrrolidin-1-yl)methyl (e.g., (2-(R)-methylpyrrolidin-1-yl)methyl), piperidin-4-yl, tetrahydro-2H-pyran-4-yl, 4-hydroxycyclohexyl, piperidin-4-ylmethyl, (4-hydroxypiperidin-1-yl)methyl, azetidin-1-ylmethyl, (3,3-difluoroazetidin-1-yl)methyl, methyl, ethyl, isopropyl, dimethylcarbamoyl, morpholinomethyl, (2-methylmorpholino)methyl (e.g. (S)-(2-methylmorpholino)methyl), (2-(hydroxymethyl)morpholino)methyl, pyrrolidin-1-ylmethyl, (3-hydroxy-3-methylpyrrolidin-1-yl)methyl (e.g., (S)-(3-hydroxy-3-methylpyrrolidin-1-yl)methyl)), and (dimethylamino)methyl.

In some embodiments, $R^{20}$ is selected from fluoro, piperazinyl, (2-hydroxyethyl)piperazinyl, methyloxopiperazinyl, methylpiperazinyl, piperazinecarbonyl, methylpiperazinecarbonyl, (methylpyrrolidinyl)methyl, piperidinyl, tetrahydropyranyl, hydroxycyclohexyl, piperidinylmethyl, hydroxypiperidinylmethyl, hydroxymethylpiperidinylmethyl, hydroxymethylazetidinylmethyl, methylpiperazinylmethyl, azetidinylmethyl, difluoroazetidinylmethyl, methyl, ethyl, isopropyl, dimethylcarbamoyl, morpholinomethyl, methylmorpholinomethyl, hydroxymethylmorpholinomethyl, pyrrolidinylmethyl, hydroxymethylpyrrolidinylmethyl, and (dimethylamino)methyl.

In some embodiments, $R^{20}$ is selected from fluoro, piperazin-1-yl, 4-(2-hydroxyethyl)piperazin-1-yl, 4-methyl-2-oxopiperazin-1-yl, 4-methylpiperazin-1-yl, piperazin-1-ylcarbonyl, 4-methylpiperazin-1-ylcarbonyl, (2-methylpyrrolidin-1-yl)methyl (e.g., (2-(R)-methylpyrrolidin-1-yl)methyl), piperidin-4-yl, tetrahydro-2H-pyran-4-yl, 4-hydroxycyclohexyl, piperidin-4-ylmethyl, (4-hydroxypiperidin-1-yl)methyl, (4-hydroxy-4-methylpiperidin-1-yl)methyl, (3-hydroxy-3-methylazetidin-1-yl)methyl, (4-methylpiperazin-1-yl)methyl, azetidin-1-ylmethyl, (3,3-difluoroazetidin-1-yl)methyl, methyl, ethyl, isopropyl, dimethylcarbamoyl, morpholinomethyl, (2-methylmorpholino)methyl (e.g. (S)-(2-methylmorpholino)methyl), (2-(hydroxymethyl)morpholino)methyl, pyrrolidin-1-ylmethyl, (3-hydroxy-3-methylpyrrolidin-1-yl)methyl (e.g., (S)-(3-hydroxy-3-methylpyrrolidin-1-yl)methyl)), and (dimethylamino)methyl.

In some embodiments, each $R^{21}$ is independently selected from $C_{1-6}$ alkyl, $C_{1-6}$ haloalkyl, $C_{3-10}$ cycloalkyl, 4-10 membered heterocycloalkyl, halo, D, CN, $OR^{a4}$, $C(O)NR^{c4}R^{d4}$ and $NR^{c4}R^{d4}$; wherein said $C_{1-6}$ alkyl, $C_{3-10}$ cycloalkyl, and 4-10 membered heterocycloalkyl, are each optionally substituted with 1, 2, 3, or 4 substituents independently selected from $R^{22}$.

In some embodiments, each $R^{21}$ is independently selected from $C_{1-6}$ alkyl, $C_{1-6}$ haloalkyl, $C_{3-6}$ cycloalkyl, 4-6 membered heterocycloalkyl, halo, D, CN, $OR^{a4}$, $C(O)NR^{c4}R^{d4}$ and $NR^{c4}R^{d4}$; wherein said $C_{1-6}$ alkyl, $C_{3-6}$ cycloalkyl, and 4-6 membered heterocycloalkyl, are each optionally substituted with 1, 2, 3, or 4 substituents independently selected from $R^{22}$.

In some embodiments, each $R^{21}$ is independently selected from $C_{1-6}$ alkyl, $C_{3-10}$ cycloalkyl, 4-10 membered heterocycloalkyl, halo, $OR^{a4}$, and $NR^{c4}R^{d4}$; wherein said $C_{1-6}$ alkyl, $C_{3-10}$ cycloalkyl, and 4-10 membered heterocycloalkyl, are each optionally substituted with 1, 2, 3, or 4 substituents independently selected from $R^{22}$.

In some embodiments, each $R^{21}$ is independently selected from $C_{1-6}$ alkyl, $C_{3-6}$ cycloalkyl, 4-6 membered heterocycloalkyl, halo, $OR^{a4}$, and $NR^{c4}R^{d4}$; wherein said $C_{1-6}$ alkyl, $C_{3-6}$ cycloalkyl, and 4-6 membered heterocycloalkyl, are each optionally substituted with 1, 2, 3, or 4 substituents independently selected from $R^{22}$.

In some embodiments, each $R^{21}$ is independently selected from $C_{1-6}$ alkyl, 4-10 membered heterocycloalkyl, and $OR^{a4}$; wherein said $C_{1-6}$ alkyl, and 4-10 membered heterocycloalkyl, are each optionally substituted with 1, 2, 3, or 4 substituents independently selected from $R^{22}$.

In some embodiments, $R^{21}$ is $C_{1-6}$ alkyl, optionally substituted with 1, 2, 3, or 4 substituents independently selected from $R^{22}$.

In some embodiments, $R^{21}$ is $C_{3-6}$ cycloalkyl, optionally substituted with 1, 2, 3, or 4 substituents independently selected from $R^{22}$.

In some embodiments, $R^{21}$ is cyclohexyl, optionally substituted with 1, 2, 3, or 4 substituents independently selected from $R^{22}$.

In some embodiments, $R^{21}$ is 4-10 membered heterocycloalkyl, optionally substituted with 1, 2, 3, or 4 substituents independently selected from $R^{22}$.

In some embodiments, $R^{21}$ is 4-6 membered heterocycloalkyl, optionally substituted with 1, 2, 3, or 4 substituents independently selected from $R^{22}$.

In some embodiments, $R^{21}$ is $OR^{a4}$.
In some embodiments, $R^{21}$ is $NR^{c4}R^{d4}$.
In some embodiments, $R^{21}$ is halo.
In some embodiments, $R^{21}$ is selected from methyl, OH, 2-hydroxy ethyl, piperazin-1-yl, piperidin-4-yl, and 2-methylpyrrolidin-1-yl (e.g., 2-(R)-methylpyrrolidin-1-yl).

In some embodiments, $R^{21}$ is selected from methyl, F, OH, dimethylamino, hydroxyethyl, piperazinyl, piperidinyl, methylpyrrolidinyl, azetidinyl, morpholino, hydroxypiperidinyl, difluoroazetidinyl, methylmorpholino, hydroxymethylmorpholino, hydroxymethylpyrrolidinyl, and pyrrolidinyl.

In some embodiments, $R^{21}$ is selected from methyl, F, OH, dimethylamino, 2-hydroxy ethyl, piperazin-1-yl, piperidin-4-yl, 2-methylpyrrolidin-1-yl (e.g., 2-(R)-methylpyrrolidin-1-yl), azetidinyl, morpholino, 4-hydroxypiperidin-1-yl, 3,3-difluoroazetidin-1-yl, 2-methylmorpholino, 2-(hydroxymethyl)morpholino, 3-hydroxy-3-methylpyrrolidin-1-yl, and pyrrolidin-1-yl.

In some embodiments, $R^{21}$ is selected from methyl, F, OH, dimethylamino, hydroxyethyl, piperazinyl, piperidinyl, methylpyrrolidinyl, azetidinyl, morpholino, hydroxypiperidinyl, hydroxymethylpiperidinyl, hydroxymethylazetidinyl, methylpiperazinyl, difluoroazetidinyl, methylmorpholino, hydroxymethylmorpholino, hydroxymethylpyrrolidinyl, and pyrrolidinyl.

In some embodiments, $R^{21}$ is selected from methyl, F, OH, dimethylamino, 2-hydroxy ethyl, piperazin-1-yl, piperidin-4-yl, 2-methylpyrrolidin-1-yl (e.g., 2-(R)-methylpyrrolidin-1-yl), azetidinyl, morpholino, 4-hydroxypiperidin-1-yl, 4-hydroxy-4-methylpiperidin-1-yl, 3-hydroxy-3-methylazetidin-1-yl, 4-methylpiperazin-1-yl, 3,3-difluoroazetidin-1-yl, 2-methylmorpholino, 2-(hydroxymethyl)morpholino, 3-hydroxy-3-methylpyrrolidin-1-yl, and pyrrolidin-1-yl.

In some embodiments, each $R^{22}$ is independently selected from $C_{1-6}$ alkyl, $C_{1-6}$ haloalkyl, halo, D, CN, $OR^{a6}$, and $NR^{c6}R^{d6}$; wherein said $C_{1-6}$ alkyl, is optionally substituted with 1, 2, 3, or 4 substituents independently selected from $R^g$.

In some embodiments, each $R^{22}$ is independently selected from $C_{1-6}$ alkyl, and $OR^{a6}$; wherein said $C_{1-6}$ alkyl, is optionally substituted with 1, 2, 3, or 4 substituents independently selected from $R^g$.

In some embodiments, each $R^{22}$ is independently selected from halo, $C_{1-6}$ alkyl, and $OR^{a6}$; wherein said $C_{1-6}$ alkyl, is optionally substituted with 1, 2, 3, or 4 substituents independently selected from $R^g$.

In some embodiments, $R^{22}$ is $C_{1-6}$ alkyl, optionally substituted with 1, 2, 3, or 4 substituents independently selected from $R^g$. In some embodiments, $R^{22}$ is $OR^{a6}$ In some embodiments, $R^{22}$ is OH or methyl.

In some embodiments, $R^{22}$ is F, OH or methyl.

In some embodiments, $R^2$ is selected from 4-(piperazin-1-yl)phenyl, 4-(4-(2-hydroxyethyl)piperazin-1-yl)phenyl, 4-(4-methyl-2-oxopiperazin-1-yl)phenyl, 3-(4-methylpiperazin-1-yl)phenyl, 4-(4-methylpiperazin-1-ylcarbonyl)phenyl, 4-(piperazin-1-ylcarbonyl)phenyl, 3-fluoro-4-((2-methylpyrrolidin-1-yl)methyl)phenyl (e.g. 3-fluoro-4-((2R-methylpyrrolidin-1-yl)methyl)phenyl), 1-(tetrahydro-2H-pyran-4-yl)-1H-pyrazol-4-yl, 1-(4-hydroxycyclohexyl)-1H-pyrazol-4-yl, and (piperidin-4-ylmethyl)-1H-pyrazol-4-yl.

In some embodiments, $R^2$ is selected from 4-(piperazin-1-yl)phenyl, 4-(4-(2-hydroxyethyl)piperazin-1-yl)phenyl, 4-(4-methyl-2-oxopiperazin-1-yl)phenyl, 3-(4-methylpiperazin-1-yl)phenyl, 4-(4-methylpiperazin-1-ylcarbonyl)phenyl, 4-(piperazin-1-ylcarbonyl)phenyl, 3-fluoro-4-((2-methylpyrrolidin-1-yl)methyl)phenyl (e.g. 3-fluoro-4-((2R-methylpyrrolidin-1-yl)methyl)phenyl), 1-(tetrahydro-2H-pyran-4-yl)-1H-pyrazol-4-yl, (piperidin-4-ylmethyl)-1H-pyrazol-4-yl, (piperidin-4-yl)-1H-pyrazol-4-yl, 1-(4-hydroxycyclohexyl)-1H-pyrazol-4-yl (e.g. 1-((1R,4R)-4-hydroxycyclohexyl)-1H-pyrazol-4-yl), 4-(azetidin-1-ylmethyl)phenyl, 1-ethyl-1H-pyrazol-4-yl, 1-isopropyl-1H-pyrazol-4-yl, 4-(dimethylcarbamoyl)phenyl, 4-(pyrrolidin-1-ylmethyl)phenyl, 4-(morpholinomethyl)phenyl, 4-((3,3-difluoroazetidin-1-yl)methyl)phenyl, 4-((2-methylmorpholino)methyl)phenyl, 4-((2-(hydroxymethyl)morpholino)methyl)phenyl, 4-((3-hydroxy-3-methylpyrrolidin-1-yl)methyl)phenyl, 4-((4-hydroxypiperidin-1-yl)methyl)phenyl and 4-((dimethylamino)methyl)phenyl.

In some embodiments, $R^2$ is selected from 4-(piperazin-1-yl)phenyl, 4-(4-(2-hydroxyethyl)piperazin-1-yl)phenyl, 4-(4-methyl-2-oxopiperazin-1-yl)phenyl, 3-(4-methylpiperazin-1-yl)phenyl, 4-(4-methylpiperazin-1-ylcarbonyl)phenyl, 4-(piperazin-1-ylcarbonyl)phenyl, 3-fluoro-4-((2-methylpyrrolidin-1-yl)methyl)phenyl (e.g. 3-fluoro-4-((2R- methylpyrrolidin-1-yl)methyl)phenyl), 1-(tetrahydro-2H-pyran-4-yl)-1H-pyrazol-4-yl, (piperidin-4-ylmethyl)-1H-pyrazol-4-yl, (piperidin-4-yl)-1H-pyrazol-4-yl, 1-(4-hydroxycyclohexyl)-1H-pyrazol-4-yl (e.g. 1-((1R,4R)-4-hydroxycyclohexyl)-1H-pyrazol-4-yl), 4-(azetidin-1-ylmethyl)phenyl, 1-ethyl-1H-pyrazol-4-yl, 1-isopropyl-1H-pyrazol-4-yl, 4-(dimethylcarbamoyl)phenyl, 4-(pyrrolidin-1-ylmethyl)phenyl, 4-(morpholinomethyl)phenyl, 4-((3,3-difluoroazetidin-1-yl)methyl)phenyl, 4-((2-methylmorpholino)methyl)phenyl, 4-((2-(hydroxymethyl)morpholino)methyl)phenyl, 4-((3-hydroxy-3-methylpyrrolidin-1-yl)methyl)phenyl, 4-((4-hydroxypiperidin-1-yl)methyl)phenyl, 4-((4-hydroxy-4-methylpiperidin-1-yl)methyl)phenyl, 4-((3-hydroxy-3-methylazetidin-1-yl)methyl)phenyl, 4-((4-methylpiperazin-1-yl)methyl)phenyl, 4-((4-hydroxypiperidin-1-yl)methyl)phenyl and 4-((dimethylamino)methyl)phenyl.

In some embodiments, $R^3$ is selected from H, D, halo, CN, $C_{1-6}$ alkyl, $OR^{a7}$ and $NR^{c7}R^{d7}$.

In some embodiments, $R^3$ is selected from H, D, halo, CN, and $C_{1-6}$ alkyl.

In some embodiments, $R^3$ is selected from H, and D.

In some embodiments, $R^3$ is H.

In some embodiments, $R^4$ is selected from H, D, halo, CN, $C_{1-6}$ alkyl, $OR^{a7}$ and $NR^{c7}R^{d7}$.

In some embodiments, $R^4$ is selected from H, D, halo, CN, and $C_{1-6}$ alkyl.

In some embodiments, $R^4$ is selected from H, and D.

In some embodiments, $R^4$ is H.

In some embodiments, $R^3$ and $R^4$ are both H.

In some embodiments, $R^5$ is $C_{6-10}$ aryl, optionally substituted with 1, 2, 3, 4 or 5 substituents independently selected from $R^{50}$.

In some embodiments, $R^5$ is a 5-10 membered heteroaryl; wherein the 5-10 membered heteroaryl has at least one ring-forming carbon atom and 1, 2, 3, or 4 ring-forming heteroatoms independently selected from N, O, and S; wherein the N and S are optionally oxidized; wherein a ring-forming carbon atom of the 5-10 membered heteroaryl is optionally substituted by oxo to form a carbonyl group; and wherein the 5-10 membered heteroaryl is optionally substituted with 1, 2, 3, 4 or 5 substituents independently selected from $R^{50}$.

In some embodiments, $R^5$ is selected from quinolinyl, naphthyridinyl, pyridinyl, and phenyl, wherein the quinolinyl, naphthyridinyl, pyridinyl, and phenyl are each optionally substituted with 1, 2, or 3 substituents independently selected from $R^{50}$.

In some embodiments, $R^5$ is selected from 1,8-naphthyridin-4-yl, quinolin-4-yl, 7-(hydroxymethyl)quinolin-4-yl, 7-(pyridin-4-yl)quinolin-4-yl, 7-(2-(hydroxymethyl)pyridin-4-yl)quinolin-4-yl, 7-morpholinoquinolin-4-yl, 7-(1-methyl-H-pyrazol-3-yl)quinolin-4-yl, 7-(6-oxa-2-azaspiro[3.4]octan-2-yl)quinolin-4-yl, 7-(methylcarbamoyl)quinolin-4-yl, 7-(pyridin-3-ylamino)quinolin-4-yl, 7-((3,5-difluorophenyl)(hydroxy)methyl)quinolin-4-yl, 7-(4-acetylpiperazin-1-yl)quinolin-4-yl, 7-(4-methylpiperazin-1-ylcarbonyl)quinolin-4-yl, 7-(morpholinomethyl)quinolin-4-yl, 7-((2-hydroxyethyl)carbamoyl)quinolin-4-yl, 7-cyanoquinolin-4-yl, 7-(6-oxohexahydropyrrolo[1,2-a]pyrazin-2(1H)-yl)quinolin-4-yl, 7-(5-acetyl-2,5-diazabicyclo[2.2.1]heptan-2-yl)quinolin-4-yl (e.g. 7-((1S,4S)-5-acetyl-2,5-diazabicyclo[2.2.1]heptan-2-yl)quinolin-4-yl), 8-cyanoquinolin-5-yl, 2,3-dihydro-[1,4]dioxino[2,3-b]pyridin-8-yl, 1-isonicotinoyl-2,3-dihydro-1H-pyrrolo[2,3-b]pyridin-4-yl, and 4-carbamoyl-3-fluorophenyl.

In some embodiments, $R^5$ is selected from 1,8-naphthyridin-4-yl, quinolin-4-yl, 7-(hydroxymethyl)quinolin-4-yl, 7-(pyridin-4-yl)quinolin-4-yl, 7-(2-(hydroxymethyl)pyridin-4-yl)quinolin-4-yl, 7-morpholinoquinolin-4-yl, 7-(1-methyl-H-pyrazol-3-yl)quinolin-4-yl, 7-(6-oxa-2-azaspiro[3.4]octan-2-yl)quinolin-4-yl, 7-(methylcarbamoyl)quinolin-4-yl, 7-(pyridin-3-ylamino)quinolin-4-yl, 7-((3,5-difluorophenyl)(hydroxy)methyl)quinolin-4-yl, 7-(4-acetylpiperazin-1-yl)quinolin-4-yl, 7-(4-methylpiperazin-1-ylcarbonyl)quinolin-4-yl, 7-(morpholinomethyl)quinolin-4-yl, 7-((2-hydroxyethyl)carbamoyl)quinolin-4-yl, 7-cyanoquinolin-4-yl, 7-(6-oxohexahydropyrrolo[1,2-a]pyrazin-2(1H)-yl)quinolin-4-yl, 7-(5-acetyl-2,5-diazabicyclo[2.2.1]heptan-2-yl)quinolin-4-yl (e.g. 7-((1S,4S)-5-acetyl-2,5-diazabicyclo[2.2.1]heptan-2-yl)quinolin-4-yl), 8-cyanoquinolin-5-yl, 2,3-dihydro-[1,4]dioxino[2,3-b]pyridin-8-yl, 1-isonicotinoyl-2,3-dihydro-1H-pyrrolo[2,3-b]pyridin-4-yl, 4-carbamoyl-3-fluorophenyl, 7-(pyridin-2-yl)-1,8-naphthyridin-4-yl, 7-(pyrimidin-2-yl)-1,8-naphthyridin-4-yl, 7-(pyrazin-2-yl)-1,8-naphthyridin-4-yl, 7-(1-methyl-H-pyrazol-3-yl)-1,8-naphthyridin-4-yl, 7-(5-methyl-1H-pyrazol-3-yl)-1,8-naphthyridin-4-yl, 7-(1-methyl-1H-pyrazol-4-yl)-1,8-naphthyridin-4-yl, 7-(1-methyl-1H-imidazol-4-yl)-1,8-naphthyridin-4-yl, 7-(1-ethyl-1H-imidazol-4-yl)-1,8-naphthyridin-4-yl, and 7-(4-methyl-2H-1,2,3-triazol-2-yl)-1,8-naphthyridin-4-yl.

In some embodiments, each $R^{50}$ is independently selected from $C_{1-6}$ alkyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $OR^{a9}$, $C(O)R^{b9}$, $C(O)NR^{c9}R^{d9}$, $C(O)OR^{a9}$, $NR^{c9}R^{d9}$, $S(O)_2R^{b9}$, and $S(O)_2NR^{c9}R^{d9}$; wherein said $C_{1-6}$ alkyl, $C_{3-10}$ cycloalkyl, 4-10 membered heterocycloalkyl, $C_{6-10}$ aryl, and 5-10 membered heteroaryl, are each optionally substituted with 1, 2, 3, or 4 substituents independently selected from $R^{51}$.

In some embodiments, each $R^{50}$ is independently selected from $C_{1-6}$ alkyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $OR^{a9}$, $C(O)R^{b9}$, $C(O)NR^{c9}R^{d9}$, $C(O)OR^{a9}$, $NR^{c9}R^{d9}$, $S(O)_2R^{b9}$, and $S(O)_2NR^{c9}R^{d9}$; wherein said $C_{1-6}$ alkyl, $C_{3-10}$ cycloalkyl, 4-10 membered heterocycloalkyl, $C_{6-10}$ aryl, and 5-10 membered heteroaryl, are each optionally substituted with 1, 2, 3, or 4 substituents independently selected from $R^{51}$; and wherein a ring-forming carbon atom of said 4-10 membered heterocycloalkyl is optionally oxidized to form a carbonyl group.

In some embodiments, each $R^{50}$ is independently selected from $C_{1-6}$ alkyl, 4-10 membered heterocycloalkyl, 5-10 membered heteroaryl, halo, CN, $C(O)R^{b9}$, $C(O)NR^{c9}R^{d9}$, and $NR^{c9}R^{d9}$; wherein said $C_{1-6}$ alkyl, 4-10 membered heterocycloalkyl, and 5-10 membered heteroaryl, are each optionally substituted with 1, 2 or 3 substituents independently selected from $R^{51}$.

In some embodiments, each $R^{50}$ is independently selected from $C_{1-6}$ alkyl, 4-10 membered heterocycloalkyl, 5-10 membered heteroaryl, halo, CN, $C(O)R^{b9}$, $C(O)NR^{c9}R^{d9}$, and $NR^{c9}R^{d9}$; wherein said $C_{1-6}$ alkyl, 4-10 membered heterocycloalkyl, and 5-10 membered heteroaryl, are each optionally substituted with 1, 2 or 3 substituents independently selected from $R^{51}$; and wherein a ring-forming carbon atom of said 4-10 membered heterocycloalkyl is optionally oxidized to form a carbonyl group.

In some embodiments, each $R^{50}$ is $C_{1-6}$ alkyl, each optionally substituted with 1, 2, 3, or 4 substituents independently selected from $R^{51}$.

In some embodiments, each $R^{50}$ is 4-10 membered heterocycloalkyl, optionally substituted with 1, 2, 3, or 4 substituents independently selected from $R^{51}$.

In some embodiments, each $R^{50}$ is 4-10 membered heterocycloalkyl, optionally substituted with 1, 2, 3, or 4 substituents independently selected from $R^{51}$, wherein a ring-forming carbon atom of said 4-10 membered heterocycloalkyl is optionally oxidized to form a carbonyl group.

In some embodiments, each $R^{50}$ is independently selected from 5-10 membered heteroaryl, optionally substituted with 1, 2, 3, or 4 substituents independently selected from $R^{51}$.

In some embodiments, each $R^{50}$ is selected from halo, CN, $OR^{a9}$, $C(O)R^{b9}$, $C(O)NR^{c9}R^{d9}$, $C(O)OR^{a9}$, and $NR^{c9}R^{d9}$.

In some embodiments, each $R^{50}$ is halo.
In some embodiments, each $R^{50}$ is CN.
In some embodiments, each $R^{50}$ is $C(O)R^{b9}$.
In some embodiments, each $R^{50}$ is $C(O)NR^{c9}R^{d9}$.
In some embodiments, each $R^{50}$ is $NR^{c9}R^{d9}$.

In some embodiments, each $R^{50}$ is independently selected from fluoro, hydroxyethyl, cyano, carbamoyl, methylcarbamoyl, pyridinyl, morpholino, morpholinomethyl, pyrazolyl, 6-oxaspiro[3.4]octanyl, pyridinylamino, benzyl, piperazinyl, piperazin-1-ylcarbonyl, pyrimidinyl, pyrazinyl, (2-hydroxyethyl)carbamoyl, hexahydropyrrolo[1,2-a]pyrazinyl, 2,5-diazabicyclo[2.2.1]heptanyl, triazolyl, imidazolyl, and pyrazinyl, wherein the methylcarbamoyl, pyridinyl, morpholino, morpholinomethyl, pyrazolyl, 6-oxaspiro[3.4]octanyl, pyridinylamino, benzyl, piperazinyl, piperazin-1-ylcarbonyl, pyrimidinyl, pyrazinyl, (2-hydroxyethyl)carbamoyl, hexahydropyrrolo[1,2-a]pyrazinyl, 2,5-diazabicyclo[2.2.1]heptanyl, triazolyl, imidazolyl, and pyrazinyl are each optionally substituted with 1, 2, 3, or 4 substituents independently selected from $R^{51}$.

In some embodiments, $R^{50}$ is selected from fluoro, hydroxyethyl, cyano, carbamoyl, methylcarbamoyl, pyridin-4-yl, 3-hydroxymethylpyridin-4-yl, 4-morpholino, 4-morpholinomethyl, 1-methyl-1H-pyrazol-3-yl, 6-oxaspiro[3.4]octan-2-yl, pyridin-3-ylamino, (3,5-difluorophenyl)(hydroxyl)methyl, 4-acetylpiperazin-1-yl, 4-methylpiperazin-1-ylcarbonyl, (2-hydroxyethyl)carbamoyl, 6-oxohexahydropyrrolo[1,2-a]pyrazin-2(1H)-yl, and 5-acetyl-2,5-diazabicyclo[2.2.1]heptan-2-yl (e.g. (1S,4S)-5-acetyl-2,5-diazabicyclo[2.2.1]heptan-2-yl).

In some embodiments, $R^{50}$ is independently selected from fluoro, hydroxyethyl, cyano, carbamoyl, methylcarbamoyl, pyridin-4-yl, 3-hydroxymethylpyridin-4-yl, 4-morpholino, 4-morpholinomethyl, 1-methyl-1H-pyrazol-3-yl, 6-oxaspiro[3.4]octan-2-yl, pyridin-3-ylamino, (3,5-difluorophenyl)(hydroxyl)methyl, 4-acetylpiperazin-1-yl, 4-methylpiperazin-1-ylcarbonyl, (2-hydroxyethyl)carbamoyl, 6-oxohexahydropyrrolo[1,2-a]pyrazin-2(1H)-yl, 5-acetyl-2,5-diazabicyclo[2.2.1]heptan-2-yl (e.g. (1S,4S)-5-acetyl-2,5-diazabicyclo[2.2.1]heptan-2-yl), pyridin-2-yl, pyrazin-2-yl, pyrimidin-2-yl, 1-methyl-1H-pyrazol-3-yl, 5-methyl-1H-pyrazol-3-yl, 1-methyl-1H-pyrazol-4-yl, 1-methyl-1H-imidazol-4-yl, 1-ethyl-1H-imidazol-4-yl, and 4-methyl-2H-1,2,3-triazol-2-yl.

In some embodiments, $R^5$ is substituted with at least two adjacent $R^{50}$ substituents, taken together with the atoms to which they are attached, to form a fused 5- or 6-membered heterocycloalkyl ring; wherein the fused 5- or 6-membered heterocycloalkyl ring each has at least one ring-forming carbon atom and 1, 2, 3, or 4 ring-forming heteroatoms independently selected from N, O, and S; wherein a ring-forming carbon atom of each fused 5- or 6-membered heterocycloalkyl ring is optionally substituted by oxo to form a carbonyl group; and wherein the fused 5 or 6-membered heterocycloalkyl ring is optionally substituted with 1, 2, 3 or 4 substituents independently selected from $R^{51}$.

In some embodiments, $R^5$ is substituted with at least two adjacent $R^{50}$ substituents, taken together with the atoms to which they are attached, to form a fused heterocycloalkyl ring selected from 2,3-dihydrodioxine; and 1-isonicotinoylpyrrolidine:

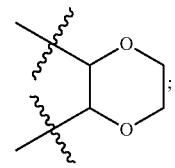

2,3-dihydrodioxime

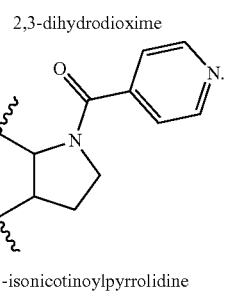

1-isonicotinoylpyrrolidine

In some embodiments, $R^5$ is selected from pyridinyl and phenyl, wherein the pyridinyl and phenyl are each optionally substituted with 1, 2, or 3 substituents independently selected from $R^{50}$; and at least two adjacent $R^{50}$ substituents, taken together with the atoms to which they are attached, to form a fused heterocycloalkyl ring selected from 2,3-dihydrodioxine; and 1-isonicotinolpyrrolidine:

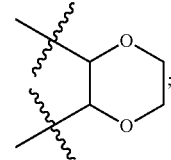

2,3-dihydrodioxime

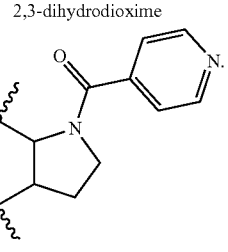

1-isonicotinoylpyrrolidine

In some embodiments, each $R^{51}$ is independently selected from $C_{1-6}$ alkyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $OR^{a10}$, $C(O)R^{b10}$, $C(O)NR^{c10}R^{d10}$, $C(O)OR^{a10}$, $NR^{c10}R^{d10}$, $S(O)_2R^{b10}$, and $S(O)_2NR^{c10}R^{d10}$; wherein said $C_{1-6}$ alkyl, $C_{3-10}$ cycloalkyl, 4-10 membered heterocycloalkyl, $C_{6-10}$ aryl, and 5-10 membered heteroaryl, are each optionally substituted with 1, 2, 3, or 4 substituents independently selected from $R^{52}$.

In some embodiments, each $R^{51}$ is independently selected from $C_{1-6}$ alkyl, 4-10 membered heterocycloalkyl, $C_{6-10}$ aryl, $OR^{a10}$, and $C(O)R^{b10}$; wherein said $C_{1-6}$ alkyl, 4-10 membered heterocycloalkyl, and $C_{6-10}$ aryl are each optionally substituted with 1, 2, 3, or 4 substituents independently selected from $R^{52}$.

In some embodiments, each $R^{51}$ is $C_{1-6}$ alkyl; wherein said $C_{1-6}$ alkyl, are each optionally substituted with 1, 2, 3, or 4 substituents independently selected from $R^{52}$.

In some embodiments, each $R^{51}$ is 4-10 membered heterocycloalkyl; wherein said 4-10 membered heterocycloalkyl are each optionally substituted with 1, 2, 3, or 4 substituents independently selected from $R^{52}$.

In some embodiments, each $R^{51}$ is $C_{6-10}$ aryl; wherein said $C_{6-10}$ aryl are each optionally substituted with 1, 2, 3, or 4 substituents independently selected from $R^{52}$. In some embodiments, each $R^{51}$ is $OR^{a10}$.

In some embodiments, each $R^{51}$ is $C(O)R^{b10}$.

In some embodiments, each $R^{51}$ is independently selected from $C_{1-6}$ alkyl, 4-10 membered heterocycloalkyl, $C_{6-10}$ aryl, OH, and $C(O)R^{b10}$; wherein said $C_{1-6}$ alkyl, 4-10 membered heterocycloalkyl, and $C_{6-10}$ aryl, are each optionally substituted with 1, 2, 3, or 4 substituents independently selected from $R^{52}$.

In some embodiments, each $R^{51}$ is selected from methyl, OH, hydroxymethyl, hydroxyethyl, acetyl, 4-morpholino, 4-methylpiperazin-1-yl, pyridin-3-yl, 3,5-difluorophenyl, and pyridin-4-yl-carbonyl.

In some embodiments, each $R^{52}$ is independently selected from $C_{1-6}$ alkyl, $C_{1-6}$ haloalkyl, halo, D, CN, $OR^{a11}$, and $NR^{c11}R^{d11}$.

In some embodiments, each $R^{52}$ is independently selected from halo, and $OR^{a11}$.

In some embodiments, each $R^{52}$ is independently selected from halo, and OH.

In some embodiments, each $R^{52}$ is selected from fluoro, and OH.

In some embodiments, A is N.

In some embodiments, A is $CR^A$ and wherein $R^A$ is selected from H, D and $C_{1-6}$ alkyl.

In some embodiments, A is CH.

In some embodiments, each $R^a$, $R^c$, and $R^d$ is independently selected from H, $C_{1-6}$ alkyl, $C_{1-6}$ haloalkyl, $C_{3-10}$ cycloalkyl and 4-10 membered heteroalkyl, wherein said $C_{1-6}$ alkyl, $C_{3-10}$ cycloalkyl, and 4-10 membered heteroalkyl are each optionally substituted with 1, 2, 3, or 4 substituents independently selected from $R^{10}$.

In some embodiments, each $R^a$, $R^c$, and $R^d$ is independently selected from H, $C_{1-6}$ alkyl, and $C_{3-10}$ cycloalkyl, wherein said $C_{1-6}$ alkyl, and $C_{3-10}$ cycloalkyl are each optionally substituted with 1, 2, 3, or 4 substituents independently selected from $R^{10}$.

In some embodiments, each $R^a$ is independently selected from H and methyl.

In some embodiments, $R^a$ is methyl.

In some embodiment, $R^c$ and $R^d$ are H or $C_{5-6}$ cycloalkyl.

In some embodiment, $R^c$ is H.

In some embodiment, $R^d$ is H or cyclohexyl. In some embodiments, any $R^c$ and $R^d$ attached to the same N atom, together with the N atom to which they are attached, form a 4-10 membered heterocycloalkyl group optionally substituted with 1, 2, 3 or 4 substituents independently selected from $R^{10}$. In some embodiments, $R^c$ and $R^d$ attached to the same N atom, together with the N atom to which they are attached, form a 5-6 membered heterocycloalkyl.

In some embodiments, $R^c$ and $R^d$ attached to the same N atom, together with the N atom to which they are attached, form a piperazinyl.

In some embodiments, each $R^b$ is independently selected from $C_{1-6}$ alkyl, and $C_{1-6}$ haloalkyl.

In some embodiments, each $R^b$ is independently selected from $C_{1-6}$ alkyl, $C_{1-6}$ haloalkyl and 4-10 membered heterocycloalkyl.

In some embodiments, each $R^{a1}$, $R^{c1}$ and $R^{d1}$ is independently selected from H, and $C_{1-6}$ alkyl, wherein said $C_{1-6}$ alkyl is optionally substituted with 1, 2, 3, or 4 substituents independently selected from $R^{11}$.

In some embodiments, $R^{a1}$ is H or $C_{1-6}$ alkyl.

In some embodiments, $R^{a1}$ is H or methyl.

In some embodiments, each $R^{b1}$ is independently selected from $C_{1-6}$ alkyl, and $C_{1-6}$ haloalkyl.

In some embodiments, each $R^{a2}$, $R^{c2}$ and $R^{d2}$ is independently selected from H, $C_{1-6}$ alkyl, and $C_{1-6}$ haloalkyl.

In some embodiments, any $R^{c2}$ and $R^{d2}$ attached to the same N atom, together with the N atom to which they are attached, form a 4-10 membered heterocycloalkyl group optionally substituted with 1, 2, 3 or 4 substituents independently selected from $R^{21}$.

In some embodiments, $R^{c2}$ and $R^{d2}$ attached to the same N atom, together with the N atom to which they are attached, form a 5-6 membered heterocycloalkyl.

In some embodiments, $R^{c2}$ and $R^{d2}$ attached to the same N atom, together with the N atom to which they are attached, form a piperazinyl.

In some embodiments, each $R^{b2}$ is independently selected from $C_{1-6}$ alkyl, and $C_{1-6}$ haloalkyl.

In some embodiments, each $R^{a4}$, $R^{c4}$ and $R^{d4}$ is independently selected from H and $C_{1-6}$ alkyl.

In some embodiments, each $R^{b4}$ is independently selected from $C_{1-6}$ alkyl, and $C_{1-6}$ haloalkyl.

In some embodiments, each $R^{a6}$, $R^{c6}$ and $R^{d6}$ is independently selected from H and $C_{1-6}$ alkyl.

In some embodiments, each $R^{a6}$, $R^{c6}$ and $R^{d6}$ is H.

In some embodiments, each $R^{a9}$, $R^{c9}$ and $R^{d9}$ is independently selected from H, $C_{1-6}$ alkyl, $C_{1-6}$ haloalkyl, 4-10 membered heterocycloalkyl, and 5-10 membered heteroaryl; wherein said $C_{1-6}$ alkyl, 4-10 membered heterocycloalkyl, and 5-10 membered heteroaryl, are each optionally substituted with 1, 2, 3, or 4 substituents independently selected from $R^{51}$.

In some embodiments, each $R^{a9}$, $R^{c9}$ and $R^{d9}$ is independently selected from H, $C_{1-6}$ alkyl, and 5-10 membered heteroaryl; wherein said $C_{1-6}$ alkyl, and 5-10 membered heteroaryl, are each optionally substituted with 1, 2, 3, or 4 substituents independently selected from $R^{51}$.

In some embodiments, any $R^{c9}$ and $R^{d9}$ attached to the same N atom, together with the N atom to which they are attached, form a 4-10 membered heterocycloalkyl group optionally substituted with 1, 2, 3 or 4 substituents independently selected from $R^{51}$.

In some embodiments, each $R^{b9}$ is independently selected from $C_{1-6}$ alkyl, and $C_{1-6}$ haloalkyl.

In some embodiments, each $R^{a10}$, $R^{c10}$ and $R^{d10}$ is independently selected from H and $C_{1-6}$ alkyl.

In some embodiments, each $R^{b10}$ is independently selected from $C_{1-6}$ alkyl, $C_{1-6}$ haloalkyl, 5-6 membered heteroaryl, and 4-7 membered heterocycloalkyl; wherein said $C_{1-6}$ alkyl 5-6 membered heteroaryl, and 4-7 membered heterocycloalkyl, are each optionally substituted with 1, 2, 3, or 4 substituents independently selected from $R^{52}$.

In some embodiments, each $R^{a11}$, $R^{c11}$ and $R^{d11}$ is independently selected from H and $C_{1-6}$ alkyl.

In some embodiments, each $R^g$ is independently selected from OH, CN, halo, $C_{1-6}$ alkyl, $C_{1-6}$ haloalkyl, $C_{1-6}$ alkoxy, $C_{1-6}$ haloalkoxy, amino, $C_{1-6}$ alkylamino and di($C_{1-6}$ alkyl) amino.

In some embodiments, the compound is a compound of Formula II:

II or a pharmaceutically acceptable salt thereof.

In some embodiments, the compound is a compound of Formula III:

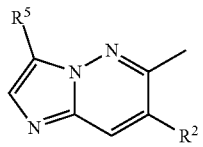

III or a pharmaceutically acceptable salt thereof.

In some embodiments, the compound is a compound of Formula IVa Formula IVb:

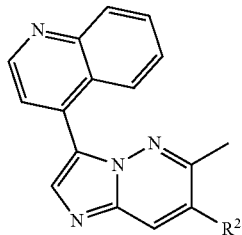

IVa

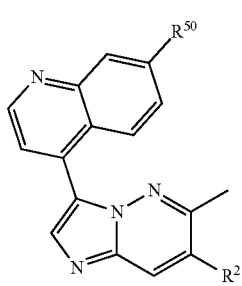

IVb or a pharmaceutically acceptable salt thereof.

In some embodiments, the compound is a compound of Formula Va, Formula Vb or Formula Vc:

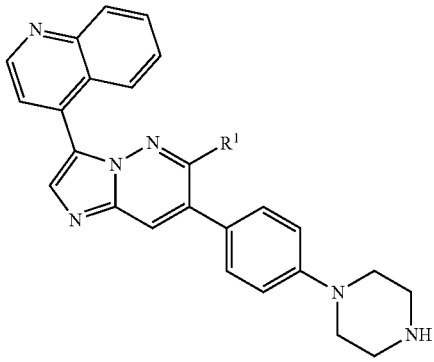

Va

Vb

Vc or a pharmaceutically acceptable salt thereof.

In some embodiments, the compound is a compound of Formula VIa or Formula VIb:

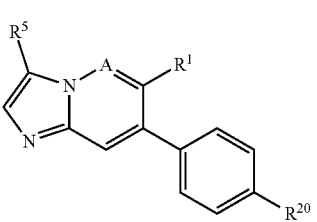

VIa

-continued

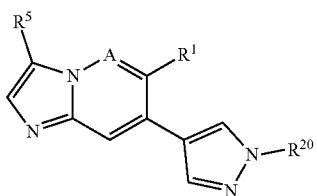

or a pharmaceutically acceptable salt thereof.

In some embodiments, the compound is a compound of Formula VIIa, Formula VIIb, Formula VIIc or Formula VIId:

VIIa

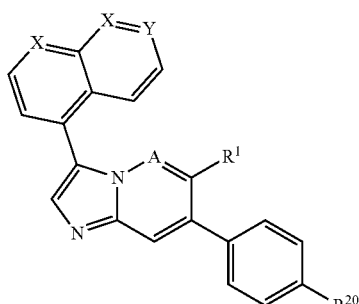

VIIb

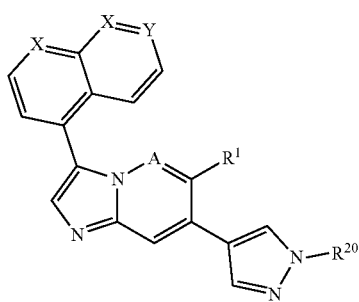

VIIc

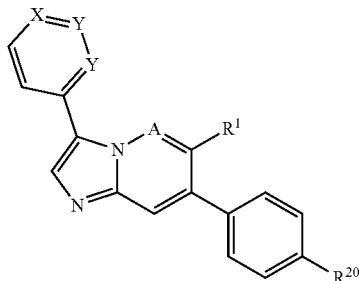

VIId

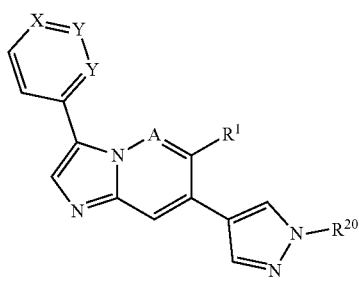

or a pharmaceutically acceptable salt thereof, wherein
each X is independently selected from CH, N and $CR^{50}$; and
each Y is independently selected from CH and $CR^{50}$.

In some embodiments, the compound is a compound of Formula VIIIa or Formula VIIIb:

VIIIa

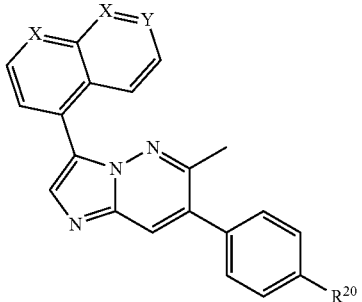

VIIIb

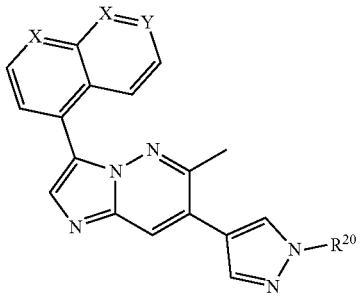

or a pharmaceutically acceptable salt thereof, wherein
each X is independently selected from CH, N and $CR^{50}$; and
each Y is independently selected from CH and $CR^{50}$.

In some embodiments, the compound of Formula I is a compound wherein:

$R^1$ is selected from $C_{1-6}$ alkyl, $C_{1-6}$ haloalkyl, CN, $OR^a$, $C(O)R^b$, $C(O)NR^cR^d$, $C(O)OR^a$, $NR^cR^d$, $S(O)_2R^b$, and $S(O)_2 NR^cR^d$; wherein said $C_{1-6}$ alkyl, is optionally substituted with 1, 2, 3, or 4 substituents independently selected from $R^{10}$;

$R^2$ is selected from $C_{6-10}$ aryl and 5-10 membered heteroaryl; wherein the 5-10 membered heteroaryl has at least one ring-forming carbon atom and 1, 2, 3, or 4 ring-forming heteroatoms independently selected from N, O, and S; wherein the N and S are optionally oxidized; wherein a ring-forming carbon atom of the 5-10 membered heteroaryl is optionally substituted by oxo to form a carbonyl group; and wherein the $C_{6-10}$ aryl and 5-10 membered heteroaryl are each optionally substituted with 1, 2, 3, 4 or 5 substituents independently selected from $R^{20}$;

$R^3$ is selected from H, D, halo, CN, and $C_{1-6}$ alkyl;

$R^4$ is selected from H, D, halo, CN, and $C_{1-6}$ alkyl;

$R^5$ is selected from $C_{6-10}$ aryl and 5-10 membered heteroaryl; wherein the 5-10 membered heteroaryl has at least one ring-forming carbon atom and 1, 2, 3, or 4 ring-forming heteroatoms independently selected from N, O, and S; wherein the N and S are optionally oxidized; wherein a ring-forming carbon atom of the 5-10 membered heteroaryl is optionally substituted by oxo to form a carbonyl group; and wherein the $C_{6-10}$ aryl and 5-10 membered heteroaryl are each optionally substituted with 1, 2, 3, 4 or 5 substituents independently selected from $R^{50}$;

or two adjacent $R^{50}$ substituents on $R^5$, taken together with the atoms to which they are attached, form a fused 4-, 5-, 6- or 7-membered heterocycloalkyl ring, or a fused $C_{3-7}$ cycloalkyl ring; wherein the fused 4-, 5-, 6- or 7-membered heterocycloalkyl ring each has at least one ring-forming carbon atom and 1, 2, 3, or 4 ring-forming heteroatoms independently selected from N, O, and S; wherein a ring-forming carbon atom of each fused 4-, 5-, 6- or 7-membered heterocycloalkyl ring is optionally substituted by oxo to form a carbonyl group; and wherein the fused 4-, 5-, 6- or 7-membered heterocycloalkyl ring and fused $C_{3-7}$ cycloalkyl ring are each optionally substituted with 1, 2, 3 or 4 substituents independently selected from $R^{51}$;

A is N or $CR^4$;

$R^4$ is selected from H, D and $C_{1-6}$ alkyl;

each $R^{10}$ is independently selected from $C_{1-6}$ alkyl, $C_{1-6}$ haloalkyl, halo, D, CN, $OR^{a1}$, $C(O)R^{b1}$, $C(O)NR^{c1}R^{d1}$, $C(O)OR^{a1}$, $NR^{c1}R^{d1}$, and $S(O)_2NR^{c1}R^{d1}$; wherein said $C_{1-6}$ alkyl is optionally substituted with 1, 2, 3, or 4 substituents independently selected from $R^{11}$;

each $R^{20}$ is independently selected from $C_{1-6}$ alkyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $OR^{a2}$, $C(O)R^{b2}$, $C(O)NR^{c2}R^{d2}$, $C(O)OR^{a2}$, $NR^{c2}R^{d2}$, $S(O)_2R^{b2}$, and $S(O)_2NR^{c2}R^{d2}$; wherein said $C_{1-6}$ alkyl, $C_{3-10}$ cycloalkyl, 4-10 membered heterocycloalkyl, $C_{6-10}$ aryl, and 5-10 membered heteroaryl, are each optionally substituted with 1, 2, 3, or 4 substituents independently selected from $R^{21}$;

each $R^{21}$ is independently selected from $C_{1-6}$ alkyl, $C_{1-6}$ haloalkyl, $C_{3-10}$ cycloalkyl, 4-10 membered heterocycloalkyl, halo, D, CN, $OR^{a4}$, $C(O)NR^{c4}R^{d4}$ and $NR^{c4}R^{d4}$; wherein said $C_{1-6}$ alkyl, $C_{3-10}$ cycloalkyl, and 4-10 membered heterocycloalkyl, are each optionally substituted with 1, 2, 3, or 4 substituents independently selected from $R^{22}$;

each $R^{22}$ is independently selected from $C_{1-6}$ alkyl, $C_{1-6}$ haloalkyl, halo, D, CN, $OR^{a6}$, and $NR^{c6}R^{d6}$; wherein said $C_{1-6}$ alkyl, is optionally substituted with 1, 2, 3, or 4 substituents independently selected from $R^g$;

each $R^{50}$ is independently selected from $C_{1-6}$ alkyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $OR^{a9}$, $C(O)R^{b9}$, $C(O)NR^{c9}R^{d9}$, $C(O)OR^{a9}$, $NR^{c9}R^{d9}$, $S(O)_2R^{b9}$, and $S(O)_2NR^{c9}R^{d9}$; wherein said $C_{1-6}$ alkyl, $C_{3-10}$ cycloalkyl, 4-10 membered heterocycloalkyl, $C_{6-10}$ aryl, and 5-10 membered heteroaryl, are each optionally substituted with 1, 2, 3, or 4 substituents independently selected from $R^{51}$;

each $R^{51}$ is independently selected from $C_{1-6}$ alkyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $OR^{a10}$, $C(O)R^{b10}$, $C(O)NR^{c10}R^{d10}$, $C(O)OR^{a10}$, $NR^{c10}R^{d10}$, $S(O)_2R^{b10}$, and $S(O)_2NR^{c10}R^{d10}$; wherein said $C_{1-6}$ alkyl, $C_{3-10}$ cycloalkyl, 4-10 membered heterocycloalkyl, $C_{6-10}$ aryl, and 5-10 membered heteroaryl, are each optionally substituted with 1, 2, 3, or 4 substituents independently selected from $R^{52}$;

each $R^{52}$ is independently selected from $C_{1-6}$ alkyl, $C_{1-6}$ haloalkyl, halo, D, CN, $OR^{a11}$, and $NR^{c11}R^{d11}$;

each $R^a$, $R^c$, and $R^d$ is independently selected from H, $C_{1-6}$ alkyl, $C_{1-6}$ haloalkyl, $C_{3-10}$ cycloalkyl, and 4-10 membered heterocycloalkyl; wherein said $C_{1-6}$ alkyl, $C_{3-10}$ cycloalkyl, and 4-10 membered heterocycloalkyl, are each optionally substituted with 1, 2, 3, or 4 substituents independently selected from $R^{10}$;

or any $R^c$ and $R^d$ attached to the same N atom, together with the N atom to which they are attached, form a 4-10 membered heterocycloalkyl group optionally substituted with 1, 2, 3 or 4 substituents independently selected from $R^{10}$;

each $R^b$ is independently selected from $C_{1-6}$ alkyl, and $C_{1-6}$ haloalkyl;

each $R^{a1}$, $R^{c1}$ and $R^{d1}$ is independently selected from H and $C_{1-6}$ alkyl;

each $R^{b1}$ is independently selected from $C_{1-6}$ alkyl, and $C_{1-6}$ haloalkyl;

each $R^{a2}$, $R^{c2}$ and $R^{d2}$ is independently selected from H, $C_{1-6}$ alkyl, and $C_{1-6}$ haloalkyl;

or any $R^{c2}$ and $R^{d2}$ attached to the same N atom, together with the N atom to which they are attached, form a 4-10 membered heterocycloalkyl group optionally substituted with 1, 2, 3 or 4 substituents independently selected from $R^{21}$;

each $R^{b2}$ is independently selected from $C_{1-6}$ alkyl, and $C_{1-6}$ haloalkyl;

each $R^{a4}$, $R^{c4}$ and $R^{d4}$ is independently selected from H and $C_{1-6}$ alkyl;

each $R^{b4}$ is independently selected from $C_{1-6}$ alkyl, and $C_{1-6}$ haloalkyl;

each $R^{a6}$, $R^{c6}$ and $R^{d6}$ is independently selected from H and $C_{1-6}$ alkyl;

each $R^{a9}$, $R^{c9}$ and $R^{d9}$ is independently selected from H, $C_{1-6}$ alkyl, $C_{1-6}$ haloalkyl, 4-10 membered heterocycloalkyl, and 5-10 membered heteroaryl; wherein said $C_{1-6}$ alkyl, 4-10 membered heterocycloalkyl, and 5-10 membered heteroaryl, are each optionally substituted with 1, 2, 3, or 4 substituents independently selected from $R^{51}$;

or any $R^{c9}$ and $R^{d9}$ attached to the same N atom, together with the N atom to which they are attached, form a 4-10 membered heterocycloalkyl group optionally substituted with 1, 2, 3 or 4 substituents independently selected from $R^{51}$;

each $R^{b9}$ is independently selected from $C_{1-6}$ alkyl, and $C_{1-6}$ haloalkyl;

each $R^{a10}$, $R^{c10}$ and $R^{d10}$ is independently selected from H and $C_{1-6}$ alkyl;

each $R^{b10}$ is independently selected from $C_{1-6}$ alkyl, $C_{1-6}$ haloalkyl, 5-6 membered heteroaryl, and 4-7 membered heterocycloalkyl; wherein said $C_{1-6}$ alkyl 5-6 membered heteroaryl, and 4-7 membered heterocycloalkyl, are each optionally substituted with 1, 2, 3, or 4 substituents independently selected from $R^{52}$; and each $R^{a11}$, $R^{c11}$ and $R^{d11}$ is independently selected from H and $C_{1-6}$ alkyl; and each $R^g$ is independently selected from OH, CN, halo, $C_{1-6}$ alkyl, $C_{1-6}$ haloalkyl, $C_{1-6}$ alkoxy, $C_{1-6}$ haloalkoxy, amino, $C_{1-6}$ alkylamino and di($C_{1-6}$ alkyl) amino.

In some embodiments, the compound of Formula I is a compound wherein:

$R^1$ is selected from $C_{1-6}$ alkyl, $C_{1-6}$ haloalkyl, CN, $C(O)R^b$, $C(O)NR^cR^d$, and $C(O)OR^a$; wherein said $C_{1-6}$ alkyl, is optionally substituted with 1, 2, 3, or 4 substituents independently selected from $R^{10}$;

$R^2$ is selected from $C_{6-10}$ aryl and 5-10 membered heteroaryl; wherein the 5-10 membered heteroaryl has at least one ring-forming carbon atom and 1, 2, 3, or 4 ring-forming heteroatoms independently selected from N, O, and S; wherein the N and S are optionally oxidized; wherein a ring-forming carbon atom of the 5-10 membered heteroaryl is optionally substituted by oxo to form a carbonyl group; and wherein the $C_{6-10}$ aryl and 5-10 membered heteroaryl are each optionally substituted with 1, 2, 3, 4 or 5 substituents independently selected from $R^{20}$;

$R^3$ is selected from H, D, halo, CN, and $C_{1-6}$ alkyl;

$R^4$ is selected from H, D, halo, CN, and $C_{1-6}$ alkyl;

$R^5$ is selected from $C_{6-10}$ aryl and 5-10 membered heteroaryl; wherein the 5-10 membered heteroaryl has at least one ring-forming carbon atom and 1, 2, 3, or 4 ring-forming heteroatoms independently selected from N, O, and S; wherein the N and S are optionally oxidized; wherein a ring-forming carbon atom of the 5-10 membered heteroaryl is optionally substituted by oxo to form a carbonyl group; and wherein the $C_{6-10}$ aryl and 5-10 membered heteroaryl are each optionally substituted with 1, 2, 3, 4 or 5 substituents independently selected from $R^{50}$;

or two adjacent $R^{50}$ substituents on $R^5$, taken together with the atoms to which they are attached, form a fused 4-, 5-, 6- or 7-membered heterocycloalkyl ring, or a fused $C_{3-7}$ cycloalkyl ring; wherein the fused 4-, 5-, 6- or 7-membered heterocycloalkyl ring each has at least one ring-forming carbon atom and 1, 2, 3, or 4 ring-forming heteroatoms independently selected from N, O, and S; wherein a ring-forming carbon atom of each fused 4-, 5-, 6- or 7-membered heterocycloalkyl ring is optionally substituted by oxo to form a carbonyl group; and wherein the fused 4-, 5-, 6- or 7-membered heterocycloalkyl ring and fused $C_{3-7}$ cycloalkyl ring are each optionally substituted with 1, 2, 3 or 4 substituents independently selected from $R^{51}$;

A is N or $CR^A$;

$R^A$ is selected from H, D and $C_{1-6}$ alkyl;

each $R^{10}$ is independently selected from $C_{1-6}$ alkyl, $C_{1-6}$ haloalkyl, halo, D, CN, $OR^{a1}$, $C(O)R^{b1}$, $C(O)NR^{c1}R^{d1}$, $C(O)OR^{a1}$, $NR^{c1}R^{d1}$, and $S(O)_2NR^{c1}R^{d1}$; wherein said $C_{1-6}$ alkyl is optionally substituted with 1, 2, 3, or 4 substituents independently selected from $R^{11}$;

each $R^{20}$ is independently selected from $C_{1-6}$ alkyl, $C_{1-6}$ haloalkyl, $C_{3-6}$ cycloalkyl, 4-6 membered heterocycloalkyl, phenyl, 5-6 membered heteroaryl, $C_{3-6}$ cycloalkyl-$C_{1-3}$ alkylene, 4-6 membered heterocycloalkyl-$C_{1-3}$ alkylene, phenyl-$C_{1-3}$ alkylene, 5-6 membered heteroaryl-$C_{1-3}$ alkylene, halo, D, CN, $OR^{a2}$, $C(O)R^{b2}$, $C(O)NR^{c2}R^{d2}$, $C(O)OR^{a2}$, $NR^{c2}R^{d2}$, $S(O)_2R^{b2}$, and $S(O)_2NR^{c2}R^{d2}$; wherein a ring-forming carbon atom of the 4-6 membered heterocycloalkyl is optionally substituted by oxo to form a carbonyl group; wherein said $C_{1-6}$ alkyl, $C_{3-6}$ cycloalkyl, 4-6 membered heterocycloalkyl, phenyl, 5-6 membered heteroaryl, $C_{3-6}$ cycloalkyl-$C_{1-3}$ alkylene, 4-6 membered heterocycloalkyl-$C_{1-3}$ alkylene, phenyl-$C_{1-3}$ alkylene, and 5-6 membered heteroaryl-$C_{1-3}$ alkylene are each optionally substituted with 1, 2, 3, or 4 substituents independently selected from $R^{21}$;

each $R^{21}$ is independently selected from $C_{1-6}$ alkyl, $C_{1-6}$ haloalkyl, $C_{3-6}$ cycloalkyl, 4-6 membered heterocycloalkyl, halo, D, CN, $OR^{a4}$, $C(O)NR^{c4}R^{d4}$ and $NR^{c4}R^{d4}$; wherein said $C_{1-6}$ alkyl, $C_{3-6}$ cycloalkyl, and 4-6 membered heterocycloalkyl, are each optionally substituted with 1, 2, 3, or 4 substituents independently selected from $R^{22}$;

each $R^{22}$ is independently selected from $C_{1-6}$ alkyl, $C_{1-6}$ haloalkyl, halo, D, CN, $OR^{a6}$, and $NR^{c6}R^{d6}$; wherein said $C_{1-6}$ alkyl, is optionally substituted with 1, 2, 3, or 4 substituents independently selected from $R^g$;

each $R^{50}$ is independently selected from $C_{1-6}$ alkyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $OR^{a9}$, $C(O)R^{b9}$, $C(O)NR^{c9}R^{d9}$, $C(O)OR^{a9}$, $NR^{c9}R^{d9}$, $S(O)_2R^{b9}$, and $S(O)_2NR^{c9}R^{d9}$; wherein said $C_{1-6}$ alkyl, $C_{3-10}$ cycloalkyl, 4-10 membered heterocycloalkyl, $C_{6-10}$ aryl, and 5-10 membered heteroaryl, are each optionally substituted with 1, 2, 3, or 4 substituents independently selected from $R^{51}$;

each $R^{51}$ is independently selected from $C_{1-6}$ alkyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $OR^{a10}$, $C(O)R^{b10}$, $C(O)NR^{c10}R^{d10}$, $C(O)OR^{a10}$, $NR^{c10}R^{d10}$, $S(O)_2R^{b10}$, and $S(O)_2NR^{c10}R^{d10}$; wherein said $C_{1-6}$ alkyl, $C_{3-10}$ cycloalkyl, 4-10 membered heterocycloalkyl, $C_{6-10}$ aryl, and 5-10 membered heteroaryl, are each optionally substituted with 1, 2, 3, or 4 substituents independently selected from $R^{52}$;

each $R^{52}$ is independently selected from $C_{1-6}$ alkyl, $C_{1-6}$ haloalkyl, halo, D, CN, $OR^{a11}$, and $NR^{c11}R^{d11}$;

each $R^a$, $R^c$, and $R^d$ is independently selected from H, $C_{1-6}$ alkyl, $C_{1-6}$ haloalkyl, $C_{3-10}$ cycloalkyl, and 4-10 membered heterocycloalkyl; wherein said $C_{1-6}$ alkyl, $C_{3-10}$ cycloalkyl, and 4-10 membered heterocycloalkyl, are each optionally substituted with 1, 2, 3, or 4 substituents independently selected from $R^{10}$;

or any $R^c$ and $R^d$ attached to the same N atom, together with the N atom to which they are attached, form a 4-10 membered heterocycloalkyl group optionally substituted with 1, 2, 3 or 4 substituents independently selected from $R^{10}$;

each $R^b$ is independently selected from $C_{1-6}$ alkyl, $C_{1-6}$ haloalkyl and 4-10 membered heterocycloalkyl, wherein the 4-10 membered heterocycloalkyl is optionally substituted with 1, 2, 3, or 4 substituents independently selected from $R^{10}$;

each $R^{a1}$, $R^{c1}$ and $R^{d1}$ is independently selected from H and $C_{1-6}$ alkyl;

each $R^{b1}$ is independently selected from $C_{1-6}$ alkyl, and $C_{1-6}$ haloalkyl;

each $R^{a2}$, $R^{c2}$ and $R^{d2}$ is independently selected from H, $C_{1-6}$ alkyl, and $C_{1-6}$ haloalkyl;

or any $R^{c2}$ and $R^{d2}$ attached to the same N atom, together with the N atom to which they are attached, form a 4-10 membered heterocycloalkyl group optionally substituted with 1, 2, 3 or 4 substituents independently selected from $R^{21}$;

each $R^{b2}$ is independently selected from $C_{1-6}$ alkyl, and $C_{1-6}$ haloalkyl;

each $R^{a4}$, $R^{c4}$ and $R^{d4}$ is independently selected from H and $C_{1-6}$ alkyl;

each $R^{b4}$ is independently selected from $C_{1-6}$ alkyl, and $C_{1-6}$ haloalkyl;

each $R^{a6}$, $R^{c6}$ and $R^{d6}$ is independently selected from H and $C_{1-6}$ alkyl;

each $R^{a9}$, $R^{c9}$ and $R^{d9}$ is independently selected from H, $C_{1-6}$ alkyl, $C_{1-6}$ haloalkyl, 4-10 membered heterocycloalkyl, and 5-10 membered heteroaryl; wherein said $C_{1-6}$ alkyl, 4-10 membered heterocycloalkyl, and 5-10 membered heteroaryl, are each optionally substituted with 1, 2, 3, or 4 substituents independently selected from $R^{51}$;

or any $R^{c9}$ and $R^{d9}$ attached to the same N atom, together with the N atom to which they are attached, form a 4-10 membered heterocycloalkyl group optionally substituted with 1, 2, 3 or 4 substituents independently selected from $R^{51}$;

each $R^{b9}$ is independently selected from $C_{1-6}$ alkyl, and $C_{1-6}$ haloalkyl;

each $R^{a10}$, $R^{c10}$ and $R^{d10}$ is independently selected from H and $C_{1-6}$ alkyl;

each $R^{b10}$ is independently selected from $C_{1-6}$ alkyl, $C_{1-6}$ haloalkyl, 5-6 membered heteroaryl, and 4-7 membered heterocycloalkyl; wherein said $C_{1-6}$ alkyl 5-6 membered heteroaryl, and 4-7 membered heterocycloalkyl, are each optionally substituted with 1, 2, 3, or 4 substituents independently selected from $R^{52}$; and each $R^{a11}$, $R^{c11}$ and $R^{d11}$ is independently selected from H and $C_{1-6}$ alkyl; and each $R^g$ is independently selected from OH, CN, halo, $C_{1-6}$ alkyl, $C_{1-6}$ haloalkyl, $C_{1-6}$ alkoxy, $C_{1-6}$ haloalkoxy, amino, $C_{1-6}$ alkylamino and di($C_{1-6}$ alkyl)amino.

In some embodiments, the compound of Formula I is a compound wherein:

$R^1$ is selected from $C_{1-6}$ alkyl, CN, C(O)$NR^cR^d$, and C(O)$OR^a$; wherein said $C_{1-6}$ alkyl, is optionally substituted with 1, 2, 3, or 4 substituents independently selected from $R^{10}$;

$R^2$ is selected from $C_{6-10}$ aryl and 5-10 membered heteroaryl; wherein the 5-10 membered heteroaryl has at least one ring-forming carbon atom and 1, 2, 3, or 4 ring-forming heteroatoms independently selected from N, O, and S; wherein the N and S are optionally oxidized; wherein a ring-forming carbon atom of the 5-10 membered heteroaryl is optionally substituted by oxo to form a carbonyl group; and wherein the $C_{6-10}$ aryl and 5-10 membered heteroaryl are each optionally substituted with 1, 2, 3, 4 or 5 substituents independently selected from $R^{20}$;

$R^3$ is H;

$R^4$ is H;

$R^5$ is selected from $C_{6-10}$ aryl and 5-10 membered heteroaryl; wherein the 5-10 membered heteroaryl has at least one ring-forming carbon atom and 1, 2, 3, or 4 ring-forming heteroatoms independently selected from N, O, and S; wherein the N and S are optionally oxidized; wherein a ring-forming carbon atom of the 5-10 membered heteroaryl is optionally substituted by oxo to form a carbonyl group; and wherein the $C_{6-10}$ aryl and 5-10 membered heteroaryl are each optionally substituted with 1, 2, 3, 4 or 5 substituents independently selected from $R^{50}$;

or two adjacent $R^{50}$ substituents on $R^5$, taken together with the atoms to which they are attached, form a fused 4-, 5-, 6- or 7-membered heterocycloalkyl ring; wherein the fused 4-, 5-, 6- or 7-membered heterocycloalkyl ring each has at least one ring-forming carbon atom and 1, 2, 3, or 4 ring-forming heteroatoms independently selected from N, O, and S; wherein a ring-forming carbon atom of each fused 4-, 5-, 6- or 7-membered heterocycloalkyl ring is optionally substituted by oxo to form a carbonyl group; and wherein the fused 4-, 5-, 6- or 7-membered heterocycloalkyl ring and fused $C_{3-7}$ cycloalkyl ring are each optionally substituted with 1, 2, 3 or 4 substituents independently selected from $R^{51}$;

A is N or CH;

each $R^{10}$ is independently selected from $C_{1-6}$ alkyl, $OR^{a1}$, and C(O)$OR^{a1}$; wherein said $C_{1-6}$ alkyl is optionally substituted with 1, 2, 3, or 4 substituents independently selected from $R^{11}$;

each $R^{20}$ is independently selected from $C_{1-6}$ alkyl, $C_{3-10}$ cycloalkyl, 4-10 membered heterocycloalkyl, halo, and C(O)$NR^{c2}R^{d2}$; wherein said $C_{1-6}$ alkyl, $C_{3-10}$ cycloalkyl, and 4-10 membered heterocycloalkyl, are each optionally substituted with 1, 2, 3, or 4 substituents independently selected from $R^{21}$;

each $R^{21}$ is independently selected from $C_{1-6}$ alkyl, 4-10 membered heterocycloalkyl, and OH; wherein said $C_{1-6}$ alkyl, and 4-10 membered heterocycloalkyl, are each optionally substituted with 1, 2, 3, or 4 substituents independently selected from $R^{22}$;

each $R^{22}$ is independently selected from $C_{1-6}$ alkyl, and OH;

each $R^{50}$ is independently selected from $C_{1-6}$ alkyl, 4-10 membered heterocycloalkyl, 5-10 membered heteroaryl, halo, CN, C(O)$NR^{c9}R^{d9}$, and $NR^{c9}R^{d9}$; wherein said $C_{1-6}$ alkyl, 4-10 membered heterocycloalkyl, and 5-10 membered heteroaryl, are each optionally substituted with 1, 2, 3, or 4 substituents independently selected from $R^{51}$;

each $R^{51}$ is independently selected from $C_{1-6}$ alkyl, 4-10 membered heterocycloalkyl, $C_{6-10}$ aryl, OH, and C(O)$R^{b10}$; wherein said $C_{1-6}$ alkyl, 4-10 membered heterocycloalkyl, and $C_{6-10}$ aryl, are each optionally substituted with 1, 2, 3, or 4 substituents independently selected from $R^{52}$;

each $R^{52}$ is independently selected from halo, and OH;

each $R^a$, $R^c$, and $R^d$ is independently selected from H, $C_{1-6}$ alkyl, and $C_{3-10}$ cycloalkyl; wherein said $C_{1-6}$ alkyl, and $C_{3-10}$ cycloalkyl, are each optionally substituted with 1, 2, 3, or 4 substituents independently selected from $R^{10}$;

or any $R^c$ and $R^d$ attached to the same N atom, together with the N atom to which they are attached, form a 4-10 membered heterocycloalkyl group optionally substituted with 1, 2, 3 or 4 substituents independently selected from $R^{10}$;

each $R^{a1}$ is independently selected from H and $C_{1-6}$ alkyl;

each $R^{a2}$, $R^{c2}$ and $R^{d2}$ is independently selected from H, $C_{1-6}$ alkyl, and $C_{1-6}$ haloalkyl;

or any $R^{c2}$ and $R^{d2}$ attached to the same N atom, together with the N atom to which they are attached, form a 4-10 membered heterocycloalkyl group optionally substituted with 1, 2, 3 or 4 substituents independently selected from $R^{21}$;

each $R^{c9}$ and $R^{d9}$ is independently selected from H, $C_{1-6}$ alkyl, and 5-10 membered heteroaryl; wherein said $C_{1-6}$ alkyl, and 5-10 membered heteroaryl, are each optionally substituted with 1, 2, 3, or 4 substituents independently selected from $R^{51}$;

or any $R^{c9}$ and $R^{d9}$ attached to the same N atom, together with the N atom to which they are attached, form a 4-10 membered heterocycloalkyl group optionally substituted with 1, 2, 3 or 4 substituents independently selected from $R^{51}$;

each $R^{b10}$ is independently selected from $C_{1-6}$ alkyl, and 5-6 membered heteroaryl; wherein said $C_{1-6}$ alkyl, and 5-6 membered heteroaryl, are each optionally substituted with 1, 2, 3, or 4 substituents independently selected from $R^{52}$.

In some embodiments, the compound of Formula I is a compound wherein:

$R^1$ is selected from $C_{1-6}$ alkyl, CN, C(O)$NR^cR^d$, C(O)$R^b$ and C(O)$OR^a$; wherein said $C_{1-6}$ alkyl, is optionally substituted with 1, 2, 3, or 4 substituents independently selected from $R^{10}$;

$R^2$ is selected from phenyl and 5-6 membered heteroaryl; wherein the 5-6 membered heteroaryl has at least one ring-forming carbon atom and 1, 2, 3, or 4 ring-forming heteroatoms independently selected from N, O, and S; wherein the N and S are optionally oxidized; wherein a ring-forming carbon atom of the 5-6 membered heteroaryl is optionally substituted by oxo to form a carbonyl group; and wherein the phenyl and 5-6 membered heteroaryl are each optionally substituted with 1, 2, 3, 4 or 5 substituents independently selected from $R^{20}$;

$R^3$ is H;

$R^4$ is H;

$R^5$ is selected from $C_{6-10}$ aryl and 5-10 membered heteroaryl; wherein the 5-10 membered heteroaryl has at least one ring-forming carbon atom and 1, 2, 3, or 4 ring-forming heteroatoms independently selected from N, O, and S; wherein the N and S are optionally oxidized; wherein a ring-forming carbon atom of the 5-10 membered heteroaryl is optionally substituted by oxo to form a carbonyl group; and wherein the $C_{6-10}$ aryl and 5-10 membered heteroaryl are each optionally substituted with 1, 2, 3, 4 or 5 substituents independently selected from $R^{50}$;

or two adjacent $R^{50}$ substituents on $R^5$, taken together with the atoms to which they are attached, form a fused 4-, 5-, 6- or 7-membered heterocycloalkyl ring; wherein the fused 4-, 5-, 6- or 7-membered heterocycloalkyl ring each has at least one ring-forming carbon atom and 1, 2, 3, or 4 ring-forming heteroatoms independently selected from N, O, and S; wherein a ring-forming carbon atom of each fused 4-, 5-, 6- or 7-membered heterocycloalkyl ring is optionally substituted by oxo to form a carbonyl group; and wherein the fused 4-, 5-, 6- or 7-membered heterocycloalkyl ring and fused $C_{3-7}$ cycloalkyl ring are each optionally substituted with 1, 2, 3 or 4 substituents independently selected from $R^{51}$;

A is N or CH;

each $R^{10}$ is independently selected from $C_{1-6}$ alkyl, $OR^{a1}$, and $C(O)OR^{a1}$; wherein said $C_{1-6}$ alkyl is optionally substituted with 1, 2, 3, or 4 substituents independently selected from $R^{11}$;

each $R^{20}$ is independently selected from $C_{1-6}$ alkyl, $C_{3-6}$ cycloalkyl, 4-6 membered heterocycloalkyl, 4-6 membered heterocycloalkyl-$C_{1-3}$ alkylene, halo, $NR^{c2}R^{d2}$, and $C(O)NR^{c2}R^{d2}$, wherein a ring-forming carbon atom of the 4-6 membered heterocycloalkyl is optionally substituted by oxo to form a carbonyl group; wherein said $C_{1-6}$ alkyl, $C_{3-6}$ cycloalkyl, 4-6 membered heterocycloalkyl and 4-6 membered heterocycloalkyl-$C_{1-3}$ alkylene are each optionally substituted with 1, 2, 3, or 4 substituents independently selected from $R^{21}$ each $R^{21}$ is independently selected from $C_{1-6}$ alkyl, $C_{3-6}$ cycloalkyl, 4-6 membered heterocycloalkyl, halo, $OR^{a4}$, and $NR^{c4}R^{d4}$; wherein said $C_{1-6}$ alkyl, $C_{3-6}$ cycloalkyl, and 4-6 membered heterocycloalkyl, are each optionally substituted with 1, 2, 3, or 4 substituents independently selected from $R^{22}$;

each $R^{22}$ is independently selected from $C_{1-6}$ alkyl, halo and OH;

each $R^{50}$ is independently selected from $C_{1-6}$ alkyl, 4-10 membered heterocycloalkyl, 5-10 membered heteroaryl, halo, CN, $C(O)NR^{c9}R^{d9}$, and $NR^{c9}R^{d9}$; wherein said $C_{1-6}$ alkyl, 4-10 membered heterocycloalkyl, and 5-10 membered heteroaryl, are each optionally substituted with 1, 2, 3, or 4 substituents independently selected from $R^{51}$;

each $R^{51}$ is independently selected from $C_{1-6}$ alkyl, 4-10 membered heterocycloalkyl, $C_{6-10}$ aryl, OH, and $C(O)R^{b10}$; wherein said $C_{1-6}$ alkyl, 4-10 membered heterocycloalkyl, and $C_{6-10}$ aryl, are each optionally substituted with 1, 2, 3, or 4 substituents independently selected from $R^{52}$;

each $R^{52}$ is independently selected from halo, and OH;

each $R^a$, $R^c$, and $R^d$ is independently selected from H, $C_{1-6}$ alkyl, and $C_{3-10}$ cycloalkyl; wherein said $C_{1-6}$ alkyl, and $C_{3-10}$ cycloalkyl, are each optionally substituted with 1, 2, 3, or 4 substituents independently selected from $R^{10}$;

or any $R^c$ and $R^d$ attached to the same N atom, together with the N atom to which they are attached, form a 4-10 membered heterocycloalkyl group optionally substituted with 1, 2, 3 or 4 substituents independently selected from $R^{10}$;

each $R^b$ is independently selected from $C_{1-6}$ alkyl, $C_{1-6}$ haloalkyl, and 4-10 membered heterocycloalkyl, wherein the 4-10 membered heterocycloalkyl is optionally substituted with 1, 2, 3, or 4 substituents independently selected from $R^{10}$;

each $R^{a1}$ is independently selected from H and $C_{1-6}$ alkyl;

each $R^{a2}$, $R^{c2}$ and $R^{d2}$ is independently selected from H, $C_{1-6}$ alkyl, and $C_{1-6}$ haloalkyl;

or any $R^{c2}$ and $R^{d2}$ attached to the same N atom, together with the N atom to which they are attached, form a 4-10 membered heterocycloalkyl group optionally substituted with 1, 2, 3 or 4 substituents independently selected from $R^{21}$;

each $R^{a4}$, $R^{c4}$ and $R^{d4}$ is independently selected from H, $C_{1-6}$ alkyl, and $C_{1-6}$ haloalkyl; or any $R^{c4}$ and $R^{d4}$ attached to the same N atom, together with the N atom to which they are attached, form a 4-10 membered heterocycloalkyl group optionally substituted with 1, 2, 3 or 4 substituents independently selected from $R^{21}$;

each $R^{c9}$ and $R^{d9}$ is independently selected from H, $C_{1-6}$ alkyl, and 5-10 membered heteroaryl; wherein said $C_{1-6}$ alkyl, and 5-10 membered heteroaryl, are each optionally substituted with 1, 2, 3, or 4 substituents independently selected from $R^{51}$;

or any $R^{c9}$ and $R^{d9}$ attached to the same N atom, together with the N atom to which they are attached, form a 4-10 membered heterocycloalkyl group optionally substituted with 1, 2, 3 or 4 substituents independently selected from $R^{51}$;

each $R^{b10}$ is independently selected from $C_{1-6}$ alkyl, and 5-6 membered heteroaryl; wherein said $C_{1-6}$ alkyl, and 5-6 membered heteroaryl, are each optionally substituted with 1, 2, 3, or 4 substituents independently selected from $R^{52}$.

In some embodiments, the compound of Formula I is a compound wherein:

$R^1$ is selected from $C_{1-6}$ alkyl, CN, $C(O)NR^cR^d$, $C(O)R^b$ and $C(O)OR^a$; wherein said $C_{1-6}$ alkyl, is optionally substituted with 1, 2, 3, or 4 substituents independently selected from $R^{10}$;

$R^2$ is selected from phenyl and pyrazolyl; wherein the phenyl and pyrazolyl are each optionally substituted with 1 or 2 substituents independently selected from $R^{20}$;

$R^3$ is H;

$R^4$ is H;

$R^5$ is selected from quinolinyl, naphthyridinyl, pyridinyl, and phenyl, wherein the quinolinyl, naphthyridinyl, pyridinyl, and phenyl are each optionally substituted with 1, 2, or 3 substituents independently selected from $R^{50}$;

or two adjacent $R^{50}$ substituents on $R^5$, taken together with the atoms to which they are attached, form a fused 4-, 5-, 6- or 7-membered heterocycloalkyl ring; wherein the fused 4-, 5-, 6- or 7-membered heterocycloalkyl ring each has at least one ring-forming carbon atom and 1, 2, 3, or 4 ring-forming heteroatoms independently selected from N, O, and S; wherein a ring-forming carbon atom of each fused 4-, 5-, 6- or 7-membered heterocycloalkyl ring is optionally substituted by oxo to form a carbonyl group; and wherein the fused 4-, 5-, 6- or 7-membered heterocycloalkyl ring and fused $C_{3-7}$ cycloalkyl ring are each optionally substituted with 1, 2, 3 or 4 substituents independently selected from $R^{51}$;

A is N or CH;

each $R^{10}$ is independently selected from $C_{1-6}$ alkyl, $OR^{a1}$, and $C(O)OR^{a1}$; wherein said $C_{1-6}$ alkyl is optionally substituted with 1, 2, 3, or 4 substituents independently selected from $R^{11}$;

each $R^{20}$ is independently selected from $C_{1-6}$ alkyl, $C_{3-6}$ cycloalkyl, 4-6 membered heterocycloalkyl, 4-6 membered heterocycloalkyl-$C_{1-3}$ alkylene, halo, $NR^{c2}R^{d2}$, and $C(O)NR^{c2}R^{d2}$, wherein a ring-forming carbon atom of the 4-6 membered heterocycloalkyl is optionally substituted by oxo to form a carbonyl group; wherein said $C_{1-6}$ alkyl, $C_{3-6}$ cycloalkyl, 4-6 membered heterocycloalkyl and 4-10 membered heterocycloalkyl-$C_{1-3}$ alkylene are each optionally substituted with 1, 2, 3, or 4 substituents independently selected from $R^{21}$;

each $R^{21}$ is independently selected from $C_{1-6}$ alkyl, $C_{3-6}$ cycloalkyl, 4-6 membered heterocycloalkyl, halo, $OR^{a4}$, and $NR^{c4}R^{d4}$; wherein said $C_{1-6}$ alkyl, $C_{3-6}$ cycloalkyl, and 4-6 membered heterocycloalkyl, are each optionally substituted with 1, 2, 3, or 4 substituents independently selected from $R^{22}$;

each $R^{22}$ is independently selected from $C_{1-6}$ alkyl, halo and OH;

each $R^{50}$ is independently selected from $C_{1-6}$ alkyl, 4-10 membered heterocycloalkyl, 5-10 membered heteroaryl, halo, CN, $C(O)NR^{c9}R^{d9}$, and $NR^{c9}R^{d9}$; wherein said $C_{1-6}$ alkyl, 4-10 membered heterocycloalkyl, and 5-10 membered heteroaryl, are each optionally substituted with 1, 2, 3, or 4 substituents independently selected from $R^{51}$;

each $R^{51}$ is independently selected from $C_{1-6}$ alkyl, 4-10 membered heterocycloalkyl, $C_{6-10}$ aryl, OH, and $C(O)R^{b10}$; wherein said $C_{1-6}$ alkyl, 4-10 membered heterocycloalkyl, and $C_{6-10}$ aryl, are each optionally substituted with 1, 2, 3, or 4 substituents independently selected from $R^{52}$;

each $R^{52}$ is independently selected from halo, and OH;

each $R^a$, $R^c$, and $R^d$ is independently selected from H, $C_{1-6}$ alkyl, and $C_{3-10}$ cycloalkyl; wherein said $C_{1-6}$ alkyl, and $C_{3-10}$ cycloalkyl, are each optionally substituted with 1, 2, 3, or 4 substituents independently selected from $R^{10}$;

or any $R^c$ and $R^d$ attached to the same N atom, together with the N atom to which they are attached, form a 4-10 membered heterocycloalkyl group optionally substituted with 1, 2, 3 or 4 substituents independently selected from $R^{10}$;

each $R^b$ is independently selected from 4-6 membered heterocycloalkyl, wherein the 4-6 membered heterocycloalkyl is optionally substituted with 1, 2, 3, or 4 substituents independently selected from $R^{10}$;

each $R^{a1}$ is independently selected from H and $C_{1-6}$ alkyl;

each $R^{a2}$, $R^{c2}$ and $R^{d2}$ is independently selected from H, $C_{1-6}$ alkyl, and $C_{1-6}$ haloalkyl;

or any $R^{c2}$ and $R^{d2}$ attached to the same N atom, together with the N atom to which they are attached, form a 4-10 membered heterocycloalkyl group optionally substituted with 1, 2, 3 or 4 substituents independently selected from $R^{21}$;

each $R^{a4}$, $R^{c4}$ and $R^{d4}$ is independently selected from H, $C_{1-6}$ alkyl, and $C_{1-6}$ haloalkyl;

or any $R^{c4}$ and $R^{d4}$ attached to the same N atom, together with the N atom to which they are attached, form a 4-10 membered heterocycloalkyl group optionally substituted with 1, 2, 3 or 4 substituents independently selected from $R^{21}$;

each $R^{c9}$ and $R^{d9}$ is independently selected from H, $C_{1-6}$ alkyl, and 5-10 membered heteroaryl; wherein said $C_{1-6}$ alkyl, and 5-10 membered heteroaryl, are each optionally substituted with 1, 2, 3, or 4 substituents independently selected from $R^{51}$;

or any $R^{c9}$ and $R^{d9}$ attached to the same N atom, together with the N atom to which they are attached, form a 4-10 membered heterocycloalkyl group optionally substituted with 1, 2, 3 or 4 substituents independently selected from $R^{51}$;

each $R^{b10}$ is independently selected from $C_{1-6}$ alkyl, and 5-6 membered heteroaryl; wherein said $C_{1-6}$ alkyl, and 5-6 membered heteroaryl, are each optionally substituted with 1, 2, 3, or 4 substituents independently selected from $R^{52}$.

In some embodiments, the compound is a compound of Formula VIa or Formula VIb:

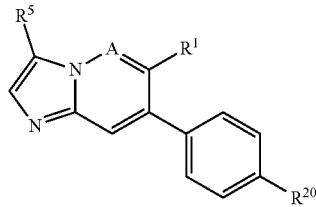

VIa

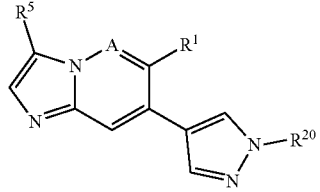

VIb or a pharmaceutically acceptable salt thereof; wherein $R^1$ is selected from $C_{1-6}$ alkyl, CN, $C(O)NR^cR^d$, $C(O)R^b$ and $C(O)OR^a$; wherein said $C_{1-6}$ alkyl, is optionally substituted with 1, 2, 3, or 4 substituents independently selected from $R^{10}$;

$R^5$ is selected from quinolinyl, naphthyridinyl, pyridinyl, and phenyl, wherein the quinolinyl, naphthyridinyl, pyridinyl, and phenyl are each optionally substituted with 1, 2, or 3 substituents independently selected from $R^{50}$;

or two adjacent $R^{50}$ substituents on $R^5$, taken together with the atoms to which they are attached, form a fused 4-, 5-, 6- or 7-membered heterocycloalkyl ring; wherein the fused 4-, 5-, 6- or 7-membered heterocycloalkyl ring each has at least one ring-forming carbon atom and 1, 2, 3, or 4 ring-forming heteroatoms independently selected from N, O, and S; wherein a ring-forming carbon atom of each fused 4-, 5-, 6- or 7-membered heterocycloalkyl ring is optionally substituted by oxo to form a carbonyl group; and wherein the fused 4-, 5-, 6- or 7-membered heterocycloalkyl ring and fused $C_{3-7}$ cycloalkyl ring are each optionally substituted with 1, 2, 3 or 4 substituents independently selected from $R^{51}$;

A is N or CH;

each $R^{10}$ is independently selected from $C_{1-6}$ alkyl, $OR^{a1}$, and $C(O)OR^{a1}$; wherein said $C_{1-6}$ alkyl is optionally substituted with 1, 2, 3, or 4 substituents independently selected from $R^{11}$;

each $R^{20}$ is independently selected from $C_{1-6}$ alkyl, $C_{3-6}$ cycloalkyl, 4-6 membered heterocycloalkyl, 4-6 membered heterocycloalkyl-$C_{1-3}$ alkylene, halo, $NR^{c2}R^{d2}$, and $C(O)NR^{c2}R^{d2}$, wherein a ring-forming carbon atom of the 4-6 membered heterocycloalkyl is optionally substituted by oxo to form a carbonyl group; wherein said $C_{1-6}$ alkyl, $C_{3-6}$ cycloalkyl, 4-6 membered heterocycloalkyl and 4-6 membered heterocycloalkyl-$C_{1-3}$ alkylene are each optionally substituted with 1, 2, 3, or 4 substituents independently selected from $R^{21}$;

each $R^{21}$ is independently selected from $C_{1-6}$ alkyl, $C_{3-6}$ cycloalkyl, 4-6 membered heterocycloalkyl, halo, $OR^{a4}$, and $NR^{c4}R^{d4}$; wherein said $C_{1-6}$ alkyl, $C_{3-6}$ cycloalkyl, and 4-6 membered heterocycloalkyl, are each optionally substituted with 1, 2, 3, or 4 substituents independently selected from $R^{22}$;

each $R^{22}$ is independently selected from $C_{1-6}$ alkyl, halo, and OH;

each $R^{50}$ is independently selected from $C_{1-6}$ alkyl, 4-10 membered heterocycloalkyl, 5-10 membered heteroaryl, halo, CN, C(O)NR$^{c9}$R$^{d9}$, and NR$^{c9}$R$^{d9}$; wherein said C$_{1-6}$ alkyl, 4-10 membered heterocycloalkyl, and 5-10 membered heteroaryl, are each optionally substituted with 1, 2, 3, or 4 substituents independently selected from R$^{51}$;

each R$^{51}$ is independently selected from C$_{1-6}$ alkyl, 4-10 membered heterocycloalkyl, C$_{6-10}$ aryl, OH, and C(O)R$^{b10}$; wherein said C$_{1-6}$ alkyl, 4-10 membered heterocycloalkyl, and C$_{6-10}$ aryl, are each optionally substituted with 1, 2, 3, or 4 substituents independently selected from R$^{52}$;

each R$^{52}$ is independently selected from halo, and OH;

each R$^{a}$, R$^{c}$, and R$^{d}$ is independently selected from H, C$_{1-6}$ alkyl, and C$_{3-10}$ cycloalkyl; wherein said C$_{1-6}$ alkyl, and C$_{3-10}$ cycloalkyl, are each optionally substituted with 1, 2, 3, or 4 substituents independently selected from R$^{10}$;

or any R$^{c}$ and R$^{d}$ attached to the same N atom, together with the N atom to which they are attached, form a 4-10 membered heterocycloalkyl group optionally substituted with 1, 2, 3 or 4 substituents independently selected from R$^{10}$;

each R$^{b}$ is independently selected from 4-6 membered heterocycloalkyl, wherein the 4-6 membered heterocycloalkyl is optionally substituted with 1, 2, 3, or 4 substituents independently selected from R$^{10}$;

each R$^{a1}$ is independently selected from H and C$_{1-6}$ alkyl;

each R$^{a2}$, R$^{c2}$ and R$^{d2}$ is independently selected from H, C$_{1-6}$ alkyl, and C$_{1-6}$ haloalkyl;

or any R$^{c2}$ and R$^{d2}$ attached to the same N atom, together with the N atom to which they are attached, form a 4-10 membered heterocycloalkyl group optionally substituted with 1, 2, 3 or 4 substituents independently selected from R$^{21}$;

each R$^{a4}$, R$^{c4}$ and R$^{d4}$ is independently selected from H, C$_{1-6}$ alkyl, and C$_{1-6}$ haloalkyl; or any R$^{c4}$ and R$^{d4}$ attached to the same N atom, together with the N atom to which they are attached, form a 4-10 membered heterocycloalkyl group optionally substituted with 1, 2, 3 or 4 substituents independently selected from R$^{21}$;

each R$^{c9}$ and R$^{d9}$ is independently selected from H, C$_{1-6}$ alkyl, and 5-10 membered heteroaryl; wherein said C$_{1-6}$ alkyl, and 5-10 membered heteroaryl, are each optionally substituted with 1, 2, 3, or 4 substituents independently selected from R$^{51}$;

or any R$^{c9}$ and R$^{d9}$ attached to the same N atom, together with the N atom to which they are attached, form a 4-10 membered heterocycloalkyl group optionally substituted with 1, 2, 3 or 4 substituents independently selected from R$^{51}$;

each R$^{b10}$ is independently selected from C$_{1-6}$ alkyl, and 5-6 membered heteroaryl; wherein said C$_{1-6}$ alkyl, and 5-6 membered heteroaryl, are each optionally substituted with 1, 2, 3, or 4 substituents independently selected from R$^{52}$.

In some embodiments, the disclosure provides a compound of Formula VIIa, Formula VIIb, Formula VIIc or Formula VIId:

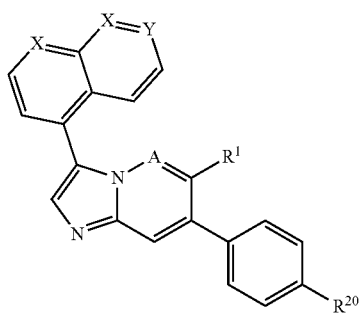

VIIa

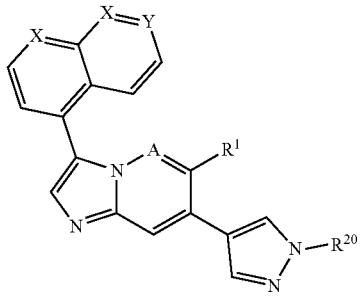

VIIb

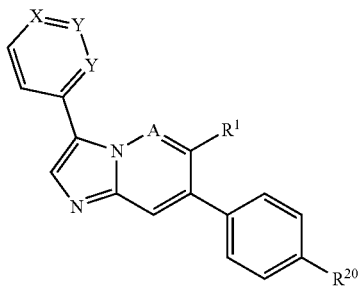

VIIc

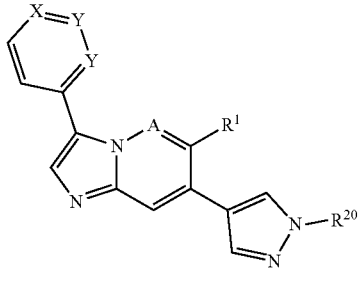

VIId or a pharmaceutically acceptable salt thereof, wherein:

each X is independently selected from CH, N and CR$^{50}$;

each Y is independently selected from CH and CR$^{50}$;

R$^{1}$ is selected from C$_{1-6}$ alkyl, CN, C(O)NR$^{c}$R$^{d}$, C(O)R$^{b}$ and C(O)OR$^{a}$; wherein said C$_{1-6}$ alkyl, is optionally substituted with 1, 2, 3, or 4 substituents independently selected from R$^{10}$;

A is N or CH;

each R$^{10}$ is independently selected from C$_{1-6}$ alkyl, OR$^{a1}$, and C(O)OR$^{a1}$; wherein said C$_{1-6}$ alkyl is optionally substituted with 1, 2, 3, or 4 substituents independently selected from R$^{11}$;

each R$^{20}$ is independently selected from C$_{1-6}$ alkyl, C$_{3-10}$ cycloalkyl, 4-10 membered heterocycloalkyl, 4-10 membered heterocycloalkyl-C$_{1-3}$ alkylene, halo, NR$^{c2}$R$^{d2}$, and C(O)NR$^{c2}$R$^{d2}$, wherein a ring-forming carbon atom of the 4-10 membered heterocycloalkyl is optionally substituted by oxo to form a carbonyl group; wherein said C$_{1-6}$ alkyl, C$_{3-10}$ cycloalkyl, 4-10 membered heterocycloalkyl and 4-10 membered heterocycloalkyl-C$_{1-3}$ alkylene are each optionally substituted with 1, 2, 3, or 4 substituents independently selected from R$^{21}$;

each R$^{21}$ is independently selected from C$_{1-6}$ alkyl, C$_{3-6}$ cycloalkyl, 4-10 membered heterocycloalkyl, halo, OR$^{a4}$, and NR$^{c4}$R$^{d4}$; wherein said C$_{1-6}$ alkyl, C$_{3-6}$ cycloalkyl, and 4-10 membered heterocycloalkyl, are each optionally substituted with 1, 2, 3, or 4 substituents independently selected from R$^{22}$;

each R$^{22}$ is independently selected from C$_{1-6}$ alkyl, halo, and OH;

each $R^{50}$ is independently selected from $C_{1-6}$ alkyl, 4-10 membered heterocycloalkyl, 5-10 membered heteroaryl, halo, CN, C(O)NR$^{c9}$R$^{d9}$, and NR$^{c9}$R$^{d9}$; wherein said $C_{1-6}$ alkyl, 4-10 membered heterocycloalkyl, and 5-10 membered heteroaryl, are each optionally substituted with 1, 2, 3, or 4 substituents independently selected from $R^{51}$;

or two adjacent $R^{50}$ substituents on $R^5$, taken together with the atoms to which they are attached, form a fused 4-, 5-, 6- or 7-membered heterocycloalkyl ring; wherein the fused 4-, 5-, 6- or 7-membered heterocycloalkyl ring each has at least one ring-forming carbon atom and 1, 2, 3, or 4 ring-forming heteroatoms independently selected from N, O, and S; wherein a ring-forming carbon atom of each fused 4-, 5-, 6- or 7-membered heterocycloalkyl ring is optionally substituted by oxo to form a carbonyl group; and wherein the fused 4-, 5-, 6- or 7-membered heterocycloalkyl ring and fused $C_{3-7}$ cycloalkyl ring are each optionally substituted with 1, 2, 3 or 4 substituents independently selected from $R^{51}$;

each $R^{51}$ is independently selected from $C_{1-6}$ alkyl, 4-10 membered heterocycloalkyl, $C_{6-10}$ aryl, OH, and C(O)R$^{b10}$; wherein said $C_{1-6}$ alkyl, 4-10 membered heterocycloalkyl, and $C_{6-10}$ aryl, are each optionally substituted with 1, 2, 3, or 4 substituents independently selected from $R^{52}$;

each $R^{52}$ is independently selected from halo, and OH;

each $R^a$, $R^c$, and $R^d$ is independently selected from H, $C_{1-6}$ alkyl, and $C_{3-10}$ cycloalkyl; wherein said $C_{1-6}$ alkyl, and $C_{3-10}$ cycloalkyl, are each optionally substituted with 1, 2, 3, or 4 substituents independently selected from $R^{10}$;

or any $R^c$ and $R^d$ attached to the same N atom, together with the N atom to which they are attached, form a 4-10 membered heterocycloalkyl group optionally substituted with 1, 2, 3 or 4 substituents independently selected from $R^{10}$;

each $R^b$ is independently selected from 4-6 membered heterocycloalkyl, wherein the 4-6 membered heterocycloalkyl is optionally substituted with 1, 2, 3, or 4 substituents independently selected from $R^{10}$;

each $R^{a1}$ is independently selected from H and $C_{1-6}$ alkyl;

each $R^{a2}$, $R^{c2}$ and $R^{d2}$ is independently selected from H, $C_{1-6}$ alkyl, and $C_{1-6}$ haloalkyl;

or any $R^{c2}$ and $R^{d2}$ attached to the same N atom, together with the N atom to which they are attached, form a 4-10 membered heterocycloalkyl group optionally substituted with 1, 2, 3 or 4 substituents independently selected from $R^{21}$;

each $R^{a4}$, $R^{c4}$ and $R^{d4}$ is independently selected from H, $C_{1-6}$ alkyl, and $C_{1-6}$ haloalkyl;

or any $R^{c4}$ and $R^{d4}$ attached to the same N atom, together with the N atom to which they are attached, form a 4-10 membered heterocycloalkyl group optionally substituted with 1, 2, 3 or 4 substituents independently selected from $R^{21}$;

each $R^{c9}$ and $R^{d9}$ is independently selected from H, $C_{1-6}$ alkyl, and 5-10 membered heteroaryl; wherein said $C_{1-6}$ alkyl, and 5-10 membered heteroaryl, are each optionally substituted with 1, 2, 3, or 4 substituents independently selected from $R^{51}$;

or any $R^{c9}$ and $R^{d9}$ attached to the same N atom, together with the N atom to which they are attached, form a 4-10 membered heterocycloalkyl group optionally substituted with 1, 2, 3 or 4 substituents independently selected from $R^{51}$;

each $R^{b10}$ is independently selected from $C_{1-6}$ alkyl, and 5-6 membered heteroaryl; wherein said $C_{1-6}$ alkyl, and 5-6 membered heteroaryl, are each optionally substituted with 1, 2, 3, or 4 substituents independently selected from $R^{52}$.

In some embodiments, the compound is a compound of Formula VIIa. In some embodiments, the compound is a compound of Formula VIIb. In some embodiments, the compound is a compound of Formula VIIc. In some embodiments, the compound is a compound of Formula VIId.

The present disclosure further provides a pharmaceutical composition comprising a compound of the disclosure, or a pharmaceutically acceptable salt thereof, and at least one pharmaceutically acceptable carrier or excipient.

The present disclosure further provides methods of inhibiting ALK2 activity, wherein said method comprises administering to a patient a therapeutically effective amount of a compound of the disclosure, or a pharmaceutically acceptable salt thereof.

The present disclosure further provides methods of treating a disease or disorder associated with inhibition of ALK2 interaction, wherein said method comprises administering to a patient in need thereof a therapeutically effective amount of a compound of the disclosure, or a pharmaceutically acceptable salt thereof.

The present disclosure further provides methods of treating a cancer in a patient, wherein said method comprises administering to the patient a therapeutically effective amount of a compound the disclosure, or a pharmaceutically acceptable salt thereof.

The present disclosure further provides methods of treating myeloproliferative diseases in a patient, wherein said method comprises administering to the patient a therapeutically effective amount of a compound of the invention, or a pharmaceutically acceptable salt thereof, and ruxolitinib, or a pharmaceutically acceptable salt thereof.

It is further appreciated that certain features of the present disclosure, which are, for clarity, described in the context of separate embodiments, can also be provided in combination in a single embodiment (while the embodiments are intended to be combined as if written in multiply dependent form). Conversely, various features of the present disclosure, which are, for brevity, described in the context of a single embodiment, can also be provided separately or in any suitable subcombination. Thus, it is contemplated as features described as embodiments of the compounds of Formula (I) can be combined in any suitable combination.

At various places in the present specification, certain features of the compounds are disclosed in groups or in ranges. It is specifically intended that such a disclosure include each and every individual subcombination of the members of such groups and ranges. For example, the term "$C_{1-6}$ alkyl" is specifically intended to individually disclose (without limitation) methyl, ethyl, $C_3$ alkyl, $C_4$ alkyl, $C_5$ alkyl and $C_6$ alkyl.

The term "n-membered," where n is an integer, typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring and 1,2,3,4-tetrahydro-naphthalene is an example of a 10-membered cycloalkyl group.

At various places in the present specification, variables defining divalent linking groups may be described. It is specifically intended that each linking substituent include both the forward and backward forms of the linking substituent. For example, —NR(CR'R")$_n$— includes both —NR(CR'R")$_n$— and —(CR'R")$_n$NR— and is intended to disclose each of the forms individually. Where the structure requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "substituted" means that an atom or group of atoms formally replaces hydrogen as a "substituent" attached to another group. The term "substituted", unless otherwise indicated, refers to any level of substitution, e.g., mono-, di-, tri-, tetra- or penta-substitution, where such substitution is permitted. The substituents are independently selected, and substitution may be at any chemically accessible position. It is to be understood that substitution at a given atom is limited by valency. It is to be understood that substitution at a given atom results in a chemically stable molecule. The phrase "optionally substituted" means unsubstituted or substituted. The term "substituted" means that a hydrogen atom is removed and replaced by a substituent. A single divalent substituent, e.g., oxo, can replace two hydrogen atoms.

The term "$C_{n-m}$" indicates a range which includes the endpoints, wherein n and m are integers and indicate the number of carbons. Examples include $C_{1-4}$, $C_{1-6}$ and the like.

The term "alkyl" employed alone or in combination with other terms, refers to a saturated hydrocarbon group that may be straight-chained or branched. The term "$C_{n-m}$ alkyl", refers to an alkyl group having n to m carbon atoms. An alkyl group formally corresponds to an alkane with one C—H bond replaced by the point of attachment of the alkyl group to the remainder of the compound. In some embodiments, the alkyl group contains from 1 to 6 carbon atoms, from 1 to 4 carbon atoms, from 1 to 3 carbon atoms, or 1 to 2 carbon atoms.

Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl and the like.

The term "alkenyl" employed alone or in combination with other terms, refers to a straight-chain or branched hydrocarbon group corresponding to an alkyl group having one or more double carbon-carbon bonds. An alkenyl group formally corresponds to an alkene with one C—H bond replaced by the point of attachment of the alkenyl group to the remainder of the compound. The term "$C_{n-m}$ alkenyl" refers to an alkenyl group having n to m carbons. In some embodiments, the alkenyl moiety contains 2 to 6, 2 to 4, or 2 to 3 carbon atoms. Example alkenyl groups include, but are not limited to, ethenyl, n-propenyl, isopropenyl, n-butenyl, sec-butenyl and the like.

The term "alkynyl" employed alone or in combination with other terms, refers to a straight-chain or branched hydrocarbon group corresponding to an alkyl group having one or more triple carbon-carbon bonds. An alkynyl group formally corresponds to an alkyne with one C—H bond replaced by the point of attachment of the alkyl group to the remainder of the compound. The term "$C_{n-m}$ alkynyl" refers to an alkynyl group having n to m carbons. Example alkynyl groups include, but are not limited to, ethynyl, propyn-1-yl, propyn-2-yl and the like. In some embodiments, the alkynyl moiety contains 2 to 6, 2 to 4, or 2 to 3 carbon atoms.

The term "alkylene", employed alone or in combination with other terms, refers to a divalent alkyl linking group. An alkylene group formally corresponds to an alkane with two C—H bond replaced by points of attachment of the alkylene group to the remainder of the compound. The term "$C_{n-m}$ alkylene" refers to an alkylene group having n to m carbon atoms. Examples of alkylene groups include, but are not limited to, ethan-1,2-diyl, ethan-1,1-diyl, propan-1,3-diyl, propan-1,2-diyl, propan-1,1-diyl, butan-1,4-diyl, butan-1,3-diyl, butan-1,2-diyl, 2-methyl-propan-1,3-diyl and the like.

The term "alkoxy", employed alone or in combination with other terms, refers to a group of formula —O-alkyl, wherein the alkyl group is as defined above. The term "$C_{n-m}$ alkoxy" refers to an alkoxy group, the alkyl group of which has n to m carbons. Example alkoxy groups include methoxy, ethoxy, propoxy (e.g., n-propoxy and isopropoxy), t-butoxy and the like. In some embodiments, the alkyl group has 1 to 6, 1 to 4, or 1 to 3 carbon atoms.

The term "alkoxylene", employed alone or in combination with other terms, refers to a divalent alkoxy linking group. An alkoxylene group formally corresponds to a group of formula —O-alkyl, wherein a C—H bond is replaced by a point of attachment of the alkoxylene group to the remainder of the compound. The term "$C_{n-m}$ alkoxylene" refers to an alkoxylene group having n to m carbon atoms.

The term "amino" refers to a group of formula —NH$_2$.

The term "carbonyl", employed alone or in combination with other terms, refers to a —C(=O)— group, which also may be written as C(O).

As used herein, the terms "carbamoyl" and "carbamyl" interchangeably refer to a group of formula —C(O)NH$_2$.

As used herein, the term "carboxy" refers to a group of formula —C(O)OH.

The term "cyano" or "nitrile" refers to a group of formula —C≡N, which also may be written as —CN.

As used herein, the term "$C_{1-3}$ alkoxy-$C_{1-3}$ alkyl" refers to a group of formula —($C_{1-3}$ alkylene)-($C_{1-3}$ alkoxy).

As used herein, the term "$C_{1-3}$ alkoxy-$C_{1-3}$ alkoxy" refers to a group of formula —($C_{1-3}$ alkoxylene)-($C_{1-3}$ alkoxy).

As used herein, the term "HO—$C_{1-3}$ alkoxy" refers to a group of formula —($C_{1-3}$ alkoxylene)-OH.

As used herein, the term "HO—$C_{1-3}$ alkyl" refers to a group of formula —($C_{1-3}$ alkylene)-OH.

As used herein, the term "cyano-$C_{1-3}$ alkyl" refers to a group of formula —($C_{1-3}$ alkylene)-CN.

As used herein, the term "H$_2$N—$C_{1-3}$ alkyl" refers to a group of formula —($C_{1-3}$ alkylene)-NH$_2$. The terms "halo" or "halogen", used alone or in combination with other terms, refers to fluoro, chloro, bromo and iodo. In some embodiments, "halo" refers to a halogen atom selected from F, Cl, or Br. In some embodiments, halo groups are F.

The term "haloalkyl" as used herein refers to an alkyl group in which one or more of the hydrogen atoms has been replaced by a halogen atom. The term "$C_{n-m}$ haloalkyl" refers to a $C_{n-m}$ alkyl group having n to m carbon atoms and from at least one up to {2(n to m)+1}halogen atoms, which may either be the same or different. In some embodiments, the halogen atoms are fluoro atoms. In some embodiments, the haloalkyl group has 1 to 6 or 1 to 4 carbon atoms. Example haloalkyl groups include CF$_3$, C$_2$F$_5$, CHF$_2$, CH$_2$F, CCl$_3$, CHCl$_2$, C$_2$Cl$_5$ and the like. In some embodiments, the haloalkyl group is a fluoroalkyl group.

The term "haloalkoxy", employed alone or in combination with other terms, refers to a group of formula —O-haloalkyl, wherein the haloalkyl group is as defined above. The term "$C_{n-m}$ haloalkoxy" refers to a haloalkoxy group, the haloalkyl group of which has n to m carbons. Example haloalkoxy groups include trifluoromethoxy and the like. In some embodiments, the haloalkoxy group has 1 to 6, 1 to 4, or 1 to 3 carbon atoms.

The term "oxo" refers to an oxygen atom as a divalent substituent, forming a carbonyl group when attached to carbon, or attached to a heteroatom forming a sulfoxide or sulfone group, or an N-oxide group. In some embodiments, heterocyclic groups may be optionally substituted by 1 or 2 oxo (=O) substituents.

The term "sulfido" refers to a sulfur atom as a divalent substituent, forming a thiocarbonyl group (C=S) when attached to carbon.

As used herein, the term "$C_{n-m}$ alkylamino" refers to a group of formula —NH(alkyl), wherein the alkyl group has n to m carbon atoms. In some embodiments, the alkyl group has 1 to 6, 1 to 4, or 1 to 3 carbon atoms.

As used herein, the term "$C_{n-m}$ alkoxycarbonyl" refers to a group of formula —C(O)O— alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylcarbonyl" refers to a group of formula —C(O)— alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylcarbonylamino" refers to a group of formula —NHC(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonylamino" refers to a group of formula —NHS(O)$_2$-alkyl, wherein the alkyl group has n to m carbon atoms. In some embodiments, the alkyl group has 1 to 6, 1 to 4, or 1 to 3 carbon atoms.

As used herein, the term "aminosulfonyl" refers to a group of formula —S(O)$_2$NH$_2$.

As used herein, the term "$C_{n-m}$ alkylaminosulfonyl" refers to a group of formula —S(O)$_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonyl" refers to a group of formula —S(O)$_2$N(alkyl)$_2$, wherein each alkyl group independently has n to m carbon atoms.

In some embodiments, each alkyl group has, independently, 1 to 6, 1 to 4, or 1 to 3 carbon atoms.

As used herein, the term "aminosulfonylamino" refers to a group of formula —NHS(O)$_2$NH$_2$.

As used herein, the term "$C_{n-m}$ alkylaminosulfonylamino" refers to a group of formula —NHS(O)$_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonylamino" refers to a group of formula —NHS(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminocarbonylamino", employed alone or in combination with other terms, refers to a group of formula —NHC(O)NH$_2$.

As used herein, the term "$C_{n-m}$ alkylaminocarbonylamino" refers to a group of formula —NHC(O)NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminocarbonylamino" refers to a group of formula —NHC(O)N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "$C_{n-m}$ alkylcarbamyl" refers to a group of formula —C(O)—NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$-alkyl)carbamyl" refers to a group of formula —C(O)N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, the term "thio" refers to a group of formula —SH.

As used herein, the term "$C_{n-m}$ alkylthio" refers to a group of formula —S-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfinyl" refers to a group of formula —S(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonyl" refers to a group of formula —S(O)$_2$-alkyl, wherein the alkyl group has n to m carbon atoms. In some embodiments, the alkyl group has 1 to 6, 1 to 4, or 1 to 3 carbon atoms.

The term "aromatic" refers to a carbocycle or heterocycle having one or more polyunsaturated rings having aromatic character (i.e., having (4n+2) delocalized π (pi) electrons where n is an integer).

The term "aryl," employed alone or in combination with other terms, refers to an aromatic hydrocarbon group, which may be monocyclic or polycyclic (e.g., having 2 fused rings). The term "$C_{n-m}$ aryl" refers to an aryl group having from n to m ring carbon atoms. Aryl groups include, e.g., phenyl, naphthyl, and the like. In some embodiments, aryl groups have from 6 to about 10 carbon atoms. In some embodiments aryl groups have 6 carbon atoms. In some embodiments aryl groups have 10 carbon atoms. In some embodiments, the aryl group is phenyl. In some embodiments, the aryl group is naphthyl.

The term "heteroaryl" or "heteroaromatic," employed alone or in combination with other terms, refers to a monocyclic or polycyclic aromatic heterocycle having at least one heteroatom ring member selected from sulfur, oxygen, nitrogen and phosphorous. In some embodiments, the heteroaryl ring has 1, 2, 3 or 4 heteroatom ring members independently selected from nitrogen, sulfur and oxygen. In some embodiments, any ring-forming N in a heteroaryl moiety can be an N-oxide. In some embodiments, the heteroaryl has 5-10 ring atoms including carbon atoms and 1, 2, 3 or 4 heteroatom ring members independently selected from nitrogen, sulfur and oxygen. In some embodiments, the heteroaryl has 5-6 ring atoms and 1 or 2 heteroatom ring members independently selected from nitrogen, sulfur and oxygen. In some embodiments, the heteroaryl is a five-membered or six-membered heteroaryl ring. In other embodiments, the heteroaryl is an eight-membered, nine-membered or ten-membered fused bicyclic heteroaryl ring. Example heteroaryl groups include, but are not limited to, pyridinyl (pyridyl), pyrimidinyl, pyrazinyl, pyridazinyl, pyrrolyl, pyrazolyl, azolyl, oxazolyl, isoxazolyl, thiazolyl, imidazolyl, furanyl, thiophenyl, quinolinyl, isoquinolinyl, naphthyridinyl (including 1,2-, 1,3-, 1,4-, 1,5-, 1,6-, 1,7-, 1,8-, 2,3- and 2,6-naphthyridine), indolyl, isoindolyl, benzothiophenyl, benzofuranyl, benzisoxazolyl, imidazo[1,2-b]thiazolyl, purinyl, pyrazolopyrimidinyl (including pyrazolo[1,5-a]pyrimidine and pyrazolo[4,3-d]pyrimidinyl), imidazopyrindinyl (i.e. imidazo[1,2-a]pyridinyl) and the like. In some embodiments, the heteroaryl group is pyridone (e.g., 2-pyridone). Exemplary five-membered ring heteroaryls include thienyl, furyl, pyrrolyl, imidazolyl, thiazolyl, oxazolyl, pyrazolyl, isothiazolyl, isoxazolyl, 1,2,3-triazolyl, tetrazolyl, 1,2, 3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl and 1,3,4-oxadiazolyl. Exemplary six-membered ring heteroaryls are pyridyl, pyrazinyl, pyrimidinyl, triazinyl, isoindolyl, and pyridazinyl.

The term "cycloalkyl," employed alone or in combination with other terms, refers to a non-aromatic hydrocarbon ring system (monocyclic, bicyclic or polycyclic), including cyclized alkyl and alkenyl groups. The term "$C_{n-m}$ cycloalkyl" refers to a cycloalkyl that has n to m ring member carbon atoms. Cycloalkyl groups can include mono- or polycyclic (e.g., having 2, 3 or 4 fused rings) groups and spirocycles. Cycloalkyl groups can have 3, 4, 5, 6 or 7 ring-forming carbons ($C_{3-7}$). Cycloalkyl groups can have 3, 4, 5, 6, 7, 8, 9 or 10 ring-forming carbons ($C_{3-10}$). In some embodiments, the cycloalkyl group has 3 to 6 ring members, 3 to 5 ring members, or 3 to 4 ring members. In some embodiments, the cycloalkyl group is monocyclic. In some embodiments, the cycloalkyl group is monocyclic or bicyclic. In some embodiments, the cycloalkyl group is a $C_{3-6}$ monocyclic cycloalkyl group. Ring-forming carbon atoms of a cycloalkyl group can be optionally oxidized to form an oxo or sulfido group. Cycloalkyl groups also include cycloalkylidenes. In some embodiments, cycloalkyl is cyclopropyl, cyclobutyl, cyclopentyl or cyclohexyl. Also included in the definition of cycloalkyl are moieties that have one or more aromatic rings fused (i.e., having a bond in common with) to the cycloalkyl ring, e.g., benzo or thienyl derivatives of cyclopentane, cyclohexane and the like. A cycloalkyl group containing a fused aromatic ring can be attached through any ring-forming atom including a ring-forming atom of the fused aromatic ring. Examples of cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, bicyclo[1.1.1]pentanyl, bicyclo[2.1.1]hexanyl, and the like. In some embodiments, the cycloalkyl group is cyclopropyl, cyclobutyl, cyclopentyl, or cyclohexyl.

The term "heterocycloalkyl," employed alone or in combination with other terms, refers to a non-aromatic ring or ring system, which may optionally contain one or more alkenylene groups as part of the ring structure, which has at least one heteroatom ring member independently selected from nitrogen, sulfur, oxygen and phosphorus, and which has 4-10 ring members, 4-7 ring members, or 4-6 ring members. Included within the term "heterocycloalkyl" are monocyclic 4-, 5-, 6- and 7-membered heterocycloalkyl groups. Heterocycloalkyl groups can include mono- or bicyclic (e.g., having two fused or bridged rings) or spirocyclic ring systems. In some embodiments, the heterocycloalkyl group is a monocyclic group having 1, 2 or 3 heteroatoms independently selected from nitrogen, sulfur and oxygen. Ring-forming carbon atoms and heteroatoms of a heterocycloalkyl group can be optionally oxidized to form an oxo or sulfido group or other oxidized linkage (e.g., C(O), S(O), C(S) or S(O)$_2$, N-oxide etc.) or a nitrogen atom can be quaternized. The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the heterocycloalkyl ring, e.g., benzo or thienyl derivatives of piperidine, morpholine, azepine, etc. A heterocycloalkyl group containing a fused aromatic ring can be attached through any ring-forming atom including a ring-forming atom of the fused aromatic ring. Examples of heterocycloalkyl groups include azetidinyl, azepanyl, dihydrobenzofuranyl, dihydrofuranyl, dihydropyranyl, morpholino, 3-oxa-9-azaspiro[5.5]undecanyl, 1-oxa-8-azaspiro[4.5]decanyl, 2,5$\lambda^2$-diazabicyclo[2.2.1]heptan-2-yl, 6-oxohexahydropyrrolo[1,2-a]pyrazin-2(1H)-yl, 6-oxa-2-azaspiro[3.4]octan-2-yl, piperidinyl, piperazinyl, oxopiperazinyl, pyranyl, pyrrolidinyl, quinuclidinyl, tetrahydrofuranyl, tetrahydropyranyl, 1,2,3,4-tetrahydroquinolinyl, 1,2,3,4-tetrahydroisoquinolinyl, 1,2,3,4-tetrahydronaphthyl, 2,3-dihydro-1H-inden-5-yl, isoindolinyl, tropanyl, and thiomorpholino.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas an azetidin-3-yl ring is attached at the 3-position.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. One method includes fractional recrystallization using a chiral resolving acid which is an optically active, salt-forming organic acid. Suitable resolving agents for fractional recrystallization methods are, e.g., optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane and the like.

Resolution of racemic mixtures can also be carried out by elution on a column packed with an optically active resolving agent (e.g., dinitrobenzoylphenylglycine). Suitable elution solvent composition can be determined by one skilled in the art.

In some embodiments, the compounds of the present disclosure have the (R)-configuration. In other embodiments, the compounds have the (S)-configuration. In compounds with more than one chiral centers, each of the chiral centers in the compound may be independently (R) or (S), unless otherwise indicated. Compounds with two chiral centers can, for example, have (R,R), (R,S), (S,R) or (S,S) configurations.

Compounds of the present disclosure also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge.

Example prototropic tautomers include ketone-enol pairs, amide-imidic acid pairs, lactam-lactim pairs, enamine-imine pairs, and annular forms where a proton can occupy two or more positions of a heterocyclic system, e.g., 1H- and 3H-imidazole, 1H-, 2H- and 4H-1,2,4-triazole, 1H- and 2H-isoindole and 1H- and 2H-pyrazole. Tautomeric forms can be in equilibrium or sterically locked into one form by appropriate substitution.

Compounds of the present disclosure can also include all isotopes of atoms occurring in the intermediates or final compounds. Isotopes include those atoms having the same atomic number but different mass numbers. For example, isotopes of hydrogen include tritium and deuterium. One or more constituent atoms of the compounds of the present disclosure can be replaced or substituted with isotopes of the atoms in natural or non-natural abundance. In some embodiments, the compound includes at least one deuterium atom. For example, one or more hydrogen atoms in a compound of the present disclosure can be replaced or substituted by deuterium. In some embodiments, the compound includes two or more deuterium atoms. In some embodiments, the compound includes 1, 2, 3, 4, 5, 6, 7, 8, 9, 10, 11 or 12 deuterium atoms. Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765). Isotopically labeled compounds can used in various studies such as NMR spectroscopy, metabolism experiments, and/or assays.

Substitution with heavier isotopes such as deuterium, may afford certain therapeutic advantages resulting from greater metabolic stability, for example, increased in vivo half-life or reduced dosage requirements, and hence may be preferred in some circumstances. (A. Kerekes et. al. *J. Med. Chem.* 2011, 54, 201-210; R. Xu et. al. *J. Label Compd. Radiopharm.* 2015, 58, 308-312).

The term, "compound," as used herein is meant to include all stereoisomers, geometric isomers, tautomers and isotopes of the structures depicted. The term is also meant to refer to compounds of the present disclosure, regardless of how they are prepared, e.g., synthetically, through biological process (e.g., metabolism or enzyme conversion), or a combination thereof.

All compounds, and pharmaceutically acceptable salts thereof, can be found together with other substances such as water and solvents (e.g., hydrates and solvates) or can be isolated. When in the solid state, the compounds described herein and salts thereof may occur in various forms and may, e.g., take the form of solvates, including hydrates. The compounds may be in any solid state form, such as a polymorph or solvate, so unless clearly indicated otherwise, reference in the specification to compounds and salts thereof should be understood as encompassing any solid state form of the compound.

In some embodiments, the compounds of the present disclosure, or salts thereof, are substantially isolated. By "substantially isolated" is meant that the compound is at least partially or substantially separated from the environment in which it was formed or detected.

Partial separation can include, e.g., a composition enriched in the compounds of the present disclosure. Substantial separation can include compositions containing at least about 50%, at least about 60%, at least about 70%, at least about 80%, at least about 90%, at least about 95%, at least about 97%, or at least about 99% by weight of the compounds of the present disclosure, or salt thereof.

The phrase "pharmaceutically acceptable" is employed herein to refer to those compounds, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g., a reaction temperature, that is about the temperature of the room in which the reaction is carried out, e.g., a temperature from about 20° C. to about 30° C.

The present invention also includes pharmaceutically acceptable salts of the compounds described herein. The term "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, e.g., from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol or butanol) or acetonitrile (MeCN) are preferred. Lists of suitable salts are found in *Remington's Pharmaceutical Sciences, 17th* Ed., (Mack Publishing Company, Easton, 1985), p. 1418, Berge et al., *J. Pharm. Sci.,* 1977, 66(1), 1-19 and in Stahl et al., *Handbook of Pharmaceutical Salts: Properties, Selection, and Use,* (Wiley, 2002). In some embodiments, the compounds described herein include the N-oxide forms.

Synthesis

Compounds of the present disclosure, including salts thereof, can be prepared using known organic synthesis techniques and can be synthesized according to any of numerous possible synthetic routes, such as those in the Schemes below.

The reactions for preparing compounds provided herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds provided herein can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, 3rd. Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), or mass spectrometry, or by chromatography such as high performance liquid chromatography (HPLC) or thin layer chromatography (TLC).

The expressions, "ambient temperature", "room temperature", and "r.t.", as used herein, are understood in the art, and refer generally to a temperature, e.g. a reaction temperature, that is about the temperature of the room in which the reaction is carried out, for example, a temperature from about 20° C. to about 30° C.

Compounds as disclosed herein can be prepared by one skilled in the art according to preparatory routes known in the literature and according to various possible synthetic routes. Example synthetic methods for preparing compounds of the present application are provided in the Schemes below.

A series of imidazo[1,2-b]pyridazine derivatives 7 can be prepared according to the procedure outlined in Scheme 1. Aminopyridazine 3 can be obtained by palladium catalytic amination (*Tetrahedron Lett.* 1997, 38, 6367-6370) of the dichloropyridazine 1 with diphenylmethanimine followed by hydrolysis under acidic conditions. Cycloaddition of the aminopyridazine 3 with 2-chloroacetaldehyde gives the imidazo[1,2-b]pyridazine 4 which can be converted to the corresponding imidazo[1,2-b]pyridazine iodide 5 by treatment with NIS. Suzuki coupling (*J. Am. Chem. Soc.* 2010, 132, 14073-14075) with the boronic acid or ester R$^5$B(OR')$_2$ affords compound 6 which can be converted to the desired imidazo[1,2-b]pyridazine derivatives 7 by further Suzuki coupling with a suitable boronic acid or ester R$^2$B(OR')$_2$. Alternatively, Suzuki coupling of imidazo[1,2-b]pyridazine 4 with the boronic acid or ester R$^2$B(OR')$_2$ affords compound 8 which can be converted to compound 9 by treatment with NIS. The imidazo[1,2-b]pyridazine iodide 9 can be subsequently converted to the desired imidazo[1,2-b]pyridazine derivatives 7 by Suzuki coupling with a suitable boronic acid or ester R$^5$B(OR')$_2$.

Scheme 1

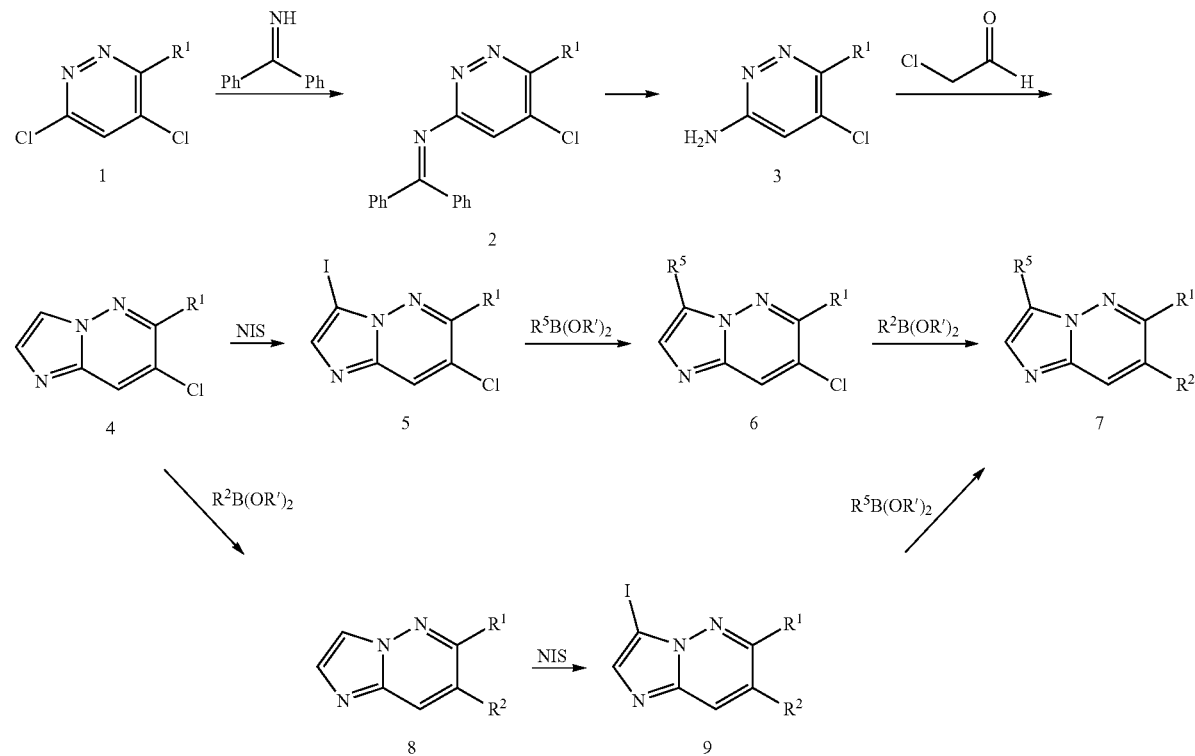

A series of imidazo[1,2-b]pyridazine-6-carboxamide derivatives 12 can be prepared according to the procedure outlined in Scheme 2. Methyl imidazo[1,2-b]pyridazine-6-carboxylate 10 prepared according to the procedure outlined in Scheme 1 can be converted to the corresponding acid 11 by hydrolysis. The acid 11 can be subsequently converted to the desired imidazo[1,2-b]pyridazine-6-carboxamide derivatives 12 by coupling with an appropriate amine using an amidation coupling reagent such as, but not limited to, (benzotriazol-1-yloxy)tris(dimethylamino)phosphonium hexafluorophosphate (BOP), (benzotriazol-1-yloxy)tripyrrolidinophosphonium hexafluorophosphate (PyBOP), 1-[bis (dimethylamino)methylene]-1H-1,2,3-triazolo[4,5-b]pyridinium 3-oxid hexafluorophosphate (HATU), or N,N,N',N'-Tetramethyl-O-(1H-benzotriazol-1-yl)uronium hexafluorophosphate (HBTU).

Scheme 2

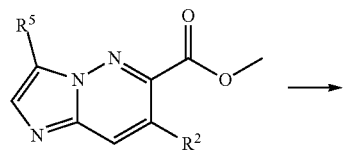

10

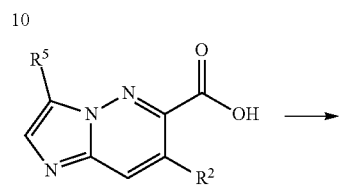

11

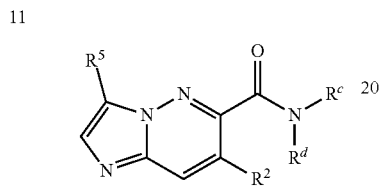

12

A series of imidazo[1,2-b]pyridazine-6-carbonitrile derivatives 18 can be prepared according to the procedure outlined in Scheme 3. Methyl imidazo[1,2-b]pyridazine-6-carboxylate 13, prepared according to the procedure outlined in Scheme 1, can be converted to the corresponding acid 14 by hydrolysis. The acid 14 can be subsequently converted to imidazo[1,2-b]pyridazine-6-carboxamide 15 by coupling with ammonium chloride using an amidation coupling reagent such as HATU. Treating compound 15 with oxalyl chloride in the presence of triethylamine and triphenylphosphine oxide can afford compound 16 which then can be converted to the corresponding iodide 17 by treatment with NIS. Suzuki coupling with a suitable boronic acid or ester R⁵B(OR')₂ affords the desired imidazo[1,2-b]pyridazine-6-carbonitrile derivatives 18.

Scheme 3

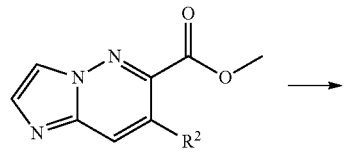

13

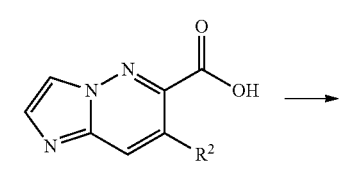

14

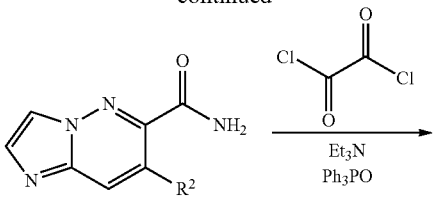

15

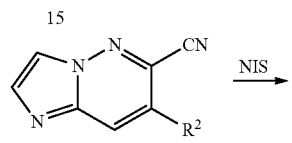

16

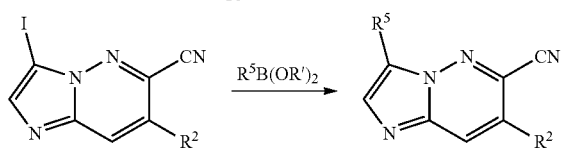

17                18

A series of imidazo[1,2-b]pyridazine derivatives 23 can be prepared according to the procedure outlined in Scheme 4. Methyl 7-chloroimidazo[1,2-b]pyridazine-6-carboxylate 19 prepared according to the procedure outlined in Scheme 1 can be converted to the corresponding alcohol 20 by reduction. The alcohol 20 can be subsequently converted to compound 21 via Suzuki coupling with the boronic acid or ester R²B(OR')₂. Treating compound 21 with NIS affords the corresponding iodide 22 which can be converted to the desired imidazo[1,2-b]pyridazine derivatives 23 through Suzuki coupling with a suitable boronic acid or ester R⁵B(OR')₂.

Scheme 4

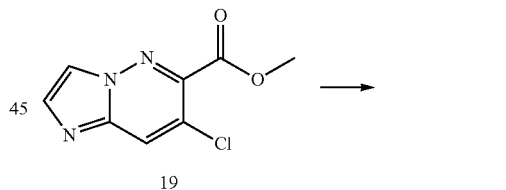

19

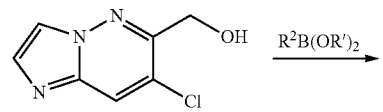

20

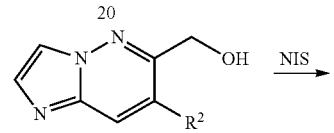

21

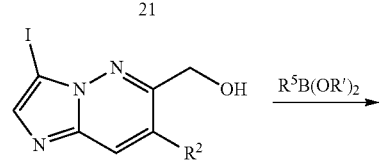

22

-continued

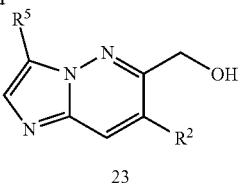
23

A series of imidazo[1,2-a]pyridine derivatives 28 can be prepared according to the procedure outlined in Scheme 5. Cycloaddition of the aminopyridine 24 with 2-chloroacetaldehyde gives compound 25 which can be converted to compound 26 via Suzuki coupling with the boronic acid or ester $R^2B(OR')_2$. Treating compound 26 with NIS affords the corresponding iodide 27 which can be converted to the desired imidazo[1,2-a]pyridine derivatives 28 through Suzuki coupling with a suitable boronic acid or ester $R^5B(OR')_2$.

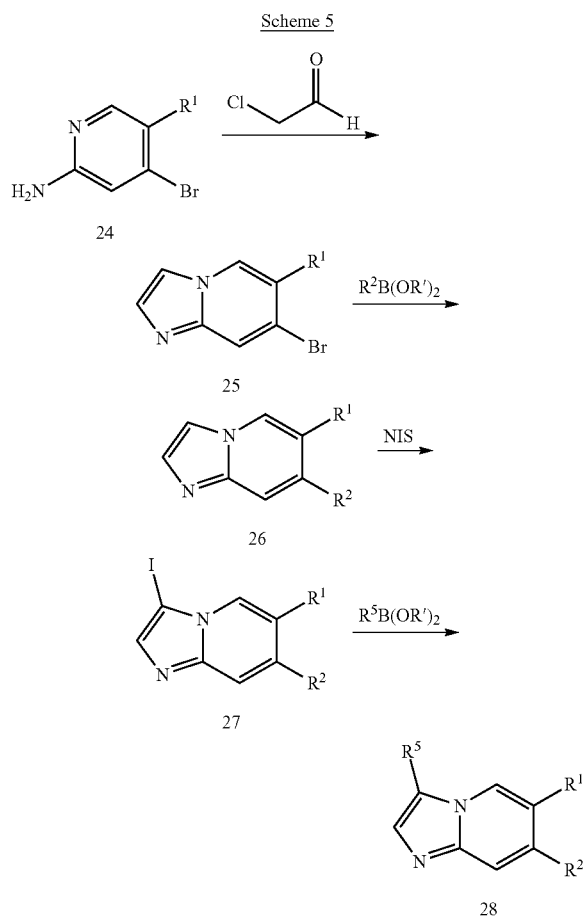

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples were described as below.

Preparatory LC-MS purifications of some of the compounds prepared were performed on Waters mass directed fractionation systems. The basic equipment setup, protocols, and control software for the operation of these systems have been described in detail in the literature. See e.g. "Two-Pump At Column Dilution Configuration for Preparative LC-MS", K. Blom, J. Combi. Chem., 4, 295 (2002); "Optimizing Preparative LC-MS Configurations and Methods for Parallel Synthesis Purification", K. Blom, R. Sparks, J. Doughty, G. Everlof, T. Haque, A. Combs, J. Combi. Chem., 5, 670 (2003); and "Preparative LC-MS Purification: Improved Compound Specific Method Optimization", K. Blom, B. Glass, R. Sparks, A. Combs, J. Combi. Chem., 6, 874-883 (2004). The compounds separated were typically subjected to analytical liquid chromatography mass spectrometry (LCMS) for purity check under the following conditions: Instrument; Agilent 1100 series, LC/MSD, Column: Waters Sunfire™ $C_{18}$ 5 µm particle size, 2.1×5.0 mm, Buffers: mobile phase A: 0.025% TFA in water and mobile phase B: acetonitrile; gradient 2% to 80% of B in 3 minutes with flow rate 2.0 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ $C_{18}$ 5 µm particle size, 30×100 mm column, eluting with mobile phase A: 0.1% TFA (trifluoroacetic acid) in water and mobile phase B: acetonitrile; the flow rate was 60 mL/minute, the separating gradient was optimized for each compound using the Compound Specific Method Optimization protocol as described in the literature [see "Preparative LCMS Purification: Improved Compound Specific Method Optimization", K. Blom, B. Glass, R. Sparks, A. Combs, J. Comb. Chem., 6, 874-883 (2004)].

pH=10 purifications: Waters XBridge $C_{18}$ 5 µm particle size, 30×100 mm column, eluting with mobile phase A: 0.15% $NH_4OH$ in water and mobile phase B: acetonitrile; the flow rate was 60 mL/minute, the separating gradient was optimized for each compound using the Compound Specific Method Optimization protocol as described in the literature [See "Preparative LCMS Purification: Improved Compound Specific Method Optimization", K. Blom, B. Glass, R. Sparks, A. Combs, J. Comb. Chem., 6, 874-883 (2004)].

Methods of Use

The present disclosure provides methods of modulating (e.g., inhibiting) ALK2 activity, said method comprising administering to a patient a compound provided herein, or a pharmaceutically acceptable salt thereof. The compounds of the present disclosure can be used alone, in combination with other agents or therapies or as an adjuvant or neoadjuvant for the treatment of diseases or disorders, including cancers. For the uses described herein, any of the compounds of the disclosure, including any of the embodiments thereof, may be used.

In myelofibrosis (MF), a significant proportion of patients develop anemia and become dependent on frequent red blood cell (RBC) transfusions (Tefferi, A. et al. Mayo Clinic Proceedings 2012 87, 25-33). Elevated serum hepcidin levels in patients with MF have been shown to be associated with hemoglobin (Hb) levels, increased requirement for RBC transfusions and reduced survival (Pardanani, A. et al. American Journal of Hematology 2013, 88, 312-316). BMP signaling plays a central role in driving hepcidin transcriptional induction by activating SMAD signaling. In anemia mouse model, the liver-specific deletion of either ALK2 or ALK3 can block the induction of hepcidin production and iron overload (Steinbicker, A. U., et al. Blood 2011, 118, 4224-4230). Therefore, ALK2 inhibition could be useful in combination with ruxolitinib in the treatment of MF patients as the hepcidin-mediated FPN1 internalization and degradation may not require the action of JAK2 (Ross, S. L., et al. Cell Metabolism 2012, 15, 905-917). The ALK2 inhibition may block the negative effect of hepcidin on iron metabolism and improve the anemia in MF patients (Asshoff, M. et al. Blood 2017, 129, 1823-1830).

Fibrodysplasia ossificans progressiva (FOP) is a human rare genetic bone disease and the patients were characterized by extraskeletal bone formation through endochondral ossification (Yu, P. B., et al. Nature Medicine 2008, 14, 1363-1369; Fukuda, T. et al. Journal of Biological Chemistry 2009 284, 7149-7156). 95% of FOP patients harbor point mutations in ACVR1/ALK2 and The responsive mutation for classic FOP is 617G>A (R206H) in the intracellular glycine and serine-rich (GS) domain of ALK2 (Shen, Q. et al. Journal of Clinical Investigation 2009, 119, 3462-3472). ALK2 mutations in atypical FOP patients have also been found in other amino acids of the GS domain or protein kinase domain (Fukuda, T. et al. Biochemical and Biophysical Research Communications 2008, 377, 905-909). The different ALK2 mutants have been shown to activate BMP signaling without exogenous BMP ligands constitutively and these ALK2 mutants can transmit much stronger BMP signaling upon ligand stimulation (Van Dinther, M. et al. Journal of Bone and Mineral Research 2010, 25, 1208-1215).

Activating mutations in ALK2 have also been identified in diffuse intrapontine gliomas (DIPG), which are highly aggressive glial neoplasms of the ventral pons in the pediatric population. ALK2 was reported as one of the most recurrently mutated gene in DIPG. ALK2 was found to carry nonsynonymous heterozygous somatic mutations in 46 of 195 (24%) cases at five specific residues. Patients with ALK2 mutations were predominantly female (approximately 2:1) and had a younger age of onset (approximately 5 years) and longer overall survival time (approximately 15 months) compared with wild-type IDPG. These ALK2 mutants are highly specific to DIPG and the ALK2 inhibitor LDN-19318917 results in significant inhibition of those ALK2 mutant DIPG cell viability (Taylor, K. R. et al. Nature Genetics 2014, 46, 457-461; Buczkowicz, P. et al. Nature Genetics 2014, 46, 451-456).

A method of treating a disease or disorder associated with inhibition of ALK2 activity can include administering to a patient in need thereof a therapeutically effective amount of a compound provided herein, or a pharmaceutically acceptable salt thereof. In some embodiments, the disease or disorder is cancer. Examples of cancers that are treatable using the compounds of the present disclosure include, but are not limited to, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, endometrial cancer, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or urethra, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers.

In some embodiments, cancers treatable with compounds of the present disclosure include melanoma (e.g., metastatic malignant melanoma), renal cancer (e.g. clear cell carcinoma), prostate cancer (e.g. hormone refractory prostate adenocarcinoma), breast cancer, triple-negative breast cancer, colon cancer and lung cancer (e.g. non-small cell lung cancer and small cell lung cancer). Additionally, the disclosure includes refractory or recurrent malignancies whose growth may be inhibited using the compounds of the disclosure.

In some embodiments, cancers that are treatable using the compounds of the present disclosure include, but are not limited to, solid tumors (e.g., prostate cancer, colon cancer, esophageal cancer, endometrial cancer, ovarian cancer, uterine cancer, renal cancer, hepatic cancer, pancreatic cancer, gastric cancer, breast cancer, lung cancer, cancers of the head and neck, thyroid cancer, glioblastoma, sarcoma, bladder cancer, etc.), hematological cancers (e.g., lymphoma, leukemia such as acute lymphoblastic leukemia (ALL), acute myelogenous leukemia (AML), chronic lymphocytic leukemia (CLL), chronic myelogenous leukemia (CML), DLBCL, mantle cell lymphoma, Non-Hodgkin lymphoma (including relapsed or refractory NHL and recurrent follicular), Hodgkin lymphoma or multiple myeloma) and combinations of said cancers.

In some embodiments, diseases and indications that are treatable using the compounds of the present disclosure include, but are not limited to hematological cancers, sarcomas, lung cancers, gastrointestinal cancers, genitourinary tract cancers, liver cancers, bone cancers, nervous system cancers, gynecological cancers, and skin cancers.

Exemplary hematological cancers include lymphomas and leukemias such as acute lymphoblastic leukemia (ALL), acute myelogenous leukemia (AML), acute promyelocytic leukemia (APL), chronic lymphocytic leukemia (CLL), chronic myelogenous leukemia (CML), diffuse large B-cell lymphoma (DLBCL), mantle cell lymphoma, Non-Hodgkin lymphoma (including relapsed or refractory NHL and recurrent follicular), Hodgkin lymphoma, myeloproliferative diseases (e.g., primary myelofibrosis (PMF), polycythemia vera (PV), essential thrombocytosis (ET)), myelodysplasia syndrome (MDS), T-cell acute lymphoblastic lymphoma (T-ALL), multiple myeloma, cutaneous T-cell lymphoma, Waldenstrom's Macroglubulinemia, hairy cell lymphoma, chronic myelogenic lymphoma and Burkitt's lymphoma.

Exemplary sarcomas include chondrosarcoma, Ewing's sarcoma, osteosarcoma, rhabdomyosarcoma, angiosarcoma, fibrosarcoma, liposarcoma, myxoma, rhabdomyoma, rhabdosarcoma, fibroma, lipoma, harmatoma, and teratoma. Exemplary sarcomas also include lymphosarcoma and leiomyosarcoma.

Exemplary lung cancers include non-small cell lung cancer (NSCLC), small cell lung cancer, bronchogenic carcinoma (squamous cell, undifferentiated small cell, undifferentiated large cell, adenocarcinoma), alveolar (bronchiolar) carcinoma, bronchial adenoma, chondromatous hamartoma, and mesothelioma. Exemplary lung cancers also include pavicellular and non-pavicellular carcinoma, bronchial adenoma and pleuropulmonary blastoma.

Exemplary gastrointestinal cancers include cancers of the esophagus (squamous cell carcinoma, adenocarcinoma, leiomyosarcoma, lymphoma), stomach (carcinoma, lymphoma, leiomyosarcoma), pancreas (exocrine pancreatic carcinoma, ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma), and colorectal cancer. Exemplary gastrointestinal cancers also include gall bladder cancer and anal cancer.

Exemplary genitourinary tract cancers include cancers of the kidney (adenocarcinoma, Wilm's tumor [nephroblastoma]), bladder and urethra (squamous cell carcinoma, transitional cell carcinoma, adenocarcinoma), prostate (adenocarcinoma, sarcoma), and testis (seminoma, teratoma, embryonal carcinoma, teratocarcinoma, choriocarcinoma, sarcoma, interstitial cell carcinoma, fibroma, fibroadenoma, adenomatoid tumors, lipoma). Exemplary genitourinary tract cancers also include renal cell carcinoma and urothelial carcinoma.

Exemplary liver cancers include hepatoma (hepatocellular carcinoma), cholangiocarcinoma, hepatoblastoma, angiosarcoma, hepatocellular adenoma, and hemangioma.

Exemplary bone cancers include, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma, and giant cell tumors Exemplary nervous system cancers include cancers of the skull (osteoma, hemangioma, granuloma, xanthoma, osteitis deformans), meninges (meningioma, meningiosarcoma, gliomatosis), brain (astrocytoma, meduoblastoma, glioma, ependymoma, germinoma (pinealoma), glioblastoma, glioblastoma multiform, oligodendroglioma, schwannoma, retinoblastoma, congenital tumors), and spinal cord (neurofibroma, meningioma, glioma, sarcoma), as well as neuroblastoma and Lhermitte-Duclos disease. Exemplary nervous system cancers also include neuro-ectodermal tumors and pineal tumors.

Exemplary gynecological cancers include cancers of the uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), and fallopian tubes (carcinoma). Exemplary nervous system cancers also include neuro-ectodermal tumors and pineal tumors.

Exemplary skin cancers include melanoma, basal cell carcinoma, squamous cell carcinoma, Kaposi's sarcoma, Merkel cell skin cancer, moles dysplastic nevi, lipoma, angioma, dermatofibroma, and keloids. In some embodiments, diseases and indications that are treatable using the compounds of the present disclosure include, but are not limited to, sickle cell disease (e.g., sickle cell anemia), triple-negative breast cancer (TNBC), myelodysplastic syndromes, testicular cancer, bile duct cancer, esophageal cancer, and urothelial carcinoma.

Exemplary head and neck cancers include glioblastoma, melanoma, rhabdosarcoma, lymphosarcoma, osteosarcoma, squamous cell carcinomas, adenocarcinomas, oral cancer, laryngeal cancer, nasopharyngeal cancer, nasal and paranasal cancers, thyroid and parathyroid cancers. Exemplary head and neck cancers also include tumors of the eye, tumors of the lips and mouth and squamous head and neck cancer.

The compounds of the present disclosure can also be useful in the inhibition of tumor metastases. In some embodiments, the compounds provided herein may be used to treat tumors producing PGE2 (e.g. Cox-2 overexpressing tumors) and/or adenosine (CD73 and CD39 over-expressing tumors). Overexpression of Cox-2 has been detected in a number of tumors, such as colorectal, breast, pancreatic and lung cancers, where it correlates with a poor prognosis. Overexpression of Cox-2 has been reported in hematological cancer models such as RAJI (Burkitt's lymphoma) and U937 (acute promonocytic leukemia) as well as in patient's blast cells. CD73 is up-regulated in various human carcinomas including those of colon, lung, pancreas and ovary. Importantly, higher expression levels of CD73 are associated with tumor neovascularization, invasiveness, and metastasis and with shorter patient survival time in breast cancer.

The terms "individual" or "patient," used interchangeably, refer to any animal, including mammals, preferably mice, rats, other rodents, rabbits, dogs, cats, swine, cattle, sheep, horses, or primates, and most preferably humans.

The phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein, the term "treating" or "treatment" refers to one or more of (1) inhibiting the disease; e.g., inhibiting a disease, condition or disorder in an individual who is experiencing or displaying the pathology or symptomatology of the disease, condition or disorder (i.e., arresting further development of the pathology and/or symptomatology); and (2) ameliorating the disease; e.g., ameliorating a disease, condition or disorder in an individual who is experiencing or displaying the pathology or symptomatology of the disease, condition or disorder (i.e., reversing the pathology and/or symptomatology) such as decreasing the severity of disease.

As used herein, the term "contacting" refers to the bringing together of the indicated compounds in an in vitro system or an in vivo system such that they are in sufficient physical proximity to interact.

In some embodiments, the compounds of the present disclosure are useful in preventing or reducing the risk of developing any of the diseases referred to herein; e.g., preventing or reducing the risk of developing a disease, condition or disorder in an individual who may be predisposed to the disease, condition or disorder but does not yet experience or display the pathology or symptomatology of the disease.

Combination Therapies

One or more additional pharmaceutical agents or treatment methods such as, for example, anti-viral agents, chemotherapeutics or other anti-cancer agents, immune enhancers, immunosuppressants, radiation, anti-tumor and anti-viral vaccines, cytokine therapy (e.g., IL2, GM-CSF, etc.), and/or tyrosine kinase inhibitors can be used in combination with compounds described herein for treatment of ALK2 associated diseases, disorders or conditions, or diseases or conditions as described herein. The agents can be combined with the present compounds in a single dosage form, or the agents can be administered simultaneously or sequentially as separate dosage forms.

I. Immune-Checkpoint Therapies

In some embodiments, the compounds provided herein can be used in combination with one or more immune checkpoint inhibitors for the treatment of cancer as described herein. Compounds of the present disclosure can be used in combination with one or more immune checkpoint inhibitors. Exemplary immune checkpoint inhibitors include inhibitors against immune checkpoint molecules such as CD20, CD28, CD39, CD40, CD122, CD96, CD73, CD47, GITR, CSF1R, JAK, PI3K delta, PI3K gamma, TAM, arginase, CD137 (also known as 4-1BB), ICOS, B7-H3, B7-H4, BTLA, CTLA-4, LAG3, TIM3, VISTA, TIGIT, PD-1, PD-L1 and PD-L2. In some embodiments, the immune checkpoint molecule is a stimulatory checkpoint molecule selected from CD27, CD28, CD40, ICOS, OX40, GITR and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, TIGIT, and VISTA. In some embodiments, the compounds of the disclosure provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the compounds provided herein can be used in combination with one or more agonists of immune checkpoint molecules, e.g., OX40, CD27, GITR, and CD137 (also known as 4-1BB).

In some embodiments, the inhibitor of an immune checkpoint molecule is anti-PD1 antibody, anti-PD-L1 antibody, or anti-CTLA-4 antibody.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), durvalumab (Imfinzi®), pidilizumab, SHR-1210, PDR001, MGA012, PDR001, AB122, or AMP-224. In some embodiments, the anti-PD-1 monoclonal antibody is nivolumab or pembrolizumab. In some embodiments, the anti-PD1 antibody is pembrolizumab. In some embodiments, the anti-PD-1 monoclonal antibody is MGA012. In some embodiments, the anti-PD1 antibody is SHR-1210. Other anti-cancer agent(s) include antibody therapeutics such as 4-1BB (e.g. urelumab, utomilumab). In some embodiments, the anti-PD-1 monoclonal antibody is ipilumimab.

In some embodiments, the compounds of the disclosure can be used in combination with INCB086550.

In some embodiments, the inhibitor of an immune checkpoint molecule is anti-PD1 antibody, anti-a small molecule PD-L1 antibody, or anti-CTLA-4 antibody. inhibitor. In some embodiments, the small molecule PD-L1 inhibitor has an $IC_{50}$ less than 1 µM, less than 100 nM, less than 10 nM or less than 1 nM in a PD-L1 assay described in US Patent Publication Nos. US 20170107216, US 20170145025, US 20170174671, US 20170174679, US 20170320875, US 20170342060, US 20170362253, US 20180016260, US 20180057486, US 20180177784, US 20180177870, US 20180179179, US 20180179197, US 20180179201, and US 20180179202, each of which is incorporated by reference in its entirety for all purposes.

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MEDI4736, MPDL3280A (also known as RG7446), or MSB0010718C. In some embodiments, the anti-PD-L1 monoclonal antibody is MPDL3280A or MEDI4736.

In some embodiments, the inhibitor of an immune checkpoint molecule is an inhibitor of PD-1 and PD-L1, e.g., an anti-PD-1/PD-L1 monoclonal antibody. In some embodiments, the anti-PD-1/PD-L1 is MCLA-136.

In some embodiments, the inhibitor is MCLA-145.

In some embodiments, the inhibitor of an immune checkpoint molecule is an inhibitor of CTLA-4, e.g., an anti-CTLA-4 antibody. In some embodiments, the anti-CTLA-4 antibody is ipilimumab, tremelimumab, AGEN1884, or CP-675,206.

In some embodiments, the inhibitor of an immune checkpoint molecule is an inhibitor of CSF1R, e.g., an anti-CSF1R antibody. In some embodiments, the anti-CSF1R antibody is IMC-CS4 or RG7155.

In some embodiments, the inhibitor of an immune checkpoint molecule is an inhibitor of LAG3, e.g., an anti-LAG3 antibody. In some embodiments, the anti-LAG3 antibody is BMS-986016, LAG525, IMP321, GSK2831781, or INCAGN2385.

In some embodiments, the inhibitor of an immune checkpoint molecule is an inhibitor of TIM3, e.g., an anti-TIM3 antibody. In some embodiments, the anti-TIM3 antibody is INCAGN2390, MBG453, or TSR-022.

In some embodiments, the inhibitor of an immune checkpoint molecule is an inhibitor of GITR, e.g., an anti-GITR antibody. In some embodiments, the anti-GITR antibody is TRX518, MK-4166, INCAGN1876, MK-1248, AMG228, BMS-986156, GWN323, or MEDI1873.

In some embodiments, the inhibitor of an immune checkpoint molecule is an agonist of OX40, e.g., OX40 agonist antibody or OX40L fusion protein. In some embodiments, the anti-OX40 antibody is MEDI0562, MEDI6469, MOXR-0916, PF-04518600, GSK3174998, or BMS-986178. In some embodiments, the OX40L fusion protein is MEDI6383.

In some embodiments, the inhibitor of an immune checkpoint molecule is an inhibitor of CD20, e.g., an anti-CD20 antibody. In some embodiments, the anti-CD20 antibody is obinutuzumab or rituximab.

The compounds of the present disclosure can be used in combination with bispecific antibodies. In some embodiments, one of the domains of the bispecific antibody targets PD-1, PD-L1, CTLA-4, GITR, OX40, TIM3, LAG3, CD137, ICOS, CD3 or TGFβ receptor.

In some embodiments, the compounds of the disclosure can be used in combination with one or more metabolic enzyme inhibitors. In some embodiments, the metabolic enzyme inhibitor is an inhibitor of IDO1, TDO, or arginase. Examples of IDO1 inhibitors include epacadostat, NLG919, BMS-986205, PF-06840003, IOM2983, RG-70099 and LY338196. An example of an arginase inhibitor is CB-1158.

As provided throughout, the additional compounds, inhibitors, agents, etc. can be combined with the present compound in a single or continuous dosage form, or they can be administered simultaneously or sequentially as separate dosage forms.

II. Cancer Therapies

Cancer cell growth and survival can be impacted by multiple signaling pathways. Thus, it is useful to combine different enzyme/protein/receptor inhibitors, exhibiting different preferences in the targets which they modulate the activities of, to treat such conditions. Examples of agents that may be combined with compounds of the present disclosure include inhibitors of the PI3K-AKT-mTOR pathway, inhibitors of the Raf-MAPK pathway, inhibitors of JAK-STAT pathway, inhibitors of beta catenin pathway, inhibitors of notch pathway, inhibitors of hedgehog pathway, inhibitors of Pim kinases, and inhibitors of protein chaperones and cell cycle progression. Targeting more than one signaling pathway (or more than one biological molecule involved in a given signaling pathway) may reduce the likelihood of drug-resistance arising in a cell population, and/or reduce the toxicity of treatment.

The compounds of the present disclosure can be used in combination with one or more other enzyme/protein/receptor inhibitors for the treatment of diseases, such as cancer. Examples of cancers include solid tumors and liquid tumors, such as blood cancers. For example, the compounds of the present disclosure can be combined with one or more inhibitors of the following kinases for the treatment of cancer: Akt1, Akt2, Akt3, TGF-βR, Pim, PKA, PKG, PKC, CaM-kinase, phosphorylase kinase, MEKK, ERK, MAPK, mTOR, EGFR, HER2, HER3, HER4, INS-R, IGF-1R, IR-R, PDGFαR, PDGFβR, CSFIR, KIT, FLK-II, KDR/FLK-1, FLK-4, flt-1, FGFR1, FGFR2, FGFR3, FGFR4, HPK, c-Met, Ron, Sea, TRKA, TRKB, TRKC, FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, and B-Raf. In some embodiments, the compounds of the present disclosure can be combined with one or more of the following inhibitors for the treatment of cancer. Non-limiting examples of inhibitors that can be combined with the compounds of the present disclosure for treatment of cancers include an FGFR inhibitor (FGFR1, FGFR2, FGFR3 or FGFR4, e.g., AZD4547, BAY1187982, ARQ087, BGJ398, BIBF1120, TKI258, lucitanib, dovitinib, TAS-120, JNJ-42756493, Debio1347, INCB54828, INCB62079 and INCB63904), a JAK inhibitor (JAK1 and/or JAK2, e.g., ruxolitinib, baricitinib or INCB39110), an IDO inhibitor (e.g., epacadostat and NLG919), an LSD1 inhibitor (e.g., GSK2979552, INCB59872 and INCB60003), a TDO inhibitor, a PI3K-delta inhibitor (e.g., INCB50797 and INCB50465), a PI3K-gamma inhibitor such as a PI3K-gamma selective inhibitor (e.g., PLX3397 and LY3022855), a TAM receptor tyrosine kinases (Tyro-3, Axl, and Mer), an angiogenesis inhibitor, an interleukin receptor inhibitor, bromo and extra terminal family members inhibitors (for example, bromodomain inhibitors or BET inhibitors such as OTX015, CPI-0610, INCB54329 and INCB57643) and an adenosine receptor antagonist or combinations thereof. Inhibitors of HDAC such as panobinostat and vorinostat. Inhibitors of c-Met such as onartumzumab, tivantnib, and INC-280. Inhibitors of BTK such as ibrutinib. Inhibitors of mTOR such as rapamycin, sirolimus, temsirolimus, and everolimus. Inhibitors of Raf, such as vemurafenib and dabrafenib. Inhibitors of MEK such as trametinib, selumetinib and GDC-0973. Inhibitors of Hsp90 (e.g., tanespimycin), cyclin dependent kinases (e.g., palbociclib), PARP (e.g., olaparib) and Pim kinases (LGH447, INCB053914 and SGI-1776) can also be combined with compounds of the present disclosure.

In some embodiments, compounds of the present disclosure can be combined with one or more JAK inhibitors (JAK1 and/or JAK2, e.g., ruxolitinib, baricitinib or INCB39110). In some embodiments, compounds of the present disclosure can be combined with one or more JAK inhibitors (JAK1 and/or JAK2, e.g., ruxolitinib, baricitinib or INCB39110) for the treatment of cancers such as myeloproliferative diseases. For example, the myeloproliferative disease is myelofibrosis. In some embodiments, compounds of the present disclosure can be combined with ruxolitinib, or a pharmaceutically acceptable salt thereof. In some embodiments, compounds of the present disclosure can be combined with ruxolitinib, or a pharmaceutically acceptable salt thereof, for the treatment of myeloproliferative disease such as myelofibrosis.

Compounds of the present disclosure can be used in combination with one or more agents for the treatment of diseases such as cancer. In some embodiments, the agent is an alkylating agent, a proteasome inhibitor, a corticosteroid, or an immunomodulatory agent. Examples of an alkylating agent include bendamustine, nitrogen mustards, ethylenimine derivatives, alkyl sulfonates, nitrosoureas and triazenes, uracil mustard, chlormethine, cyclophosphamide (Cytoxan™), ifosfamide, melphalan, chlorambucil, pipobroman, triethylene-melamine, triethylenethiophosphoramine, busulfan, carmustine, lomustine, streptozocin, dacarbazine, and temozolomide. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM).

The compounds of the present disclosure can further be used in combination with other methods of treating cancers, for example by chemotherapy, irradiation therapy, tumor-targeted therapy, adjuvant therapy, immunotherapy or surgery. Examples of immunotherapy include cytokine treatment (e.g., interferons, GM-CSF, G-CSF, IL-2), CRS-207 immunotherapy, cancer vaccine, monoclonal antibody, adoptive T cell transfer, CAR (Chimeric antigen receptor) T cell treatment as a booster for T cell activation, oncolytic virotherapy and immunomodulating small molecules, including thalidomide or JAK1/2 inhibitor and the like. The compounds can be administered in combination with one or more anti-cancer drugs, such as a chemotherapeutics. Example chemotherapeutics include any of: abarelix, abiraterone, afatinib, aflibercept, aldesleukin, alemtuzumab, alitretinoin, allopurinol, altretamine, amsacrine, anastrozole, aphidicolon, arsenic trioxide, asparaginase, axitinib, azacitidine, bevacizumab, bexarotene, baricitinib, bicalutamide, bleomycin, bortezombi, bortezomib, brivanib, buparlisib, busulfan intravenous, busulfan oral, calusterone, camptosar, capecitabine, carboplatin, carmustine, cediranib, cetuximab, chlorambucil, cisplatin, cladribine, clofarabine, crizotinib, cyclophosphamide, cytarabine, dacarbazine, dacomitinib, dactinomycin, dalteparin sodium, dasatinib, dactinomycin, daunorubicin, decitabine, degarelix, denileukin, denileukin diftitox, deoxycoformycin, dexrazoxane, docetaxel, doxorubicin, droloxafine, dromostanolone propionate, eculizumab, enzalutamide, epidophyllotoxin, epirubicin, epothilones, erlotinib, estramustine, etoposide phosphate, etoposide, exemestane, fentanyl citrate, filgrastim, floxuridine, fludarabine, fluorouracil, flutamide, fulvestrant, gefitinib, gemcitabine, gemtuzumab ozogamicin, goserelin acetate, histrelin acetate, ibritumomab tiuxetan, idarubicin, idelalisib, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mithramycin, mitomycin C, mitotane, mitoxantrone, nandrolone phenpropionate, navelbene, necitumumab, nelarabine, neratinib, nilotinib, nilutamide, nofetumomab, oserelin, oxaliplatin, paclitaxel, pamidronate, panitumumab, pazopanib, pegaspargase, pegfilgrastim, pemetrexed disodium, pentostatin, pilaralisib, pipobroman, plicamycin, ponatinib, porfimer, prednisone, procarbazine, quinacrine, ranibizumab, rasburicase, regorafenib, reloxafine, revlimid, rituximab, ruxolitinib, sorafenib, streptozocin, sunitinib, sunitinib maleate, tamoxifen, tegafur, temozolomide, teniposide, testolactone, thalidomide, thioguanine, thiotepa, topotecan, toremifene, tositumomab, trastuzumab, tretinoin, triptorelin, uracil mustard, valrubicin, vandetanib, vinblastine, vincristine, vindesine, vinorelbine, vorinostat and zoledronate.

Other anti-cancer agent(s) include antibody therapeutics such as trastuzumab (Herceptin), antibodies to costimulatory molecules such as CTLA-4 (e.g., ipilimumab or tremelimumab), 4-1BB, antibodies to PD-1 and PD-L1, or antibodies to cytokines (IL-10, TGF-β, etc.). Examples of antibodies to PD-1 and/or PD-L1 that can be combined with compounds of the present disclosure for the treatment of cancer or infections such as viral, bacteria, fungus and parasite infections include, but are not limited to, nivolumab, pembrolizumab, MPDL3280A, MEDI-4736 and SHR-1210.

Other anti-cancer agents include inhibitors of kinases associated cell proliferative disorder. These kinases include but not limited to Aurora-A, CDK1, CDK2, CDK3, CDK5, CDK7, CDK8, CDK9, ephrin receptor kinases, CHK1, CHK2, SRC, Yes, Fyn, Lck, Fer, Fes, Syk, Itk, Bmx, GSK3, JNK, PAK1, PAK2, PAK3, PAK4, PDK1, PKA, PKC, Rsk and SGK.

Other anti-cancer agents also include those that block immune cell migration such as antagonists to chemokine receptors, including CCR2 and CCR4.

The compounds of the present disclosure can further be used in combination with one or more anti-inflammatory agents, steroids, immunosuppressants or therapeutic antibodies. The steroids include but are not limited to 17 alpha-ethinylestradiol, diethylstilbestrol, testosterone, prednisone, fluoxymesterone, methylprednisolone, methyltestosterone, prednisolone, triamcinolone, chlorotrianisene, hydroxyprogesterone, aminoglutethimide, and medroxyprogesteroneacetate.

The compounds of the present disclosure can also be used in combination with lonafarnib (SCH6636), tipifarnib (R115777), L778123, BMS 214662, tezacitabine (MDL 101731), Sml1, triapine, didox, trimidox and amidox.

The compounds described herein can be combined with another immunogenic agent, such as cancerous cells, purified tumor antigens (including recombinant proteins, peptides, and carbohydrate molecules), cells, and cells transfected with genes encoding immune stimulating cytokines. Non-limiting examples of tumor vaccines that can be used include peptides of melanoma antigens, such as peptides of gp100, MAGE antigens, Trp-2, MARTI and/or tyrosinase, or tumor cells transfected to express the cytokine GM-CSF.

The compounds described herein can be used in combination with a vaccination protocol for the treatment of cancer. In some embodiments, the tumor cells are transduced to express GM-CSF. In some embodiments, tumor vaccines include the proteins from viruses implicated in human cancers such as Human Papilloma Viruses (HPV), Hepatitis Viruses (HBV and HCV) and Kaposi's Herpes Sarcoma Virus (KHSV). In some embodiments, the compounds of the present disclosure can be used in combination with tumor specific antigen such as heat shock proteins isolated from tumor tissue itself. In some embodiments, the compounds described herein can be combined with dendritic cells immunization to activate potent anti-tumor responses.

The compounds of the present disclosure can be used in combination with bispecific macrocyclic peptides that target Fe alpha or Fe gamma receptor-expressing effectors cells to tumor cells. The compounds of the present disclosure can also be combined with macrocyclic peptides that activate host immune responsiveness.

The compounds of the present disclosure can be used in combination with bone marrow transplant for the treatment of a variety of tumors of hematopoietic origin.

Suitable antiviral agents contemplated for use in combination with the compounds of the present disclosure can comprise nucleoside and nucleotide reverse transcriptase inhibitors (NRTIs), non-nucleoside reverse transcriptase inhibitors (NNRTIs), protease inhibitors and other antiviral drugs.

Example suitable NRTIs include zidovudine (AZT); didanosine (ddI); zalcitabine (ddC); stavudine (d4T); lamivudine (3TC); abacavir (1592U89); adefovir dipivoxil [bis(POM)-PMEA]; lobucavir (BMS-180194); BCH-10652; emitricitabine [(−)-FTC]; beta-L-FD4 (also called beta-L-D4C and named beta-L-2',3'-dicleoxy-5-fluoro-cytidene); DAPD, ((−)-beta-D-2,6,-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4 (1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfnavir (AG-1343); amprenavir (141W94); lasinavir (BMS-234475); DMP-450; BMS-2322623; ABT-378; and AG-1 549. Other antiviral agents include hydroxyurea, ribavirin, IL-2, IL-12, pentafuside and Yissum Project No. 11607.

The compounds described herein may be combined with or in sequence with other agents against membrane receptor kinases especially for patients who have developed primary or acquired resistance to the targeted therapy. These therapeutic agents include inhibitors or antibodies against EGFR, Her2, VEGFR, c-Met, Ret, IGFR1, or Flt-3 and against cancer-associated fusion protein kinases such as Bcr-Abl and EML4-Alk. Inhibitors against EGFR include gefitinib and erlotinib, and inhibitors against EGFR/Her2 include but are not limited to dacomitinib, afatinib, lapitinib and neratinib. Antibodies against the EGFR include but are not limited to cetuximab, panitumumab and necitumumab. Inhibitors of c-Met may be used in combination with compound disclosed herein. These include onartumzumab, tivantnib, and INC-280. Agents against Abl (or Bcr-Abl) include imatinib, dasatinib, nilotinib, and ponatinib and those against Alk (or EML4-ALK) include crizotinib.

Angiogenesis inhibitors may be efficacious in some tumors in combination with compounds disclosed herein. These include antibodies against VEGF or VEGFR or kinase inhibitors of VEGFR. Antibodies or other therapeutic proteins against VEGF include bevacizumab and aflibercept. Inhibitors of VEGFR kinases and other anti-angiogenesis inhibitors include but are not limited to sunitinib, sorafenib, axitinib, cediranib, pazopanib, regorafenib, brivanib, and vandetanib Activation of intracellular signaling pathways is frequent in cancer, and agents targeting components of these pathways have been combined with receptor targeting agents to enhance efficacy and reduce resistance. Examples of agents that may be combined with compounds described herein include inhibitors of the PI3K-AKT-mTOR pathway, inhibitors of the Raf-MAPK pathway, inhibitors of JAK-STAT pathway, and inhibitors of protein chaperones and cell cycle progression.

Agents against the PI3 kinase include but are not limited to pilaralisib, idelalisib, buparlisib. Inhibitors of mTOR such as rapamycin, sirolimus, temsirolimus, and everolimus may be combined with compounds of the invention. Other suitable examples include but are not limited to vemurafenib and dabrafenib (Raf inhibitors) and trametinib, selumetinib and GDC-0973 (MEK inhibitors). Inhibitors of one or more JAKs (e.g., ruxolitinib, baricitinib, tofacitinib), Hsp90 (e.g., tanespimycin), cyclin dependent kinases (e.g., palbociclib), HDACs (e.g., panobinostat), PARP (e.g., olaparib), and proteasomes (e.g., bortezomib, carfilzomib) can also be combined with compounds described herein. In some embodiments, the JAK inhibitor is selective for JAK1 over JAK2 and JAK3.

Other suitable agents for use in combination with compounds described herein include chemotherapy combinations such as platinum-based doublets used in lung cancer and other solid tumors (cisplatin or carboplatin plus gemcitabine; cisplatin or carboplatin plus docetaxel; cisplatin or carboplatin plus paclitaxel; cisplatin or carboplatin plus pemetrexed) or gemcitabine plus paclitaxel bound particles (Abraxane®).

Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (Cytoxan™), ifosfamide, melphalan, chlorambucil, pipobroman, triethylene-melamine, triethylenethiophosphoramine, busulfan, carmustine, lomustine, streptozocin, dacarbazine, and temozolomide.

Other suitable agents for use in combination with compounds described herein include steroids including 17 alpha-ethinylestradiol, diethylstilbestrol, testosterone, prednisone, fluoxymesterone, methylprednisolone, methyltestosterone, prednisolone, triamcinolone, chlorotrianisene, hydroxyprogesterone, aminoglutethimide, and medroxyprogesteroneacetate.

Other suitable agents for use in combination with compounds described herein include: dacarbazine (DTIC), optionally, along with other chemotherapy drugs such as carmustine (BCNU) and cisplatin; the "Dartmouth regimen," which consists of DTIC, BCNU, cisplatin and tamoxifen; a combination of cisplatin, vinblastine, and DTIC; or temozolomide. Compounds described herein may also be combined with immunotherapy drugs, including cytokines such as interferon alpha, interleukin 2, and tumor necrosis factor (TNF) inhibitors.

Suitable chemotherapeutic or other anti-cancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anti-cancer agents further include, for example, certain natural products and their derivatives (for example, vinca alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (TAXOL™), mithramycin, deoxycoformycin, mitomycin-C, L-asparaginase, interferons (especially IFN-a), etoposide, and teniposide.

Other cytotoxic agents include navelbene, CPT-11, anastrazole, letrazole, capecitabine, reloxafine, cyclophosphamide, ifosamide, and droloxafine.

Also suitable are cytotoxic agents such as epidophyllotoxin; an antineoplastic enzyme; a topoisomerase inhibitor; procarbazine; mitoxantrone; platinum coordination complexes such as cis-platin and carboplatin; biological response modifiers; growth inhibitors; antihormonal therapeutic agents; leucovorin; tegafur; and haematopoietic growth factors.

Other anti-cancer agent(s) include antibody therapeutics such as trastuzumab (Herceptin), antibodies to costimulatory molecules such as CTLA-4, 4-1BB, PD-L1 and PD-1 antibodies, or antibodies to cytokines (IL-10, TGF-β, etc.).

Other anti-cancer agents also include those that block immune cell migration such as antagonists to chemokine receptors, including CCR2 and CCR4.

Other anti-cancer agents also include those that augment the immune system such as adjuvants or adoptive T cell transfer.

Anti-cancer vaccines include dendritic cells, synthetic peptides, DNA vaccines and recombinant viruses. In some embodiments, tumor vaccines include the proteins from viruses implicated in human cancers such as Human Papilloma Viruses (HPV), Hepatitis Viruses (HBV and HCV) and Kaposi's Herpes Sarcoma Virus (KHSV). Non-limiting examples of tumor vaccines that can be used include peptides of melanoma antigens, such as peptides of gp100, MAGE antigens, Trp-2, MARTI and/or tyrosinase, or tumor cells transfected to express the cytokine GM-CSF.

The compounds of the present disclosure can be used in combination with bone marrow transplant for the treatment of a variety of tumors of hematopoietic origin.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, N.J.), the disclosure of which is incorporated herein by reference as if set forth in its entirety.

When more than one pharmaceutical agent is administered to a patient, they can be administered simultaneously, separately, sequentially, or in combination (e.g., for more than two agents).

In some embodiments, the compounds of the present disclosure can be used in combination with INCB086550.

Formulation, Dosage Forms and Administration

When employed as pharmaceuticals, the compounds of the present disclosure can be administered in the form of pharmaceutical compositions. Thus the present disclosure provides a composition comprising a compound of Formula (I) or any of the formulas as described herein, a compound as recited in any of the claims and described herein, or a pharmaceutically acceptable salt thereof, or any of the embodiments thereof, and at least one pharmaceutically acceptable carrier or excipient. The pharmaceutical compositions can comprise of a compound described herein and one or more second therapeutic agents as described herein. For example, the second therapeutic agent is a JAK inhibitor such as ruxolitinib. The compositions can be prepared in a manner well known in the pharmaceutical art, and can be administered by a variety of routes, depending upon whether local or systemic treatment is indicated and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, e.g., by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the compound of the present disclosure or a pharmaceutically acceptable salt thereof, in combination with one or more pharmaceutically acceptable carriers or excipients. In some embodiments, the composition is suitable for topical administration. In making the compositions of the present disclosure, the active ingredient is typically mixed with an excipient, diluted by an excipient or enclosed within such a carrier in the form of, e.g., a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, e.g., up to 10% by weight of the active compound, soft and hard gelatin capsules, suppositories, sterile injectable solutions and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

The compounds of the present disclosure may be milled using known milling procedures such as wet milling to obtain a particle size appropriate for tablet formation and for other formulation types. Finely divided (nanoparticulate) preparations of the compounds of the present disclosure can be prepared by processes known in the art see, e.g., WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup and methyl cellulose. The formulations can additionally include: lubricating agents such as talc, magnesium stearate and mineral oil; wetting agents; emulsifying and suspending agents; preserving agents such as methyl- and propylhydroxy-benzoates; sweetening agents; and flavoring agents. The compositions of the present disclosure can be formulated so as to provide quick, sustained or delayed release of the active ingredient after administration to the patient by employing procedures known in the art.

In some embodiments, the pharmaceutical composition comprises silicified microcrystalline cellulose (SMCC) and at least one compound described herein, or a pharmaceutically acceptable salt thereof. In some embodiments, the silicified microcrystalline cellulose comprises about 98% microcrystalline cellulose and about 2% silicon dioxide w/w.

In some embodiments, the composition is a sustained release composition comprising at least one compound described herein, or a pharmaceutically acceptable salt thereof, and at least one pharmaceutically acceptable carrier or excipient. In some embodiments, the composition comprises at least one compound described herein, or a pharmaceutically acceptable salt thereof, and at least one component selected from microcrystalline cellulose, lactose monohydrate, hydroxypropyl methylcellulose and polyethylene oxide. In some embodiments, the composition comprises at least one compound described herein, or a pharmaceutically acceptable salt thereof, and microcrystalline cellulose, lactose monohydrate and hydroxypropyl methylcellulose. In some embodiments, the composition comprises at least one compound described herein, or a pharmaceutically acceptable salt thereof, and microcrystalline cellulose, lactose monohydrate and polyethylene oxide. In some embodiments, the composition further comprises magnesium stearate or silicon dioxide. In some embodiments, the microcrystalline cellulose is Avicel PH102™. In some embodiments, the lactose monohydrate is Fast-flo 316™. In some embodiments, the hydroxypropyl methylcellulose is hydroxypropyl methylcellulose 2208 K4M (e.g., Methocel K4 M Premier™) and/or hydroxypropyl methylcellulose 2208 K100LV (e.g., Methocel K00LV™). In some embodiments, the polyethylene oxide is polyethylene oxide WSR 1105 (e.g., Polyox WSR 1105™).

In some embodiments, a wet granulation process is used to produce the composition. In some embodiments, a dry granulation process is used to produce the composition.

The compositions can be formulated in a unit dosage form, each dosage containing from about 5 to about 1,000 mg (1 g), more usually about 100 mg to about 500 mg, of the active ingredient. In some embodiments, each dosage contains about 10 mg of the active ingredient. In some embodiments, each dosage contains about 50 mg of the active ingredient. In some embodiments, each dosage contains about 25 mg of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The components used to formulate the pharmaceutical compositions are of high purity and are substantially free of potentially harmful contaminants (e.g., at least National Food grade, generally at least analytical grade, and more typically at least pharmaceutical grade). Particularly for human consumption, the composition is preferably manufactured or formulated under Good Manufacturing Practice standards as defined in the applicable regulations of the U.S. Food and Drug Administration. For example, suitable formulations may be sterile and/or substantially isotonic and/or in full compliance with all Good Manufacturing Practice regulations of the U.S. Food and Drug Administration.

The active compound may be effective over a wide dosage range and is generally administered in a therapeutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms and the like.

The therapeutic dosage of a compound of the present invention can vary according to, e.g., the particular use for which the treatment is made, the manner of administration of the compound, the health and condition of the patient, and the judgment of the prescribing physician. The proportion or concentration of a compound of the present disclosure in a pharmaceutical composition can vary depending upon a number of factors including dosage, chemical characteristics (e.g., hydrophobicity), and the route of administration. For example, the compounds of the present disclosure can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, e.g., about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, e.g., liquid paraffin, polyoxyethylene alkyl ether, propylene glycol, white Vaseline, and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, e.g., glycerol, hydroxyethyl cellulose, and the like. In some embodiments, topical formulations contain at least about 0.1, at least about 0.25, at least about 0.5, at least about 1, at least about 2 or at least about 5 wt % of the compound of the present disclosure. The topical formulations can be suitably packaged in tubes of, e.g., 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers or stabilizers will result in the formation of pharmaceutical salts.

The therapeutic dosage of a compound of the present invention can vary according to, e.g., the particular use for which the treatment is made, the manner of administration of the compound, the health and condition of the patient, and the judgment of the prescribing physician. The proportion or concentration of a compound of the present disclosure in a pharmaceutical composition can vary depending upon a number of factors including dosage, chemical characteristics (e.g., hydrophobicity), and the route of administration. For example, the compounds of the present disclosure can be provided in an aqueous physiological buffer solution containing about 0.1 to about 10% w/v of the compound for parenteral administration. Some typical dose ranges are from about 1 rig/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

Labeled Compounds and Assay Methods

The compounds of the present disclosure can further be useful in investigations of biological processes in normal and abnormal tissues. Thus, another aspect of the present invention relates to fluorescent dye, spin label, heavy metal or radio-labeled compounds provided herein that would be useful not only in imaging techniques but also in assays, both in vitro and in vivo, for localizing and quantitating ALK2 protein in tissue samples, including human, and for identifying ALK2 ligands by inhibition binding of a labeled compound. Accordingly, the present invention includes ALK2 binding assays that contain such labeled compounds.

The present invention further includes isotopically-substituted compounds of the disclosure. An "isotopically-substituted" compound is a compound of the present disclosure where one or more atoms are replaced or substituted by an atom having the same atomic number but a different atomic mass or mass number. Compounds of the present disclosure may contain isotopes in a natural abundance as found in nature. Compounds of the present disclosure may also have isotopes in amounts greater to that found in nature, e.g., synthetically incorporating low natural abundance isotopes into the compounds of the present disclosure so they are enriched in a particularly useful isotope (e.g., $^2$H and $^{13}$C). It is to be understood that a "radio-labeled" compound is a compound that has incorporated at least one isotope that is radioactive (e.g., radionuclide), e.g., $^3$H and $^{14}$C. Suitable radionuclides that may be incorporated in compounds of the present invention include but are not limited to $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. The radionuclide that is incorporated in the instant radio-labeled compounds will depend on the specific application of that radio-labeled compound. In some embodiments, the radionuclide is selected from the group consisting of $^3$H, $^{14}$C, $^{125}$I, $^{35}$S and $^{82}$Br. For in vitro ALK2 labeling and competition assays, compounds that incorporate $^3$H, $^{14}$C, $^{82}$Br, $^{125}$I, $^{131}$I, or $^{35}$S will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful. The present disclosure can further include synthetic methods for incorporating radio-isotopes into compounds of the disclosure. Synthetic methods for incorporating radio-isotopes into organic compounds are well known in the art and a person of ordinary skill in the art will readily recognize the methods applicable for the compounds of disclosure.

One or more constituent atoms of the compounds presented herein can be replaced or substituted with isotopes of the atoms in natural or non-natural abundance. In some embodiments, the compound includes at least one deuterium atom. In some embodiments, the compound includes two or more deuterium atoms. In some embodiments, the compound includes 1-2, 1-3, 1-4, 1-5, or 1-6 deuterium atoms. In some embodiments, all of the hydrogen atoms in a compound can be replaced or substituted by deuterium atoms.

Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can be used in various studies such as NMR spectroscopy, metabolism experiments, and/or assays.

Substitution with heavier isotopes, such as deuterium, may afford certain therapeutic advantages resulting from greater metabolic stability, for example, increased in vivo half-life or reduced dosage requirements, and hence may be preferred in some circumstances. (see e.g., A. Kerekes et. al. *J. Med. Chem.* 2011, 54, 201-210; R. Xu et. al. *J. Label Compd. Radiopharm.* 2015, 58, 308-312). In particular, substitution at one or more metabolism sites may afford one or more of the therapeutic advantages. Specifically, a labeled compound of the present disclosure can be used in a screening assay to identify and/or evaluate compounds. For example, a newly synthesized or identified compound (i.e., test compound) which is labeled can be evaluated for its ability to bind a ALK2 protein by monitoring its concentration variation when contacting with the ALK2, through tracking of the labeling. For example, a test compound (labeled) can be evaluated for its ability to reduce binding of another compound which is known to bind to a ALK2 protein (i.e., standard compound). Accordingly, the ability of a test compound to compete with the standard compound for binding to the ALK2 protein directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present disclosure also includes pharmaceutical kits useful, e.g., in the treatment or prevention of diseases or disorders associated with the activity of ALK2, such as cancer or infections, which include one or more containers containing a pharmaceutical composition comprising a therapeutically effective amount of a compound of Formula I, or any of the embodiments thereof. Such kits can further include one or more of various conventional pharmaceutical kit components, such as, e.g., containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples have been found to inhibit the activity of ALK2 according to at least one assay described herein.

EXAMPLES

Experimental procedures for compounds of the present disclosure are provided below. Preparatory LC-MS purifications of some of the compounds prepared were performed on Waters mass directed fractionation systems. The basic equipment setup, protocols, and control software for the operation of these systems have been described in detail in the literature. See e.g. "Two-Pump At Column Dilution Configuration for Preparative LC-MS", K. Blom, *J. Combi. Chem.*, 4, 295 (2002); "Optimizing Preparative LC-MS Configurations and Methods for Parallel Synthesis Purification", K. Blom, R. Sparks, J. Doughty, G. Everlof, T. Haque, A. Combs, *J. Combi. Chem.*, 5, 670 (2003); and "Preparative LC-MS Purification: Improved Compound Specific Method Optimization", K. Blom, B. Glass, R. Sparks, A. Combs, *J. Combi. Chem.*, 6, 874-883 (2004). The compounds separated were typically subjected to analytical liquid chromatography mass spectrometry (LCMS) for purity check under the following conditions: Instrument; Agilent 1100 series, LC/MSD, Column: Waters Sunfire™ $C_{18}$ 5 μm particle size, 2.1×5.0 mm, Buffers: mobile phase A: 0.025% TFA in water and mobile phase B: acetonitrile; gradient 2% to 80% of B in 3 minutes with flow rate 2.0 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ $C_{18}$ 5 μm particle size, 30×100 mm column, eluting with mobile phase A: 0.1% TFA (trifluoroacetic acid) in water and mobile phase B: acetonitrile; the flow rate was 60 mL/minute, the separating gradient was optimized for each compound using the Compound Specific Method Optimization protocol as described in the literature [see "Preparative LCMS Purification: Improved Compound Specific Method Optimization", K. Blom, B. Glass, R. Sparks, A. Combs, *J. Comb. Chem.*, 6, 874-883 (2004)].

pH=10 purifications: Waters XBridge $C_{18}$ 5 μm particle size, 30×100 mm column, eluting with mobile phase A: 0.15% $NH_4OH$ in water and mobile phase B: acetonitrile; the flow rate was 60 mL/minute, the separating gradient was optimized for each compound using the Compound Specific Method Optimization protocol as described in the literature [See "Preparative LCMS Purification: Improved Compound Specific Method Optimization", K. Blom, B. Glass, R. Sparks, A. Combs, *J. Comb. Chem.*, 6, 874-883 (2004)].

Example 1. 4-(6-Methyl-7-(4-(piperazin-1-yl)phenyl)imidazo[1,2-b]pyridazin-3-yl)quinoline

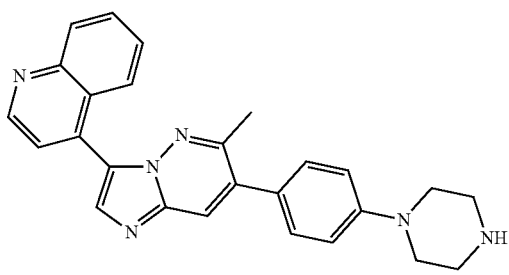 [SMILES: Cc1nn2c(-c3ccnc4ccccc34)cnc2cc1-c1ccc(N2CCNCC2)cc1]

Step 1: N-(5-Chloro-6-methylpyridazin-3-yl)-1,1-diphenylmethanimine

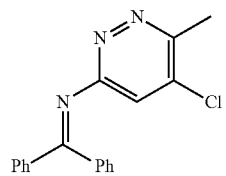 [SMILES: Cc1nnc(N=C(c2ccccc2)c2ccccc2)cc1Cl]

A screw-cap vial equipped with a magnetic stir bar was charged with 4,6-dichloro-3-methylpyridazine (AURUM Pharmatech, 1.121 g, 6.88 mmol), $Cs_2CO_3$ (4.34 g, 13.32 mmol), Xantphos (454.8 mg, 0.786 mmol) and $Pd_2(dba)_3$ (318.7 mg, 0.348 mmol). The vial was sealed with a Teflon-lined septum, evacuated and backfilled with nitrogen (this process was repeated a total of three times). A solution of diphenylmethanimine (1.290 g, 7.12 mmol) in 1,4-dioxane (20.0 mL) was added via syringe. The mixture was stirred at 90° C. for 16 h. After cooling to room temperature, the reaction mixture was diluted with $CH_2Cl_2$ (100 mL), filtered and concentrated. The residue was purified on silica gel (40 g, 0-100% EtOAc in $CH_2Cl_2$) to give the desired product as an orange foamy solid (1.263 g, 60%). LCMS calculated for $C_{18}H_{15}ClN_3$ $(M+H)^+$ m/z=308.1. found 308.1.

Step 2: 7-Chloro-6-methylimidazo[1,2-b]pyridazine

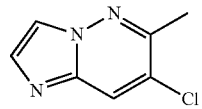

A solution of N-(5-chloro-6-methylpyridazin-3-yl)-1,1-diphenylmethanimine (1.263 g, 4.10 mmol) in THF (20.0 mL) was treated with HCl (4.0 N in water) (10.0 mL, 40.0 mmol). The mixture was stirred at room temperature for 90 min. The mixture was then adjusted to pH=7 with NaOH (4 N in water). The resulting mixture was concentrated under reduced pressure to about the volume of 20 mL. Isopropanol (24 mL) was added followed by chloroacetaldehyde (50 wt % in water) (7.694 g, 49.0 mmol). The mixture was stirred at 85° C. for 24 h. After cooling to room temperature, the mixture was diluted with $CH_2Cl_2$, and washed with aqueous $K_2CO_3$ (2 M). The separated organic phase was dried over anhydrous $Na_2SO_4$, filtered and concentrated. The residue was purified on silica gel (40 g, 0-100% EtOAc in $CH_2Cl_2$) to give the desired product as a beige solid (536.8 mg, 78%). LCMS calculated for $C_7H_7ClN_3$ $(M+H)^+$ m/z=168.0. found 168.0.

Step 3: 7-Chloro-3-iodo-6-methylimidazo[1,2-b]pyridazine

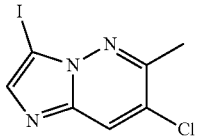

A solution of 7-chloro-6-methylimidazo[1,2-b]pyridazine (102.2 mg, 0.610 mmol) in DMF (3.0 mL) was treated with NIS (208.3 mg, 0.926 mmol). The mixture was stirred at 80° C. for 1 h. After cooling to room temperature, the mixture was concentrated in vacuo. The residue was purified on silica gel (20 g, 0-100% EtOAc in $CH_2Cl_2$) to give the desired product as a white solid (156.6 mg, 87%). LCMS calculated for $C_7H_6ClIN_3$ $(M+H)^+$ m/z=293.9. found 293.9.

Step 4: 4-(7-Chloro-6-methylimidazo[1,2-b]pyridazin-3-yl)quinoline

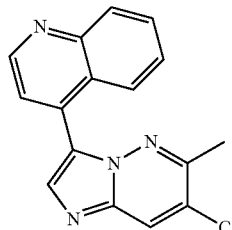

A screw-cap vial equipped with a magnetic stir bar was charged with 7-chloro-3-iodo-6-methylimidazo[1,2-b]pyridazine (156.6 mg, 0.534 mmol), 4-(4,4,5,5-tetramethyl-1,3,2-dioxaborolan-2-yl)quinoline (138.4 mg, 0.542 mmol), $PdCl_2(dppf)\text{-}CH_2Cl_2$ adduct (43.6 mg, 0.053 mmol) and cesium carbonate (522 mg, 1.601 mmol). The vial was sealed with a Teflon-lined septum, evacuated and backfilled with nitrogen (this process was repeated a total of three times). 1,4-Dioxane (6.0 ml) was added via syringe followed by water (600.0 µl, 33.3 mmol). The mixture was stirred at 90° C. for 4 h. After cooling to room temperature, the reaction mixture was concentrated. The residue was purified on silica gel (20 g, 0-100% EtOAc in $CH_2Cl_2$) to give the desired product as a yellow solid (108.8 mg, 69%). LCMS calculated for $C_{16}H_{12}ClN_4$ $(M+H)^+$ m/z=295.1. found 295.0.

Step 5: 4-(6-Methyl-7-(4-(piperazin-1-yl)phenyl)imidazo[1,2-b]pyridazin-3-yl)quinoline A screw-cap vial equipped with a magnetic stir bar was charged with 4-(7-chloro-6-methylimidazo[1,2-b]pyridazin-3-yl)quinoline (17.9 mg, 0.061 mmol), tert-butyl 4-(4-(4,4,5,5-tetramethyl-1,3,2-dioxaborolan-2-yl)phenyl)piperazine-1-carboxylate (35.4 mg, 0.091 mmol), chloro(2-dicyclohexylphosphino-2',4',6'-triisopropyl-1,1'-biphenyl)[2-(2'-amino-1,1'-biphenyl)]palladium(II) (XPhos Pd G2, 5.0 mg, 6.35 µmol) and cesium carbonate (60.2 mg, 0.185 mmol). The vial was sealed with a Teflon-lined septum, evacuated and backfilled with nitrogen (this process was repeated a total of three times). 1,4-Dioxane (2.0 ml) was added via syringe, followed by water (200.0 µl, 11.10 mmol). The mixture was heated at 80° C. for 6 h. After cooling to room temperature, the reaction was concentrated. The residue was treated with $CH_2Cl_2$ (2.0 mL) followed by TFA (2.0 mL). The mixture was stirred at room temperature for 15 min, and then concentrated. The residue was purified using prep-LCMS (XBridge C18 column, eluting with a gradient of acetonitrile/water containing 0.1% TFA, at flow rate of 60 mL/min) to afford the desired product as its TFA salt. LCMS calculated for $C_{26}H_{25}N_6(M+H)^+$: m/z=421.2. found: 421.2. $^1$H NMR (TFA salt, 500 MHz, DMSO) δ 9.12 (d, J=4.7 Hz, 1H), 8.80 (br, 2H), 8.26 (s, 1H), 8.19 (d, J=8.4 Hz, 1H), 8.09 (s, 1H), 8.06 (d, J=8.5 Hz, 1H), 8.00 (d, J=4.7 Hz, 1H), 7.91 (m, 1H), 7.70 (m, 1H), 7.49 (d, J=8.7 Hz, 2H), 7.14 (d, J=8.7 Hz, 2H), 3.46 (m, 4H), 3.28 (m, 4H), 2.43 (s, 3H).

Example 2. Methyl 7-(4-(piperazin-1-yl)phenyl)-3-(quinolin-4-yl)imidazo[1,2-b]pyridazine-6-carboxylate

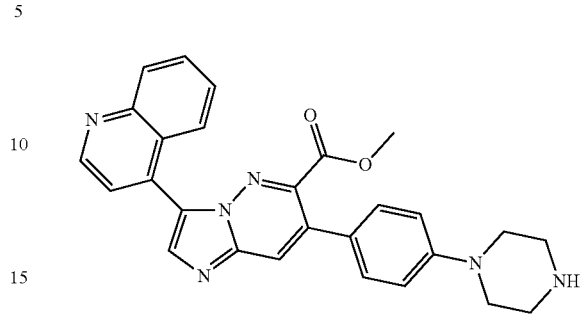

Step 1: Methyl 4-chloro-6-((diphenylmethylene)amino)pyridazine-3-carboxylate

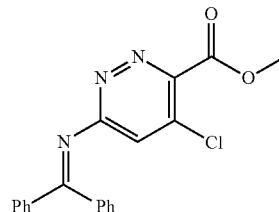

A screw-cap vial equipped with a magnetic stir bar was charged with methyl 4,6-dichloropyridazine-3-carboxylate (Combi-Blocks, 1.204 g, 5.82 mmol), cesium carbonate (3.835 g, 11.77 mmol), Xantphos (380.6 mg, 0.658 mmol) and $Pd_2(dba)_3$ (268.9 mg, 0.294 mmol). The vial was sealed with a Teflon-lined septum, evacuated and backfilled with nitrogen (this process was repeated a total of three times). A solution of diphenylmethanimine (1.089 g, 6.01 mmol) in 1,4-dioxane (20.0 mL) was added via syringe. The mixture was stirred at 90° C. for 16 h. After cooling to room temperature, the reaction mixture was diluted with $CH_2Cl_2$ (100 mL), filtered and concentrated. The residue was purified on silica gel (40 g, 0-100% EtOAc in $CH_2Cl_2$) to give the desired product as a yellow foamy solid (631.3 mg, 31%). LCMS calculated for $C_{19}H_{15}ClN_3O_2(M+H)^+$ m/z=352.1. found 352.1.

Step 2: Methyl 7-chloroimidazo[1,2-b]pyridazine-6-carboxylate

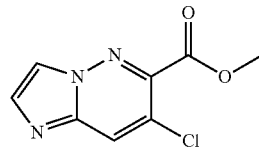

A solution of methyl 4-chloro-6-((diphenylmethylene)amino)pyridazine-3-carboxylate (631.3 mg, 1.795 mmol) in THF (15.0 mL) was treated with HCl (4.0 N in water) (5.0 mL, 20.00 mmol). The mixture was stirred at room temperature for 90 min. The mixture was then adjusted to pH=7 with NaOH (4 N in water). The resulting mixture was concentrated under reduced pressure to about the volume of 10 mL. Isopropanol (15 mL) was added followed by chloroacetaldehyde (50 wt % in water) (3.473 g, 22.12 mmol). The mixture was stirred at 80° C. for 1 h. After cooling to room temperature, the mixture was diluted with $CH_2Cl_2$, and washed with aqueous $K_2CO_3$ (2 M). The separated organic phase was dried over anhydrous $Na_2SO_4$, filtered and concentrated. The residue was purified on silica gel (40 g, 0-100% EtOAc in $CH_2Cl_2$) to give the desired product as a yellow solid (178.7 mg, 47%). LCMS calculated for $C_8H_7ClN_3O_2(M+H)^+$ m/z=212.0. found 212.0.

Step 3: Methyl 7-(4-(4-(tert-butoxycarbonyl)piperazin-1-yl)phenyl)imidazo[1,2-b]pyridazine-6-carboxylate

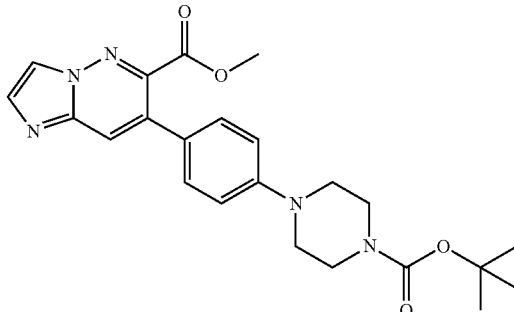

A screw-cap vial equipped with a magnetic stir bar was charged with methyl 7-chloroimidazo[1,2-b]pyridazine-6-carboxylate (178.7 mg, 0.844 mmol), tert-butyl 4-(4-(4,4,5,5-tetramethyl-1,3,2-dioxaborolan-2-yl)phenyl)piperazine-1-carboxylate (492 mg, 1.267 mmol), bis(di-tert-butyl(4-dimethylaminophenyl)phosphine)dichloropalladium(II) (90.9 mg, 0.128 mmol) and CsF (513.0 mg, 3.38 mmol). The vial was sealed with a Teflon-lined septum, evacuated and backfilled with nitrogen (this process was repeated a total of three times). Butan-1-ol (6.0 ml) was added via syringe, followed by water (2.0 ml). The reaction was stirred at 60° C. for 5 h. After cooling to room temperature, the reaction mixture was concentrated. The residue was purified on silica gel (40 g, 0-100% EtOAc in $CH_2Cl_2$) to give the desired product as a yellow semi-solid (341.0 mg, 92%). LCMS calculated for $C_{23}H_{28}N_5O_4$ $(M+H)^+$ m/z=438.2. found 438.2.

Step 4: Methyl 7-(4-(4-(tert-butoxycarbonyl)piperazin-1-yl)phenyl)-3-iodoimidazo[1,2-b]pyridazine-6-carboxylate

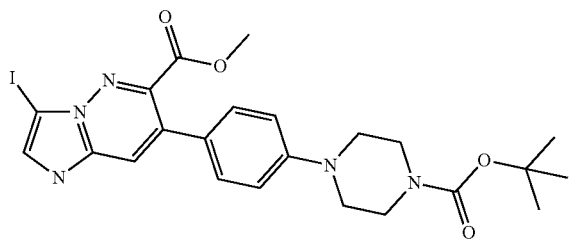

A solution of methyl 7-(4-(4-(tert-butoxycarbonyl)piperazin-1-yl)phenyl)imidazo[1,2-b]pyridazine-6-carboxylate (341.0 mg, 0.779 mmol) in DMF (5.0 mL) was treated with NIS (267.6 mg, 1.189 mmol). The mixture was stirred at 50° C. for 1 h. After cooling to room temperature, the mixture was concentrated in vacuo. The residue was purified on silica gel (20 g, 0-100% EtOAc in $CH_2Cl_2$) to give the desired product as a yellow foamy solid (186.1 mg, 42%). LCMS calculated for $C_{23}H_{27}IN_5O_4(M+H)^+$ m/z=564.1. found 564.1.

Step 5: Methyl 7-(4-(4-(tert-butoxycarbonyl)piperazin-1-yl)phenyl)-3-(quinolin-4-yl) imidazo[1,2-b]pyridazine-6-carboxylate

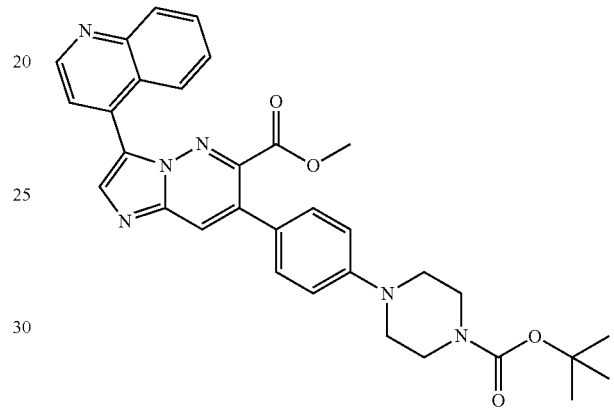

A screw-cap vial equipped with a magnetic stir bar was charged with methyl 7-(4-(4-(tert-butoxycarbonyl)piperazin-1-yl)phenyl)-3-iodoimidazo[1,2-b]pyridazine-6-carboxylate (186.1 mg, 0.330 mmol), 4-(4,4,5,5-tetramethyl-1,3,2-dioxaborolan-2-yl)quinoline (126 mg, 0.495 mmol), bis(di-tert-butyl(4-dimethylaminophenyl)phosphine)dichloropalladium(II) (35.1 mg, 0.050 mmol) and CsF (201 mg, 1.321 mmol). The vial was sealed with a Teflon-lined septum, evacuated and backfilled with nitrogen (this process was repeated a total of three times). Butan-1-ol (6.0 ml) was added via syringe, followed by water (2.0 ml). The reaction was stirred at 60° C. for 5 h. After cooling to room temperature, the reaction mixture was concentrated. The residue was purified on silica gel (40 g, 0-100% EtOAc in $CH_2Cl_2$) to give the desired product as a yellow foamy solid (165.5 mg, 89%). LCMS calculated for $C_{32}H_{33}N_6O_4$ $(M+H)^+$ m/z=565.3. found 565.2.

Step 6: Methyl 7-(4-(piperazin-1-yl)phenyl)-3-(quinolin-4-yl)imidazo[1,2-b]pyridazine-6-carboxylate A solution of methyl 7-(4-(4-(tert-butoxycarbonyl)piperazin-1-yl)phenyl)-3-(quinolin-4-yl)imidazo[1,2-b]pyridazine-6-carboxylate (15.0 mg, 0.027 mmol) in $CH_2Cl_2$ (2.0 mL) was treated with TFA (2.0 mL). The mixture was stirred at room temperature for 15 min, and then concentrated. The residue was purified using prep-LCMS (XBridge C18 column, eluting with a gradient of acetonitrile/water containing 0.1% TFA, at flow rate of 60 mL/min) to afford the desired product as its TFA salt. LCMS calculated for $C_{27}H_{25}N_6O_2$ $(M+H)^+$: m/z=465.2. found: 465.2. $^1$H NMR (TFA salt, 600 MHz, DMSO) δ 9.10 (d, J=4.5 Hz, 1H), 8.77 (br, 2H), 8.44 (s, 1H), 8.38 (s, 1H), 8.18 (d, J=8.5 Hz, 1H), 7.97

(d, J=8.4, 1H), 7.90 (d, J=4.5 Hz, 1H), 7.88 (m, 1H), 7.67 (m, 1H), 7.41 (d, J=8.7 Hz, 2H), 7.13 (d, J=8.7 Hz, 2H), 3.69 (s, 3H), 3.46 (m, 4H), 3.27 (m, 4H).

Example 3. N-((1R,4R)-4-Hydroxy-4-methylcyclohexyl)-7-(4-(piperazin-1-yl)phenyl)-3-(quinolin-4-yl)imidazo[1,2-b]pyridazine-6-carboxamide

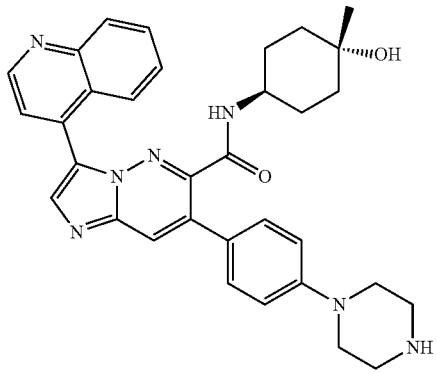 [SMILES: C[C@]1(O)CC[C@H](NC(=O)c2nn3c(-c4ccnc5ccccc45)cnc3cc2-c2ccc(N3CCNCC3)cc2)CC1]

Step 1: 7-(4-(4-(tert-Butoxycarbonyl)piperazin-1-yl)phenyl)-3-(quinolin-4-yl)imidazo[1,2-b]pyridazine-6-carboxylic Acid

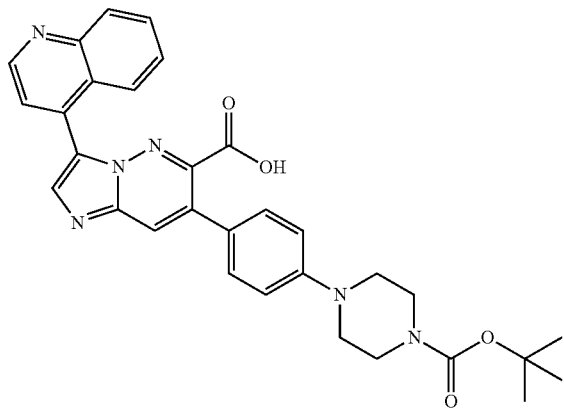 [SMILES: CC(C)(C)OC(=O)N1CCN(c2ccc(-c3cc4ncc(-c5ccnc6ccccc56)n4nc3C(=O)O)cc2)CC1]

A vial containing methyl 7-(4-(4-(tert-butoxycarbonyl)piperazin-1-yl)phenyl)-3-(quinolin-4-yl)imidazo[1,2-b]pyridazine-6-carboxylate (122.3 mg, 0.217 mmol, see step 5 in Example 2) was treated with lithium hydroxide, monohydrate (44.7 mg, 1.065 mmol), followed by MeOH (3.0 mL), THF (2.0 mL) and water (3.00 mL). The solution was stirred at 60° C. for 3 h, and then was allowed to cool to room temperature. CH$_2$Cl$_2$ (10 mL) was added followed by water (10 mL). The mixture was adjusted to pH=5 with 1 N HCl (aq). The separated aqueous phase was extracted with CH$_2$Cl$_2$ (3×). The combined organic phases were dried over anhydrous Na$_2$SO$_4$, filtered and concentrated to give the crude product as a red semi-oil (123.1 mg) which was used directly in the next step without further purification. LCMS calculated for C$_{31}$H$_{31}$N$_6$O$_4$ (M+H)$^+$: m/z=551.2. found: 551.2.

Step 2: N-((1R,4R)-4-Hydroxy-4-methylcyclohexyl)-7-(4-(piperazin-1-yl)phenyl)-3-(quinolin-4-yl)imidazo[1,2-b]pyridazine-6-carboxamide A solution of 7-(4-(4-(tert-butoxycarbonyl)piperazin-1-yl)phenyl)-3-(quinolin-4-yl)imidazo[1,2-b]pyridazine-6-carboxylic acid (20.0 mg, 0.036 mmol) in DMF (1.0 ml) was treated with HATU (55.2 mg, 0.145 mmol). The mixture was stirred at room temperature for 10 min, then cis-4-amino-1-methylcyclohexanol (48.9 mg, 0.378 mmol) was added followed by DIPEA (100.0 μL, 0.573 mmol). The reaction mixture was stirred to 50° C. for 16 h. After cooling to room temperature, the reaction was concentrated. The residue was treated with CH$_2$Cl$_2$ (2.0 mL) followed by TFA (2.0 mL). The mixture was stirred at room temperature for 15 min, and then concentrated. The residue was purified using prep-LCMS (XBridge C18 column, eluting with a gradient of acetonitrile/water containing 0.1% TFA, at flow rate of 60 mL/min) to afford the desired product as its TFA salt. LCMS calculated for C$_{33}$H$_{36}$N$_7$O$_2$ (M+H)$^+$: m/z=562.3. found: 562.3.

Example 4. Ethyl 4-(7-(4-(piperazin-1-yl)phenyl)-3-(quinolin-4-yl)imidazo[1,2-b]pyridazine-6-carbonyl)piperazine-1-carboxylate

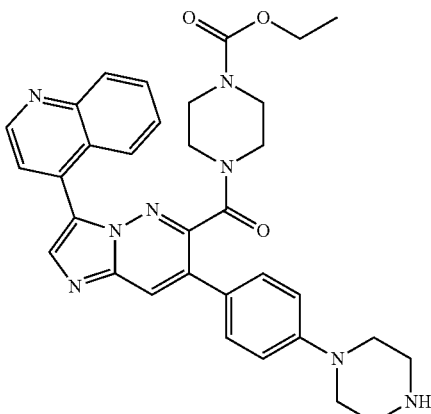

This compound was prepared according to the procedure described in Example 3 (step 2), using ethyl 1-piperazinecarboxylate instead of cis-4-amino-1-methylcyclohexanol as the starting material. LCMS calculated for C$_{33}$H$_{35}$N$_8$O$_3$ (M+H)+: m/z=591.3. found: 591.3.

Example 5. 7-(4-(Piperazin-1-yl)phenyl)-3-(quinolin-4-yl)imidazo[1,2-b]pyridazine-6-carboxamide

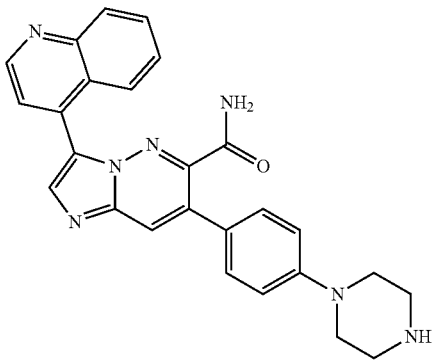 [SMILES: NC(=O)c1nn2c(-c3ccnc4ccccc34)cnc2cc1-c1ccc(N2CCNCC2)cc1]

Step 1: 7-(4-(4-(tert-Butoxycarbonyl)piperazin-1-yl)phenyl)-3-iodoimidazo[1,2-b]pyridazine-6-carboxylic Acid

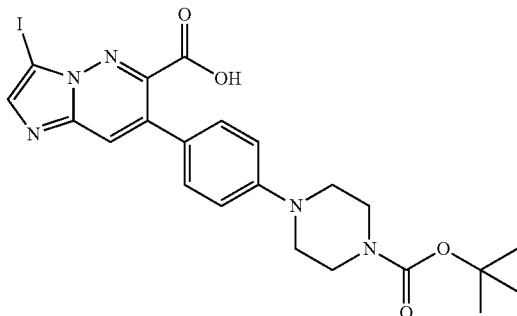

A vial containing methyl 7-(4-(4-(tert-butoxycarbonyl)piperazin-1-yl)phenyl)-3-iodoimidazo[1,2-b]pyridazine-6-carboxylate (147.2 mg, 0.261 mmol, see step 4 in Example 2) was treated with lithium hydroxide, monohydrate (44.7 mg, 1.065 mmol), followed by MeOH (3.0 mL), THF (2.0 mL) and water (3.00 mL). The solution was stirred at 60° C. for 3 h, and then was allowed to cool to room temperature. $CH_2Cl_2$ (10 mL) was added followed by water (10 mL). The mixture was adjusted to pH=5 with 1 N HCl (aq). The separated aqueous phase was extracted with $CH_2Cl_2$ (3×). The combined organic phases were dried over anhydrous $Na_2SO_4$, filtered and concentrated to give the crude product as a yellow semi-solid (127.7 mg) which was used directly in the next step without further purification. LCMS calculated for $C_{22}H_{25}IN_5O_4(M+H)^+$: m/z=550.1. found: 550.1.

Step 2: tert-Butyl 4-(4-(6-carbamoyl-3-iodoimidazo[1,2-b]pyridazin-7-yl)phenyl)piperazine-1-carboxylate

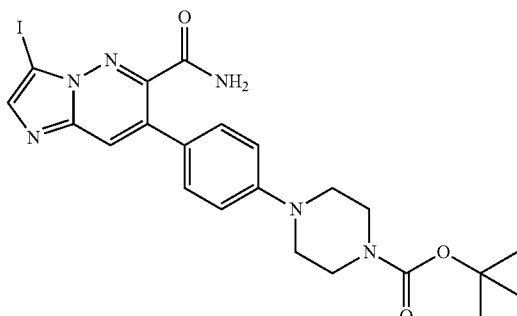

A solution of 7-(4-(4-(tert-butoxycarbonyl)piperazin-1-yl)phenyl)-3-iodoimidazo[1,2-b]pyridazine-6-carboxylic acid (127.7 mg, 0.232 mmol) in DMF (5.0 mL) was treated with HATU (178.0 mg, 0.468 mmol). The mixture was stirred at room temperature for 10 min. Ammonium chloride (67.2 mg, 1.256 mmol) was added followed by DIPEA (387.9 mg, 3.00 mmol). After stirring at room temperature for 1 h, the reaction mixture was concentrated. The residue was purified on silica gel (20 g, 0-100% EtOAc in $CH_2Cl_2$) to give the desired product as a yellow solid (113.5 mg, 89%). LCMS calculated for $C_{22}H_{26}IN_6O_3(M+H)^+$: m/z=549.1. found: 549.1.

Step 3: 7-(4-(Piperazin-1-yl)phenyl)-3-(quinolin-4-yl)imidazo[1,2-b]pyridazine-6-carboxamide A screw-cap vial equipped with a magnetic stir bar was charged with tert-butyl 4-(4-(6-carbamoyl-3-iodoimidazo[1,2-b]pyridazin-7-yl)phenyl)piperazine-1-carboxylate (14.7 mg, 0.027 mmol), 4-(4,4,5,5-tetramethyl-1,3,2-dioxaborolan-2-yl)quinoline (10.3 mg, 0.040 mmol), dicyclohexyl(2',4',6'-triisopropylbiphenyl-2-yl)phosphine-(2'-aminobiphenyl-2-yl)(chloro)palladium (1:1) (XPhos Pd G2, 5.00 mg, 6.35 µmol) and cesium carbonate (34.9 mg, 0.107 mmol). The vial was sealed with a Teflon-lined septum, evacuated and backfilled with nitrogen (this process was repeated a total of three times). 1,4-Dioxane (2.0 ml) was added via syringe, followed by water (200.0 µl, 11.10 mmol). The mixture was heated at 80° C. for 2 h. After cooling to room temperature, the reaction was concentrated. The residue was treated with $CH_2Cl_2$ (2.0 mL) followed by TFA (2.0 mL). The mixture was stirred at room temperature for 15 min, and then concentrated. The residue was purified using prep-LCMS (XBridge C18 column, eluting with a gradient of acetonitrile/water containing 0.1% TFA, at flow rate of 60 mL/min) to afford the desired product as its TFA salt. LCMS calculated for $C_{26}H_{24}N_7O$ $(M+H)^+$: m/z=450.2. found: 450.2.

Example 6. 7-(4-(piperazin-1-yl)phenyl)-3-(quinolin-4-yl)imidazo[1,2-b]pyridazine-6-carbonitrile

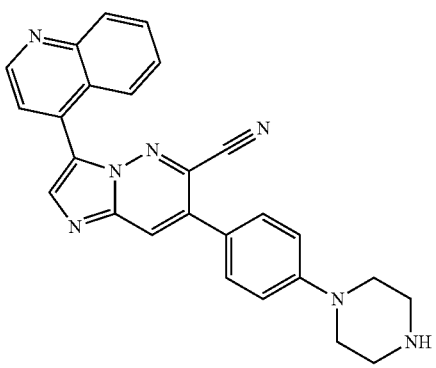 [SMILES: N#Cc1nn2c(-c3ccnc4ccccc34)cnc2cc1-c1ccc(N2CCNCC2)cc1]

Step 1: 7-(4-(4-(tert-Butoxycarbonyl)piperazin-1-yl)phenyl)-3-iodoimidazo[1,2-b]pyridazine-6-carboxylic Acid

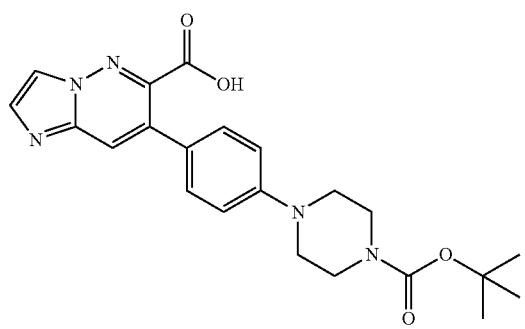 [SMILES: CC(C)(C)OC(=O)N1CCN(c2ccc(-c3cc4nccn4nc3C(=O)O)cc2)CC1]

A vial containing methyl 7-(4-(4-(tert-butoxycarbonyl)piperazin-1-yl)phenyl)imidazo-[1,2-b]pyridazine-6-carboxylate (555.3 mg, 1.269 mmol, see step 3 in Example 2) was treated with lithium hydroxide, monohydrate (269.1 mg, 6.41 mmol), followed by MeOH (5.0 mL), THF (5.0 mL) and water (5.0 mL). The solution was stirred at 60° C. for 3 h, and then was allowed to cool to room temperature. CH$_2$Cl$_2$ (20 mL) was added, followed by water (20 mL). The mixture was adjusted to pH=5 with 1 N HCl (aq). The separated aqueous phase was extracted with CH$_2$Cl$_2$ (3×). The combined organic phases were dried over anhydrous Na$_2$SO$_4$, filtered and concentrated to give the crude product as a yellow solid (312.5 mg) which was used directly in the next step without further purification. LCMS calculated for C$_{22}$H$_{26}$N$_5$O$_4$ (M+H)$^+$: m/z=424.2. found: 424.2.

Step 2: tert-Butyl 4-(4-(6-carbamoylimidazo[1,2-b]pyridazin-7-yl)phenyl)piperazine-1-carboxylate

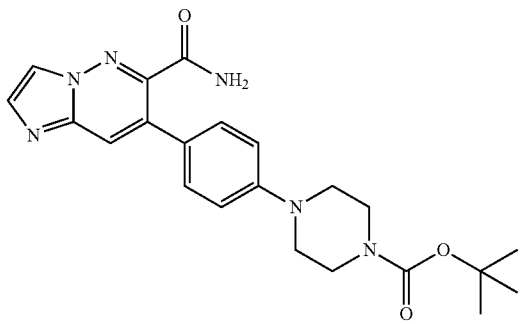 [SMILES: CC(C)(C)OC(=O)N1CCN(c2ccc(-c3cc4nccn4nc3C(N)=O)cc2)CC1]

A solution of 7-(4-(4-(tert-butoxycarbonyl)piperazin-1-yl)phenyl)imidazo[1,2-b]pyridazine-6-carboxylic acid (312.5 mg, 0.738 mmol) in DMF (5.0 mL) was treated with HATU (424.9 mg, 1.117 mmol). The mixture was stirred at room temperature for 10 min. Ammonium chloride (208.9 mg, 3.91 mmol) was added followed by DIPEA (1104 mg, 8.54 mmol). After stirring at room temperature for 1 h, the reaction mixture was diluted with CH$_2$C$_2$ and washed with water. The separated organic phase was dried over anhydrous Na$_2$SO$_4$, filtered and concentrated. The residue was purified on silica gel (20 g, 0-100% EtOAc in CH$_2$Cl$_2$) to give the desired product as a yellow solid (274.3 mg, 88%). LCMS calculated for C$_{22}$H$_{27}$N$_6$O$_3$ (M+H)$^+$: m/z=423.2. found: 423.2.

Step 3: tert-Butyl 4-(4-(6-cyanoimidazo[1,2-b]pyridazin-7-yl)phenyl)piperazine-1-carboxylate

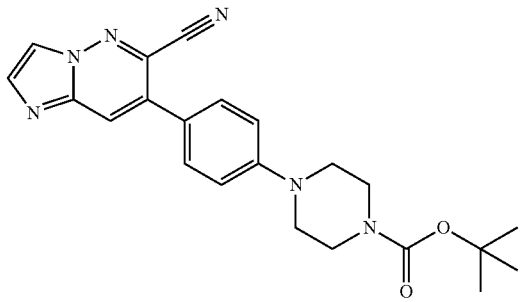 [SMILES: CC(C)(C)OC(=O)N1CCN(c2ccc(-c3cc4nccn4nc3C#N)cc2)CC1]

A solution of tert-butyl 4-(4-(6-carbamoylimidazo[1,2-b]pyridazin-7-yl)phenyl)-piperazine-1-carboxylate (274.3 mg, 0.649 mmol) in acetonitrile (8.0 mL) was treated with triethylamine (316.6 mg, 3.13 mmol) and triphenylphosphine oxide (18.6 mg, 0.067 mmol). Then a solution of oxalyl chloride (168.0 mg, 1.324 mmol) in acetonitrile (2.0 mL) was added dropwise. After stirring at room temperature for 1 h, the reaction mixture was diluted with Et$_2$O and washed with water. The separated organic phase was dried over anhydrous Na$_2$SO$_4$, filtered and concentrated. The residue was purified on silica gel (20 g, 0-100% EtOAc in CH$_2$Cl$_2$) to give the desired product as a yellow solid (124.2 mg, 47%). LCMS calculated for C$_{22}$H$_{25}$N$_6$O$_2$ (M+H)$^+$: m/z=405.2. found: 405.2.

Step 4: tert-Butyl 4-(4-(6-cyano-3-iodoimidazo[1,2-b]pyridazin-7-yl)phenyl)piperazine-1-carboxylate

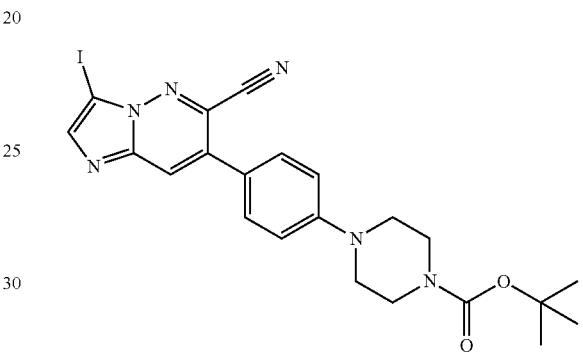

A solution of tert-butyl 4-(4-(6-cyanoimidazo[1,2-b]pyridazin-7-yl)phenyl)piperazine-1-carboxylate (24.6 mg, 0.061 mmol) in DMF (1.5 mL) was treated with NIS (22.3 mg, 0.099 mmol) After stirring at room temperature for 16 h, the reaction was concentrated. The residue was purified on silica gel (10 g, 0-100% EtOAc in CH$_2$Cl$_2$) to give the desired product as a white solid (6.5 mg, 20%). LCMS calculated for C$_{22}$H$_{24}$IN$_6$O$_2$ (M+H)$^+$: m/z=531.1. found: 531.1.

Step 5: 7-(4-(Piperazin-1-yl)phenyl)-3-(quinolin-4-yl)imidazo[1,2-b]pyridazine-6-carbonitrile A screw-cap vial equipped with a magnetic stir bar was charged with tert-butyl 4-(4-(6-cyano-3-iodoimidazo[1,2-b]pyridazin-7-yl)phenyl)piperazine-1-carboxylate (6.5 mg, 0.012 mmol), 4-(4,4,5,5-tetramethyl-1,3,2-dioxaborolan-2-yl)quinoline (4.8 mg, 0.019 mmol), dicyclohexyl(2',4',6'-triisopropylbiphenyl-2-yl)phosphine-(2'-aminobiphenyl-2-yl)(chloro)palladium (1:1) (XPhos Pd G2, 3.1 mg, 3.94 µmol) and cesium carbonate (15.5 mg, 0.048 mmol). The vial was sealed with a Teflon-lined septum, evacuated and backfilled with nitrogen (this process was repeated a total of three times). 1,4-Dioxane (1.0 ml) was added via syringe, followed by water (100.0 µl, 5.55 mmol). The mixture was heated at 80° C. for 2 h. After cooling to room temperature, the reaction was concentrated. The residue was treated with CH$_2$Cl$_2$ (2.0 mL) followed by TFA (2.0 mL). The mixture was stirred at room temperature for 15 min, and then concentrated. The residue was purified using prep-LCMS (XBridge C18 column, eluting with a gradient of acetonitrile/water containing 0.15% NH$_4$OH, at flow rate of 60 mL/min) to afford the desired product as its TFA salt. LCMS calculated for $C_{26}H_{22}N_7(M+H)^+$: m/z=432.2. found: 432.2.

Example 7. (7-(4-(Piperazin-1-yl)phenyl)-3-(quinolin-4-yl)imidazo[1,2-b]pyridazin-6-yl)methanol

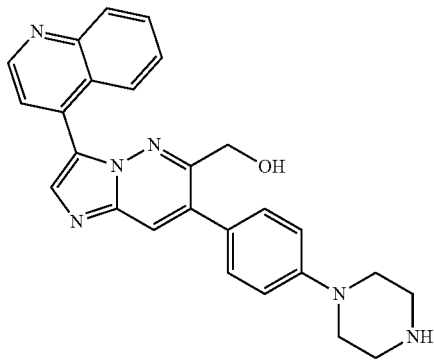 [SMILES: OCc1nn2c(-c3ccnc4ccccc34)cnc2cc1-c1ccc(N2CCNCC2)cc1]

Step 1: (7-Chloroimidazo[1,2-b]pyridazin-6-yl)methanol

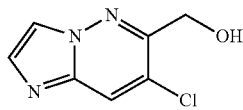 [SMILES: OCc1nn2ccnc2cc1Cl]

A solution of methyl 7-chloroimidazo[1,2-b]pyridazine-6-carboxylate (900.0 mg, 4.25 mmol, see step 2 in Example 2) in THF (20.0 mL) was treated with MeOH (10.00 mL). LiBH$_4$ (93.5 mg, 4.29 mmol) was added. The reaction was stirred at room temperature for 30 min, and then additional LiBH$_4$ (94.6 mg, 4.34 mmol) was added. After the reaction was stirred at room temperature for another 30 min, acetone (60.0 ml, 817 mmol) was added. The mixture was stirred at rt for 1 h, and then concentrated. The residue was diluted with Et$_2$O and washed with water. The separated organic phases were dried over anhydrous Na$_2$SO$_4$, filtered and concentrated. The residue was purified on silica gel (40 g, 0-100% EtOAc in CH$_2$Cl$_2$) to give the desired product as a white solid (179.2 mg, 23%). LCMS calculated for $C_7H_7ClN_3O (M+H)^+$: m/z=184.0. found: 184.0.

Step 2: tert-Butyl 4-(4-(6-(hydroxymethyl)imidazo[1,2-b]pyridazin-7-yl)phenyl)piperazine-1-carboxylate

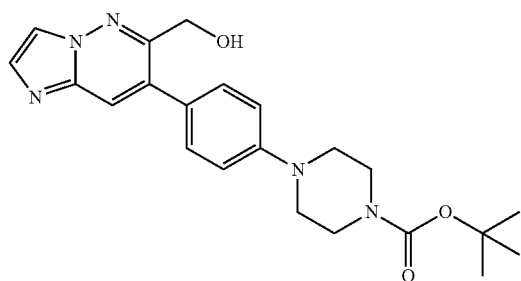 [SMILES: CC(C)(C)OC(=O)N1CCN(c2ccc(-c3cc4nccn4nc3CO)cc2)CC1]

A screw-cap vial equipped with a magnetic stir bar was charged with (7-chloroimidazo[1,2-b]pyridazin-6-yl)methanol (179.0 mg, 0.975 mmol), tert-butyl 4-(4-(4,4,5,5-tetramethyl-1,3,2-dioxaborolan-2-yl)phenyl)piperazine-1-carboxylate (568 mg, 1.462 mmol), dicyclohexyl(2',4',6'-triisopropylbiphenyl-2-yl)phosphine-(2'-aminobiphenyl-2-yl)(chloro)palladium (1:1) (XPhos Pd G2, 84.0 mg, 0.107 mmol) and cesium carbonate (1088 mg, 3.34 mmol). The vial was sealed with a Teflon-lined septum, evacuated and backfilled with nitrogen (this process was repeated a total of three times). 1,4-Dioxane (10.0 mL) was added via syringe, followed by water (1.0 mL, 55.5 mmol). The mixture was heated at 80° C. for 2 h. After cooling to room temperature, the reaction was concentrated. The residue was treated with CH$_2$Cl$_2$ (2.0 mL) followed by TFA (2.0 mL). The mixture was stirred at room temperature for 15 min, and then concentrated. The residue was purified on silica gel (40 g, 0-100% EtOAc in CH$_2$Cl$_2$, then 10% MeOH in CH$_2$Cl$_2$) to provide the desired product as a yellow solid (348.0 mg, 87%). LCMS calculated for $C_{22}H_{28}N_5O_3 (M+H)^+$: m/z=410.2. found: 410.2.

Step 3: tert-Butyl 4-(4-(6-(hydroxymethyl)-3-iodoimidazo[1,2-b]pyridazin-7-yl)phenyl)piperazine-1-carboxylate

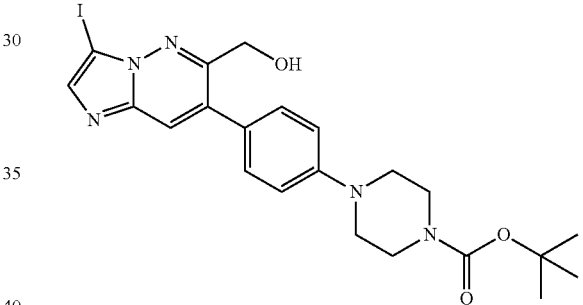

A solution of tert-butyl 4-(4-(6-(hydroxymethyl)imidazo[1,2-b]pyridazin-7-yl)phenyl)piperazine-1-carboxylate (348.0 mg, 0.850 mmol) in DMF (7.0 mL) was treated with NIS (233.6 mg, 1.038 mmol). After stirring at 50° C. for 1 h, the reaction was concentrated. The residue was purified on silica gel (40 g, 0-100% EtOAc in CH$_2$Cl$_2$) to give the desired product as a yellow foamy solid (222.3 mg, 49%). LCMS calculated for $C_{22}H_{27}IN_5O_3(M+H)^+$: m/z=536.1. found: 536.1.

Step 4: (7-(4-(Piperazin-1-yl)phenyl)-3-(quinolin-4-yl) imidazo[1,2-b]pyridazin-6-yl)methanol A screw-cap vial equipped with a magnetic stir bar was charged with tert-butyl 4-(4-(6-(hydroxymethyl)-3-iodoimidazo[1,2-b]pyridazin-7-yl)phenyl)piperazine-1-carboxylate (74.4 mg, 0.139 mmol), 4-(4,4,5,5-tetramethyl-1,3,2-dioxaborolan-2-yl)quinoline (42.6 mg, 0.167 mmol), dicyclohexyl(2',4',6'-triisopropylbiphenyl-2-yl)phosphine-(2'-aminobiphenyl-2-yl)(chloro)-palladium (1:1) (XPhos Pd G2, 16.4 mg, 0.021 mmol) and cesium carbonate (152.9 mg, 0.469 mmol). The vial was sealed with a Teflon-lined septum, evacuated and backfilled with nitrogen (this process was repeated a total of three times). 1,4-Dioxane (3.0 ml) was added via syringe, followed by water (300.0 µl, 16.65 mmol). The mixture was heated at 80° C. for 2 h. After cooling to room temperature, the reaction was concentrated. The residue was treated with CH$_2$Cl$_2$ (2.0 mL) followed by TFA (2.0 mL). The mixture was stirred at room temperature for 15 min, and then concentrated. The residue was purified using prep-LCMS (XBridge C18 column, eluting with a gradient of acetonitrile/water containing 0.15% NH$_4$OH, at flow rate of 60 mL/min) to afford the desired product (9.3 mg, 15%). LCMS calculated for C$_{26}$H$_{25}$N$_6$O (M+H)$^+$: m/z=437.2. found: 437.1. $^1$H NMR (600 MHz, DMSO) δ 9.06 (d, J=4.4 Hz, 1H), 8.22 (s, 1H), 8.15 (d, J=8.4 Hz, 1H), 8.09 (s, 1H), 8.03 (d, J=8.4 Hz, 1H), 7.97 (d, J=4.4 Hz, 1H), 7.85 (m, 1H), 7.65 (m, 1H), 7.55 (d, J=8.3 Hz, 2H), 7.04 (d, J=8.3 Hz, 2H), 5.41 (t, J=5.6 Hz, 1H), 4.49 (d, J=5.6 Hz, 2H), 3.17 (m, 4H), 2.88 (m, 4H).

Example 8. 4-(6-(Methoxymethyl)-7-(4-(piperazin-1-yl)phenyl)imidazo[1,2-b]pyridazin-3-yl)quinoline

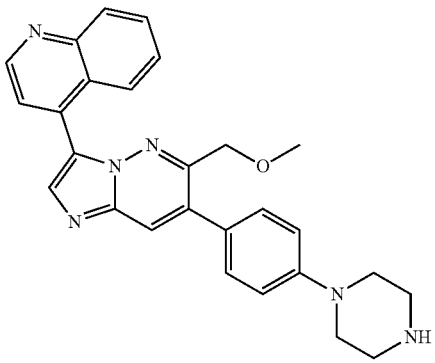 [SMILES: COCc1nn2c(-c3ccnc4ccccc34)cnc2cc1-c1ccc(N2CCNCC2)cc1]

Step 1: tert-Butyl 4-(4-(6-(hydroxymethyl)-3-(quinolin-4-yl)imidazo[1,2-b]pyridazin-7-yl)phenyl)piperazine-1-carboxylate

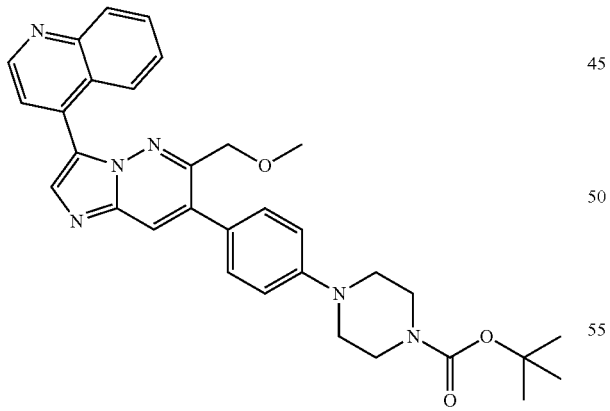

A solution of (7-(4-(piperazin-1-yl)phenyl)-3-(quinolin-4-yl)imidazo[1,2-b]pyridazin-6-yl)methanol (9.3 mg, 0.021 mmol, see step 4 in Example 7) in CH$_2$Cl$_2$ (2.0 mL) at room temperature was treated with a solution of Boc-anhydride (5.0 mg, 0.023 mmol) in THF (0.5 mL) followed by DMAP (2.60 mg, 0.021 mmol). After stirring at room temperature for 1 h, the reaction mixture was purified using prep-LCMS (XBridge C18 column, eluting with a gradient of acetonitrile/water containing 0.15% NH$_4$OH, at flow rate of 60 mL/min) to afford the desired product (5.0 mg, 44%). LCMS calculated for C$_{31}$H$_{33}$N$_6$O$_3$ (M+H)$^+$: m/z=537.3. found: 537.3.

Step 2: 4-(6-(Methoxymethyl)-7-(4-(4-(piperazin-1-yl)phenyl)imidazo[1,2-b]pyridazin-3-yl)quinoline A solution of tert-butyl 4-(4-(6-(hydroxymethyl)-3-(quinolin-4-yl)imidazo[1,2-b]pyridazin-7-yl)phenyl)piperazine-1-carboxylate (5.0 mg, 9.32 μmol) in THF (3.0 mL) at −78° C. under N$_2$ atmosphere was treated with a solution of KHMDS (1.0 M in THF) (100.0 μL, 0.100 mmol). The mixture was then allowed to warm to room temperature and stirred for 20 min. The mixture was cooled back to −78° C., then a solution of MeI (1.0 M in MTBE) (50.0 μL, 0.050 mmol) was added. The mixture was allowed to warm to room temperature. After the reaction was stirred at room temperature for 30 min, MeOH (2.0 mL) was added. The reaction was concentrated. The residue was treated with CH$_2$Cl$_2$ (2.0 mL) followed by TFA (2.0 mL). The mixture was stirred at room temperature for 15 min, and then concentrated. The residue was purified using prep-LCMS (XBridge C18 column, eluting with a gradient of acetonitrile/water containing 0.1% TFA, at flow rate of 60 mL/min) to afford the desired product as its TFA salt. LCMS calculated for C$_{27}$H$_{27}$N$_6$O (M+H)$^+$: m/z=451.2. found: 451.2. $^1$H NMR (TFA salt, 400 MHz, DMSO) δ 9.12 (d, J=4.7 Hz, 1H), 877 (br, 2H), 8.33 (s, 1H), 8.22-8.15 (overlap, 2H), 8.05 (d, J=7.9 Hz, 1H), 7.99 (d, J=4.7 Hz, 1H), 7.91 (m, 1H), 7.68 (m, 1H), 7.55 (d, J=8.7 Hz, 2H), 7.14 (d, J=8.7 Hz, 2H), 4.41 (s, 2H), 3.46 (m, 4H), 3.27 (m, 4H), 3.19 (s, 3H).

Example 9. 4-(6-Methyl-7-(1-(piperidin-4-ylmethyl)-1H-pyrazol-4-yl)imidazo[1,2-b]pyridazin-3-yl)-7-(pyridin-4-yl)quinolone

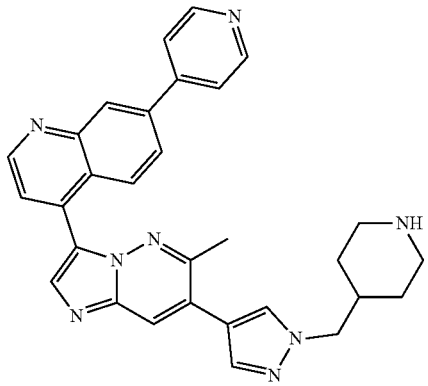 [SMILES: Cc1nn2c(-c3ccnc4cc(-c5ccncc5)ccc34)cnc2cc1-c1cnn(CC2CCNCC2)c1]

Step 1. 4-chloro-7-(pyridin-4-yl)quinoline

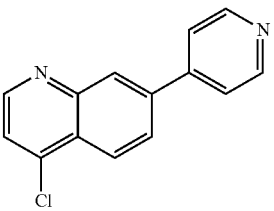 [SMILES: Clc1ccnc2cc(-c3ccncc3)ccc12]

A vial was charged with of 4-chloro-7-iodoquinoline (0.579 g, 2.0 mmol), 4-(4,4,5,5-tetramethyl-1,3,2-dioxaborolan-2-yl)pyridine (0.410 g, 2.000 mmol), potassium phosphate (0.849 g, 4.00 mmol), PdCl$_2$(dppf) (0.117 g, 0.160 mmol) and 1,4-dioxane (8.0 ml)/water (1.50 ml). The vial was sealed with a Teflon-lined septum, evacuated and backfilled with nitrogen (this process was repeated a total of three times). The reaction was stirred at 100° C. for 3 h. The mixture was extracted with ethyl acetate and then the product was purified on silica gel (24 g) eluting with CH$_2$Cl$_2$/MeOH (max MeOH 10%). The desired product was isolated as its TFA salt. LC-MS calculated for C$_{14}$H$_{10}$ClN$_2$ (M+H)$^+$: m/z=241.1. found 241.1.

Step 2. (7-(pyridin-4-yl)quinolin-4-yl)boronic Acid

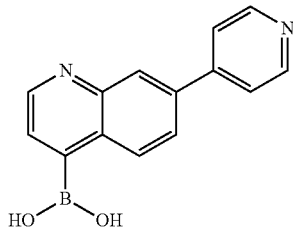 [SMILES: OB(O)c1ccnc2cc(-c3ccncc3)ccc12]

A vial was charged with mixture of 4,4,5,5,4',4',5',5'-Octamethyl-[2,2']bi[[1,3,2]-dioxaborolanyl] (0.380 g, 1.496 mmol), potassium acetate (0.196 g, 1.994 mmol), 4-chloro-7-(pyridin-4-yl)quinoline (0.240 g, 0.997 mmol) and PdCl$_2$(dppf) (0.073 g, 0.100 mmol) in 1,4-dioxane (5.0 mL). The vial was sealed with a Teflon-lined septum, evacuated and backfilled with nitrogen (this process was repeated a total of three times). The mixture was stirred at 105° C. for 6 h. The mixture was used in the next step directly without concentration of the solvent. LC-MS calculated for C$_{14}$H$_{12}$BN$_2$O$_2$ (M+H)$^+$: m/z=251.1. found 251.1.

Step 3. 4-(7-chloro-6-methylimidazo[1,2-b]pyridazin-3-yl)-7-(pyridin-4-yl)quinoline

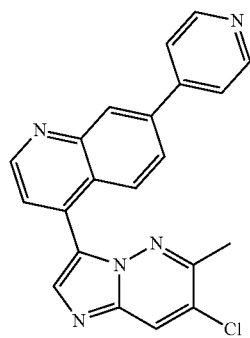 [SMILES: Cc1nn2c(-c3ccnc4cc(-c5ccncc5)ccc34)cnc2cc1Cl]

A vial was charged with a mixture of (7-(pyridin-4-yl)quinolin-4-yl)boronic acid (0.128 g, 0.511 mmol), 7-chloro-3-iodo-6-methylimidazo[1,2-b]pyridazine (0.15 g, 0.511 mmol, see step 3 in Example 1), potassium phosphate (0.217 g, 1.022 mmol) and PdCl$_2$(dppf) (0.037 g, 0.051 mmol) in 1,4-dioxane (4.0 ml)/water (0.6 ml). The vial was sealed with a Teflon-lined septum and backfilled with nitrogen (this process was repeated a total of three times). The reaction was stirred at 100° C. for 3 h. The mixture was extracted with ethyl acetate and then the product was purified on silica gel (12 g) eluting with CH$_2$Cl$_2$/MeOH (max MeOH 10%). LC-MS calculated for C$_{21}$H$_{15}$ClN$_5$ (M+H)$^+$: m/z=372.1. found 372.1.

Step 4. 4-(6-methyl-7-(1-(piperidin-4-ylmethyl)-1H-pyrazol-4-yl) imidazo[1,2-b]pyridazin-3-yl)-7-(pyridin-4-yl)quinoline A vial was charged with a mixture of 4-(7-chloro-6-methylimidazo[1,2-b]pyridazin-3-yl)-7-(pyridin-4-yl)quinoline (12.0 mg, 0.032 mmol), tert-butyl 4-((4-(4,4,5,5-tetramethyl-1,3,2-dioxaborolan-2-yl)-1H-pyrazol-1-yl)methyl)piperidine-1-carboxylate (18.94 mg, 0.048 mmol), potassium phosphate (13.70 mg, 0.065 mmol) and chloro(2-dicyclohexylphosphino-2',4',6'-tri-isopropyl-1,1'-biphenyl)(2'-amino-1,1'-biphenyl-2-yl) palladium(II) (XPhos Pd G2, 1.5 mg, 3.23 μmol) in dioxane (0.8 ml)/water (0.20 ml). The vial was sealed with a Teflon-lined septum, evacuated and backfilled with nitrogen (this process was repeated a total of three times). The reaction mixture was stirred at 70° C. for 1 h. The solvent was removed and the residue was treated with CH$_2$Cl$_2$/TFA (0.5/0.5 mL) for 30 min. The solvent was concentrated and the mixture was diluted with acetonitrile/water and purified using prep-LCMS (XBridge C18 column, eluting with a gradient of acetonitrile/water containing 0.1% TFA, at flow rate of 60 mL/min) to afford the desired compound as its TFA salt. LC-MS calculated for C$_{30}$H$_{29}$N$_8$(M+H)$^+$: m/z=501.3. found 501.4.

Example 10. (trans)-4-(4-(6-Methyl-3-(7-(pyridin-4-yl)quinolin-4-yl)imidazo[1,2-b]pyridazin-7-yl)-1H-pyrazol-1-yl)cyclohexan-1-ol

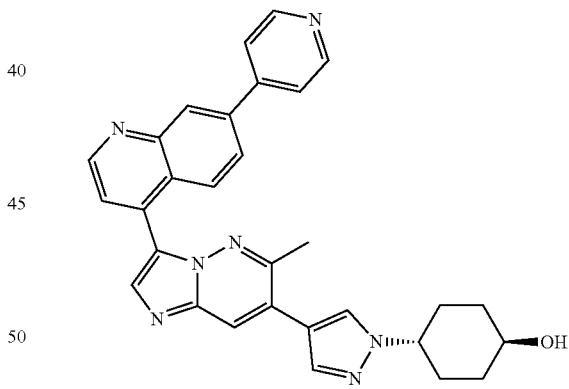

A screw-cap vial equipped with a magnetic stir bar was charged with 4-(7-chloro-6-methylimidazo[1,2-b]pyridazin-3-yl)-7-(pyridin-4-yl)quinoline (12.0 mg, 0.032 mmol, see step 3 in Example 9), 1-(trans)-4-((tert-butyldimethylsilyl)oxy)cyclohexyl)-4-(4,4,5,5-tetramethyl-1,3,2-dioxaborolan-2-yl)-1H-pyrazole (19.68 mg, 0.048 mmol), potassium phosphate (13.70 mg, 0.065 mmol) and chloro(2-dicyclohexylphosphino-2',4',6'-tri-isopropyl-1,1'-biphenyl)(2'-amino-1,1'-biphenyl-2-yl) palladium(II) (XPhos Pd G2, 1.5 mg, 3.23 μmol) in dioxane (0.800 ml)/water (0.20 ml). The vial was sealed with a Teflon-lined septum, evacuated and backfilled with nitrogen (this process was repeated a total of three times). The reaction mixture was stirred at 70° C. for 1 h. The mixture was then treated with conc. HCl (0.4 mL)

and stirred at rt for 2 h. The mixture was diluted with acetonitrile/water and purified using prep-LCMS (XBridge C18 column, eluting with a gradient of acetonitrile/water containing 0.1% TFA, at flow rate of 60 mL/min) to afford the desired product as its TFA salt. LC-MS calculated for $C_{30}H_{28}N_7O_3$ (M+H)$^+$: m/z=502.3. found 502.4.

Example 11. 2-(4-(4-(6-Methyl-3-(7-(pyridin-4-yl)quinolin-4-yl)imidazo[1,2-b]pyridazin-7-yl)phenyl)piperazin-1-yl)ethan-1-ol

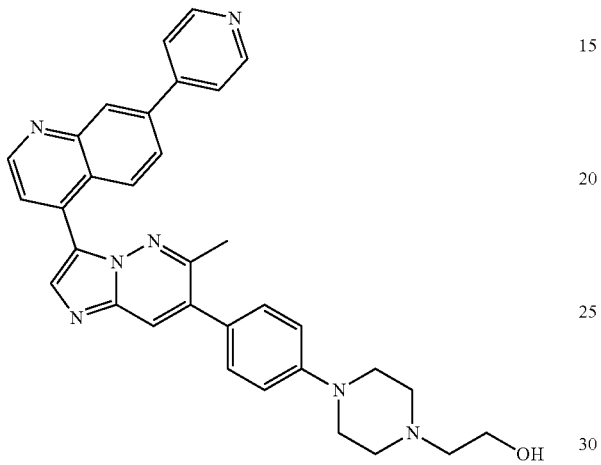

This compound was prepared according to the procedure described in Example 10, using 1-(2-((tert-butyldimethylsilyl)oxy)ethyl)-4-(4-(4,4,5,5-tetramethyl-1,3,2-dioxaborolan-2-yl)phenyl)piperazine instead of 1-(trans)-4-((tert-butyldimethylsilyl)oxy)cyclohexyl)-4-(4,4,5,5-tetramethyl-1,3,2-dioxaborolan-2-yl)-1H-pyrazole as the starting material. LC-MS calculated for $C_{33}H_{32}N_7O$ (M+H)$^+$: m/z=542.3. found 542.5.

Example 12. 4-Methyl-1-(4-(6-methyl-3-(7-(pyridin-4-yl)quinolin-4-yl)imidazo[1,2-b]pyridazin-7-yl)phenyl)piperazin-2-one

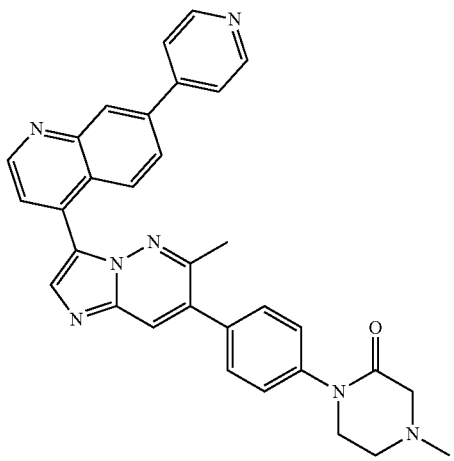 [SMILES: Cc1nn2c(-c3ccnc4cc(-c5ccncc5)ccc34)cnc2cc1-c1ccc(N2CCN(C)CC2=O)cc1]

A screw-cap vial equipped with a magnetic stir bar was charged with 4-(7-chloro-6-methylimidazo[1,2-b]pyridazin-3-yl)-7-(pyridin-4-yl)quinoline (12.0 mg, 0.032 mmol), 4-methyl-1-(4-(4,4,5,5-tetramethyl-1,3,2-dioxaborolan-2-yl)phenyl)piperazin-2-one (15.31 mg, 0.048 mmol), potassium phosphate (13.70 mg, 0.065 mmol) and chloro(2-dicyclohexylphosphino-2',4',6'-tri-isopropyl-1,1'-biphenyl)(2'-amino-1,1'-biphenyl-2-yl) palladium(II) (XPhos Pd G2, 1.5 mg, 3.23 μmol) in dioxane (0.80 ml)/water (0.20 ml). The vial was sealed with a Teflon-lined septum, evacuated and backfilled with nitrogen (this process was repeated a total of three times). The reaction mixture was stirred at 70° C. for 1 h. The solvent was concentrated and the mixture was diluted with acetonitrile/water and purified using prep-LCMS (XBridge C18 column, eluting with a gradient of acetonitrile/water containing 0.1% TFA, at flow rate of 60 mL/min) to afford the desired product as its TFA salt. LC-MS calculated for $C_{32}H_{28}N_7O$ (M+H)$^+$: m/z=526.3. found 526.5.

Example 13. 4-(6-Methyl-7-(3-(4-methylpiperazin-1-yl)phenyl)imidazo[1,2-b]pyridazin-3-yl)-7-(pyridin-4-yl)quinolone

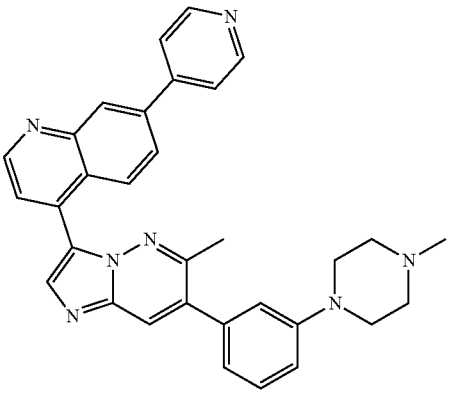 [SMILES: Cc1nn2c(-c3ccnc4cc(-c5ccncc5)ccc34)cnc2cc1-c1cccc(N2CCN(C)CC2)c1]

This compound was prepared according to the procedure described in Example 12, using (3-(4-methylpiperazin-1-yl)phenyl)boronic acid instead of 4-methyl-1-(4-(4,4,5,5-tetramethyl-1,3,2-dioxaborolan-2-yl)phenyl)piperazin-2-one as the starting material. The desired product was isolated as its TFA salt. LC-MS calculated for $C_{32}H_{30}N_7$(M+H)$^+$: m/z=512.3. found 512.3.

Example 14. (4-(6-Methyl-3-(7-(pyridin-4-yl)quinolin-4-yl)imidazo[1,2-b]pyridazin-7-yl)phenyl)(4-methylpiperazin-1-yl)methanone

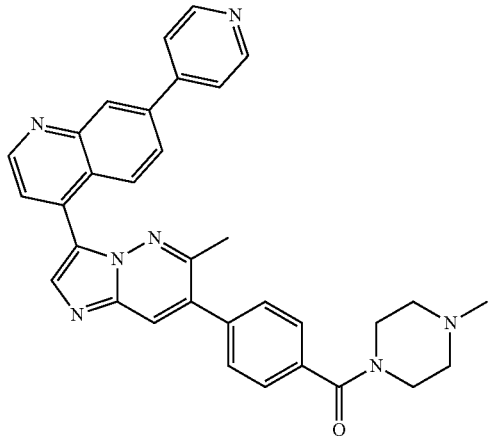 [SMILES: Cc1nn2c(-c3ccnc4cc(-c5ccncc5)ccc34)cnc2cc1-c1ccc(C(=O)N2CCN(C)CC2)cc1]

This compound was prepared according to the procedure described in Example 12, using (4-methylpiperazin-1-yl)(4-(4,4,5,5-tetramethyl-1,3,2-dioxaborolan-2-yl)phenyl)methanone instead of 4-methyl-1-(4-(4,4,5,5-tetramethyl-1,3,2-dioxaborolan-2-yl)phenyl)piperazin-2-one as the starting material. The desired product was isolated as its TFA salt. LC-MS calculated for $C_{33}H_{30}N_7O$ (M+H)$^+$: m/z=540.2. found 540.3.

Example 15. (R)-4-(7-(3-fluoro-4-((2-methylpyrrolidin-1-yl)methyl)phenyl)-6-methylimidazo[1,2-b]pyridazin-3-yl)-7-(pyridin-4-yl)quinoline

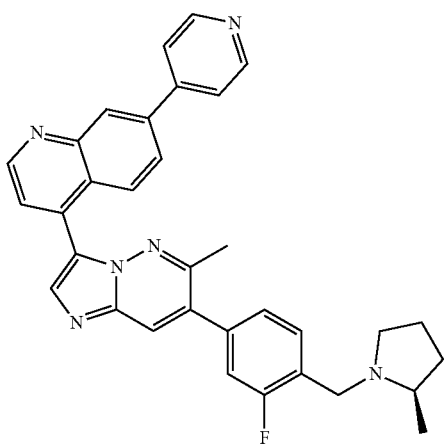 [SMILES: Cc1nn2c(-c3ccnc4cc(-c5ccncc5)ccc34)cnc2cc1-c1ccc(CN2CCC[C@H]2C)c(F)c1]

Step 1 (R)-1-(2-fluoro-4-(4,4,5,5-tetramethyl-1,3,2-dioxaborolan-2-yl)benzyl)-2-methylpyrrolidine

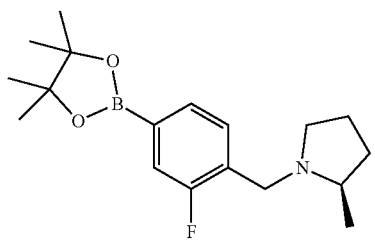 [SMILES: C[C@@H]1CCCN1Cc1ccc(B2OC(C)(C)C(C)(C)O2)cc1F]

A mixture of 2-fluoro-4-(4,4,5,5-tetramethyl-1,3,2-dioxaborolan-2-yl)benzaldehyde (0.125 g, 0.500 mmol) and (R)-2-methylpyrrolidine (0.047 g, 0.550 mmol) in $CH_2Cl_2$ (3.0 ml) was stirred at rt for 10 min and then treated with sodium triacetoxyborohydride (0.212 g, 1.00 mmol). The reaction mixture and stirred at rt for 2 h. The mixture was diluted with $CH_2Cl_2$, and washed with saturated $NaHCO_3$. The separated organic layer was dried over anhydrous $Na_2SO_4$, filtered and concentrated to provide the crude product which was used in the next step directly. LC-MS calculated for $C_{18}H_{28}BFNO_2$ (M+H)$^+$: m/z=320.2. found 320.3.

Step 2 (R)-4-(7-(3-fluoro-4-((2-methylpyrrolidin-1-yl)methyl)phenyl)-6-methylimidazo[1,2-b]pyridazin-3-yl)-7-(pyridin-4-yl)quinoline This compound was prepared according to the procedure described in Example 12, using (R)-1-(2-fluoro-4-(4,4,5,5-tetramethyl-1,3,2-dioxaborolan-2-yl)benzyl)-2-methylpyrrolidine instead of 4-methyl-1-(4-(4,4,5,5-tetramethyl-1,3,2-dioxaborolan-2-yl)phenyl)piperazin-2-one as the starting material. The desired product was isolated as its TFA salt. LC-MS calculated for $C_{33}H_{30}FN_6$ (M+H)$^+$: m/z=529.3. found 529.3.

Example 16. N-methyl-4-(6-methyl-7-(4-(piperazin-1-yl)phenyl)imidazo[1,2-b]pyridazin-3-yl)quinoline-7-carboxamide

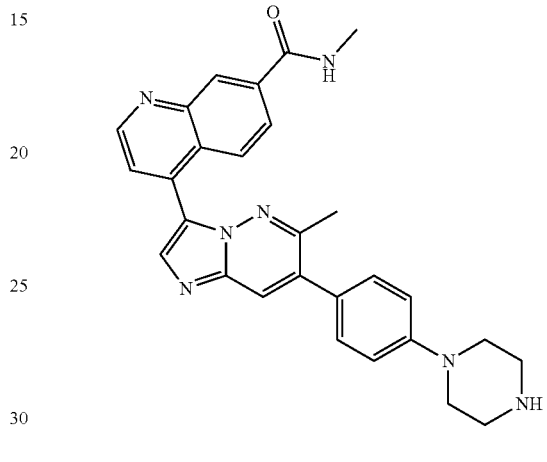

Step 1. (7-(methoxycarbonyl)quinolin-4-yl)boronic Acid

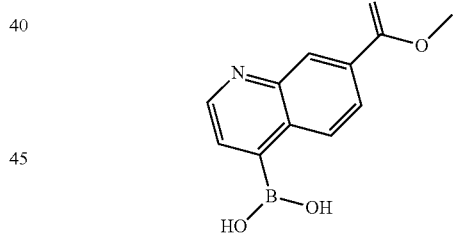

A vial was charged with methyl 4-chloroquinoline-7-carboxylate (0.3 g, 1.354 mmol), 4,4,4',4',5,5,5',5'-octamethyl-2,2'-bi(1,3,2-dioxaborolane) (0.412 g, 1.624 mmol), potassium acetate (0.266 g, 2.71 mmol), Tris(dibenzylideneacetone)dipalladium(0) (0.124 g, 0.135 mmol) and 2-(Dicyclohexylphosphino)biphenyl (0.095 g, 0.271 mmol). The vial was sealed, evacuated and backfilled with nitrogen (this process was repeated a total of three times). The mixture was treated with THF (2 ml). The mixture was heated at 80° C. for 4 h. After cooling to room temperature, the mixture was concentrated. The residue was purified on silica gel column (0-100% EtOAc/Hexanes) to give (7-(methoxycarbonyl)quinolin-4-yl)boronic acid (0.25 g, 1.082 mmol, 80% yield). LCMS calculated for $C_{11}H_{11}BNO_4$ (M+H)+: m/z=232.2. found 232.2.

Step 2. tert-butyl 4-(4-(6-methylimidazo[1,2-b]pyridazin-7-yl)phenyl)piperazine-1-carboxylate

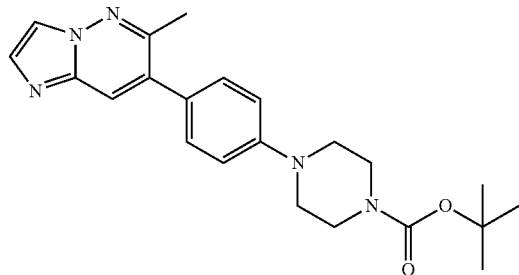 [SMILES: Cc1nn2ccnc2cc1-c1ccc(N2CCN(C(=O)OC(C)(C)C)CC2)cc1]

A vial was charged with 7-chloro-6-methylimidazo[1,2-b]pyridazine (252 mg, 1.504 mmol, see step 2 in Example 1), tert-butyl 4-(4-(4,4,5,5-tetramethyl-1,3,2-dioxaborolan-2-yl)phenyl)piperazine-1-carboxylate (670.1 mg, 1.726 mmol), cesium carbonate (980 mg, 3.01 mmol) and dicyclohexyl(2',4',6'-triisopropylbiphenyl-2-yl)phosphine-(2'-aminobiphenyl-2-yl)(chloro)palladium (1:1) (177 mg, 0.226 mmol). The vial was sealed, evacuated and backfilled with nitrogen (this process was repeated a total of three times). 1,4-Dioxane (10 ml) and water (2 ml) were added. The reaction was heated at 80° C. for 1 h. After cooling to room temperature, the mixture was concentrated. The residue was purified on silica gel column (0-100% EtOAc in Hexanes) to give tert-butyl 4-(4-(6-methylimidazo[1,2-b]pyridazin-7-yl)phenyl)piperazine-1-carboxylate (590 mg, 1.499 mmol, 100% yield). LCMS calculated for $C_{22}H_{28}N_5O_2$ (M+H)+: m/z=394.1. found: 394.1.

Step 3. tert-butyl 4-(4-(3-iodo-6-methylimidazo[1,2-b]pyridazin-7-yl)phenyl)piperazine-1-carboxylate

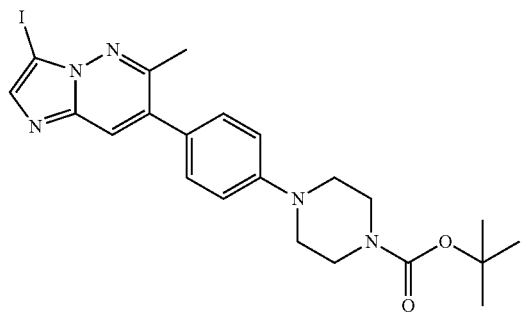 [SMILES: Cc1nn2c(I)cnc2cc1-c1ccc(N2CCN(C(=O)OC(C)(C)C)CC2)cc1]

A mixture of tert-butyl 4-(4-(6-methylimidazo[1,2-b]pyridazin-7-yl)phenyl)piperazine-1-carboxylate (590 mg, 1.499 mmol) and NIS (405 mg, 1.799 mmol) was treated with DMF (8.0 ml). The mixture was stirred at 50° C. for 90 min. The mixture was concentrated and purified on silica gel column (0-75% EtOAc in Hexanes) to give tert-butyl 4-(4-(3-iodo-6-methylimidazo[1,2-b]pyridazin-7-yl)phenyl)piperazine-1-carboxylate (450 mg, 0.866 mmol, 57.8% yield). LCMS calculated for $C_{22}H_{27}IN_5O_2$(M+H)+: m/z=520.1. found: 520.1.

Step 4. Methyl 4-(7-(4-(4-(tert-butoxycarbonyl)piperazin-1-yl)phenyl)-6-methylimidazo[1,2-b]pyridazin-3-yl)quinoline-7-carboxylate

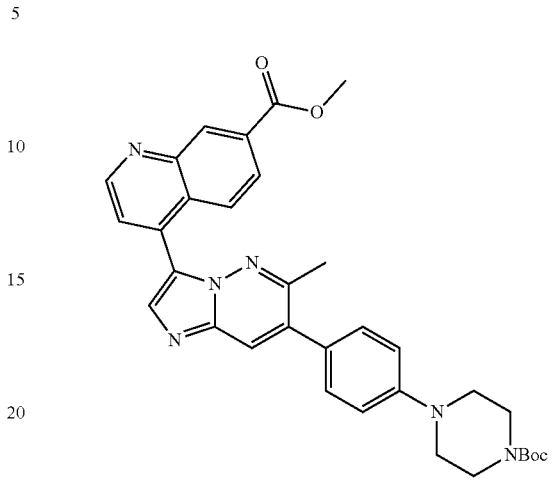

A mixture of tert-butyl 4-(4-(3-iodo-6-methylimidazo[1,2-b]pyridazin-7-yl)phenyl)piperazine-1-carboxylate (0.105 g, 0.202 mmol), (7-(methoxycarbonyl)quinolin-4-yl)boronic acid (0.095 g, 0.303 mmol), (1,1'-Bis(diphenylphosphino)ferrocene)-dichloropalladium(II) (0.015 g, 0.020 mmol), potassium carbonate (0.056 g, 0.404 mmol) in 1,4-Dioxane (1 ml) and water (0.5 ml) was heated at 90° C. for 1 h. After cooling, the mixture was purified on silica gel column (0-100% EtOAc/Hexnanes) to give methyl 4-(7-(4-(4-(tert-butoxycarbonyl)piperazin-1-yl)phenyl)-6-methylimidazo[1,2-b]pyridazin-3-yl)quinoline-7-carboxylate (0.052 g, 0.090 mmol, 44.5% yield). LCMS calculated for $C_{33}H_{35}N_6O_4$ (M+H)+: m/z=579.2. found 579.2.

Step 5. 4-(7-(4-(4-(tert-butoxycarbonyl)piperazin-1-yl)phenyl)-6-methylimidazo[1,2-b]pyridazin-3-yl)quinoline-7-carboxylic Acid

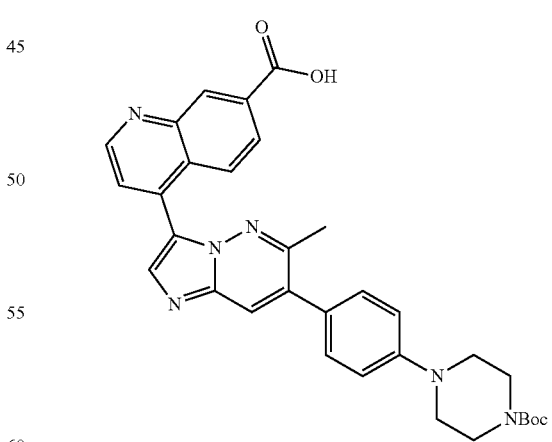

A solution of methyl 4-(7-(4-(4-(tert-butoxycarbonyl)piperazin-1-yl)phenyl)-6-methylimidazo[1,2-b]pyridazin-3-yl)quinoline-7-carboxylate (30 mg, 0.052 mmol) in THF (1 mL) was treated with a 1N aq. solution of sodium hydroxide (0.207 ml, 0.207 mmol) at room temperature. After being stirred at room temperature for 1 h, the reaction mixture was neutralized and concentrated to give 4-(7-(4-(4-(tert-butoxycarbonyl)piperazin-1-yl)phenyl)-6-methylimidazo[1,2-b]pyridazin-3-yl)quinoline-7-carboxylic acid. LCMS calculated for $C_{32}H_{33}N_6O_4$ (M+H)+ m/z=565.2. found 565.2.

Step 6. N-methyl-4-(6-methyl-7-(4-(piperazin-1-yl)phenyl) imidazo[1,2-b]pyridazin-3-yl)quinoline-7-carboxamide A solution of 4-(7-(4-(4-(tert-butoxycarbonyl)piperazin-1-yl)phenyl)-6-methylimidazo[1,2-b]pyridazin-3-yl)quinoline-7-carboxylic acid (6 mg, 10.63 μmol), methanamine (0.396 mg, 0.013 mmol), HATU (6.06 mg, 0.016 mmol) and DIPEA (3.71 μl, 0.021 mmol) in DMF (0.5 ml) was stirred at room temperature for 1 h. The reaction mixture was treated with water. The mixture was concentrated to give tert-butyl 4-(4-(6-methyl-3-(7-(methylcarbamoyl)quinolin-4-yl)imidazo[1,2-b]pyridazin-7-yl)phenyl)piperazine-1-carboxylate. The intermediate was treated with trifluoroacetic acid (0.5 ml, 6.49 mmol) in DCM (0.500 ml) at room temperature for 30 min. The mixture was purified on prep-LCMS (XBridge C18 column, eluting with a gradient of acetonitrile/water containing 0.1% TFA, at flow rate of 60 mL/min) to give N-methyl-4-(6-methyl-7-(4-(piperazin-1-yl)phenyl)imidazo[1,2-b]pyridazin-3-yl)quinoline-7-carboxamide (4.8 mg, 10.05 μmol, 95% yield). LCMS calculated for $C_{28}H_{28}N_7O$ (M+H)+ m/z=478.1. found 478.2.

Example 17. (4-(6-methyl-7-(4-(piperazin-1-yl)phenyl)imidazo[1,2-b]pyridazin-3-yl)quinolin-7-yl)(4-methylpiperazin-1-yl)methanone

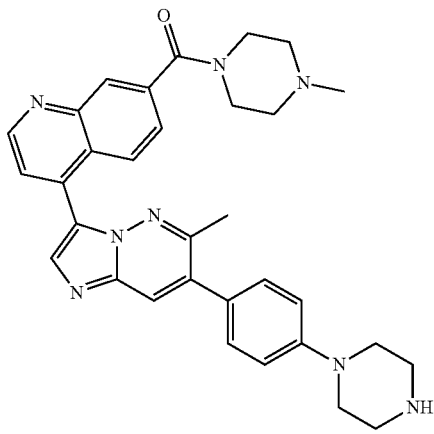 [SMILES: Cc1nn2c(-c3ccnc4cc(C(=O)N5CCN(C)CC5)ccc34)cnc2cc1-c1ccc(N2CCNCC2)cc1]

This compound was prepared according to the procedure described in Example 16 (step 6), using 1-methylpiperazine instead of methanamine as the starting material. LCMS calculated for $C_{32}H_{35}N_8O$ (M+H)+ m/z=547.0. found 547.0.

Example 18. 7-(1-methyl-1H-pyrazol-3-yl)-4-(6-methyl-7-(4-(piperazin-1-yl)phenyl)imidazo[1,2-b]pyridazin-3-yl)quinoline

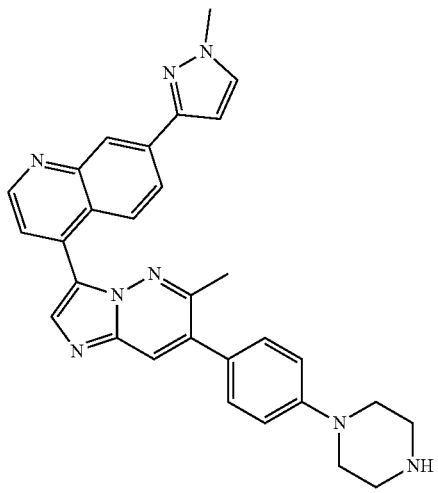 [SMILES: Cc1nn2c(-c3ccnc4cc(-c5ccn(C)n5)ccc34)cnc2cc1-c1ccc(N2CCNCC2)cc1]

Step 1. tert-butyl 4-(4-(3-(7-chloroquinolin-4-yl)-6-methylimidazo[1,2-b]pyridazin-7-yl)phenyl)piperazine-1-carboxylate

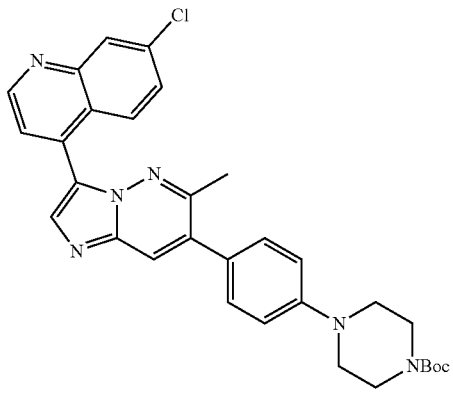 [SMILES: Cc1nn2c(-c3ccnc4cc(Cl)ccc34)cnc2cc1-c1ccc(N2CCN(C(=O)OC(C)(C)C)CC2)cc1]

A mixture of tert-butyl 4-(4-(3-iodo-6-methylimidazo[1,2-b]pyridazin-7-yl)phenyl)piperazine-1-carboxylate (0.28 g, 0.539 mmol), 7-chloro-4-(4,4,5,5-tetramethyl-1,3,2-dioxaborolan-2-yl)quinoline (0.172 g, 0.593 mmol), (1,1'-Bis(diphenylphosphino)ferrocene)-dichloropalladium(II) (0.394 g, 0.539 mmol), potassium carbonate (0.149 g, 1.078 mmol) in 1,4-Dioxane (1 ml) and water (0.2 ml) was heated at 90° C. for 1 h. After cooling, the mixture was purified on silica gel column (0-100% EtOAc/Hexnanes) to give tert-butyl 4-(4-(3-(7-chloroquinolin-4-yl)-6-methylimidazo[1,2-b]pyridazin-7-yl)phenyl)piperazine-1-carboxylate (0.22 g, 0.396 mmol, 73.5% yield). LCMS calculated for $C_{31}H_{32}ClN_6O_2$(M+H)+: m/z=555.1. found: 555.1.

Step 2. 7-(1-methyl-1H-pyrazol-3-yl)-4-(6-methyl-7-(4-(piperazin-1-yl)phenyl)imidazo[1,2-b]pyridazin-3-yl)quinoline A mixture of tert-butyl 4-(4-(3-(7-chloroquinolin-4-yl)-6-methylimidazo[1,2-b]pyridazin-7-yl)phenyl)piperazine-1-carboxylate (11 mg, 0.020 mmol), 1-methyl-3-(4,4,5,5-tetramethyl-1,3,2-dioxaborolan-2-yl)-1H-pyrazole (4.12 mg, 0.020 mmol), Chloro(2-dicyclohexylphosphino-2',4',6'-triisopropyl-1,1'-biphenyl) [2-(2'-amino-1,1'-biphenyl)]palladium(II) (15.59 mg, 0.020 mmol) and potassium carbonate (5.48 mg, 0.040 mmol) in 1,4-Dioxane (1 ml)/Water (0.2 ml) was heated at 100° C. for 1 h. After cooling, the mixture was concentrated to give tert-butyl 4-(4-(6-methyl-3-(7-(1-methyl-1H-pyrazol-3-yl)quinolin-4-yl)imidazo[1,2-b]pyridazin-7-yl)phenyl)piperazine-1-carboxylate. The residue was treated with TFA (1.0 ml) in DCM (1.0 ml) at room temperature for 15 min. The mixture was purified on prep-LCMS (XBridge C18 column, eluting with a gradient of acetonitrile/water containing 0.1% TFA, at flow rate of 60 mL/min) to give 7-(1-methyl-1H-pyrazol-3-yl)-4-(6-methyl-7-(4-(piperazin-1-yl)phenyl)imidazo[1,2-b]pyridazin-3-yl)quinoline (5.3 mg, 10.59 μmol, 53.4% yield). LCMS calculated for $C_{30}H_{29}N_8$(M+H)+: m/z=501.2. found: 501.2.

Example 19. (4-(4-(6-methyl-7-(4-(piperazin-1-yl)phenyl)imidazo[1,2-b]pyridazin-3-yl)quinolin-7-yl)pyridin-2-yl)methanol

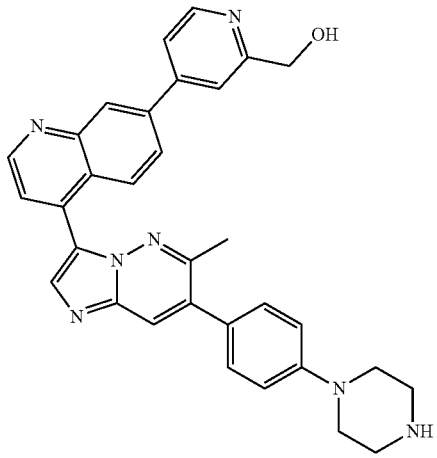 [SMILES: Cc1nn2c(-c3ccnc4cc(-c5ccnc(CO)c5)ccc34)cnc2cc1-c1ccc(N2CCNCC2)cc1]

This compound was prepared according to the procedure described in Example 18 (step 2), using (4-(4,4,5,5-tetramethyl-1,3,2-dioxaborolan-2-yl)pyridin-2-yl)methanol instead of 1-methyl-3-(4,4,5,5-tetramethyl-1,3,2-dioxaborolan-2-yl)-1H-pyrazole as the starting material. LCMS calculated for $C_{32}H_{30}N_7O$ (M+H)$^+$: m/z=528.2. found: 528.2.

Example 20. 4-(4-(6-methyl-7-(4-(piperazin-1-yl)phenyl)imidazo[1,2-b]pyridazin-3-yl)quinolin-7-yl)morpholine

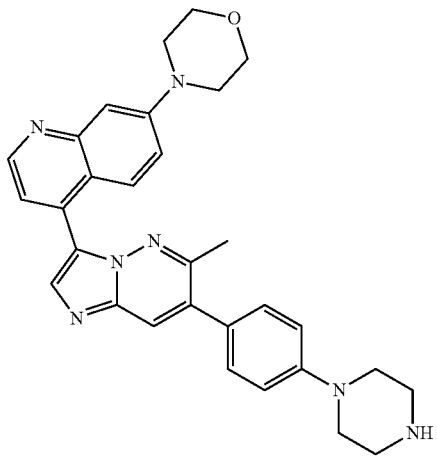 [SMILES: Cc1nn2c(-c3ccnc4cc(N5CCOCC5)ccc34)cnc2cc1-c1ccc(N2CCNCC2)cc1]

A mixture of tert-butyl 4-(4-(3-(7-chloroquinolin-4-yl)-6-methylimidazo[1,2-b]pyridazin-7-yl)phenyl)piperazine-1-carboxylate (11 mg, 0.020 mmol, see step 1 in Example 18), morpholine (1.726 mg, 0.020 mmol), Chloro-(2-dicyclohexylphosphino-2',6'-diisopropoxy-1,1'-biphenyl)[2-(2'-amino-1,1'-biphenyl)]palladium(II) (15.39 mg, 0.020 mmol) and cesium carbonate (6.46 mg, 0.020 mmol) in 1,4-Dioxane (1 ml) was heated at 110° C. for 2 h. After cooling, the mixture was concentrated. The residue was treated with TFA (1 ml) in DCM (1.0 ml) at room temperature for 15 min. The mixture was purified on prep-LCMS (XBridge C18 column, eluting with a gradient of acetonitrile/water containing 0.1% TFA, at flow rate of 60 mL/min) to give 4-(4-(6-methyl-7-(4-(piperazin-1-yl)phenyl)imidazo[1,2-b]pyridazin-3-yl)quinolin-7-yl)morpholine (5.5 mg, 10.88 μmol, 54.9% yield). LCMS calculated for $C_{30}H_{32}N_7O$ (M+H)+: m/z=506.3. found: 506.1. $^1$H NMR (TFA salt, 500 MHz, DMSO) δ 8.97 (d, J=5.6 Hz, 1H), 8.89 (br, 2H), 8.33 (s, 1H), 8.11 (overlap, 2H), 7.97 (d, J=5.6 Hz, 1H), 7.68 (m, 1H), 7.49 (d, J=8.6 Hz, 2H), 7.33 (d, J=2.6 Hz, 1H), 7.14 (d, J=8.6 Hz, 2H), 3.82 (m, 4H), 3.47 (overlap, 8H), 3.28 (m, 4H), 2.48 (s, 3H).

Example 21. 2-(4-(6-methyl-7-(4-(piperazin-1-yl)phenyl)imidazo[1,2-b]pyridazin-3-yl)quinolin-7-yl)-6-oxa-2-azaspiro[3.4]octane

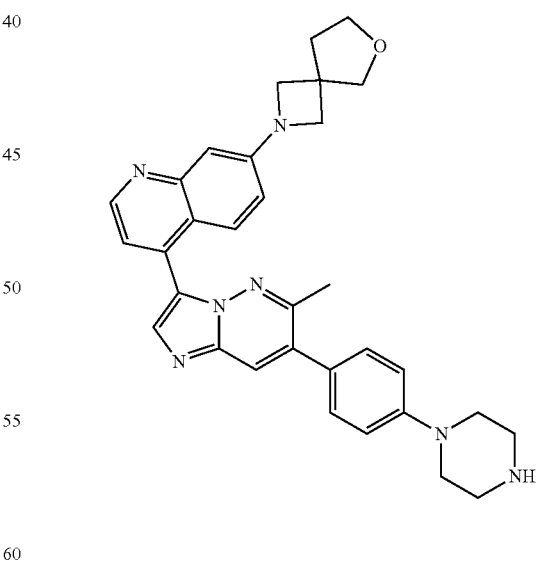

This compound was prepared according to the procedure described in Example 20, using 6-oxa-2-azaspiro[3.4]octane instead of morpholine as the starting material. LCMS calculated for $C_{32}H_{34}N_7O$ (M+H)$^+$: m/z=532.2. found: 532.2.

Example 22. 4-(6-methyl-7-(4-(piperazin-1-yl)phenyl)imidazo[1,2-b]pyridazin-3-yl)-N-(pyridin-3-yl)quinolin-7-amine

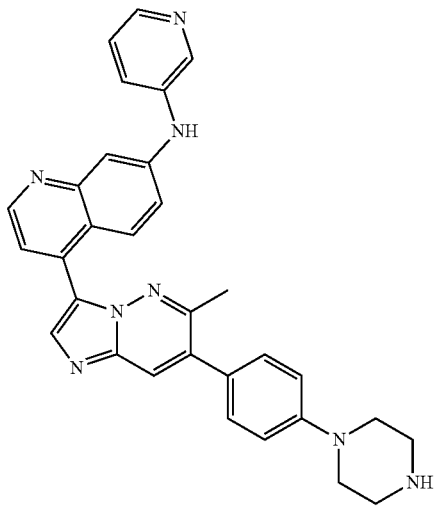 [SMILES: Cc1nn2c(-c3ccnc4cc(Nc5cccnc5)ccc34)cnc2cc1-c1ccc(N2CCNCC2)cc1]

This compound was prepared according to the procedure described in Example 20, using pyridin-3-amine instead of morpholine as the starting material. LCMS calculated for $C_{31}H_{29}N_8(M+H)^+$: m/z=513.2. found: 513.2.

Example 23. 1-(4-(4-(6-methyl-7-(4-(piperazin-1-yl)phenyl)imidazo[1,2-b]pyridazin-3-yl)quinolin-7-yl)piperazin-1-yl)ethan-1-one

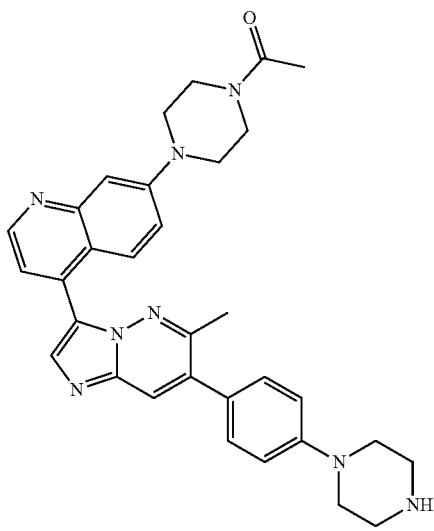 [SMILES: CC(=O)N1CCN(c2ccc3c(-c4cnc5cc(-c6ccc(N7CCNCC7)cc6)c(C)nn45)ccnc3c2)CC1]

This compound was prepared according to the procedure described in Example 20, using 1-(piperazin-1-yl)ethan-1-one instead of morpholine as the starting material. LCMS calculated for $C_{32}H_{35}N_8O$ (M+H)$^+$: m/z=547.2. found: 547.2.

Example 24. 4-((4-(6-methyl-7-(4-(piperazin-1-yl)phenyl)imidazo[1,2-b]pyridazin-3-yl)quinolin-7-yl)methyl)morpholine

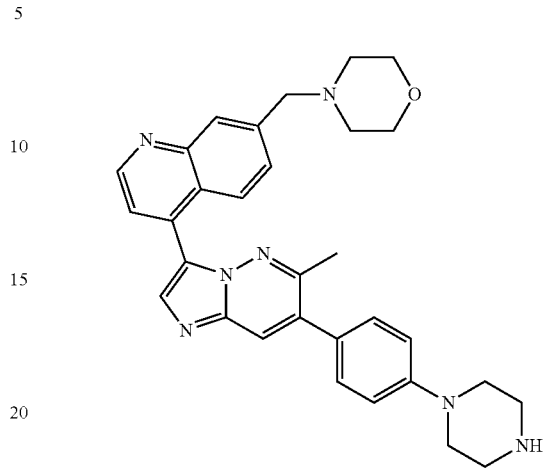

Step 1. tert-butyl 4-(4-(6-methyl-3-(7-vinylquinolin-4-yl)imidazo[1,2-b]pyridazin-7-yl)phenyl)piperazine-1-carboxylate

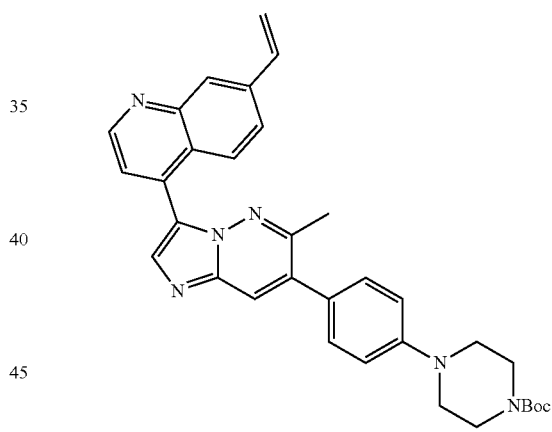

A mixture of tert-butyl 4-(4-(3-(7-chloroquinolin-4-yl)-6-methylimidazo[1,2-b]pyridazin-7-yl)phenyl)piperazine-1-carboxylate (120 mg, 0.216 mmol, see step 1 in Example 18), 4,4,5,5-tetramethyl-2-vinyl-1,3,2-dioxaborolane (0.044 ml, 0.259 mmol), Chloro(2-dicyclohexyl-phosphino-2',4',6'-triisopropyl-1,1'-biphenyl)[2-(2'-amino-1,1'-biphenyl)]palladium(II) (17.01 mg, 0.022 mmol) and potassium carbonate (59.8 mg, 0.432 mmol) in 1,4-Dioxane (1 ml)/Water (0.2 ml) was heated at 100° C. for 2 h. After cooling, the mixture was concentrated. The residue was purified on silica gel column (0-100% EtOAc/Hexanes) to give tert-butyl 4-(4-(6-methyl-3-(7-vinylquinolin-4-yl)imidazo[1,2-b]pyridazin-7-yl)phenyl)piperazine-1-carboxylate (100 mg, 0.183 mmol, 85% yield). LCMS calculated for $C_{33}H_{35}N_6O_2$ (M+H)$^+$: m/z=547.2. found: 547.2.

Step 2. tert-butyl 4-(4-(3-(7-formylquinolin-4-yl)-6-methylimidazo[1,2-b]pyridazin-7-yl)phenyl)piperazine-1-carboxylate

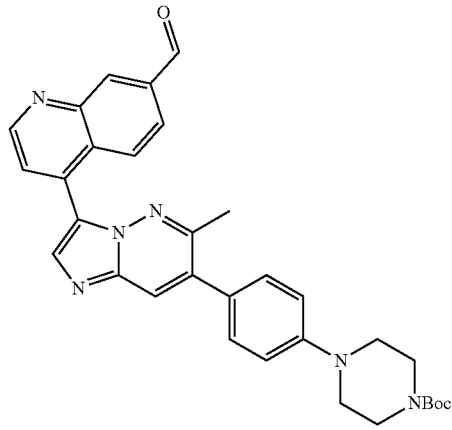 [SMILES: Cc1nn2c(-c3ccnc4cc(C=O)ccc34)cnc2cc1-c1ccc(N2CCN(C(=O)OC(C)(C)C)CC2)cc1]

A mixture of tert-butyl 4-(4-(6-methyl-3-(7-vinylquinolin-4-yl)imidazo[1,2-b]pyridazin-7-yl)phenyl)piperazine-1-carboxylate (100 mg, 0.183 mmol) in THF (5 ml)/Water (1.250 ml) cooled in an ice bath was treated with a 4% aq. solution of osmium tetroxide (0.224 ml, 0.037 mmol). The reaction was stirred for 5 min, then sodium periodate (117 mg, 0.549 mmol) was added. After stirring at room temperature for 2 h, the reaction was treated with $Na_2S_2O_3$, extracted with EtOAc, and concentrated. The residue was purified on silica gel column (0-100% EtOAc/Hexanes followed by 10% MeOH/DCM) to give tert-butyl 4-(4-(3-(7-formylquinolin-4-yl)-6-methylimidazo[1,2-b]pyridazin-7-yl)phenyl)piperazine-1-carboxylate (90 mg, 0.164 mmol, 90% yield). LCMS calculated for $C_{32}H_{33}N_6O_3$ $(M+H)^+$: m/z=549.2. found: 549.2.

Step 3. 4-((4-(6-methyl-7-(4-(piperazin-1-yl)phenyl)imidazo[1,2-b]pyridazin-3-yl)quinolin-7-yl)methyl)morpholine A solution of tert-butyl 4-(4-(3-(7-formylquinolin-4-yl)-6-methylimidazo[1,2-b]pyridazin-7-yl)phenyl)piperazine-1-carboxylate (6 mg, 10.94 μmol) and morpholine (0.953 mg, 10.94 μmol) in DCM (1 ml) was stirred at room temperature for 10 min. The reaction mixture was then treated with sodium triacetoxyborohydride (2.318 mg, 10.94 μmol). The reaction mixture was stirred at room temperature for 2 h. The mixture was concentrated to dryness to give tert-butyl 4-(4-(6-methyl-3-(7-(morpholinomethyl)quinolin-4-yl)imidazo[1,2-b]pyridazin-7-yl)phenyl)piperazine-1-carboxylate. This intermediate was treated with trifluoroacetic acid (0.5 ml, 6.49 mmol) in DCM (1 ml) at room temperature for 30 min. The mixture was purified on prep-LCMS (XBridge C18 column, eluting with a gradient of acetonitrile/water containing 0.1% TFA, at flow rate of 60 mL/min) to give 4-((4-(6-methyl-7-(4-(piperazin-1-yl)phenyl)imidazo[1,2-b]pyridazin-3-yl)quinolin-7-yl)methyl)morpholine (3.3 mg, 6.35 μmol, 58.1% yield). LCMS calculated for $C_{31}H_{34}N_7O$ $(M+H)^+$: m/z=520.3. found: 520.3.

Example 25. (3,5-difluorophenyl)(4-(6-methyl-7-(4-(piperazin-1-yl)phenyl)imidazo[1,2-b]pyridazin-3-yl)quinolin-7-yl)methanol

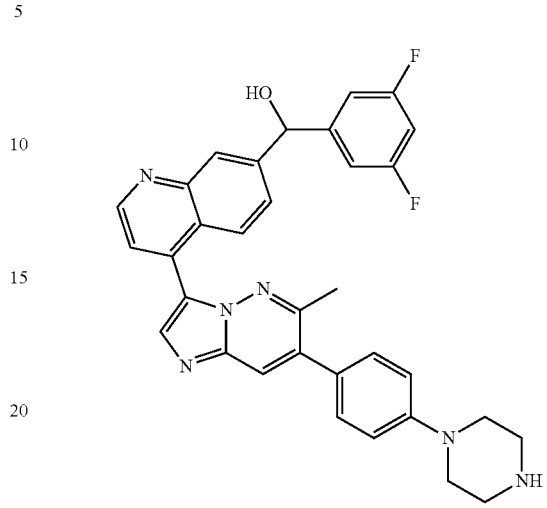

A suspension of tert-butyl 4-(4-(3-(7-formylquinolin-4-yl)-6-methylimidazo[1,2-b]pyridazin-7-yl)phenyl)piperazine-1-carboxylate (6 mg, 10.94 μmol, see step 2 in Example 24) in THF (0.5 ml) at −78° C. was treated with a 0.5 M THF solution of (3,5-difluorophenyl)-magnesium bromide (0.028 ml, 0.014 mmol). The mixture was stirred at room temperature for 1 h, and then concentrated to dryness. The residue was treated with trifluoroacetic acid (0.1 ml, 1.298 mmol) in DCM (0.5 ml) at room temperature for 1 h. The mixture was purified on prep-LCMS (XBridge C18 column, eluting with a gradient of acetonitrile/water containing 0.1% TFA, at flow rate of 60 mL/min) to give (3,5-difluorophenyl)(4-(6-methyl-7-(4-(piperazin-1-yl)phenyl)imidazo[1,2-b]pyridazin-3-yl)quinolin-7-yl)methanol (4.3 mg, 7.64 mol, 69.9% yield). LCMS calculated for $C_{33}H_{29}F_2N_6O$ $(M+H)^+$: m/z=563.2. found: 563.1.

Example 26. (4-(6-methyl-7-(4-(piperazin-1-yl)phenyl)imidazo[1,2-b]pyridazin-3-yl)quinolin-7-yl)methanol

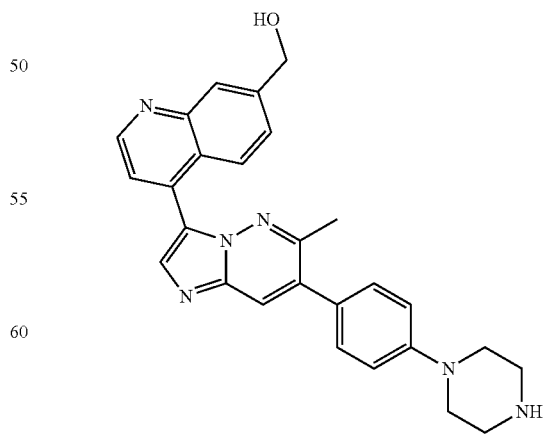

A solution of tert-butyl 4-(4-(3-(7-formylquinolin-4-yl)-6-methylimidazo[1,2-b]pyridazin-7-yl)phenyl)piperazine- 1-carboxylate (6 mg, 10.94 μmol, see step 2 in Example 24) and sodium borohydride (0.414 mg, 10.94 μmol) in MeOH (1 ml) was stirred at room temperature for 1 h. The mixture was concentrated to dryness to give tert-butyl 4-(4-(3-(7-(hydroxymethyl)quinolin-4-yl)-6-methylimidazo[1,2-b]pyridazin-7-yl)phenyl)piperazine-1-carboxylate. This intermediate was treated with trifluoroacetic acid (0.5 ml, 6.49 mmol) in DCM (1.000 ml) at room temperature for 30 min. The mixture was purified on prep-LCMS (XBridge C18 column, eluting with a gradient of acetonitrile/water containing 0.1% TFA, at flow rate of 60 mL/min) to give (4-(6-methyl-7-(4-(piperazin-1-yl)phenyl)imidazo[1,2-b]pyridazin-3-yl)quinolin-7-yl)methanol (2.5 mg, 5.55 μmol, 50.7% yield). LCMS calculated for $C_{27}H_{27}N_6O$ (M+H)$^+$: m/z=451.2. found: 451.1.

Example 27. 4-(6-methyl-7-(4-(piperazin-1-yl)phenyl)imidazo[1,2-b]pyridazin-3-yl)-1,8-naphthyridine

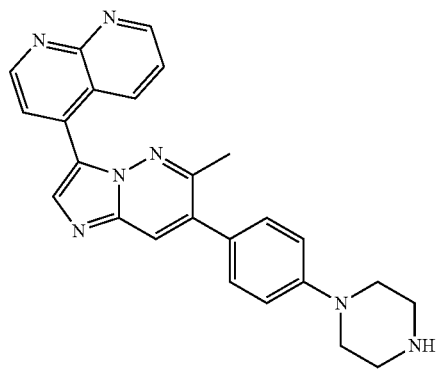 [SMILES: Cc1nn2c(-c3ccnc4ncccc34)cnc2cc1-c1ccc(N2CCNCC2)cc1]

A mixture of tert-butyl 4-(4-(3-iodo-6-methylimidazo[1,2-b]pyridazin-7-yl)phenyl)piperazine-1-carboxylate (0.010 g, 0.019 mmol), 4-(4,4,5,5-tetramethyl-1,3,2-dioxaborolan-2-yl)-1,8-naphthyridine (5.42 mg, 0.021 mmol), (1,1'-Bis(diphenylphosphino)-ferrocene)dichloropalladium(II) (1.409 mg, 1.925 μmol) and potassium carbonate (5.32 mg, 0.039 mmol) in 1,4-Dioxane (1 ml)/Water (0.2 ml) was heated at 100° C. for 1 h. After cooling, the mixture was concentrated. The residue was treated with trifluoroacetic acid (1.0 ml) in DCM (1.0 ml) at room temperature for 30 min. The mixture was purified on prep-LCMS (XBridge C18 column, eluting with a gradient of acetonitrile/water containing 0.1% TFA, at flow rate of 60 mL/min) to give 4-(6-methyl-7-(4-(piperazin-1-yl)phenyl)imidazo[1,2-b]pyridazin-3-yl)-1,8-naphthyridine (4.0 mg, 9.49 μmol, 49.3% yield). LCMS calculated for $C_{25}H_{24}N_7$(M+H)$^+$: m/z=422.2. found: 422.1.

Example 28. 5-(6-methyl-7-(4-(piperazin-1-yl)phenyl)imidazo[1,2-b]pyridazin-3-yl)quinoline-8-carbonitrile

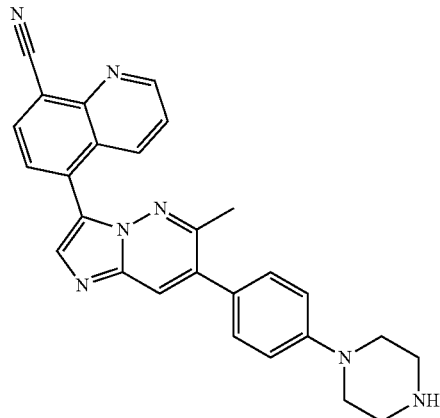 [SMILES: Cc1nn2c(-c3ccc(C#N)c4ncccc34)cnc2cc1-c1ccc(N2CCNCC2)cc1]

Step 1. 5-(4,4,5,5-tetramethyl-1,3,2-dioxaborolan-2-yl)quinoline-8-carbonitrile

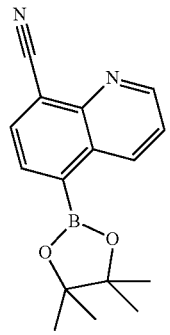 [SMILES: CC1(C)OB(c2ccc(C#N)c3ncccc23)OC1(C)C]

A vial was charged with a mixture of 5-bromoquinoline-8-carbonitrile (0.036 g, 0.154 mmol), 4,4,4',4',5,5,5',5'-octamethyl-2,2'-bi(1,3,2-dioxaborolane) (0.047 g, 0.185 mmol), potassium acetate (0.030 g, 0.309 mmol) and (1,1'-Bis(diphenylphosphino)ferrocene)-dichloropalladium(II) (0.011 g, 0.015 mmol). The vial was sealed, evacuated and backfilled with nitrogen (this process was repeated a total of three times). The mixture was treated with Dioxane (1 ml). The mixture was heated at 90° C. for 1 h. The mixture was filtered to give 5-(4,4,5,5-tetramethyl-1,3,2-dioxaborolan-2-yl)quinoline-8-carbonitrile (0.035 g) which was used directly in the next step without further purification. LCMS calculated for $C_{16}H_{18}BN_2O_2$ (M+H)$^+$: m/z=281.1. found: 281.0.

Step 2. 5-(6-methyl-7-(4-(piperazin-1-yl)phenyl)imidazo[1,2-b]pyridazin-3-yl)quinoline-8-carbonitrile This compound was prepared according to the procedure described in Example 27, using 5-(4,4,5,5-tetramethyl-1,3,2-dioxaborolan-2-yl)quinoline-8-carbonitrile instead of 4-(4,4,5,5-tetramethyl-1,3,2-dioxaborolan-2-yl)-1,8-naphthyridine as the starting material. LCMS calculated for C₂₇H₂₄N₇(M+H)⁺: m/z=446.2. found: 446.3.

Example 29. 8-(6-methyl-7-(4-(piperazin-1-yl)phenyl)imidazo[1,2-b]pyridazin-3-yl)-2,3-dihydro-[1,4]dioxino[2,3-b]pyridine

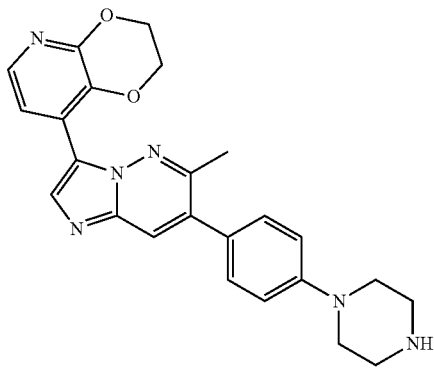 [SMILES: Cc1nn2c(-c3ccnc4c3OCCO4)cnc2cc1-c1ccc(N2CCNCC2)cc1]

This compound was prepared according to the procedure described in Example 27, using 8-(4,4,5,5-tetramethyl-1,3,2-dioxaborolan-2-yl)-2,3-dihydro-[1,4]dioxino[2,3-b]pyridine instead of 4-(4,4,5,5-tetramethyl-1,3,2-dioxaborolan-2-yl)-1,8-naphthyridine as the starting material. LCMS calculated for C₂₄H₂₅N₆O₂ (M+H)+: m/z=429.2. found: 429.0.

Example 30. 4-(6-methyl-7-(4-(piperazin-1-yl)phenyl)imidazo[1,2-b]pyridazin-3-yl)quinoline-7-carbonitrile

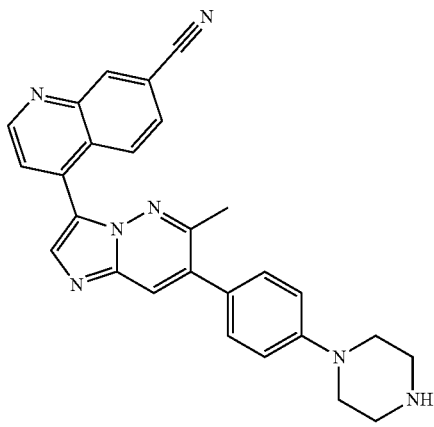 [SMILES: Cc1nn2c(-c3ccnc4cc(C#N)ccc34)cnc2cc1-c1ccc(N2CCNCC2)cc1]

A vial charged with a mixture of tert-butyl 4-(4-(3-(7-chloroquinolin-4-yl)-6-methylimidazo[1,2-b]pyridazin-7-yl)phenyl)piperazine-1-carboxylate (10 mg, 0.018 mmol, see step 1 in Example 18), dicyanozinc (2.115 mg, 0.018 mmol), Tris(dibenzylideneacetone)dipalladium(0) (0.825 mg, 0.901 μmol) and 4,5-Bis(diphenylphosphino)-9,9-dimethylxanthene (1.042 mg, 1.802 μmol). The vial was sealed with a teflon screw-cap, evacuated and backfilled with nitrogen (this process was repeated a total of three times). A solution of TMEDA (0.540 μl, 3.60 μmol) in DMF (1 ml) was added. The reaction mixture was heated at 110° C. overnight. After cooling to room temperature, the reaction was filtered and concentrated. The resultant intermediate was treated with trifluoroacetic acid (0.5 ml, 6.49 mmol) in DCM (1.000 ml) at room temperature for 30 min. The mixture was purified on prep-LCMS (XBridge C18 column, eluting with a gradient of acetonitrile/water containing 0.1% TFA, at flow rate of 60 mL/min) to give 4-(6-methyl-7-(4-(piperazin-1-yl)phenyl)imidazo[1,2-b]pyridazin-3-yl)quinoline-7-carbonitrile (0.6 mg, 1.347 μmol, 7.48% yield). LCMS calculated for C₂₇H₂₄N₇(M+H)⁺: m/z=446.2. found: 446.1.

Example 31. N-(2-hydroxyethyl)-4-(6-methyl-7-(4-(piperazin-1-yl)phenyl)imidazo[1,2-b]pyridazin-3-yl)quinoline-8-carboxamide

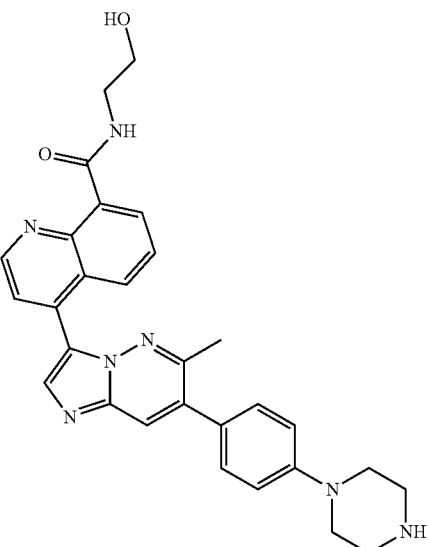

Step 1. (8-(methoxycarbonyl)quinolin-4-yl)boronic Acid

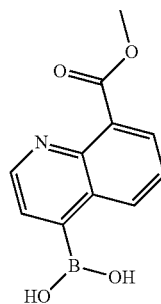

A vial was charged with a mixture of methyl 4-bromoquinoline-8-carboxylate (0.19 g, 0.714 mmol), 4,4,4',4',5,5,5',5'-octamethyl-2,2'-bi(1,3,2-dioxaborolane) (0.218 g, 0.857 mmol), potassium acetate (0.140 g, 1.428 mmol) and (1,1'-Bis(diphenylphosphino)ferrocene)-dichloropalladium (II) (0.052 g, 0.071 mmol). The vial was sealed, evacuated and backfilled with nitrogen (this process was repeated a total of three times). The mixture was treated with Dioxane (2 ml). The mixture was heated at 90° C. for 1 h. The mixture was filtered to give (8-(methoxycarbonyl)quinolin-4-yl)boronic acid which was used directly in the next step without further purification. LCMS calculated for $C_{11}H_{11}BNO_4$ (M+H)+: m/z=232.1. found: 232.2.

Step 2. Methyl 4-(7-(4-(4-(tert-butoxycarbonyl) piperazin-1-yl)phenyl)-6-methylimidazo[1,2-b] pyridazin-3-yl)quinoline-8-carboxylate

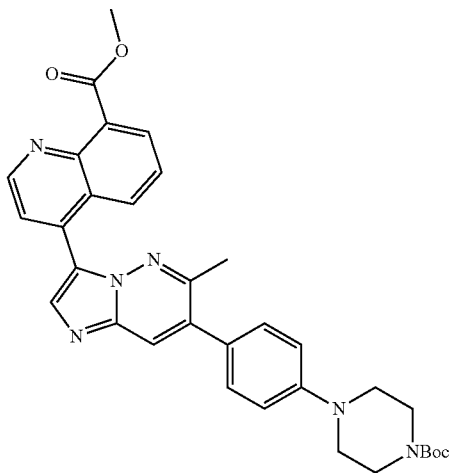 [SMILES: COC(=O)c1cccc2c(-c3cnc4cc(-c5ccc(N6CCN(C(=O)OC(C)(C)C)CC6)cc5)c(C)nn34)ccnc12]

A mixture of tert-butyl 4-(4-(3-iodo-6-methylimidazo[1,2-b]pyridazin-7-yl)phenyl)piperazine-1-carboxylate (0.060 g, 0.116 mmol), (8-(methoxycarbonyl)quinolin-4-yl)boronic acid (0.040 g, 0.173 mmol), (1,1'-Bis(diphenylphosphino)ferrocene)-dichloropalladium(II) (8.45 mg, 0.012 mmol), potassium carbonate (0.032 g, 0.231 mmol) in 1,4-Dioxane (1 ml) and water (0.2 ml) was heated at 90° C. for 1 h. After cooling, the mixture was purified on silica gel column (0-100% EtOAc/Hexanes) to give methyl 4-(7-(4-(4-(tert-butoxycarbonyl)piperazin-1-yl)phenyl)-6-methylimidazo[1,2-b]pyridazin-3-yl)quinoline-8-carboxylate (0.032 g, 0.055 mmol, 47.9% yield). LCMS calculated for $C_{33}H_{35}N_6O_4$ (M+H)+: m/z=579.3. found: 579.2.

Step 3. 4-(7-(4-(4-(tert-butoxycarbonyl)piperazin-1-yl)phenyl)-6-methylimidazo[1,2-b]pyridazin-3-yl) quinoline-8-carboxylic Acid

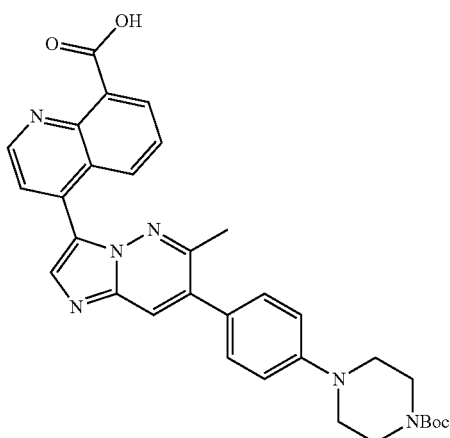

A solution of methyl 4-(7-(4-(4-(tert-butoxycarbonyl)piperazin-1-yl)phenyl)-6-methylimidazo[1,2-b]pyridazin-3-yl) quinoline-8-carboxylate (15 mg, 0.026 mmol) in THF (1 mL) was treated with 1N aq. solution of sodium hydroxide (0.5 ml, 0.500 mmol) at room temperature. After being stirred at room temperature for 3 h, the reaction mixture was neutralized and concentrated to give 4-(7-(4-(4-(tert-butoxycarbonyl)piperazin-1-yl)phenyl)-6-methylimidazo[1,2-b] pyridazin-3-yl)quinoline-8-carboxylic acid. LCMS calculated for $C_{32}H_{33}N_6O_4$ (M+H)+: m/z=565.3. found: 565.2.

Step 4. N-(2-hydroxyethyl)-4-(6-methyl-7-(4-(piperazin-1-yl)phenyl)imidazo[1,2-b]pyridazin-3-yl)quinoline-8-carboxamide A solution of 4-(7-(4-(4-(tert-butoxycarbonyl)piperazin-1-yl)phenyl)-6-methylimidazo[1,2-b]pyridazin-3-yl)quinoline-8-carboxylic acid (3.3 mg, 5.84 µmol), 2-aminoethan-1-ol (0.428 mg, 7.01 µmol), HATU (3.33 mg, 8.77 µmol) and DIPEA (2.042 µl, 0.012 mmol) in DMF (0.5 ml) was stirred at room temperature for 1 h. The reaction mixture was treated with water, extracted with DCM and concentrated to give tert-butyl 4-(4-(3-(8-((2-hydroxyethyl)carbamoyl)quinolin-4-yl)-6-methylimidazo[1,2-b]pyridazin-7-yl)phenyl) piperazine-1-carboxylate. The resultant intermediate was treated with trifluoroacetic acid (0.5 ml, 6.49 mmol) in DCM (0.500 ml) at room temperature for 30 min. The mixture was purified on prep-LCMS (XBridge C18 column, eluting with a gradient of acetonitrile/water containing 0.1% TFA, at flow rate of 60 mL/min) to give N-(2-hydroxyethyl)-4-(6-methyl-7-(4-(piperazin-1-yl)phenyl)imidazo[1,2-b]pyridazin-3-yl) quinoline-8-carboxamide (0.4 mg, 0.788 µmol, 13.48% yield). LCMS calculated for $C_{29}H_{30}N_7O_2$ (M+H)+ m/z=508.2. found 508.2.

Example 32. (4-(6-methyl-7-(1-(tetrahydro-2H-pyran-4-yl)-1H-pyrazol-4-yl)imidazo[1,2-b] pyridazin-3-yl)-2,3-dihydro-1H-pyrrolo[2,3-b]pyridin-1-yl)(pyridin-4-yl)methanone

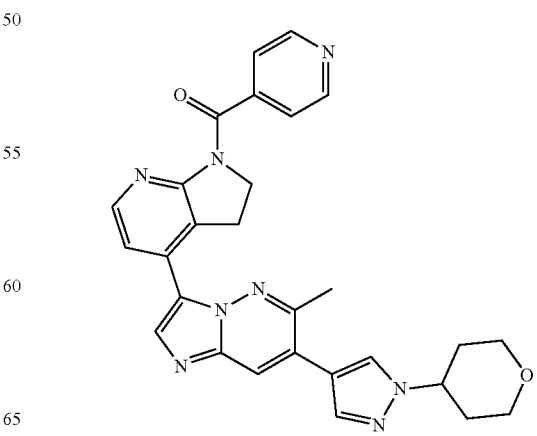

Step 1. 6-methyl-7-(1-(tetrahydro-2H-pyran-4-yl)-H-pyrazol-4-yl)imidazo[1,2-b]pyridazine

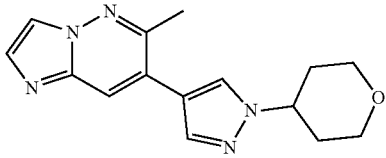 [SMILES: Cc1nn2ccnc2cc1-c1cnn(C2CCOCC2)c1]

A vial was charged with 7-chloro-6-methylimidazo[1,2-b]pyridazine (80 mg, 0.477 mmol, see step 2 in Example 1), 1-(tetrahydro-2H-pyran-4-yl)-4-(4,4,5,5-tetramethyl-1,3,2-dioxaborolan-2-yl)-1H-pyrazole (159 mg, 0.573 mmol), cesium carbonate (311 mg, 0.955 mmol) and dicyclohexyl (2',4',6'-triisopropylbiphenyl-2-yl)phosphine-(2'-aminobiphenyl-2-yl)(chloro)palladium (1:1) (56.3 mg, 0.072 mmol). The vial was sealed, evacuated and backfilled with nitrogen (this process was repeated a total of three times). 1,4-Dioxane (1 ml) and Water (0.2 ml) were added. The reaction was heated at 80° C. for 1 h. The reaction was purified on silica gel column (0-100% EtOAc in Hexanes followed by 10% MeOH/DCM) to give 6-methyl-7-(1-(tetrahydro-2H-pyran-4-yl)-1H-pyrazol-4-yl)imidazo[1,2-b]pyridazine (130 mg, 0.459 mmol, 96% yield). LCMS calculated for $C_{15}H_{18}N_5O$ (M+H)$^+$: m/z=284.2. found: 284.1.

Step 2. 3-iodo-6-methyl-7-(1-(tetrahydro-2H-pyran-4-yl)-1H-pyrazol-4-yl)imidazo[1,2-b]pyridazine

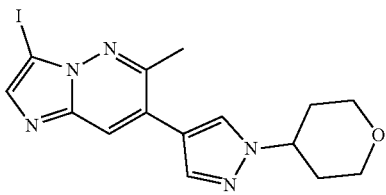 [SMILES: Cc1nn2c(I)cnc2cc1-c1cnn(C2CCOCC2)c1]

A mixture of 6-methyl-7-(1-(tetrahydro-2H-pyran-4-yl)-1H-pyrazol-4-yl)imidazo[1,2-b]pyridazine (134 mg, 0.473 mmol) and NIS (112 mg, 0.497 mmol) was treated with DMF (8.0 ml). The mixture was stirred at 50° C. for 90 min. The mixture was concentrated and purified on silica gel (0-75% EtOAc in Hexanes) to give 3-iodo-6-methyl-7-(1-(tetrahydro-2H-pyran-4-yl)-1H-pyrazol-4-yl)imidazo[1,2-b]pyridazine (180 mg, 0.440 mmol, 93% yield). LCMS calculated for $C_{15}H_{17}IN_5O$ (M+H)$^+$: m/z=410.1. found: 410.1.

Step 3. (1-(tert-butoxycarbonyl)-2,3-dihydro-1H-pyrrolo[2,3-b]pyridin-4-yl)boronic Acid

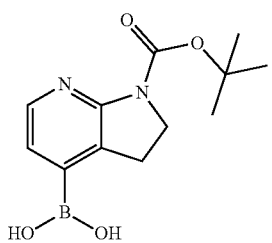 [SMILES: CC(C)(C)OC(=O)N1CCc2c(B(O)O)ccnc21]

A vial was charged with a mixture of tert-butyl 4-bromo-2,3-dihydro-1H-pyrrolo[2,3-b]pyridine-1-carboxylate (0.082 g, 0.274 mmol), 4,4,4',4',5,5,5',5'-octamethyl-2,2'-bi(1,3,2-dioxaborolane) (0.104 g, 0.411 mmol), potassium acetate (0.054 g, 0.548 mmol) and (1,1'-Bis(diphenylphosphino)ferrocene)-dichloropalladium(II) (0.020 g, 0.027 mmol). The vial was sealed, evacuated and backfilled with nitrogen (this process was repeated a total of three times). The mixture was treated with Dioxane (2 ml). The mixture was heated at 100° C. for 2 h. The mixture was filtered to give (1-(tert-butoxycarbonyl)-2,3-dihydro-1H-pyrrolo[2,3-b]pyridin-4-yl)boronic acid (0.060 g) which was used directly in the next step without further purification. LCMS calculated for $C_{12}H_{18}BN_2O_4$(M+H)$^+$: m/z=265.0. found: 265.1.

Step 4. tert-butyl 4-(6-methyl-7-(1-(tetrahydro-2H-pyran-4-yl)-H-pyrazol-4-yl)imidazo[1,2-b]pyridazin-3-yl)-2,3-dihydro-1H-pyrrolo[2,3-b]pyridine-1-carboxylate

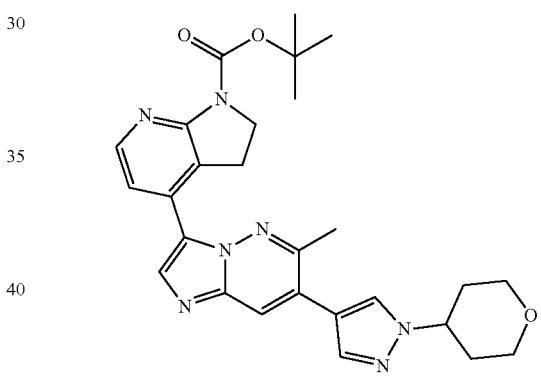

A mixture of 3-iodo-6-methyl-7-(1-(tetrahydro-2H-pyran-4-yl)-1H-pyrazol-4-yl)imidazo[1,2-b]pyridazine (0.040 g, 0.098 mmol), (1-(tert-butoxycarbonyl)-2,3-dihydro-1H-pyrrolo[2,3-b]pyridin-4-yl)boronic acid (0.052 g, 0.195 mmol), (1,1'-Bis(diphenylphosphino)-ferrocene)-dichloropalladium(II) (7.15 mg, 9.77 µmol) and potassium carbonate (0.027 g, 0.195 mmol) in 1,4-Dioxane (1 ml)/Water (0.2 ml) was heated at 90° C. for 1 h. After cooling, the mixture was concentrated. The residue was purified on silica gel column (0-100% EtOAc/Hexanes followed by 0-10% MeOH/DCM) to give tert-butyl 4-(6-methyl-7-(1-(tetrahydro-2H-pyran-4-yl)-1H-pyrazol-4-yl)imidazo[1,2-b]pyridazin-3-yl)-2,3-dihydro-1H-pyrrolo[2,3-b]pyridine-1-carboxylate (0.040 g, 0.080 mmol, 82% yield). LCMS calculated for $C_{27}H_{32}N_7O_3$ (M+H)$^+$: m/z=502.3. found: 502.1.

Step 5. 3-(2,3-dihydro-1H-pyrrolo[2,3-b]pyridin-4-yl)-6-methyl-7-(1-(tetrahydro-2H-pyran-4-yl)-1H-pyrazol-4-yl)imidazo[1,2-b]pyridazine

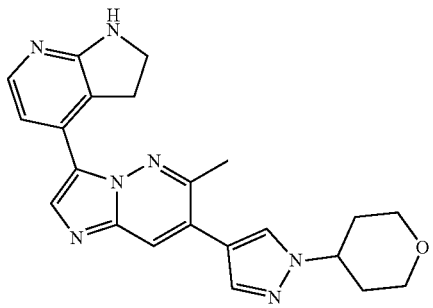 [SMILES: Cc1nn2c(-c3ccnc4c3CCN4)cnc2cc1-c1cnn(C2CCOCC2)c1]

A solution of tert-butyl 4-(6-methyl-7-(1-(tetrahydro-2H-pyran-4-yl)-1H-pyrazol-4-yl)imidazo[1,2-b]pyridazin-3-yl)-2,3-dihydro-1H-pyrrolo[2,3-b]pyridine-1-carboxylate (40 mg, 0.080 mmol) in DCM (0.5 M) was treated with 4N HCl solution in dioxane (1 ml, 4.00 mmol). After stirring at room temperature for 2 h, the mixture was purified on prep-LCMS (XBridge C18 column, eluting with a gradient of acetonitrile/water containing 0.1% TFA, at flow rate of 60 mL/min) to give 3-(2,3-dihydro-1H-pyrrolo[2,3-b]pyridin-4-yl)-6-methyl-7-(1-(tetrahydro-2H-pyran-4-yl)-1H-pyrazol-4-yl)imidazo[1,2-b]pyridazine (12 mg, 0.030 mmol, 37.5% yield). LCMS calculated for $C_{22}H_{24}N_7O$ $(M+H)^+$: m/z=402.2. found: 402.1.

Step 6. (4-(6-methyl-7-(1-(tetrahydro-2H-pyran-4-yl)-1H-pyrazol-4-yl)imidazo[1,2-b]pyridazin-3-yl)-2,3-dihydro-1H-pyrrolo[2,3-b]pyridin-1-yl) (pyridin-4-yl)methanone A solution of 3-(2,3-dihydro-1H-pyrrolo[2,3-b]pyridin-4-yl)-6-methyl-7-(1-(tetrahydro-2H-pyran-4-yl)-1H-pyrazol-4-yl)imidazo[1,2-b]pyridazine (3 mg, 7.47 μmol) and triethylamine (3.12 μl, 0.022 mmol) in DCM (0.5 ml) was treated with isonicotinoyl chloride (1.587 mg, 0.011 mmol). The mixture was stirred at room temperature for 1 h. The mixture was purified on prep-LCMS (XBridge C18 column, eluting with a gradient of acetonitrile/water containing 0.1% TFA, at flow rate of 60 mL/min) to give (4-(6-methyl-7-(1-(tetrahydro-2H-pyran-4-yl)-1H-pyrazol-4-yl)imidazo[1,2-b]pyridazin-3-yl)-2,3-dihydro-1H-pyrrolo[2,3-b]pyridin-1-yl)(pyridin-4-yl)methanone (1.5 mg, 2.96 μmol, 39.6% yield). LCMS calculated for $C_{28}H_{27}N_8O_2$ $(M+H)^+$: m/z=507.2. found: 507.2.

Example 33. 1-((1S,4S)-5-(4-(7-(1-((1R,4R)-4-hydroxycyclohexyl)-1H-pyrazol-4-yl)-6-methylimidazo[1,2-b]pyridazin-3-yl)quinolin-7-yl)-2,5-diazabicyclo[2.2.1]heptan-2-yl)ethan-1-one

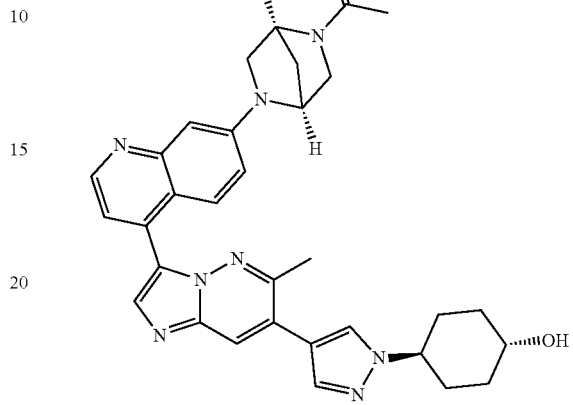

Step 1. 7-(1-((1R,4R)-4-((tert-butyldimethylsilyl)oxy)cyclohexyl)-1H-pyrazol-4-yl)-6-methylimidazo[1,2-b]pyridazine

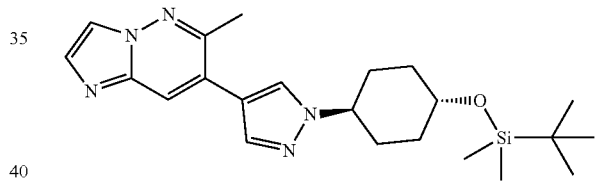

A vial was charged with 7-chloro-6-methylimidazo[1,2-b]pyridazine (35 mg, 0.209 mmol, see step 2 in Example 1), 1-((1R,4R)-4-((tert-butyldimethylsilyl)oxy)cyclohexyl)-4-(4,4,5,5-tetramethyl-1,3,2-dioxaborolan-2-yl)-1H-pyrazole (102 mg, 0.251 mmol), cesium carbonate (136 mg, 0.418 mmol) and dicyclohexyl(2',4',6'-triisopropylbiphenyl-2-yl)phosphine-(2'-aminobiphenyl-2-yl)(chloro)palladium (1:1) (24.65 mg, 0.031 mmol). The vial was sealed, evacuated and backfilled with nitrogen (this process was repeated a total of three times). 1,4-Dioxane (10 ml) and water (2 ml) were added. The reaction was heated at 80° C. for 1 h. The reaction was purified on silica gel column (0-100% EtOAc in Hexanes followed by 10% MeOH/DCM) to give 7-(1-((1R,4R)-4-((tert-butyldimethylsilyl)oxy)cyclohexyl)-1H-pyrazol-4-yl)-6-methylimidazo[1,2-b]pyridazine (77 mg, 0.187 mmol, 90% yield). LCMS calculated for $C_{22}H_{34}N_5OSi$ $(M+H)^+$: m/z=412.3. found: 412.1.

Step 2. 7-(1-((1R,4R)-4-((tert-butyldimethylsilyl) oxy)cyclohexyl)-1H-pyrazol-4-yl)-3-iodo-6-methylimidazo[1,2-b]pyridazine

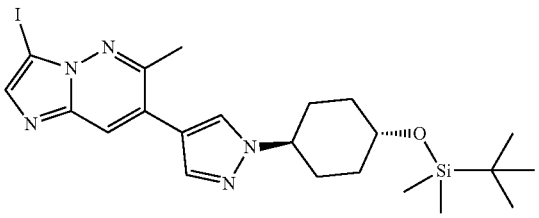 [SMILES: Cc1nn2c(I)cnc2cc1-c1cnn([C@H]2CC[C@H](O[Si](C)(C)C(C)(C)C)CC2)c1]

A mixture of 7-(1-((1R,4R)-4-((tert-butyldimethylsilyl) oxy)cyclohexyl)-1H-pyrazol-4-yl)-6-methylimidazo[1,2-b] pyridazine (77 mg, 0.187 mmol) and NIS (44.2 mg, 0.196 mmol) was treated with DMF (8.0 ml). The mixture was stirred at 50° C. for 90 min. The mixture was concentrated and purified on silica gel column (0-70% EtOAc in Hexanes) to give 7-(1-((1R,4R)-4-((tert-butyldimethylsilyl) oxy)cyclohexyl)-1H-pyrazol-4-yl)-3-iodo-6-methylimidazo [1,2-b]pyridazine (44 mg, 0.082 mmol, 43.8% yield). LCMS calculated for $C_{22}H_{33}IN_5OSi$ (M+H)$^+$: m/z=538.1. found: 538.1.

Step 3. 4-(7-(1-((1R,4R)-4-((tert-butyldimethylsilyl) oxy)cyclohexyl)-1H-pyrazol-4-yl)-6-methylimidazo [1,2-b]pyridazin-3-yl)-7-chloroquinoline

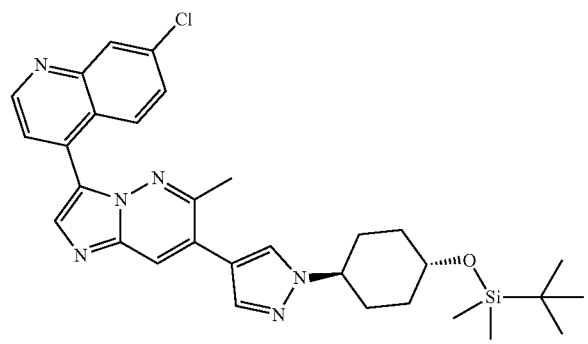 [SMILES: Cc1nn2c(-c3ccnc4cc(Cl)ccc34)cnc2cc1-c1cnn([C@H]2CC[C@H](O[Si](C)(C)C(C)(C)C)CC2)c1]

A mixture of 7-(1-((1R,4R)-4-((tert-butyldimethylsilyl) oxy)cyclohexyl)-1H-pyrazol-4-yl)-3-iodo-6-methylimidazo [1,2-b]pyridazine (0.044 g, 0.082 mmol), 7-chloro-4-(4,4,5, 5-tetramethyl-1,3,2-dioxaborolan-2-yl)quinoline (0.028 g, 0.098 mmol), (1,1'-Bis(diphenyl-phosphino)ferrocene)dichloropalladium(II) (5.99 mg, 8.19 µmol) and potassium carbonate (0.023 g, 0.164 mmol) in 1,4-Dioxane (1 ml)/ Water (0.2 ml) was heated at 90° C. for 1 h. After cooling, the mixture was concentrated. The residue was purified on silica gel column (0-100% EtOAc/Hexanes followed by 0-10% MeOH/DCM) to give 4-(7-(1-((1R,4R)-4-((tert-butyldimethylsilyl)oxy)cyclohexyl)-1H-pyrazol-4-yl)-6-methylimidazo[1,2-b]pyridazin-3-yl)-7-chloroquinoline (0.040 g, 0.070 mmol, 85% yield). LCMS calculated for $C_{31}H_{38}ClN_6OSi$ (M+H)$^+$: m/z=573.3. found: 573.3.

Step 4. (1R,4R)-4-(4-(3-(7-((1S,4S)-2,5-diazabicyclo[2.2.1]heptan-2-yl)quinolin-4-yl)-6-methylimidazo[1,2-b]pyridazin-7-yl)-1H-pyrazol-1-yl)cyclohexan-1-ol

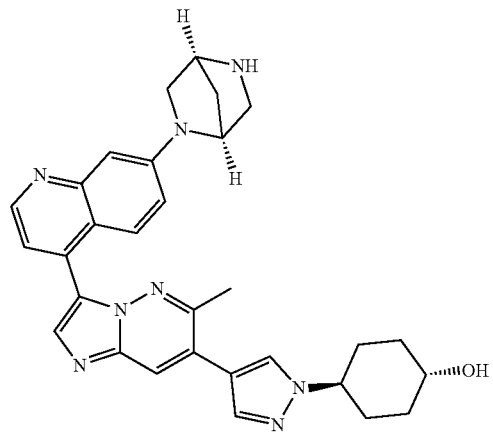 [SMILES: Cc1nn2c(-c3ccnc4cc(N5C[C@@H]6C[C@H]5CN6)ccc34)cnc2cc1-c1cnn([C@H]2CC[C@H](O)CC2)c1]

A mixture of 4-(7-(1-((1R,4R)-4-((tert-butyldimethylsilyl)oxy)cyclohexyl)-1H-pyrazol-4-yl)-6-methylimidazo[1, 2-b]pyridazin-3-yl)-7-chloroquinoline (8 mg, 0.014 mmol), tert-butyl (1 S,4S)-2,5-diazabicyclo[2.2.1]heptane-2-carboxylate (5.53 mg, 0.028 mmol), chloro-(2-dicyclohexylphosphino-2',6'-diisopropoxy-1,1'-biphenyl)[2-(2'-amino-1,1'-biphenyl)]-palladium(II) (1.084 mg, 1.396 µmol) and cesium carbonate (9.09 mg, 0.028 mmol) in 1,4-dioxane (1 ml) was heated at 110° C. for 1 h. The mixture was concentrated. The residue was dissolved in THF (1.0 m) and treated with 4M HCl solution in dioxane (0.5 ml, 2.000 mmol). After stirring at room temperature for 2 h, the mixture was purified on prep-LCMS (XBridge C18 column, eluting with a gradient of acetonitrile/water containing 0.1% TFA, at flow rate of 60 mL/min) to give (1R,4R)-4-(4-(3-(7-((1S,4S)-2,5-diazabicyclo[2.2.1]heptan-2-yl)quinolin-4-yl)-6-methylimidazo[1,2-b]pyridazin-7-yl)-1H-pyrazol-1-yl)cyclohexan-1-ol. LCMS calculated for $C_{30}H_{33}N_8O$ (M+H)$^+$: m/z=521.3; found: 521.0.

Step 5. 1-((1S,4S)-5-(4-(7-(1-((1R,4R)-4-hydroxycyclohexyl)-1H-pyrazol-4-yl)-6-methylimidazo[1,2-b]pyridazin-3-yl)quinolin-7-yl)-2,5-diazabicyclo [2.2.1]heptan-2-yl)ethan-1-one A solution of (1R,4R)-4-(4-(3-(7-((1S,4S)-2,5-diazabicyclo[2.2.1]heptan-2-yl)quinolin-4-yl)-6-methylimidazo[1,2-b]pyridazin-7-yl)-1H-pyrazol-1-yl)cyclohexan-1-ol (3.6 mg, 6.91 µmol) and triethylamine (2.89 µl, 0.021 mmol) in DCM (0.5 ml) was treated with acetyl chloride (0.814 mg, 10.37 µmol). The mixture was stirred at room temperature for 1 h. The mixture was purified on prep-LCMS (XBridge C18 column, eluting with a gradient of acetonitrile/water containing 0.1% TFA, at flow rate of 60 mL/min) to give 1-((1S,4S)-5-(4-(7-(1-((1R,4R)-4-hydroxycyclohexyl)-1H-pyrazol-4-yl)-6-methylimidazo[1,2-b]pyridazin-3-yl)quinolin-7-yl)-2,5-diazabicyclo[2.2.1]heptan-2-yl)ethan-1-one (1.7 mg, 3.02 µmol, 43.7% yield). LCMS calculated for $C_{32}H_{35}N_8O_2$ (M+H)$^+$: m/z=563.3. found: 563.0.

Example 34. 2-(4-(7-(1-((1R,4R)-4-hydroxycyclohexyl)-1H-pyrazol-4-yl)-6-methylimidazo[1,2-b]pyridazin-3-yl)quinolin-7-yl)hexahydropyrrolo[1,2-a]pyrazin-6(2H)-one

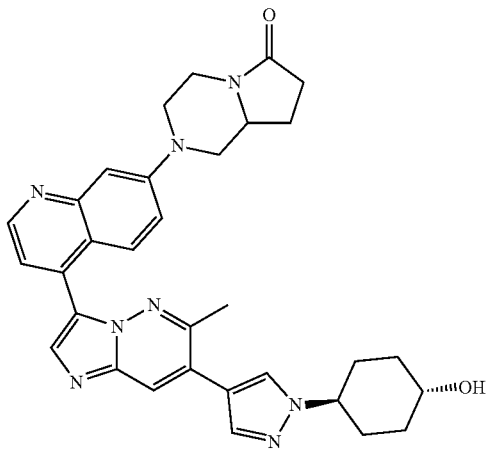 [SMILES: Cc1nn2c(-c3ccnc4cc(N5CCN6C(=O)CCC6C5)ccc34)cnc2cc1-c1cnn([C@H]2CC[C@H](O)CC2)c1]

A mixture of 4-(7-(1-((1R,4R)-4-((tert-butyldimethylsilyl)oxy)cyclohexyl)-1H-pyrazol-4-yl)-6-methylimidazo[1,2-b]pyridazin-3-yl)-7-chloroquinoline (8 mg, 0.014 mmol), hexahydro-pyrrolo[1,2-a]pyrazin-6(2H)-one (3.91 mg, 0.028 mmol), chloro-(2-dicyclohexylphosphino-2',6'-diisopropoxy-1,1'-biphenyl)[2-(2'-amino-1,1'-biphenyl)]palladium(II) (1.084 mg, 1.396 µmol) and cesium carbonate (9.09 mg, 0.028 mmol) in 1,4-Dioxane (1 ml) was heated at 110° C. for 1 h. The mixture was concentrated. The residue was treated with 4M HCl solution in dioxane (0.5 ml, 2.000 mmol) at room temperature for 2 h. The mixture was purified on prep-LCMS (XBridge C18 column, eluting with a gradient of acetonitrile/water containing 0.1% TFA, at flow rate of 60 mL/min) to give 2-(4-(7-(1-((1R,4R)-4-hydroxycyclohexyl)-1H-pyrazol-4-yl)-6-methylimidazo[1,2-b]pyridazin-3-yl)quinolin-7-yl)hexahydropyrrolo[1,2-a]pyrazin-6(2H)-one (1.5 mg, 2.67 mol, 19.10% yield). LCMS calculated for $C_{32}H_{35}N_8O_2$ (M+H)$^+$: m/z=563.3. found: 563.0.

Example 35. 4-(6-methyl-7-(1-(piperidin-4-yl)-1H-pyrazol-4-yl)imidazo[1,2-a]pyridin-3-yl)quinoline

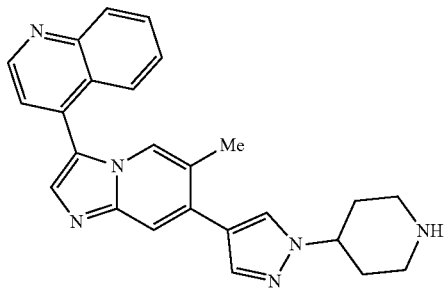 [SMILES: Cc1cn2c(-c3ccnc4ccccc34)cnc2cc1-c1cnn(C2CCNCC2)c1]

Step 1: 7-bromo-6-methylimidazo[1,2-a]pyridine

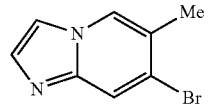

A solution of 4-bromo-5-methylpyridin-2-amine (893 mg, 4.77 mmol) in ethanol (9.5 mL), was treated with 2-chloroacetaldehyde (1.6 mL, 14.32 mmol) as a 50% by weight solution in water. This mixture was stirred at 80° C. for 3 h. The reaction mixture was cooled and concentrated under vacuum. The resulting residue was dissolved in dichloromethane and washed with saturated aqueous sodium bicarbonate. The aqueous phase was extracted twice with additional dichloromethane and the organic fractions were combined. The solution was dried with magnesium sulfate, filtered, concentrated under vacuum, and chromatographed over 100 g of silica in an eluent of 0-100% ethyl acetate/dichloromethane. Fractions containing the product were combined and concentrated to give 7-bromo-6-methylimidazo[1,2-a]pyridine (841 mg, 3.98 mmol, 83% yield) as a faintly yellow solid. LCMS calculated for $C_8H_8BrN_2$ (M+H)$^+$: m/z=211.0, 213.0. Found: 211.0, 213.0.

Step 2: tert-butyl 4-(4-(6-methylimidazo[1,2-a]pyridin-7-yl)-1H-pyrazol-1-yl)piperidine-1-carboxylate

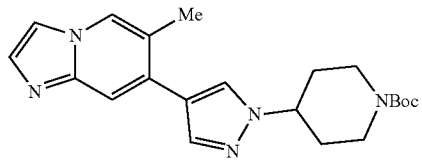 [SMILES: Cc1cn2ccnc2cc1-c1cnn(C2CCN(C(=O)OC(C)(C)C)CC2)c1]

A solution of 7-bromo-6-methylimidazo[1,2-a]pyridine (115 mg, 0.545 mmol) in dioxane (2.3 mL) was treated with water (0.5 mL), potassium phosphate, tribasic (231 mg, 1.090 mmol), and tert-butyl 4-(4-(4,4,5,5-tetramethyl-1,3,2-dioxaborolan-2-yl)-1H-pyrazol-1-yl)piperidine-1-carboxylate (267 mg, 0.708 mmol). This solution was de-gassed with bubbling nitrogen for 5 minutes. PdCl$_2$(dppf)-dichloromethane adduct (44.5 mg, 0.054 mmol) was then added, the vial was capped, and the mixture was stirred at 50° C. for 90 minutes. The reaction mixture was then cooled, diluted with ethyl acetate, and treated with saturated aqueous ammonium chloride. The phases were separated and the aqueous phase was extracted twice more with additional ethyl acetate. The organic phases were combined, washed with saturated aqueous sodium chloride, dried over magnesium sulfate, filtered, and concentrated under vacuum. The residue was chromatographed over 20 g of silica with an eluent of 0-9% methanol/dichloromethane. The fractions containing the product were combined to give tert-butyl 4-(4-(6-methylimidazo[1,2-a]pyridin-7-yl)-1H-pyrazol-1-yl)piperidine-1-carboxylate (193 mg, 0.506 mmol, 93% yield) as a brown solid. LCMS calculated for $C_{21}H_{28}N_5O_2$ (M+H)$^+$: m/z=382.2. Found: 382.3.

Step 3: tert-butyl 4-(4-(3-bromo-6-methylimidazo[1,2-a]pyridin-7-yl)-1H-pyrazol-1-yl)piperidine-1-carboxylate

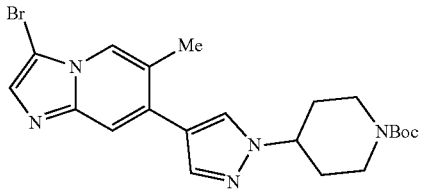 [SMILES: Cc1cn2c(Br)cnc2cc1-c1cnn(C2CCN(C(=O)OC(C)(C)C)CC2)c1]

A vial containing tert-butyl 4-(4-(6-methylimidazo[1,2-a]pyridin-7-yl)-1H-pyrazol-1-yl)piperidine-1-carboxylate (190 mg, 0.498 mmol) was treated with N,N-dimethylformamide (3 mL). This solution was cooled to 0° C. In a separate flask, a solution of N-bromosuccinimide (133 mg, 0.747 mmol) in DMF (2.5 mL) was prepared. The NBS solution was added to the vial containing the starting material in a dropwise fashion. After stirring at 0° C. for 5 minutes, the vial was removed from the ice bath and allowed to warm to 22° C. This mixture was stirred at 22° C. for 1 hour. The solution was diluted with water and ethyl acetate, and saturated aqueous sodium bicarbonate was added to the biphasic mixture. The phases were separated and the aqueous phase was extracted twice with additional ethyl acetate. The organic fractions were combined, washed with saturated aqueous sodium chloride, dried over magnesium sulfate, filtered, and concentrated under vacuum. The resulting residue was chromatographed over 20 g of silica with an eluent of 0-9% methanol/dichloromethane. The fractions containing the product were combined and concentrated to give tert-butyl 4-(4-(3-bromo-6-methylimidazo[1,2-a]pyridin-7-yl)-1H-pyrazol-1-yl)piperidine-1-carboxylate (77 mg, 0.167 mmol, 33.6% yield) as a brown solid. LCMS calculated for $C_{21}H_{27}BrN_5O_2$ $(M+H)^+$: m/z=460.1, 462.1. Found: 460.2, 462.2.

Step 4: 4-(6-methyl-7-(1-(piperidin-4-yl)-H-pyrazol-4-yl)imidazo[1,2-a]pyridin-3-yl)quinoline A solution of tert-butyl 4-(4-(3-bromo-6-methylimidazo[1,2-a]pyridin-7-yl)-1H-pyrazol-1-yl)piperidine-1-carboxylate (35 mg, 0.076 mmol) in DMF (317 μL) was treated with water (63.4 μL), cesium carbonate (61.9 mg, 0.190 mmol), and quinolin-4-ylboronic acid (28.9 mg, 0.167 mmol). The solution was de-gassed with bubbling nitrogen for 5 minutes. $PdCl_2$(dppf)-dichloromethane adduct (9.31 mg, 0.011 mmol) was added, the vial was capped, and the mixture was stirred at 90° C. for 30 minutes. The reaction mixture was then cooled, diluted with ethyl acetate, and treated with saturated aqueous ammonium chloride. The phases were separated and the aqueous phase was extracted twice more with additional ethyl acetate. The organic phases were combined, washed with saturated aqueous sodium chloride, dried over magnesium sulfate, filtered, and concentrated under vacuum to give crude tert-butyl 4-(4-(6-methyl-3-(quinolin-4-yl)imidazo[1,2-a]pyridin-7-yl)-1H-pyrazol-1-yl)piperidine-1-carboxylate as a brown solid. LCMS calculated for $C_{30}H_{33}N_6O_2$ $(M+H)^+$: m/z=509.3. Found: 509.2. Crude tert-butyl 4-(4-(6-methyl-3-(quinolin-4-yl)imidazo[1,2-a]pyridin-7-yl)-1H-pyrazol-1-yl)piperidine-1-carboxylate was then dissolved in dichloromethane (1 mL) and treated with trifluoroacetic acid (1 mL). This mixture was stirred at 22° C. for 1 hour. The mixture was diluted with methanol (3 mL), filtered, and purified by prep LC-MS (pH=2 method; XBridge™ PrepC18 5 μm OBD™ column, 30×100 mm, 60 mL/min, eluting with a gradient of MeCN and water with 0.1% TFA) to give the desired product, but insufficiently pure. The partially purified mixture was then re-purified by prep LC-MS (pH=10 method; XBridge™ PrepC18 5 μm OBD™ column, 30×100 mm, 60 mL/min, eluting with a gradient of MeCN and water with 0.15% $NH_4OH$) to give 4-(6-methyl-7-(1-(piperidin-4-yl)-1H-pyrazol-4-yl)imidazo[1,2-a]pyridin-3-yl)quinoline as an orange solid. LCMS calculated for $C_{25}H_{25}N_6(M+H)^+$: 409.2. Found: 409.2.

Example 36. 2-fluoro-4-(6-methyl-7-(1-(piperidin-4-yl)-1H-pyrazol-4-yl)imidazo[1,2-a]pyridin-3-yl)benzamide

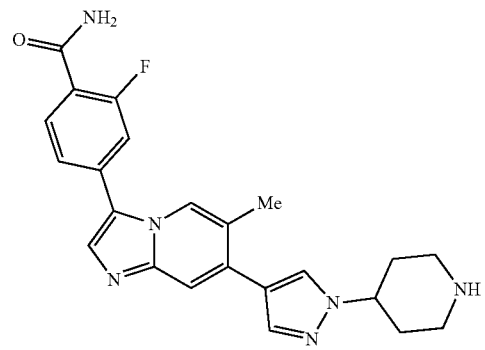 [SMILES: Cc1cn2c(-c3ccc(C(N)=O)c(F)c3)cnc2cc1-c1cnn(C2CCNCC2)c1]

A solution of tert-butyl 4-(4-(3-bromo-6-methylimidazo[1,2-a]pyridin-7-yl)-1H-pyrazol-1-yl)piperidine-1-carboxylate (35 mg, 0.076 mmol) [prepared in step 3, example 35] in DMF (317 μl) was treated with water (63.4 μl), cesium carbonate (61.9 mg, 0.190 mmol), and (4-carbamoyl-3-fluorophenyl)boronic acid (30.6 mg, 0.167 mmol). This solution was de-gassed with bubbling nitrogen for 5 minutes. $PdCl_2$(dppf)-dichloromethane adduct (9.31 mg, 0.011 mmol) was added, the vial was capped, and the mixture was stirred at 90° C. for 30 minutes. The reaction mixture was then cooled, diluted with ethyl acetate, and treated with saturated aqueous ammonium chloride. The phases were separated and the aqueous phase was extracted twice more with additional ethyl acetate. The organic phases were combined, washed with saturated aqueous sodium chloride, dried over magnesium sulfate, filtered, and concentrated under vacuum to give crude tert-butyl 4-(4-(3-(4-carbamoyl-3-fluorophenyl)-6-methylimidazo[1,2-a]pyridin-7-yl)-1H-pyrazol-1-yl)piperidine-1-carboxylate as a brown solid. LCMS calculated for $C_{28}H_{32}FN_6O_3(M+H)^+$: m/z=519.3. Found: 519.3. The crude tert-butyl 4-(4-(3-(4-carbamoyl-3-fluorophenyl)-6-methylimidazo[1,2-a]pyridin-7-yl)-1H-pyrazol-1-yl)piperidine-1-carboxylate was then dissolved in dichloromethane (1 mL) and treated with trifluoroacetic acid (1 mL). This mixture was stirred at 22° C. for 1 hour. The mixture was diluted with methanol (3 mL), filtered, and purified by prep LC-MS (pH=2 method; XBridge™ PrepC18 5 μm OBD™ column, 30×100 mm, 60 mL/min, eluting with a gradient of MeCN and water with 0.1% TFA) to give the desired product, but insufficiently pure. The partially purified mixture was then purified by prep LC-MS (pH=10 method; XBridge™ PrepC18 5 μm OBD™ column, 30×100 mm, 60 mL/min, eluting with a gradient of MeCN and water with 0.15% NH₄OH) to give 2-fluoro-4-(6-methyl-7-(1-(piperidin-4-yl)-1H-pyrazol-4-yl)imidazo[1,2-a]pyridin-3-yl)benzamide as an off-white solid. LCMS calculated for $C_{23}H_{24}FN_6O$ (M+H)⁺: 419.2. Found: 419.2.

Example 37. (1R,4R)-4-(4-(6-Methyl-3-(7-(pyridin-2-yl)-1,8-naphthyridin-4-yl)imidazo[1,2-b]pyridazin-7-yl)-1H-pyrazol-1-yl)cyclohexan-1-ol

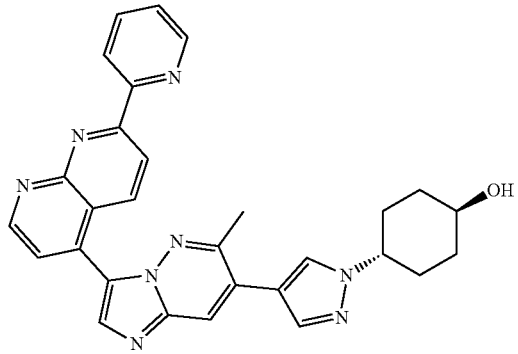 [SMILES: Cc1nn2c(-c3ccnc4nc(-c5ccccn5)ccc34)cnc2cc1-c1cnn([C@H]2CC[C@H](O)CC2)c1]

Step 1: 5-Chloro-2-(pyridin-2-yl)-1,8-naphthyridine

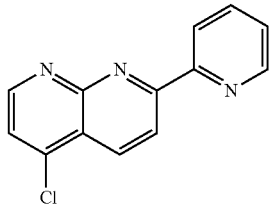 [SMILES: Clc1ccnc2nc(-c3ccccn3)ccc12]

To a screw-cap vial equipped with a magnetic stir bar was added 2,5-dichloro-1,8-naphthyridine (2571.1 mg, 12.92 mmol), and tetrakis(triphenylphosphine)palladium(0) (2239 mg, 1.938 mmol). The vial was sealed with a Teflon-lined septum, evacuated and backfilled with nitrogen (this process was repeated a total of three times). A solution of 2-(tributylstannyl)pyridine (4786 mg, 13.00 mmol) in 1,4-Dioxane (100.0 ml) was added via syringe. The mixture was stirred at 100° C. for 16 h. After cooling at room temperature, the mixture was concentrated. The residue was purified on silica gel (120 g, 0-100% EtOAc in CH₂Cl₂) to give the desired product as a white solid (2.030 g, 65%). LCMS calculated for $C_{13}H_9ClN_3$ (M+H)⁺ m/z=242.0. found 242.0.

Step 2: 2-(Pyridin-2-yl)-5-(4,4,5,5-tetramethyl-1,3,2-dioxaborolan-2-yl)-1,8-naphthyridine

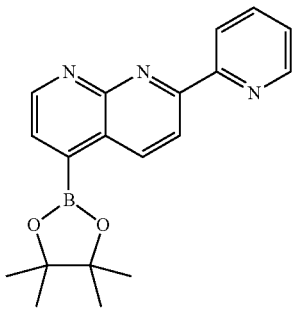 [SMILES: CC1(C)OB(c2ccnc3nc(-c4ccccn4)ccc23)OC1(C)C]

To a screw-cap vial equipped with a magnetic stir bar was added 4,4,5,5,4',4',5',5'-octamethyl-[2,2']bi[[1,3,2]dioxaborolanyl] (1115 mg, 4.39 mmol), potassium acetate (1158 mg, 11.80 mmol), 5-chloro-2-(pyridin-2-yl)-1,8-naphthyridine (833.2 mg, 3.45 mmol) and dichloro[1,1'-bis(diphenylphosphino)ferrocene]palladium (II) dichloromethane adduct (563 mg, 0.690 mmol). The vial was sealed with a Teflon-lined septum, evacuated and backfilled with nitrogen (this process was repeated a total of three times). 1,4-Dioxane (14.0 ml) was added via syringe. The mixture was stirred at 105° C. for 16 h. After cooling at room temperature, the mixture was filtered. The filtrate was used directly in the next step without further purification.

Step 3: 5-(7-Chloro-6-methylimidazo[1,2-b]pyridazin-3-yl)-2-(pyridin-2-yl)-1,8-naphthyridine

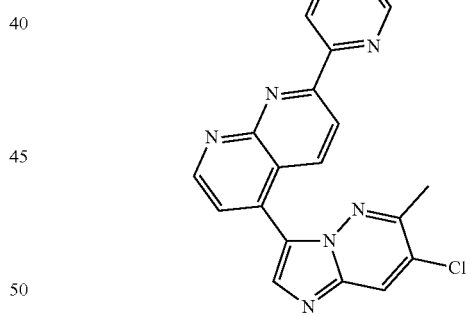

To a screw-cap vial equipped with a magnetic stir bar was added 7-chloro-3-iodo-6-methylimidazo[1,2-b]pyridazine (1006.1 mg, 3.43 mmol, see step 3 in Example 1), PdCl₂(dppf)-CH₂Cl₂ adduct (560 mg, 0.686 mmol) and cesium carbonate (4274 mg, 13.12 mmol). The vial was sealed with a Teflon-lined septum, evacuated and backfilled with nitrogen (this process was repeated a total of three times). A solution of 2-(pyridin-2-yl)-5-(4,4,5,5-tetramethyl-1,3,2-dioxaborolan-2-yl)-1,8-naphthyridine (1149 mg, 3.45 mmol, see above step 2) in 1,4-Dioxane (14.0 ml) was added via syringe followed by water (4.0 ml, 222 mmol). The mixture was stirred at 80° C. for 3 h. After cooling to room temperature, the reaction mixture was concentrated. The residue was purified on silica gel (40 g, 0-100% EtOAc in CH₂Cl₂, then 5% MeOH in CH₂Cl₂) to give the desired product as a brown solid (604.7 mg, 47%). LCMS calculated for $C_{20}H_{14}ClN_6$ (M+H)$^+$ m/z=373.1. found 373.1.

Step 4: (1R,4R)-4-(4-(6-Methyl-3-(7-(pyridin-2-yl)-1,8-naphthyridin-4-yl) imidazo[1,2-b]pyridazin-7-yl)-1H-pyrazol-1-yl)cyclohexan-1-ol To a screw-cap vial equipped with a magnetic stir bar was added 5-(7-chloro-6-methylimidazo[1,2-b]pyridazin-3-yl)-2-(pyridin-2-yl)-1,8-naphthyridine (21.8 mg, 0.058 mmol), 1-((1R,4R)-4-((tert-butyldimethylsilyl)oxy)cyclohexyl)-4-(4,4,5,5-tetramethyl-1,3,2-dioxaborolan-2-yl)-1H-pyrazole (39.0 mg, 0.096 mmol), dicyclohexyl(2',4',6'-triisopropylbiphenyl-2-yl)phosphine-(2'-aminobiphenyl-2-yl)(chloro)palladium (1:1) (XPhos Pd G2, 4.60 mg, 5.85 µmol) and cesium carbonate (59.0 mg, 0.181 mmol). The vial was sealed with a Teflon-lined septum, evacuated and backfilled with nitrogen (this process was repeated a total of three times). 1,4-Dioxane (2.0 ml) was added via syringe, followed by water (200.0 µl, 11.10 mmol). The mixture was heated at 80° C. for 6 h. After cooling to room temperature, HCl (4.0 N in 1,4-dioxane) (1.0 ml, 4.00 mmol) was added followed by MeOH (1.0 ml). The reaction was stirred at room temperature for 1 h, and then concentrated. The residue was purified using prep-LCMS (XBridge C18 column, eluting with a gradient of acetonitrile/water containing 0.1% TFA, at flow rate of 60 mL/min) to afford the desired product as its TFA salt. LCMS calculated for $C_{29}H_{27}N_8O$ (M+H)$^+$: m/z=503.2. found: 503.2. $^1$H NMR (TFA salt, 600 MHz, DMSO) δ 9.30 (d, J=4.7 Hz, 1H), 8.81 (d, J=4.2 Hz, 1H), 8.71 (overlap, 2H), 8.69 (d, J=8.0 Hz, 1H), 8.37 (s, 1H), 8.36 (overlap, 2H), 8.15 (d, J=4.7 Hz, 1H), 8.11 (m, 1H), 8.02 (s, 1H), 7.61 (m, 1H), 4.22 (m, 1H), 3.53 (m, 1H), 2.64 (s, 3H), 2.08 (m, 2H), 1.95 (m, 2H), 1.86 (m, 2H), 1.38 (m, 2H).

Example 38. 5-(7-(4-(Azetidin-1-ylmethyl)phenyl)-6-methylimidazo[1,2-b]pyridazin-3-yl)-2-(pyridin-2-yl)-1,8-naphthyridine

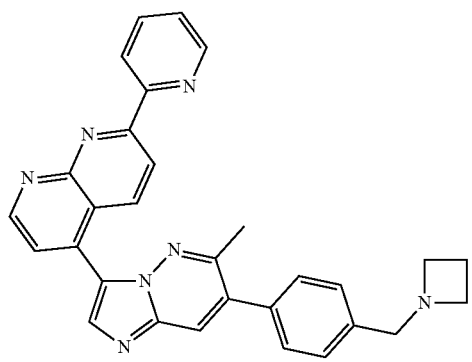 [SMILES: Cc1nn2c(-c3ccnc4nc(-c5ccccn5)ccc34)cnc2cc1-c1ccc(CN2CCC2)cc1]

This compound was prepared according to the procedure described in Example 37, using 1-(4-(4,4,5,5-tetramethyl-1,3,2-dioxaborolan-2-yl)benzyl)azetidine instead of 1-((1R,4R)-4-((tert-butyldimethylsilyl)oxy)cyclohexyl)-4-(4,4,5,5-tetramethyl-1,3,2-dioxaborolan-2-yl)-1H-pyrazole as the starting material. LC-MS calculated for $C_{30}H_{26}N_7$ (M+H)$^+$: m/z=484.2. found 484.2. $^1$H NMR (TFA salt, 600 MHz, DMSO) δ 9.27 (d, J=4.5 Hz, 1H), 8.80 (d, J=4.1 Hz, 1H), 8.68 (overlap, 2H), 8.61 (d, J=8.7 Hz, 1H), 8.26 (s, 1H), 8.11 (s, 1H), 8.08 (m, 1H), 8.04 (d, J=4.5 Hz, 1H), 7.58 (m, 1H), 7.49 (d, J=8.1 Hz, 2H), 7.41 (d, J=8.1 Hz, 2H), 3.60 (s, 2H), 3.17 (t, J=6.9 Hz, 4H), 2.39 (s, 3H), 2.00 (m, 2H).

Example 39. 5-(7-(1-Ethyl-1H-pyrazol-4-yl)-6-methylimidazo[1,2-b]pyridazin-3-yl)-2-(pyridin-2-yl)-1,8-naphthyridine

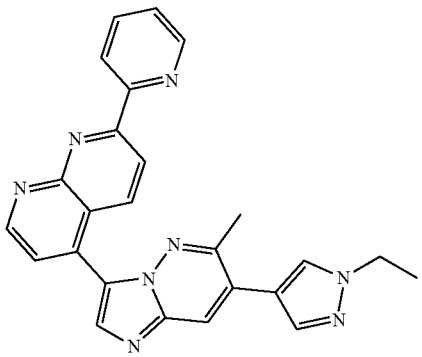 [SMILES: CCn1cc(-c2cc3ncc(-c4ccnc5nc(-c6ccccn6)ccc45)n3nc2C)cn1]

This compound was prepared according to the procedure described in Example 37, using 1-ethyl-4-(4,4,5,5-tetramethyl-1,3,2-dioxaborolan-2-yl)-1H-pyrazole instead of 1-((1R,4R)-4-((tert-butyldimethylsilyl)oxy)cyclohexyl)-4-(4,4,5,5-tetramethyl-1,3,2-dioxaborolan-2-yl)-1H-pyrazole as the starting material. LC-MS calculated for $C_{25}H_{21}N_8$ (M+H)$^+$: m/z=433.2. found 433.2. $^1$H NMR (TFA salt, 600 MHz, DMSO) δ 9.31 (d, J=4.7 Hz, 1H), 8.82 (d, J=4.2 Hz, 1H), 8.72 (overlap, 2H), 8.69 (d, J=7.9 Hz, 1H), 8.39 (overlap, 3H), 8.16 (d, J=4.7 Hz, 1H), 8.11 (m, 1H), 8.05 (s, 1H), 7.62 (m, 1H), 4.23 (q, J=7.3 Hz, 2H), 2.65 (s, 3H), 1.45 (t, J=7.3 Hz, 3H).

Example 40. 5-(7-(1-Isopropyl-1H-pyrazol-4-yl)-6-methylimidazo[1,2-b]pyridazin-3-yl)-2-(pyrimidin-2-yl)-1,8-naphthyridine

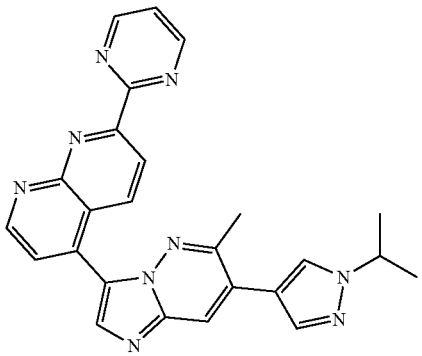 [SMILES: Cc1nn2c(-c3ccnc4nc(-c5ncccn5)ccc34)cnc2cc1-c1cnn(C(C)C)c1]

Step 1: 5-Chloro-2-(pyrimidin-2-yl)-1,8-naphthyridine

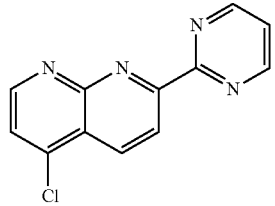 [SMILES: Clc1ccnc2nc(-c3ncccn3)ccc12]

To a screw-cap vial equipped with a magnetic stir bar was added 2,5-dichloro-1,8-naphthyridine (5.270 g, 26.5 mmol), 2-(tributylstannyl)pyrimidine (9.872 g, 26.7 mmol) and tetrakis(triphenylphosphine)palladium(0) (8.312 g, 7.19 mmol). The vial was sealed with a Teflon-lined septum, evacuated and backfilled with nitrogen (this process was repeated a total of three times). A solution of 2-(tributylstannyl)pyrimidine (9.872 g, 26.7 mmol) in 1,4-Dioxane (100.0 ml) was added via syringe. The mixture was stirred at 100° C. for 16 h. After cooling at room temperature, the mixture was concentrated. The residue was purified on silica gel (120 g, 0-100% EtOAc in CH$_2$Cl$_2$) to give the desired product as a solid (1.583 g, 25%). LCMS calculated for C$_{12}$H$_8$ClN$_4$ (M+H)$^+$ m/z=243.0. found 243.0.

Step 2: 2-(Pyrimidin-2-yl)-5-(4,4,5,5-tetramethyl-1,3,2-dioxaborolan-2-yl)-1,8-naphthyridine

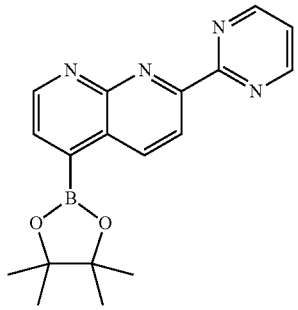 [SMILES: CC1(C)OB(c2ccnc3nc(-c4ncccn4)ccc23)OC1(C)C]

To a screw-cap vial equipped with a magnetic stir bar was added 4,4,5,5,4',4',5',5'-octamethyl-[2,2']bi[[1,3,2]dioxaborolanyl] (427.7 mg, 1.684 mmol), potassium acetate (412.2 mg, 4.20 mmol), 5-chloro-2-(pyrimidin-2-yl)-1,8-naphthyridine (304.7 mg, 1.256 mmol) and dichloro[1,1'-bis(diphenylphosphino)ferrocene]palladium (II) dichloromethane adduct (205 mg, 0.251 mmol). The vial was sealed with a Teflon-lined septum, evacuated and backfilled with nitrogen (this process was repeated a total of three times). 1,4-Dioxane (12.0 ml) was added via syringe. The mixture was stirred at 105° C. for 4 h. After cooling at room temperature, the mixture was filtered. The filtrate was used directly in the next step without further purification.

Step 3: 7-(1-Isopropyl-1H-pyrazol-4-yl)-6-methyl-imidazo[1,2-b]pyridazine

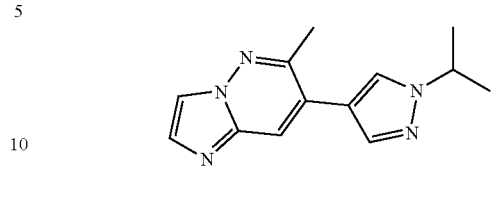

To a screw-cap vial equipped with a magnetic stir bar was added 7-chloro-6-methylimidazo[1,2-b]pyridazine (1711 mg, 10.21 mmol), 1-isopropyl-4-(4,4,5,5-tetramethyl-1,3,2-dioxaborolan-2-yl)-1H-pyrazole (2527 mg, 10.70 mmol), dicyclohexyl(2',4',6'-triisopropylbiphenyl-2-yl)phosphine-(2'-aminobiphenyl-2-yl)(chloro)palladium (1:1) (XPhos Pd G2, 1788 mg, 2.272 mmol) and cesium carbonate (10.01 g, 30.7 mmol). The vial was sealed with a Teflon-lined septum, evacuated and backfilled with nitrogen (this process was repeated a total of three times). 1,4-Dioxane (30.0 ml) was added via syringe followed by water (8.0 ml). The mixture was stirred at 80° C. for 16 h. After cooling at room temperature, the reaction was concentrated. The residue was purified by on silica gel (40 g, 0-100% EtOAc in DCM, then 5% MeOH in CH$_2$Cl$_2$) to provide the desired product (1.938 g, 79%). LCMS calculated for C$_{13}$H$_{16}$N$_5$(M+H)$^+$ m/z=242.1. found 242.0.

Step 4: 3-Iodo-7-(1-isopropyl-1H-pyrazol-4-yl)-6-methylimidazo[1,2-b]pyridazine

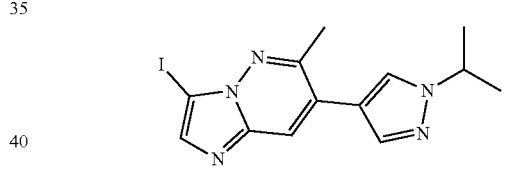

To a mixture of 7-(1-isopropyl-1H-pyrazol-4-yl)-6-methylimidazo[1,2-b]pyridazine (1938 mg, 8.03 mmol) and NIS (1808 mg, 8.04 mmol) was added DMF (40.0 ml). The mixture was stirred at room temperature for 16 h. The mixture was concentrated. The residue was purified on silica gel (120 g, 0-100% EtOAc in CH$_2$Cl$_2$) to give the desired product as a yellow solid (2.53 g, 86%). LCMS calculated for C$_{13}$H$_{15}$IN$_5$ (M+H)$^+$ m/z=368.0. found 368.1.

Step 5: 5-(7-(1-Isopropyl-H-pyrazol-4-yl)-6-methyl-imidazo[1,2-b]pyridazin-3-yl)-2-(pyrimidin-2-yl)-1,8-naphthyridine To a screw-cap vial equipped with a magnetic stir bar was added 3-iodo-7-(1-isopropyl-1H-pyrazol-4-yl)-6-methyl-imidazo[1,2-b]pyridazine (349.8 mg, 0.953 mmol), Dichloro[1,1'-bis(diphenylphosphino)ferrocene]palladium (II) dichloromethane adduct (156 mg, 0.191 mmol) and cesium carbonate (1287 mg, 3.95 mmol). The vial was sealed with a Teflon-lined septum, evacuated and backfilled with nitrogen (this process was repeated a total of three times). A solution of 2-(pyrimidin-2-yl)-5-(4,4,5,5-tetramethyl-1,3,2-dioxaborolan-2-yl)-1,8-naphthyridine (420 mg, 1.257 mmol, see above step 2) in 1,4-Dioxane (12 ml) was added via syringe followed by water (2.0 ml). The mixture was stirred at 70° C. for 16 h. After cooling to room temperature, the reaction mixture was concentrated. The residue was purified using prep-LCMS (XBridge C18 column, eluting with a gradient of acetonitrile/water containing 0.1% TFA, at flow rate of 60 mL/min) to afford the desired product as its TFA salt. LCMS calculated for $C_{25}H_{22}N_9$ (M+H)$^+$: m/z=448.2. found: 448.2. $^1$H NMR (TFA salt, 400 MHz, DMSO) δ 9.34 (d, J=4.7 Hz, 1H), 9.11 (d, J=4.8 Hz, 2H), 8.73 (d, J=8.8 Hz, 1H), 8.63 (d, J=8.8 Hz, 1H), 8.38 (s, 1H), 8.36 (s, 1H), 8.33 (s, 1H), 8.17 (d, J=4.7 Hz, 1H), 8.02 (s, 1H), 7.70 (t, J=4.8 Hz, 1H), 4.59 (m, 1H), 2.65 (s, 3H), 1.49 (d, J=6.7 Hz, 6H).

Example 41. (1R,4R)-4-(4-(6-Methyl-3-(7-(pyrazin-2-yl)-1,8-naphthyridin-4-yl)imidazo[1,2-b]pyridazin-7-yl)-1H-pyrazol-1-yl)cyclohexan-1-ol

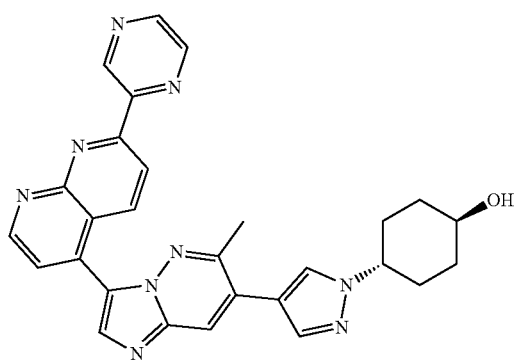 [SMILES: Cc1nn2c(-c3ccnc4nc(-c5cnccn5)ccc34)cnc2cc1-c1cnn([C@H]2CC[C@H](O)CC2)c1]

Step 1: 5-Chloro-2-(pyrazin-2-yl)-1,8-naphthyridine

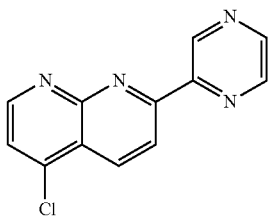 [SMILES: Clc1ccnc2nc(-c3cnccn3)ccc12]

To a screw-cap vial equipped with a magnetic stir bar was added 2,5-dichloro-1,8-naphthyridine (1078.0 mg, 5.42 mmol), 2-(tributylstannyl)pyrazine (1978 mg, 5.36 mmol) and tetrakis(triphenylphosphine)palladium(0) (1929 mg, 1.669 mmol). The vial was sealed with a Teflon-lined septum, evacuated and backfilled with nitrogen (this process was repeated a total of three times). A solution of 2-(tributylstannyl)pyrazine (1978 mg, 5.36 mmol) in 1,4-Dioxane (20.0 ml) was added via syringe. The mixture was stirred at 100° C. for 4 h. After cooling at room temperature, the mixture was concentrated. The residue was purified on silica gel (120 g, 0-100% EtOAc in $CH_2Cl_2$, then 5% MeOH in $CH_2Cl_2$) to give the desired product as a yellow solid (524.7 mg, 40%). LCMS calculated for $C_{12}H_8ClN_4$ (M+H)$^+$ m/z=243.0. found 243.0.

Step 2: 2-(Pyrazin-2-yl)-5-(4,4,5,5-tetramethyl-1,3,2-dioxaborolan-2-yl)-1,8-naphthyridine

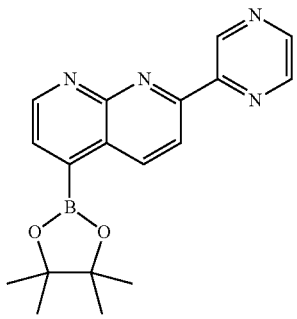 [SMILES: CC1(C)OB(c2ccnc3nc(-c4cnccn4)ccc23)OC1(C)C]

To a screw-cap vial equipped with a magnetic stir bar was added 4,4,5,5,4',4',5',5'-octamethyl-[2,2']bi[[1,3,2]dioxaborolanyl] (293.5 mg, 1.156 mmol), potassium acetate (271.6 mg, 2.77 mmol), 5-chloro-2-(pyrazin-2-yl)-1,8-naphthyridine (220.1 mg, 0.907 mmol) and dichloro[1,1'-bis(diphenylphosphino)ferrocene]palladium (II) dichloromethane adduct (156 mg, 0.190 mmol). The vial was sealed with a Teflon-lined septum, evacuated and backfilled with nitrogen (this process was repeated a total of three times). 1,4-Dioxane (6.0 ml) was added via syringe. The mixture was stirred at 105° C. for 16 h. After cooling at room temperature, the mixture was filtered. The filtrate was used directly in the next step without further purification.

Step 3: 5-(7-Chloro-6-methylimidazo[1,2-b]pyridazin-3-yl)-2-(pyrazin-2-yl)-1,8-naphthyridine

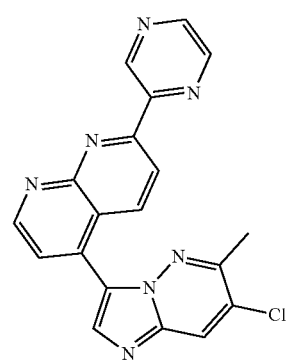 [SMILES: Cc1nn2c(-c3ccnc4nc(-c5cnccn5)ccc34)cnc2cc1Cl]

To a screw-cap vial equipped with a magnetic stir bar was added 7-chloro-3-iodo-6-methylimidazo[1,2-b]pyridazine (266.2 mg, 0.907 mmol, see step 3 in Example 1), PdCl$_2$(dppf)-CH$_2$Cl$_2$ adduct (148 mg, 0.181 mmol) and cesium carbonate (1102 mg, 3.38 mmol). The vial was sealed with a Teflon-lined septum, evacuated and backfilled with nitrogen (this process was repeated a total of three times). A solution of 2-(pyrazin-2-yl)-5-(4,4,5,5-tetramethyl-1,3,2-dioxaborolan-2-yl)-1,8-naphthyridine (303.0 mg, 0.907 mmol, see above step 2) in 1,4-Dioxane (6.0 ml) was added via syringe followed by water (3.0 ml). The mixture was stirred at 80° C. for 4 h. After cooling to room temperature, the reaction mixture was concentrated. The residue was purified on silica gel (40 g, 0-100% EtOAc in $CH_2Cl_2$, then 5% MeOH in $CH_2Cl_2$) to give the desired product as a brown solid (85.0 mg, 25%). LCMS calculated for C₁₉H₁₃ClN₇ (M+H)⁺ m/z=374.1. found 374.1.

Step 4: (1R,4R)-4-(4-(6-Methyl-3-(7-(pyrazin-2-yl)-1,8-naphthyridin-4-yl) imidazo[1,2-b]pyridazin-7-yl)-1H-pyrazol-1-yl)cyclohexan-1-ol To a screw-cap vial equipped with a magnetic stir bar was added 5-(7-chloro-6-methylimidazo[1,2-b]pyridazin-3-yl)-2-(pyrazin-2-yl)-1,8-naphthyridine (17.0 mg, 0.045 mmol), 1-((1R,4R)-4-((tert-butyldimethylsilyl)oxy)cyclohexyl)-4-(4,4,5,5-tetramethyl-1,3,2-dioxaborolan-2-yl)-1H-pyrazole (30.2 mg, 0.074 mmol), dicyclohexyl(2',4',6'-triisopropylbiphenyl-2-yl)phosphine-(2'-aminobiphenyl-2-yl)(chloro)palladium (1:1) (XPhos Pd G2, 7.16 mg, 9.10 µmol) and cesium carbonate (43.6 mg, 0.134 mmol). The vial was sealed with a Teflon-lined septum, evacuated and backfilled with nitrogen (this process was repeated a total of three times). 1,4-Dioxane (2.0 ml) was added via syringe, followed by water (200.0 µl). The mixture was heated at 80° C. for 6 h. After cooling to room temperature, HCl (4.0 N in 1,4-dioxane) (1.0 ml, 4.00 mmol) was added followed by MeOH (1.0 ml). The reaction was stirred at room temperature for 1 h, and then concentrated. The residue was purified using prep-LCMS (XBridge C18 column, eluting with a gradient of acetonitrile/water containing 0.1% TFA, at flow rate of 60 mL/min) to afford the desired product as its TFA salt. LCMS calculated for C₂₈H₂₆N₉O (M+H)⁺: m/z=504.2. found: 504.2. ¹H NMR (TFA salt, 500 MHz, DMSO) δ 9.80 (d, J=1.5 Hz, 1H), 9.32 (d, J=4.6 Hz, 1H), 8.86 (overlap, 2H), 8.72 (d, J=8.8 Hz, 1H), 8.51 (d, J=8.8 Hz, 1H), 8.36 (overlap, 2H), 8.34 (s, 1H), 8.13 (d, J=4.6 Hz, 1H), 8.02 (s, 1H), 4.22 (m, 1H), 3.52 (m, 1H), 2.63 (s, 3H), 2.07 (m, 2H), 1.96 (m, 2H), 1.86 (m, 2H), 1.38 (m, 2H).

Example 42. 5-(7-(4-(Azetidin-1-ylmethyl)phenyl)-6-methylimidazo[1,2-b]pyridazin-3-yl)-2-(pyrazin-2-yl)-1,8-naphthyridine

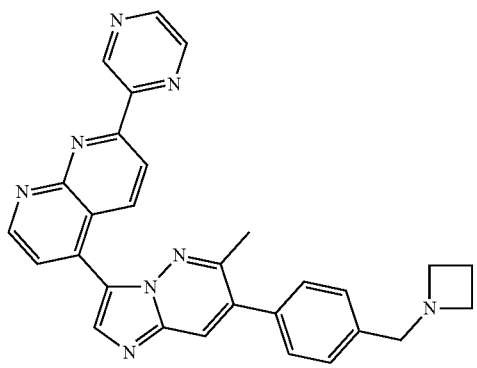 [SMILES: Cc1nn2c(-c3ccnc4nc(-c5cnccn5)ccc34)cnc2cc1-c1ccc(CN2CCC2)cc1]

This compound was prepared according to the procedure described in Example 41, using 1-(4-(4,4,5,5-tetramethyl-1,3,2-dioxaborolan-2-yl)benzyl)azetidine instead of 1-((1R,4R)-4-((tert-butyldimethylsilyl)oxy)cyclohexyl)-4-(4,4,5,5-tetramethyl-1,3,2-dioxaborolan-2-yl)-1H-pyrazole as the starting material. LC-MS calculated for C₂₉H₂₅N₈ (M+H)⁺: m/z=485.2. found 485.2.

Example 43. 5-(7-(1-Isopropyl-1H-pyrazol-4-yl)-6-methylimidazo[1,2-b]pyridazin-3-yl)-2-(pyrazin-2-yl)-1,8-naphthyridine

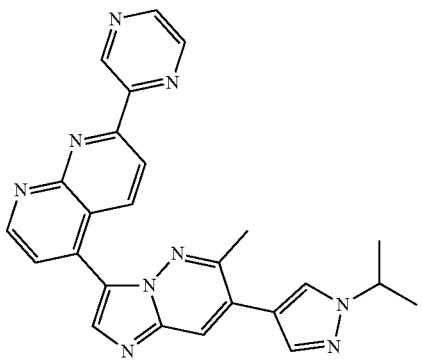 [SMILES: Cc1nn2c(-c3ccnc4nc(-c5cnccn5)ccc34)cnc2cc1-c1cnn(C(C)C)c1]

This compound was prepared according to the procedure described in Example 41, using 1-isopropyl-4-(4,4,5,5-tetramethyl-1,3,2-dioxaborolan-2-yl)-1H-pyrazole instead of 1-((1R,4R)-4-((tert-butyldimethylsilyl)oxy)cyclohexyl)-4-(4,4,5,5-tetramethyl-1,3,2-dioxaborolan-2-yl)-1H-pyrazole as the starting material. LC-MS calculated for C₂₅H₂₂N₉ (M+H)⁺: m/z=448.2. found 448.2.

Example 44. 5-(6-Methyl-7-(1-(tetrahydro-2H-pyran-4-yl)-1H-pyrazol-4-yl)imidazo[1,2-b]pyridazin-3-yl)-2-(pyrazin-2-yl)-1,8-naphthyridine

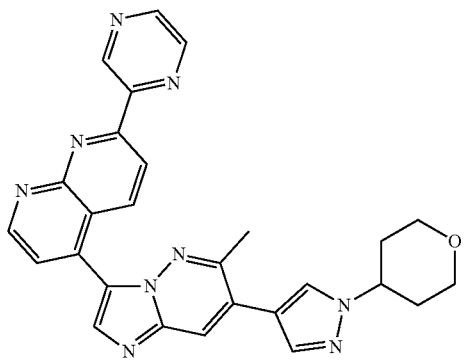 [SMILES: Cc1nn2c(-c3ccnc4nc(-c5cnccn5)ccc34)cnc2cc1-c1cnn(C2CCOCC2)c1]

This compound was prepared according to the procedure described in Example 41, using 1-(tetrahydro-2H-pyran-4-yl)-4-(4,4,5,5-tetramethyl-1,3,2-dioxaborolan-2-yl)-1H-pyrazole instead of 1-((1R,4R)-4-((tert-butyldimethylsilyl)oxy)cyclohexyl)-4-(4,4,5,5-tetramethyl-1,3,2-dioxaborolan-2-yl)-1H-pyrazole as the starting material. LC-MS calculated for C₂₇H₂₄N₉O (M+H)⁺: m/z=490.2. found 490.2.

Example 45. 5-(7-(1-Isopropyl-1H-pyrazol-4-yl)-6-methylimidazo[1,2-b]pyridazin-3-yl)-2-(1-methyl-1H-pyrazol-3-yl)-1,8-naphthyridine

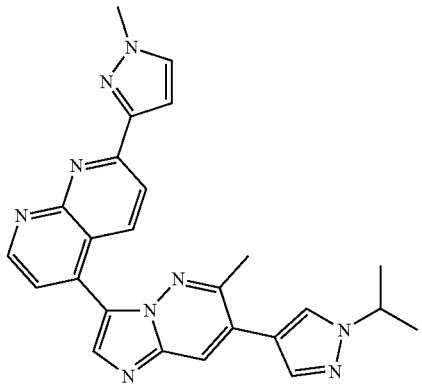 [SMILES: Cc1nn2c(-c3ccnc4nc(-c5ccn(C)n5)ccc34)cnc2cc1-c1cnn(C(C)C)c1]

Step 1: 5-Chloro-2-(1-methyl-1H-pyrazol-3-yl)-1,8-naphthyridine

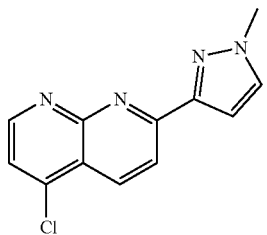 [SMILES: Cn1ccc(-c2ccc3c(Cl)ccnc3n2)n1]

To a screw-cap vial equipped with a magnetic stir bar was added 2,5-dichloro-1,8-naphthyridine (1004 mg, 5.04 mmol), 1-methyl-3-(4,4,5,5-tetramethyl-1,3,2-dioxaborolan-2-yl)-1H-pyrazole (1098 mg, 5.28 mmol), tetrakis(triphenylphosphine)palladium(0) (1166 mg, 1.009 mmol) and cesium carbonate (5390 mg, 16.54 mmol). The vial was sealed with a Teflon-lined septum, evacuated and backfilled with nitrogen (this process was repeated a total of three times). 1,4-Dioxane (18.0 ml) was added via syringe, followed by water (3.0 ml). The mixture was stirred at 80° C. for 16 h. After cooling at room temperature, the mixture was concentrated. The residue was purified on silica gel (120 g, 0-100% EtOAc in $CH_2Cl_2$) to give the desired product as a white solid (742.6 mg, 60%). LCMS calculated for $C_{12}H_{10}ClN_4$ (M+H)$^+$ m/z=245.1. found 245.0.

Step 2: 2-(1-Methyl-1H-pyrazol-3-yl)-5-(4,4,5,5-tetramethyl-1,3,2-dioxaborolan-2-yl)-1,8-naphthyridine

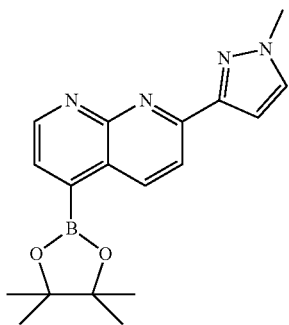 [SMILES: Cn1ccc(-c2ccc3c(B4OC(C)(C)C(C)(C)O4)ccnc3n2)n1]

To a screw-cap vial equipped with a magnetic stir bar was added 4,4,5,5,4',4',5',5'-Octamethyl-[2,2']bi[[1,3,2]dioxaborolanyl] (408.8 mg, 1.610 mmol), potassium acetate (447.2 mg, 4.56 mmol), 5-chloro-2-(1-methyl-1H-pyrazol-3-yl)-1,8-naphthyridine (300.6 mg, 1.229 mmol) and dichloro[1,1'-bis(diphenylphosphino)ferrocene]palladium (II) dichloromethane adduct (201 mg, 0.246 mmol). The vial was sealed with a Teflon-lined septum, evacuated and backfilled with nitrogen (this process was repeated a total of three times). 1,4-Dioxane (8.0 ml) was added via syringe. The mixture was stirred at 105° C. for 16 h. After cooling at room temperature, the mixture was filtered. The filtrate was used directly in the next step without further purification. LCMS calculated for $C_{18}H_{22}BN_4O_2$(M+H)$^+$ m/z=337.2. found 337.2.

Step 3: 5-(7-Chloro-6-methylimidazo[1,2-b]pyridazin-3-yl)-2-(1-methyl-1H-pyrazol-3-yl)-1,8-naphthyridine

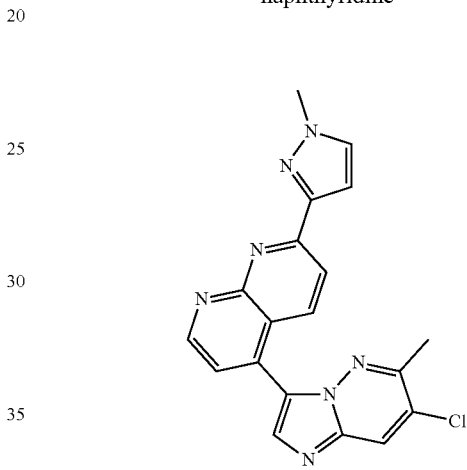

To a screw-cap vial equipped with a magnetic stir bar was added 7-chloro-3-iodo-6-methylimidazo[1,2-b]pyridazine (350.2 mg, 1.193 mmol, see step 3 in Example 1), $PdCl_2$(dppf)-$CH_2Cl_2$ adduct (195 mg, 0.239 mmol) and cesium carbonate (1307 mg, 4.01 mmol). The vial was sealed with a Teflon-lined septum, evacuated and backfilled with nitrogen (this process was repeated a total of three times). A solution of 2-(1-methyl-1H-pyrazol-3-yl)-5-(4,4,5,5-tetramethyl-1,3,2-dioxaborolan-2-yl)-1,8-naphthyridine (413 mg, 1.228 mmol, see above step 2) in 1,4-Dioxane (8.0 ml) was added via syringe followed by water (3.0 ml). The mixture was stirred at 80° C. for 4 h. After cooling to room temperature, the reaction mixture was concentrated. The residue was purified on silica gel (40 g, 0-100% EtOAc in $CH_2Cl2$, then 5% MeOH in $CH_2Cl_2$) to give the desired product as a solid (239.1 mg, 53%). LCMS calculated for $C_{19}H_{15}ClN_7$ (M+H)$^+$ m/z=376.1. found 376.1.

Step 4: 5-(7-(1-Isopropyl-1H-pyrazol-4-yl)-6-methylimidazo[1,2-b]pyridazin-3-yl)-2-(1-methyl-1H-pyrazol-3-yl)-1,8-naphthyridine To a screw-cap vial equipped with a magnetic stir bar was added 5-(7-chloro-6-methylimidazo[1,2-b]pyridazin-3-yl)-2-(1-methyl-1H-pyrazol-3-yl)-1,8-naphthyridine (15.1 mg, 0.040 mmol), 1-isopropyl-4-(4,4,5,5-tetramethyl-1,3,2-dioxaborolan-2-yl)-1H-pyrazole (21.4 mg, 0.091 mmol), dicyclohexyl(2',4',6'-triisopropylbiphenyl-2-yl)phosphine-(2'-aminobiphenyl-2-yl)(chloro)palladium (1:1) (XPhos Pd G2, 4.7 mg, 5.97 μmol) and cesium carbonate (43.7 mg, 0.134 mmol). The vial was sealed with a Teflon-lined septum, evacuated and backfilled with nitrogen (this process was repeated a total of three times). 1,4-Dioxane (2.0 ml) was added via syringe, followed by water (200.0 μl). The mixture was heated at 80° C. for 6 h. After cooling to room temperature, HCl (4.0 N in 1,4-dioxane) (1.0 ml, 4.00 mmol) was added followed by MeOH (1.0 ml). The reaction was stirred at room temperature for 1 h, and then concentrated. The residue was purified using prep-LCMS (XBridge C18 column, eluting with a gradient of acetonitrile/water containing 0.1% TFA, at flow rate of 60 mL/min) to afford the desired product as its TFA salt. LCMS calculated for $C_{25}H_{24}N_9$ (M+H)$^+$: m/z=450.2. found: 450.2. $^1$H NMR (TFA salt, 600 MHz, DMSO) δ 9.22 (d, J=4.9 Hz, 1H), 8.61 (d, J=8.8 Hz, 1H), 8.39 (s, 1H), 8.37 (s, 1H), 8.35 (s, 1H), 8.27 (d, J=8.8 Hz, 1H), 8.14 (d, J=4.9 Hz, 1H), 8.04 (s, 1H), 7.93 (d, J=2.3 Hz, 1H), 7.10 (d, J=2.3 Hz, 1H), 4.59 (m, 1H), 4.01 (s, 3H), 2.66 (s, 3H), 1.49 (d, J=6.7 Hz, 6H).

Example 46. 5-(7-(4-(Azetidin-1-ylmethyl)phenyl)-6-methylimidazo[1,2-b]pyridazin-3-yl)-2-(1-methyl-1H-pyrazol-3-yl)-1,8-naphthyridine

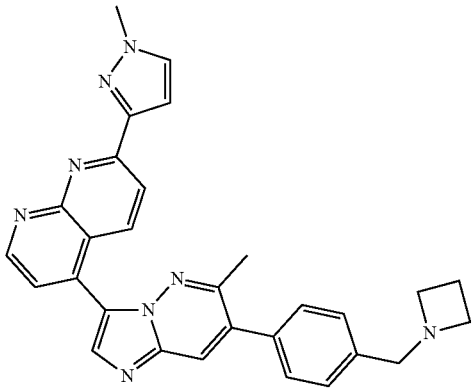 [SMILES: Cc1nn2c(-c3ccnc4nc(-c5ccn(C)n5)ccc34)cnc2cc1-c1ccc(CN2CCC2)cc1]

This compound was prepared according to the procedure described in Example 45, using 1-(4-(4,4,5,5-tetramethyl-1,3,2-dioxaborolan-2-yl)benzyl)azetidine instead of 1-isopropyl-4-(4,4,5,5-tetramethyl-1,3,2-dioxaborolan-2-yl)-1H-pyrazole as the starting material. LC-MS calculated for $C_{29}H_{27}N_8$(M+H)$^+$: m/z=487.2. found 487.2.

Example 47. N,N-dimethyl-4-(6-methyl-3-(7-(1-methyl-1H-pyrazol-3-yl)-1,8-naphthyridin-4-yl)imidazo[1,2-b]pyridazin-7-yl)benzamide

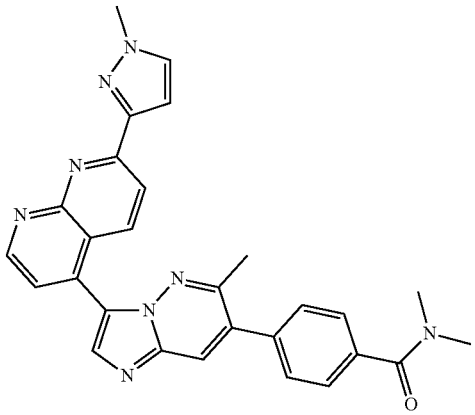 [SMILES: Cc1nn2c(-c3ccnc4nc(-c5ccn(C)n5)ccc34)cnc2cc1-c1ccc(C(=O)N(C)C)cc1]

This compound was prepared according to the procedure described in Example 45, using N,N-dimethyl-4-(4,4,5,5-tetramethyl-1,3,2-dioxaborolan-2-yl)benzamide instead of 1-isopropyl-4-(4,4,5,5-tetramethyl-1,3,2-dioxaborolan-2-yl)-1H-pyrazole as the starting material. LC-MS calculated for $C_{28}H_{25}N_8O$ (M+H)$^+$: m/z=489.2. found 489.2. $^1$H NMR (TFA salt, 500 MHz, DMSO) δ 9.23 (d, J=4.8 Hz, 1H), 8.56 (d, J=8.8 Hz, 1H), 8.34 (s, 1H), 8.26 (d, J=8.8 Hz, 1H), 8.23 (s, 1H), 8.09 (d, J=4.8 Hz, 1H), 7.92 (d, J=2.3 Hz, 1H), 7.64 (d, J=8.2 Hz, 2H), 7.57 (d, J=8.2 Hz, 2H), 7.10 (d, J=2.3 Hz, 1H), 4.00 (s, 3H), 3.03 (s, 3H), 3.98 (s, 3H), 2.43 (s, 3H).

Example 48. 5-(7-(4-(Azetidin-1-ylmethyl)phenyl)-6-methylimidazo[1,2-b]pyridazin-3-yl)-2-(5-methyl-1H-pyrazol-3-yl)-1,8-naphthyridine

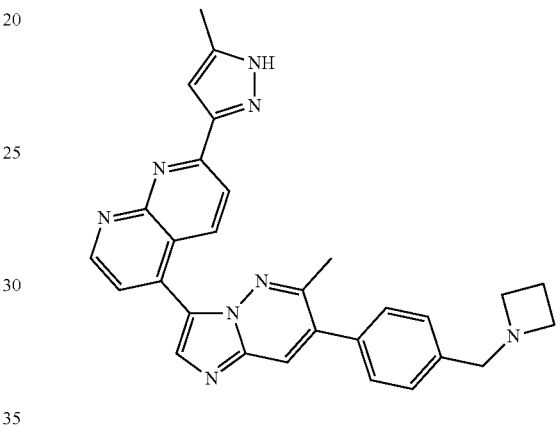

Step 1: 5-Chloro-2-(5-methyl-1H-pyrazol-3-yl)-1,8-naphthyridine

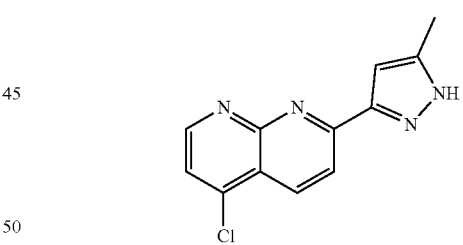

To a screw-cap vial equipped with a magnetic stir bar was added 2,5-dichloro-1,8-naphthyridine (1549.8 mg, 7.79 mmol), (5-methyl-1H-pyrazol-3-yl)boronic acid (989.1 mg, 7.85 mmol), tetrakis(triphenylphosphine)palladium(0) (1800 mg, 1.557 mmol) and cesium carbonate (9077 mg, 27.9 mmol). The vial was sealed with a Teflon-lined septum, evacuated and backfilled with nitrogen (this process was repeated a total of three times). 1,4-Dioxane (50.0 ml) was added via syringe, followed by water (10.0 ml). The mixture was stirred at 80° C. for 16 h. After cooling at room temperature, the mixture was concentrated. The residue was purified on silica gel (120 g, 0-100% EtOAc in $CH_2Cl_2$, then 5% MeOH in $CH_2Cl_2$) to give the desired product as a yellow solid (499.0 mg, 26%). LCMS calculated for $C_{12}H_{10}ClN_4$ (M+H)$^+$ m/z=245.1. found 245.1.

Step 2: 2-(5-Methyl-1H-pyrazol-3-yl)-5-(4,4,5,5-tetramethyl-1,3,2-dioxaborolan-2-yl)-1,8-naphthyridine

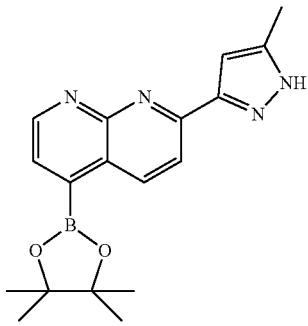 [SMILES: Cc1cc(-c2ccc3c(B4OC(C)(C)C(C)(C)O4)ccnc3n2)n[nH]1]

To a screw-cap vial equipped with a magnetic stir bar was added 4,4,5,5,4',4',5',5'-Octamethyl-[2,2']bi[[1,3,2]dioxaborolanyl] (506.8 mg, 1.996 mmol), potassium acetate (530.3 mg, 5.40 mmol), 5-chloro-2-(5-methyl-1H-pyrazol-3-yl)-1,8-naphthyridine (390.4 mg, 1.596 mmol) and dichloro[1,1'-bis(diphenylphosphino)ferrocene]palladium (II) dichloromethane adduct (275 mg, 0.337 mmol). The vial was sealed with a Teflon-lined septum, evacuated and backfilled with nitrogen (this process was repeated a total of three times). 1,4-Dioxane (8.0 ml) was added via syringe. The mixture was stirred at 105° C. for 16 h. After cooling at room temperature, the mixture was filtered. The filtrate was used directly in the next step without further purification. LCMS calculated for $C_{18}H_{22}BN_4O_2(M+H)^+$ m/z=337.2. found 337.2.

Step 3: 5-(7-Chloro-6-methylimidazo[1,2-b]pyridazin-3-yl)-2-(5-methyl-1H-pyrazol-3-yl)-1,8-naphthyridine

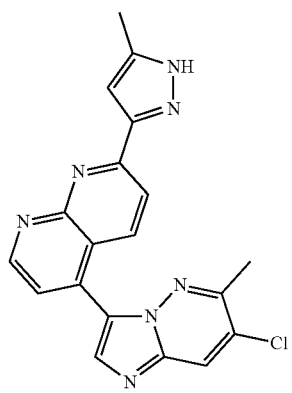 [SMILES: Cc1cc(-c2ccc3c(-c4cnc5cc(Cl)c(C)nn45)ccnc3n2)n[nH]1]

To a screw-cap vial equipped with a magnetic stir bar was added 7-chloro-3-iodo-6-methylimidazo[1,2-b]pyridazine (466.9 mg, 1.591 mmol, see step 3 in Example 1), PdCl$_2$(dppf)-CH$_2$Cl$_2$ adduct (326 mg, 0.399 mmol) and cesium carbonate (1950 mg, 5.98 mmol). The vial was sealed with a Teflon-lined septum, evacuated and backfilled with nitrogen (this process was repeated a total of three times). A solution of 2-(5-methyl-1H-pyrazol-3-yl)-5-(4,4,5,5-tetramethyl-1,3,2-dioxaborolan-2-yl)-1,8-naphthyridine (536 mg, 1.594 mmol, see above step 2) in 1,4-Dioxane (8.0 ml) was added via syringe followed by water (3.0 ml). The mixture was stirred at 80° C. for 4 h. After cooling to room temperature, the reaction mixture was concentrated. The residue was purified on silica gel (40 g, 0-100% EtOAc in CH$_2$Cl$_2$, then 10% MeOH in CH$_2$Cl$_2$) to give the desired product as a solid (181.5 mg, 30%). LCMS calculated for $C_{19}H_{15}ClN_7$ (M+H)+ m/z=376.1. found 376.1.

Step 4: 5-(7-(4-(Azetidin-1-ylmethyl)phenyl)-6-methylimidazo[1,2-b]pyridazin-3-yl)-2-(5-methyl-1H-pyrazol-3-yl)-1,8-naphthyridine To a screw-cap vial equipped with a magnetic stir bar was added 5-(7-chloro-6-methylimidazo[1,2-b]pyridazin-3-yl)-2-(5-methyl-1H-pyrazol-3-yl)-1,8-naphthyridine (19.9 mg, 0.053 mmol), 1-(4-(4,4,5,5-tetramethyl-1,3,2-dioxaborolan-2-yl)benzyl)azetidine (27.5 mg, 0.101 mmol), dicyclohexyl(2',4',6'-triisopropylbiphenyl-2-yl)phosphine-(2'-aminobiphenyl-2-yl)(chloro)palladium (1:1) (XPhos Pd G2, 6.3 mg, 8.01 μmol) and cesium carbonate (57.8 mg, 0.177 mmol). The vial was sealed with a Teflon-lined septum, evacuated and backfilled with nitrogen (this process was repeated a total of three times). 1,4-Dioxane (2.0 ml) was added via syringe, followed by water (200.0 μl). The mixture was heated at 80° C. for 6 h. After cooling to room temperature, HCl (4.0 N in 1,4-dioxane) (1.0 ml, 4.00 mmol) was added followed by MeOH (1.0 ml). The reaction was stirred at room temperature for 1 h, and then concentrated. The residue was purified using prep-LCMS (XBridge C18 column, eluting with a gradient of acetonitrile/water containing 0.1% TFA, at flow rate of 60 mL/min) to afford the desired product as its TFA salt. LCMS calculated for $C_{29}H_{27}N_8$ (M+H)$^+$: m/z=487.2. found: 487.2.

Example 49. 4-(4-(6-methyl-3-(7-(5-methyl-1H-pyrazol-3-yl)-1,8-naphthyridin-4-yl)imidazo[1,2-b]pyridazin-7-yl)benzyl)morpholine

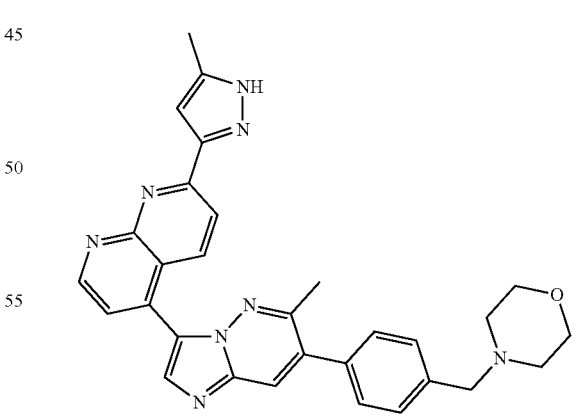

This compound was prepared according to the procedure described in Example 48, using 4-(4-(4,4,5,5-tetramethyl-1,3,2-dioxaborolan-2-yl)benzyl)morpholine instead of 1-(4-(4,4,5,5-tetramethyl-1,3,2-dioxaborolan-2-yl)benzyl)azetidine as the starting material. LC-MS calculated for $C_{30}H_{29}N_8O$ (M+H)$^+$: m/z=517.2. found 517.1.

Example 50. 5-(7-(1-Isopropyl-1H-pyrazol-4-yl)-6-methylimidazo[1,2-b]pyridazin-3-yl)-2-(5-methyl-1H-pyrazol-3-yl)-1,8-naphthyridine

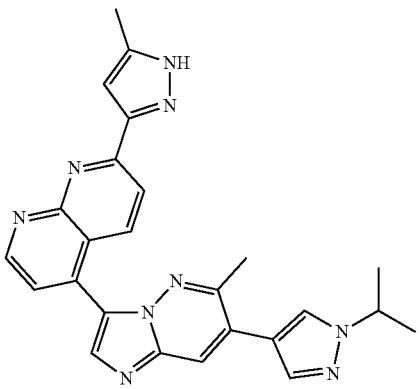 [SMILES: Cc1cc(-c2ccc3c(-c4cnc5cc(-c6cnn(C(C)C)c6)c(C)nn45)ccnc3n2)n[nH]1]

This compound was prepared according to the procedure described in Example 48, using 1-isopropyl-4-(4,4,5,5-tetramethyl-1,3,2-dioxaborolan-2-yl)-1H-pyrazole instead of 1-(4-(4,4,5,5-tetramethyl-1,3,2-dioxaborolan-2-yl)benzyl)azetidine as the starting material. LC-MS calculated for $C_{25}H_{24}N_9(M+H)^+$: m/z=450.2. found 450.2. $^1$H NMR (TFA salt, 600 MHz, DMSO) δ 9.22 (d, J=5.0 Hz, 1H), 8.61 (d, J=8.7 Hz, 1H), 8.39 (s, 1H), 8.38 (s, 1H), 8.36 (s, 1H), 8.29 (d, J=8.7 Hz, 1H), 8.15 (d, J=5.0 Hz, 1H), 8.04 (s, 1H), 6.88 (s, 1H), 4.59 (m, 1H), 2.66 (s, 3H), 2.36 (s, 3H), 1.49 (d, J=6.7 Hz, 6H).

Example 51. 5-(7-(1-Isopropyl-1H-pyrazol-4-yl)-6-methylimidazo[1,2-b]pyridazin-3-yl)-2-(1-methyl-1H-pyrazol-4-yl)-1,8-naphthyridine

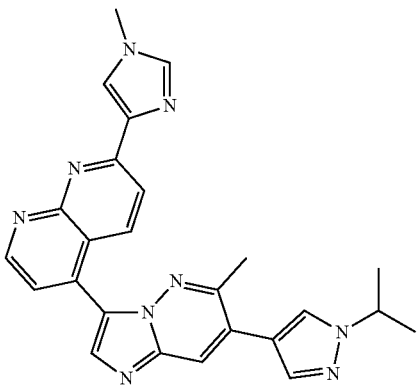 [SMILES: Cc1nn2c(-c3ccnc4nc(-c5cn(C)cn5)ccc34)cnc2cc1-c1cnn(C(C)C)c1]

Step 1: 5-Chloro-2-(1-methyl-1H-pyrazol-4-yl)-1,8-naphthyridine

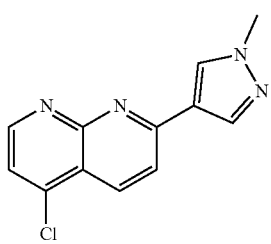 [SMILES: Cn1cc(-c2ccc3c(Cl)ccnc3n2)cn1]

To a screw-cap vial equipped with a magnetic stir bar was added 2,5-dichloro-1,8-naphthyridine (506.3 mg, 2.54 mmol), 1-methyl-4-(4,4,5,5-tetramethyl-1,3,2-dioxaborolan-2-yl)-1H-pyrazole (558.9 mg, 2.69 mmol), tetrakis(triphenylphosphine)palladium(0) (611 mg, 0.529 mmol) and cesium carbonate (2799 mg, 8.59 mmol). The vial was sealed with a Teflon-lined septum, evacuated and backfilled with nitrogen (this process was repeated a total of three times). 1,4-Dioxane (10.0 ml) was added via syringe, followed by water (2.0 ml). The mixture was stirred at 80° C. for 16 h. After cooling at room temperature, the mixture was concentrated. The residue was purified on silica gel (40 g, 0-100% EtOAc in $CH_2Cl_2$, then 5% MeOH in $CH_2Cl_2$) to give the desired product as a white solid (486.5 mg, 78%). LCMS calculated for $C_{12}H_{10}ClN_4$ $(M+H)^+$ m/z=245.1. found 245.1.

Step 2: 2-(1-Methyl-1H-pyrazol-4-yl)-5-(4,4,5,5-tetramethyl-1,3,2-dioxaborolan-2-yl)-1,8-naphthyridine

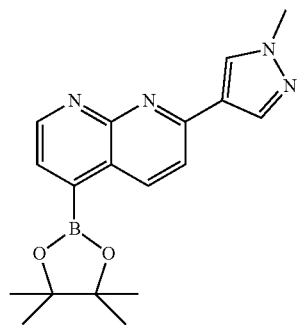 [SMILES: Cn1cc(-c2ccc3c(B4OC(C)(C)C(C)(C)O4)ccnc3n2)cn1]

To a screw-cap vial equipped with a magnetic stir bar was added 4,4,5,5,4',4',5',5'-Octamethyl-[2,2']bi[[1,3,2]dioxaborolanyl] (407.2 mg, 1.604 mmol), potassium acetate (453.7 mg, 4.62 mmol), 5-chloro-2-(1-methyl-1H-pyrazol-4-yl)-1,8-naphthyridine (304.2 mg, 1.243 mmol) and dichloro[1,1'-bis(diphenylphosphino)ferrocene]palladium (II) dichloromethane adduct (214 mg, 0.262 mmol). The vial was sealed with a Teflon-lined septum, evacuated and backfilled with nitrogen (this process was repeated a total of three times). 1,4-Dioxane (8.0 ml) was added via syringe. The mixture was stirred at 105° C. for 16 h. After cooling at room temperature, the mixture was filtered. The filtrate was used directly in the next step without further purification. LCMS calculated for $C_{18}H_{22}BN_4O_2(M+H)^+$ m/z=337.2. found 337.2.

Step 3: 5-(7-Chloro-6-methylimidazo[1,2-b]pyridazin-3-yl)-2-(1-methyl-1H-pyrazol-4-yl)-1,8-naphthyridine

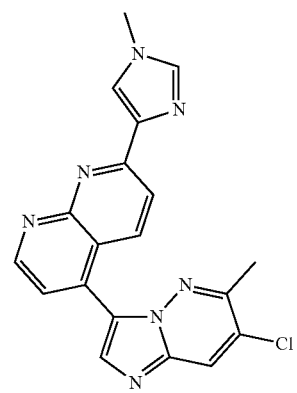 [SMILES: Cc1nn2c(-c3ccnc4nc(-c5cn(C)cn5)ccc34)cnc2cc1Cl]

To a screw-cap vial equipped with a magnetic stir bar was added 7-chloro-3-iodo-6-methylimidazo[1,2-b]pyridazine (322.1 mg, 1.097 mmol, see step 3 in Example 1), PdCl₂(dppf)-CH₂Cl₂ adduct (179 mg, 0.220 mmol) and cesium carbonate (1324 mg, 4.06 mmol). The vial was sealed with a Teflon-lined septum, evacuated and backfilled with nitrogen (this process was repeated a total of three times). A solution of 2-(1-methyl-1H-pyrazol-4-yl)-5-(4,4,5,5-tetramethyl-1,3,2-dioxaborolan-2-yl)-1,8-naphthyridine (418 mg, 1.243 mmol, see above step 2) in 1,4-Dioxane (8.0 ml) was added via syringe followed by water (3.0 ml). The mixture was stirred at 80° C. for 4 h. After cooling to room temperature, the reaction mixture was concentrated. The residue was purified on silica gel (40 g, 0-100% EtOAc in CH₂Cl₂, then 5% MeOH in CH₂Cl₂) to give the desired product as a solid (267.0 mg, 65%). LCMS calculated for $C_{19}H_{15}ClN_7$ (M+H)⁺ m/z=376.1. found 376.1.

Step 4: 5-(7-(1-Isopropyl-H-pyrazol-4-yl)-6-methyl-imidazo[1,2-b]pyridazin-3-yl)-2-(1-methyl-1H-pyrazol-4-yl)-1,8-naphthyridine To a screw-cap vial equipped with a magnetic stir bar was added 5-(7-chloro-6-methylimidazo[1,2-b]pyridazin-3-yl)-2-(1-methyl-1H-pyrazol-4-yl)-1,8-naphthyridine (19.6 mg, 0.052 mmol), 1-isopropyl-4-(4,4,5,5-tetramethyl-1,3,2-dioxaborolan-2-yl)-1H-pyrazole (26.3 mg, 0.111 mmol), dicyclohexyl(2',4',6'-triisopropylbiphenyl-2-yl)phosphine-(2'-aminobiphenyl-2-yl)(chloro)palladium (1:1) (XPhos Pd G2, 6.2 mg, 7.88 µmol) and cesium carbonate (54.6 mg, 0.168 mmol). The vial was sealed with a Teflon-lined septum, evacuated and backfilled with nitrogen (this process was repeated a total of three times). 1,4-Dioxane (2.0 ml) was added via syringe, followed by water (200.0 µl). The mixture was heated at 80° C. for 6 h. After cooling to room temperature, HCl (4.0 N in 1,4-dioxane) (1.0 ml, 4.00 mmol) was added followed by MeOH (1.0 ml). The reaction was stirred at room temperature for 1 h, and then concentrated. The residue was purified using prep-LCMS (XBridge C18 column, eluting with a gradient of acetonitrile/water containing 0.1% TFA, at flow rate of 60 mL/min) to afford the desired product as its TFA salt. LCMS calculated for $C_{25}H_{24}N_9$ (M+H)⁺: m/z=450.2. found: 450.2. ¹H NMR (TFA salt, 600 MHz, DMSO) δ 9.17 (d, J=5.0 Hz, 1H), 8.64 (s, 1H), 8.57 (d, J=8.7 Hz, 1H), 8.39 (s, 1H), 8.37 (s, 1H), 8.35 (s, 1H), 8.30 (s, 1H), 8.12 (d, J=5.0 Hz, 1H), 8.04 (overlap, 2H), 4.59 (m, 1H), 3.97 (s, 3H), 2.66 (s, 3H), 1.49 (d, J=6.7 Hz, 6H).

Example 52. 2-(1-Ethyl-1H-imidazol-4-yl)-5-(6-methyl-7-(4-(pyrrolidin-1-ylmethyl)phenyl)imidazo[1,2-b]pyridazin-3-yl)-1,8-naphthyridine

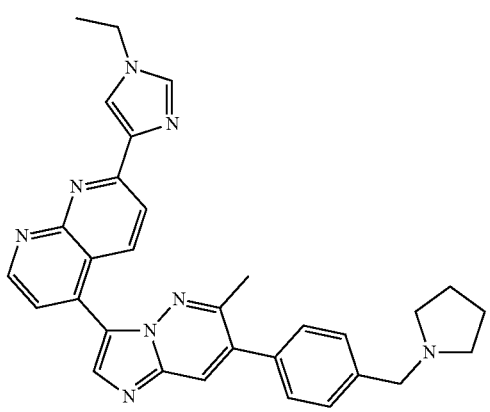 [SMILES: CCn1cnc(-c2ccc3c(-c4cnc5cc(-c6ccc(CN7CCCC7)cc6)c(C)nn45)ccnc3n2)c1]

Step 1: 5-Chloro-2-(1-ethyl-1H-imidazol-4-yl)-1,8-naphthyridine

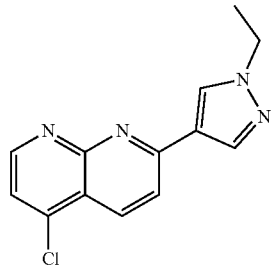 [SMILES: CCn1cc(-c2ccc3c(Cl)ccnc3n2)cn1]

To a screw-cap vial equipped with a magnetic stir bar was added 2,5-dichloro-1,8-naphthyridine (956.8 mg, 4.81 mmol), 1-ethyl-4-(4,4,5,5-tetramethyl-1,3,2-dioxaborolan-2-yl)-1H-imidazole (1048 mg, 4.72 mmol), tetrakis(triphenylphosphine)palladium(0) (1117 mg, 0.966 mmol) and cesium carbonate (4788 mg, 14.70 mmol). The vial was sealed with a Teflon-lined septum, evacuated and backfilled with nitrogen (this process was repeated a total of three times). 1,4-Dioxane (20.0 ml) was added via syringe, followed by water (3.0 ml). The mixture was stirred at 70° C. for 6 h. After cooling at room temperature, the mixture was concentrated. The residue was purified on silica gel (40 g, 0-100% EtOAc in CH₂Cl₂, then 15% MeOH in CH₂Cl₂) to give the desired product as a yellow solid (394.2 mg, 32%). LCMS calculated for $C_{13}H_{12}ClN_4$ (M+H)⁺ m/z=259.1. found 259.1.

Step 2: 2-(1-Ethyl-1H-imidazol-4-yl)-5-(4,4,5,5-tetramethyl-1,3,2-dioxaborolan-2-yl)-1,8-naphthyridine

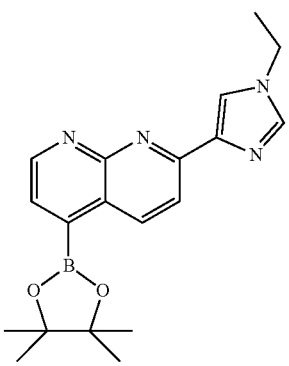 [SMILES: CCn1cnc(-c2ccc3c(B4OC(C)(C)C(C)(C)O4)ccnc3n2)c1]

To a screw-cap vial equipped with a magnetic stir bar was added 4,4,5,5,4',4',5',5'-Octamethyl-[2,2']bi[[1,3,2]dioxaborolanyl] (515.0 mg, 2.028 mmol), potassium acetate (496.8 mg, 5.06 mmol), 5-chloro-2-(1-ethyl-1H-imidazol-4-yl)-1,8-naphthyridine (394.2 mg, 1.524 mmol) and dichloro[1,1'-bis(diphenylphosphino)ferrocene]palladium (II) dichloromethane adduct (258 mg, 0.315 mmol). The vial was sealed with a Teflon-lined septum, evacuated and backfilled with nitrogen (this process was repeated a total of three times). 1,4-Dioxane (12.0 ml) was added via syringe. The mixture was stirred at 105° C. for 16 h. After cooling at room temperature, the mixture was filtered. The filtrate was used directly in the next step without further purification. LCMS calculated for $C_{19}H_{24}BN_4O_2$ (M+H)$^+$ m/z=351.2. found 351.2.

Step 3: 5-(7-Chloro-6-methylimidazo[1,2-b]pyridazin-3-yl)-2-(1-ethyl-1H-imidazol-4-yl)-1,8-naphthyridine

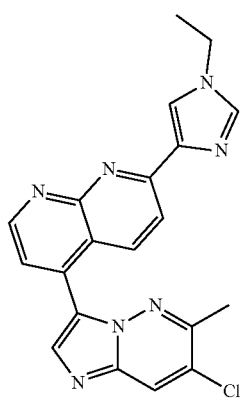 [SMILES: CCn1cnc(-c2ccc3c(-c4cnc5cc(Cl)c(C)nn45)ccnc3n2)c1]

To a screw-cap vial equipped with a magnetic stir bar was added 7-chloro-3-iodo-6-methylimidazo[1,2-b]pyridazine (497.4 mg, 1.695 mmol, see step 3 in Example 1), dichloro[1,1'-bis(diphenylphosphino)ferrocene]palladium (II) dichloromethane adduct (253 mg, 0.310 mmol) and cesium carbonate (1987 mg, 6.10 mmol). The vial was sealed with a Teflon-lined septum, evacuated and backfilled with nitrogen (this process was repeated a total of three times). A solution of 2-(1-ethyl-1H-imidazol-4-yl)-5-(4,4,5,5-tetramethyl-1,3,2-dioxaborolan-2-yl)-1,8-naphthyridine (534 mg, 1.525 mmol, see above step 2) in 1,4-Dioxane (12.0 ml) was added via syringe followed by water (3.0 ml). The mixture was stirred at 80° C. for 16 h. After cooling to room temperature, the reaction mixture was concentrated. The residue was purified on silica gel (40 g, 0-100% EtOAc in $CH_2Cl_2$, then 0-15% MeOH in $CH_2Cl_2$) to give the desired product as a solid (341.3 mg, 57%). LCMS calculated for $C_{20}H_{17}ClN_7$ (M+H)$^+$ m/z=390.1. found 390.1.

Step 4: 2-(1-Ethyl-1H-imidazol-4-yl)-5-(6-methyl-7-(4-(pyrrolidin-1-ylmethyl)phenyl)imidazo[1,2-b]pyridazin-3-yl)-1,8-naphthyridine To a screw-cap vial equipped with a magnetic stir bar was added 5-(7-chloro-6-methylimidazo[1,2-b]pyridazin-3-yl)-2-(1-ethyl-1H-imidazol-4-yl)-1,8-naphthyridine (20.0 mg, 0.051 mmol), 1-(4-(4,4,5,5-tetramethyl-1,3,2-dioxaborolan-2-yl)benzyl)pyrrolidine (26.4 mg, 0.092 mmol), dicyclohexyl(2',4',6'-triisopropylbiphenyl-2-yl)phosphine-(2'-aminobiphenyl-2-yl)(chloro)palladium (1:1) (XPhos Pd G2, 9.6 mg, 0.012 mmol) and cesium carbonate (64.2 mg, 0.197 mmol). The vial was sealed with a Teflon-lined septum, evacuated and backfilled with nitrogen (this process was repeated a total of three times). 1,4-Dioxane (2.0 ml) was added via syringe, followed by water (200.0 µl). The mixture was heated at 80° C. for 6 h. After cooling to room temperature, HCl (4.0 N in 1,4-dioxane) (1.0 ml, 4.00 mmol) was added followed by MeOH (1.0 ml). The reaction was stirred at room temperature for 1 h, and then concentrated. The residue was purified using prep-LCMS (XBridge C18 column, eluting with a gradient of acetonitrile/water containing 0.1% TFA, at flow rate of 60 mL/min) to afford the desired product as its TFA salt. LCMS calculated for $C_{31}H_{31}N_8$ (M+H)$^+$: m/z=515.3. found: 515.3.

Example 53. 4-(4-(3-(7-(1-Ethyl-1H-imidazol-4-yl)-1,8-naphthyridin-4-yl)-6-methylimidazo[1,2-b]pyridazin-7-yl)benzyl)morpholine

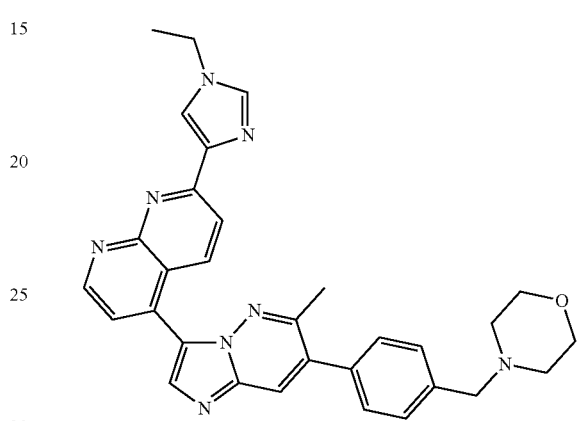

This compound was prepared according to the procedure described in Example 52, using 4-(4-(4,4,5,5-tetramethyl-1,3,2-dioxaborolan-2-yl)benzyl)morpholine instead of 1-(4-(4,4,5,5-tetramethyl-1,3,2-dioxaborolan-2-yl)benzyl)pyrrolidine as the starting material. LC-MS calculated for $C_{31}H_{31}N_8O$ (M+H)$^+$: m/z=531.3. found 531.3.

Example 54. 1-(4-(3-(7-(1-Ethyl-1H-imidazol-4-yl)-1,8-naphthyridin-4-yl)-6-methylimidazo[1,2-b]pyridazin-7-yl)phenyl)-N,N-dimethylmethanamine

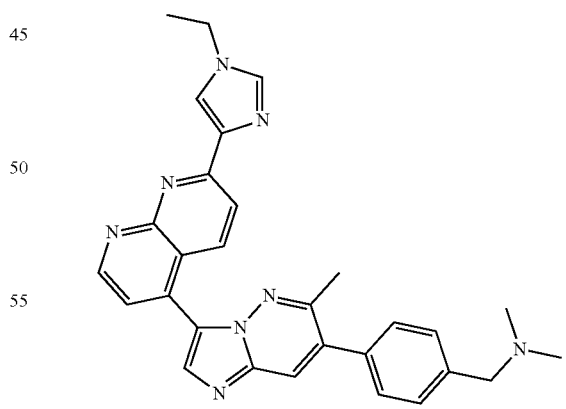

This compound was prepared according to the procedure described in Example 52, using N,N-dimethyl-1-(4-(4,4,5,5-tetramethyl-1,3,2-dioxaborolan-2-yl)phenyl)methanamine instead of 1-(4-(4,4,5,5-tetramethyl-1,3,2-dioxaborolan-2-yl)benzyl)pyrrolidine as the starting material. LC-MS calculated for $C_{29}H_{29}N_8$(M+H)$^+$: m/z=489.3. found 489.3.

Example 55. 2-(1-Ethyl-1H-imidazol-4-yl)-5-(7-(1-isopropyl-1H-pyrazol-4-yl)-6-methylimidazo[1,2-b]pyridazin-3-yl)-1,8-naphthyridine

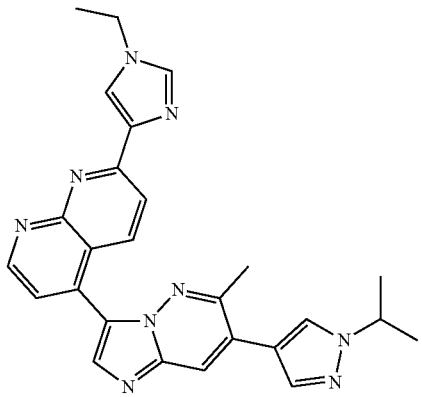 [SMILES: CCn1cnc(-c2ccc3c(-c4cnc5cc(-c6cnn(C(C)C)c6)c(C)nn45)ccnc3n2)c1]

This compound was prepared according to the procedure described in Example 52, using 1-isopropyl-4-(4,4,5,5-tetramethyl-1,3,2-dioxaborolan-2-yl)-1H-pyrazole instead of 1-(4-(4,4,5,5-tetramethyl-1,3,2-dioxaborolan-2-yl)benzyl)pyrrolidine as the starting material. LC-MS calculated for $C_{26}H_{26}N_9(M+H)^+$: m/z=464.2. found 464.2. $^1$H NMR (TFA salt, 600 MHz, DMSO) δ 9.26 (d, J=4.7 Hz, 1H), 8.98 (s, 1H), 8.68 (d, J=8.8 Hz, 1H), 8.66 (s, 1H), 8.38 (s, 1H), 8.37 (s, 1H), 8.31 (s, 1H), 8.19 (d, J=8.8 Hz, 1H), 8.11 (d, J=4.7 Hz, 1H), 8.02 (s, 1H), 4.59 (m, 1H), 4.27 (q, J=7.3 Hz, 2H), 2.64 (s, 3H), 1.52 (t, J=7.3 Hz, 3H), 1.49 (d, J=6.8 Hz, 6H).

Example 56. 5-(7-(4-(Azetidin-1-ylmethyl)phenyl)-6-methylimidazo[1,2-b]pyridazin-3-yl)-2-(1-ethyl-1H-imidazol-4-yl)-1,8-naphthyridine

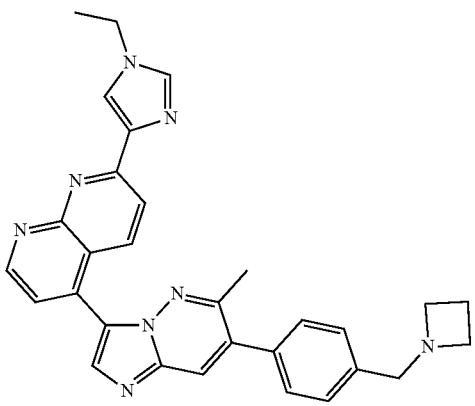 [SMILES: CCn1cnc(-c2ccc3c(-c4cnc5cc(-c6ccc(CN7CCC7)cc6)c(C)nn45)ccnc3n2)c1]

This compound was prepared according to the procedure described in Example 52, using 1-(4-(4,4,5,5-tetramethyl-1,3,2-dioxaborolan-2-yl)benzyl)azetidine instead of 1-(4-(4,4,5,5-tetramethyl-1,3,2-dioxaborolan-2-yl)benzyl)pyrrolidine as the starting material. LC-MS calculated for $C_{30}H_{29}N_8$ $(M+H)^+$: m/z=501.3. found 501.2.

Example 57. 5-(7-(4-((3,3-Difluoroazetidin-1-yl)yl)methyl)phenyl)-6-methylimidazo[1,2-b]pyridazin-3-yl)-2-(1-ethyl-1H-imidazol-4-yl)-1,8-naphthyridine

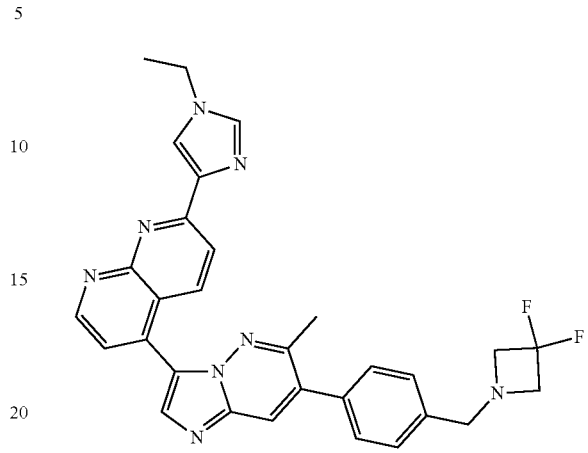

Step 1: 3,3-Difluoro-1-(4-(4,4,5,5-tetramethyl-1,3,2-dioxaborolan-2-yl)benzyl)azetidine

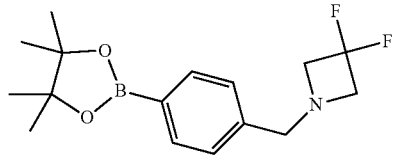 [SMILES: CC1(C)OB(c2ccc(CN3CC(F)(F)C3)cc2)OC1(C)C]

To a mixture of 2-(4-(bromomethyl)phenyl)-4,4,5,5-tetramethyl-1,3,2-dioxaborolane (102.6 mg, 0.345 mmol), $Cs_2CO_3$ (453.1 mg, 1.391 mmol) and 3,3-difluoroazetidine (HCl salt, 54.2 mg, 0.418 mmol) was added 1,4-dioxane (2.50 ml). The mixture was heated to 80° C. for 4 h. After cooling to room temperature, the mixture was filtered. The filtrate was used directly in the next step without further purification.

Step 2: 5-(7-(4-((3,3-Difluoroazetidin-1-yl)methyl)phenyl)-6-methylimidazo[1,2-b]pyridazin-3-yl)-2-(1-ethyl-1H-imidazol-4-yl)-1,8-naphthyridine This compound was prepared according to the procedure described in Example 52, using 3,3-difluoro-1-(4-(4,4,5,5-tetramethyl-1,3,2-dioxaborolan-2-yl)benzyl)azetidine instead of 1-(4-(4,4,5,5-tetramethyl-1,3,2-dioxaborolan-2-yl)benzyl)pyrrolidine as the starting material. LC-MS calculated for $C_{30}H_{27}F_2N_8$ $(M+H)^+$: m/z=537.2. found 537.2. $^1$H NMR (600 MHz, DMSO) δ 9.15 (d, J=4.5 Hz, 1H), 8.40z (d, J=8.8 Hz, 1H), 8.22 (s, 1H), 8.20 (d, J=8.8 Hz, 1H), 8.13 (s, 1H), 8.11 (s, 1H), 7.89 (d, J=4.5 Hz, 1H), 7.87 (s, 1H), 7.53 (d, J=8.1 Hz, 2H), 7.46 (d, J=7.9 Hz, 2H), 4.13 (q, J=7.3 Hz, 2H), 3.82 (s, 2H), 3.66 (t, J=12.4 Hz, 4H), 2.39 (s, 3H), 1.45 (t, J=7.3 Hz, 3H).

Example 58. (S)-4-(4-(3-(7-(1-ethyl-1H-imidazol-4-yl)-1,8-naphthyridin-4-yl)-6-methylimidazo[1,2-b]pyridazin-7-yl)benzyl)-2-methylmorpholine

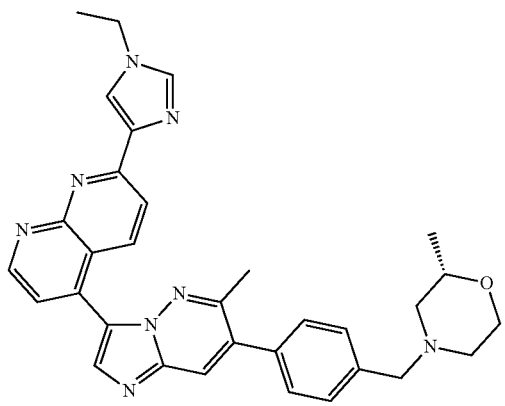 [SMILES: CCn1cnc(-c2ccc3c(-c4cnc5cc(-c6ccc(CN7CCO[C@@H](C)C7)cc6)c(C)nn45)ccnc3n2)c1]

Step 1: 3, (S)-2-methyl-4-(4-(4,4,5,5-tetramethyl-1,3,2-dioxaborolan-2-yl)benzyl)morpholine

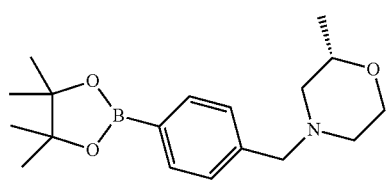 [SMILES: C[C@H]1CN(Cc2ccc(B3OC(C)(C)C(C)(C)O3)cc2)CCO1]

To a mixture of 2-(4-(bromomethyl)phenyl)-4,4,5,5-tetramethyl-1,3,2-dioxaborolane (115.6 mg, 0.389 mmol), $Cs_2CO_3$ (406.3 mg, 1.247 mmol) and (S)-2-methylmorpholine (47.8 mg, 0.473 mmol) was added 1,4-dioxane (2.50 ml). The mixture was heated to 80° C. for 2 h. After cooling to room temperature, the mixture was filtered. The filtrate was used directly in the next step without further purification.

Step 2: (S)-4-(4-(3-(7-(1-ethyl-1H-imidazol-4-yl)-1,8-naphthyridin-4-yl)-6-methylimidazo[1,2-b]pyridazin-7-yl)benzyl)-2-methylmorpholine This compound was prepared according to the procedure described in Example 52, using (S)-2-methyl-4-(4-(4,4,5,5-tetramethyl-1,3,2-dioxaborolan-2-yl)benzyl)morpholine instead of 1-(4-(4,4,5,5-tetramethyl-1,3,2-dioxaborolan-2-yl)benzyl)pyrrolidine as the starting material. LC-MS calculated for $C_{32}H_{33}N_8O$ $(M+H)^+$: m/z=545.3. found 545.2. $^1$H NMR (500 MHz, DMSO) δ 9.15 (d, J=4.5 Hz, 1H), 8.40 (d, J=8.7 Hz, 1H), 8.22 (s, 1H), 8.20 (d, J=8.7 Hz, 1H), 8.13 (s, 1H), 8.11 (s, 1H), 7.89 (d, J=4.5 Hz, 1H), 7.87 (s, 1H), 7.52 (d, J=7.7 Hz, 2H), 7.46 (d, J=7.7 Hz, 2H), 4.14 (q, J=7.3 Hz, 2H), 3.75 (m, 1H), 3.54 (overlap, 4H), 2.74 (d, J=11.0 Hz, 1H), 2.65 (m, 1H), 2.39 (s, 3H), 2.07 (m, 1H), 1.78 (t, J=10.5 Hz, 1H), 1.45 (t, J=7.3 Hz, 3H), 1.05 (d, J=6.1 Hz, 3H).

Example 59. (S)-(4-(4-(3-(7-(1-ethyl-1H-imidazol-4-yl)-1,8-naphthyridin-4-yl)-6-methylimidazo[1,2-b]pyridazin-7-yl)benzyl)morpholin-2-yl)methanol

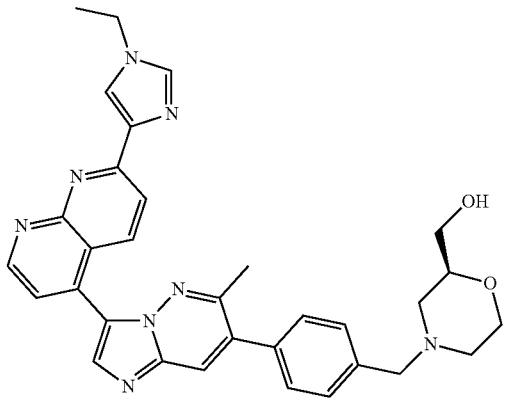 [SMILES: CCn1cnc(-c2ccc3c(-c4cnc5cc(-c6ccc(CN7CCO[C@H](CO)C7)cc6)c(C)nn45)ccnc3n2)c1]

Step 1: 3, (S)-(4-(4-(4,4,5,5-tetramethyl-1,3,2-dioxaborolan-2-yl)benzyl)morpholin-2-yl)methanol

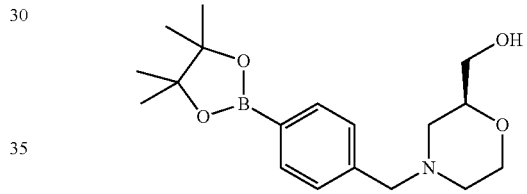

To a mixture of 2-(4-(bromomethyl)phenyl)-4,4,5,5-tetramethyl-1,3,2-dioxaborolane (115.6 mg, 0.389 mmol), $Cs_2CO_3$ (402.5 mg, 1.235 mmol) and (S)-morpholin-2-ylmethanol (54.8 mg, 0.468 mmol) was added 1,4-dioxane (2.50 ml). The mixture was heated to 80° C. for 2 h. After cooling to room temperature, the mixture was filtered. The filtrate was used directly in the next step without further purification.

Step 2: (S)-(4-(4-(3-(7-(1-ethyl-1H-imidazol-4-yl)-1,8-naphthyridin-4-yl)-6-methylimidazo[1,2-b]pyridazin-7-yl)benzyl)morpholin-2-yl) methanol This compound was prepared according to the procedure described in Example 52, using (S)-(4-(4-(4,4,5,5-tetramethyl-1,3,2-dioxaborolan-2-yl)benzyl)morpholin-2-yl)methanol instead of 1-(4-(4,4,5,5-tetramethyl-1,3,2-dioxaborolan-2-yl)benzyl)pyrrolidine as the starting material. LC-MS calculated for $C_{32}H_{33}N_8O_2$ $(M+H)^+$: m/z=561.3. found 561.3. $^1$H NMR (500 MHz, DMSO) δ 9.14 (d, J=4.5 Hz, 1H), 8.40 (d, J=8.8 Hz, 1H), 8.21 (s, 1H), 8.20 (d, J=8.8 Hz, 1H), 8.13 (d, J=1.3 Hz, 1H), 8.11 (s, 1H), 7.89 (d, J=4.5 Hz, 1H), 7.87 (d, J=1.3 Hz, 1H), 7.52 (d, J=8.1 Hz, 2H), 7.46 (d, J=8.2 Hz, 2H), 4.64 (br, 1H), 4.13 (q, J=7.3 Hz, 2H), 3.78 (m, 1H), 3.55 (overlap, 3H), 3.43 (overlap, 2H), 3.29 (m, 1H), 2.82 (d, J=11.2 Hz, 1H), 2.67 (m, 1H), 2.39 (s, 3H), 2.11 (m, 1H), 1.84 (m, 1H), 1.45 (t, J=7.3 Hz, 3H).

Example 60. 2-(4-Methyl-2H-1,2,3-triazol-2-yl)-5-(6-methyl-7-(4-(pyrrolidin-1-ylmethyl)phenyl)imidazo[1,2-b]pyridazin-3-yl)-1,8-naphthyridine

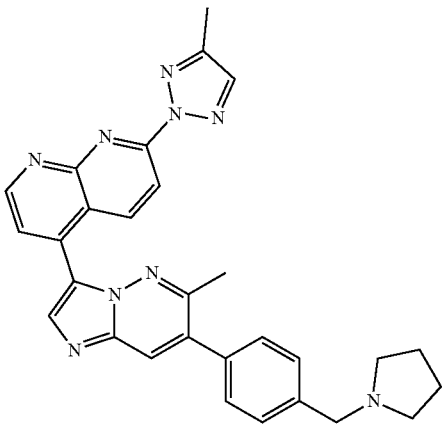 [SMILES: Cc1cnn(-c2ccc3c(-c4cnc5cc(-c6ccc(CN7CCCC7)cc6)c(C)nn45)ccnc3n2)n1]

Step 1: 5-Chloro-2-(4-methyl-2H-1,2,3-triazol-2-yl)-1,8-naphthyridine

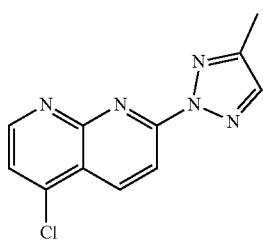 [SMILES: Cc1cnn(-c2ccc3c(Cl)ccnc3n2)n1]

To a 100 ml round bottom flask equipped with a magnetic stir bar was charged 4-methyl-2H-1,2,3-triazole (ENAMINE, 1 g, 12.03 mmol), $Cs_2CO_3$ (7.82 g, 24.07 mmol), and 5-chloro-2-(4-methyl-2H-1,2,3-triazol-2-yl)-1,8-naphthyridine (1.61 g, 6.55 mmol, 54.5% yield). To this flask was added 60 ml acetonitrile. The flask was sealed with a rubber septum and added 65 ml acetonitrile. The mixture was stirred at room temperature for 16 h. The resulting solution was diluted with $CH_2Cl_2$ (100 ml), and filtered through Celite and then concentrated. The residue was purified on silica gel (50 g, 0-100% EtOAc in $CH_2Cl_2$) to give the desired product as yellow foamy solid (1.61 g, 55% yield). LCMS calculated for $C_{11}H_9ClN_5$ $(M+H)^+$ m/z=246.1. found 246.1.

Step 2: 2-(4-Methyl-2H-1,2,3-triazol-2-yl)-5-(4,4,5,5-tetramethyl-1,3,2-dioxaborolan-2-yl)-1,8-naphthyridine

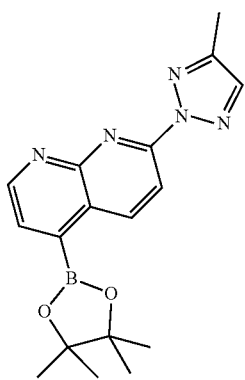 [SMILES: Cc1cnn(-c2ccc3c(B4OC(C)(C)C(C)(C)O4)ccnc3n2)n1]

To a 100 ml round bottom flask was charged with a mixture of 5-chloro-2-(4-methyl-2H-1,2,3-triazol-2-yl)-1,8-naphthyridine (1.61 g, 6.55 mmol), potassium acetate (1.286 g, 13.11 mmol), bis(pinacolato)diboron (2.496 g, 9.83 mmol) and $Pd(dppf)Cl_2.DCM$ (0.532 g, 0.655 mmol). The flask was sealed, evacuated and backfilled with nitrogen (this process was repeated a total of three times). To this flask was added 60 ml degassed 1,4-Dioxane. The mixture was heated to 100° C. for 16 h. The resulting mixture was cooled down to room temperature and diluted with 100 ml DCM, and then filtered through Celite. The filtrate was then concentrated to give the crude product, which was used directly in the next step without further purification. LCMS calculated for $C_{17}H_{21}BN_5O_2(M+H)^+$: m/z=338.2. found: 338.1.

Step 3: 5-(7-Chloro-6-methylimidazo[1,2-b]pyridazin-3-yl)-2-(4-methyl-2H-1,2,3-triazol-2-yl)-1,8-naphthyridine

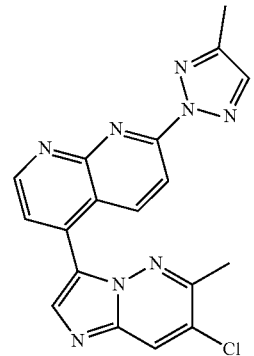 [SMILES: Cc1cnn(-c2ccc3c(-c4cnc5cc(Cl)c(C)nn45)ccnc3n2)n1]

To a 100 ml round bottom flask equipped with a magnetic stir bar was charged, 2-(4-methyl-2H-1,2,3-triazol-2-yl)-5-(4,4,5,5-tetramethyl-1,3,2-dioxaborolan-2-yl)-1,8-naphthyridine (1.608 g, 4.77 mmol), 7-chloro-3-iodo-6-methylimidazo[1,2-b]pyridazine (Example 1, Step 3, 1 g, 3.41 mmol), $Pd(dppf)Cl_2.DCM$ (0.692 g, 0.852 mmol) and $Cs_2CO_3$ (3.88 g, 11.93 mmol). The flask was sealed, evacuated and backfilled with nitrogen (this process was repeated a total of three times). To this flask was added 40 ml degassed 1,4-Dioxane and 10 ml degassed water. The mixture was heated to 80° C. for 3 h. The resulting mixture was cooled down to room temperature and diluted with DCM, and then filtered through Celite and concentrated. The residue was purified on silica gel (50 g, 0-100% EtOAc in $CH_2Cl_2$, then, 0-15% MeOH in $CH_2Cl_2$) to give the desired product as a brown solid (0.68 g, 53%). LCMS calculated for $C_{18}H_{14}ClN_8$ $(M+H)^+$: m/z=377.1. found: 377.1.

Step 4: 2-(4-methyl-2H-1,2,3-triazol-2-yl)-5-(6-methyl-7-(4-(pyrrolidin-1-ylmethyl)phenyl)imidazo[1,2-b]pyridazin-3-yl)-1,8-naphthyridine To a 25 ml flask was charged 5-(7-chloro-6-methylimidazo[1,2-b]pyridazin-3-yl)-2-(4-methyl-2H-1,2,3-triazol-2-yl)-1,8-naphthyridine (200 mg, 0.531 mmol)), 1-(4-(4,4,5,5-tetramethyl-1,3,2-dioxaborolan-2-yl)benzyl)pyrrolidine (COMBI-BLOCKS, 152 mg, 0.531 mmol), Xphos Pd G2 (84 mg, 0.106 mmol) and potassium phosphate tribasic (563 mg, 2.65 mmol). The flask was flashed with $N_2$ for 3 times. Then 4 ml degassed 1,4-Dioxane and 1 ml degassed water was added. The resulting mixture was heated to 80° C. for 1 h, then cooled down to room temperature and diluted with 20 ml DCM and 5 ml MeOH. The mixture was filtered through Celite and concentrated. The residue was purified using prep-LCMS (Waters Sunfire C18 column, eluting with a gradient of acetonitrile/water containing 0.1% TFA, at flow rate of 60 mL/min) to afford the desired product. LCMS calculated for $C_{29}H_{28}N_9$ (M+H)$^+$: m/z=502.3. found: 502.4. $^1$H NMR (TFA salt, 500 MHz, DMSO-d6) δ 9.29 (d, J=4.6 Hz, 1H), 8.70 (d, J=9.0 Hz, 1H), 8.41-8.26 (m, 2H), 8.19 (s, 1H), 8.14 (s, 1H), 8.07 (d, J=4.6 Hz, 1H), 7.69 (s, 4H), 4.47 (d, J=5.7 Hz, 2H), 3.55-3.32 (m, 2H), 3.17 (dt, J=13.7, 6.7 Hz, 2H), 2.46 (s, 3H), 2.42 (s, 3H), 2.08 (t, J=7.0 Hz, 2H), 2.02-1.80 (m, 2H).

Example 61. 5-(7-(1-Isopropyl-1H-pyrazol-4-yl)-6-methylimidazo[1,2-b]pyridazin-3-yl)-2-(4-methyl-2H-1,2,3-triazol-2-yl)-1,8-naphthyridine

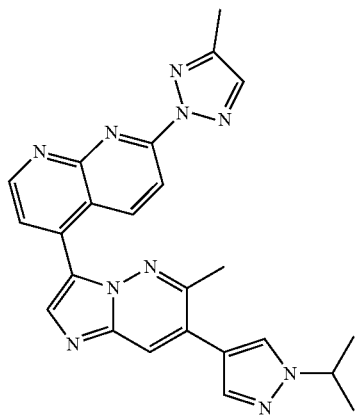 [SMILES: Cc1cnn(-c2ccc3c(-c4cnc5cc(-c6cnn(C(C)C)c6)c(C)nn45)ccnc3n2)n1]

This compound was prepared according to the procedure described in Example 60, using 1-isopropyl-4-(4,4,5,5-tetramethyl-1,3,2-dioxaborolan-2-yl)-1H-pyrazole instead of 1-(4-(4,4,5,5-tetramethyl-1,3,2-dioxaborolan-2-yl)benzyl)pyrrolidine as the starting material. LCMS calculated for $C_{24}H_{23}N_{10}$ (M+H)$^+$: m/z=451.2. found: 451.3. $^1$H NMR (TFA salt, 600 MHz, DMSO-d6) δ 9.25 (d, J=4.5 Hz, 1H), 8.70 (d, J=9.0 Hz, 1H), 8.34 (d, J=11.6 Hz, 2H), 8.29-8.23 (m, 2H), 8.12 (s, 1H), 8.06 (d, J=4.6 Hz, 1H), 8.00 (s, 1H), 4.58 (p, J=6.7 Hz, 1H), 2.62 (s, 3H), 2.45 (s, 3H), 1.48 (d, J=6.7 Hz, 6H).

Example 62. 2-(4-Methyl-2H-1,2,3-triazol-2-yl)-5-(6-methyl-7-(1-(tetrahydro-2H-pyran-4-yl)-1H-pyrazol-4-yl)imidazo[1,2-b]pyridazin-3-yl)-1,8-naphthyridine

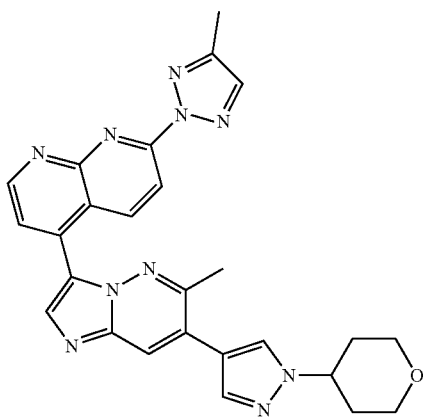 [SMILES: Cc1cnn(-c2ccc3c(-c4cnc5cc(-c6cnn(C7CCOCC7)c6)c(C)nn45)ccnc3n2)n1]

This compound was prepared according to the procedure described in Example 60, using 1-(tetrahydro-2H-pyran-4-yl)-4-(4,4,5,5-tetramethyl-1,3,2-dioxaborolan-2-yl)-1H-pyrazole instead of 1-(4-(4,4,5,5-tetramethyl-1,3,2-dioxaborolan-2-yl)benzyl)pyrrolidine as the starting material. LCMS calculated for $C_{26}H_{25}N_{10}O$ (M+H)$^+$: m/z=493.2. found: 493.3. $^1$H NMR (TFA salt, 500 MHz, DMSO-d6) δ 9.27 (d, J=4.7 Hz, 1H), 8.72 (d, J=9.0 Hz, 1H), 8.41 (s, 1H), 8.36 (s, 1H), 8.29 (t, J=4.5 Hz, 2H), 8.13 (s, 1H), 8.08 (d, J=4.7 Hz, 1H), 8.05 (s, 1H), 4.51 (tt, J=10.5, 5.5 Hz, 1H), 4.04-3.97 (m, 2H), 3.50 (dd, J=11.0, 3.4 Hz, 2H), 2.64 (s, 3H), 2.46 (s, 3H), 2.09-1.99 (m, 4H).

Example 63. N,N-dimethyl-1-(4-(6-methyl-3-(7-(4-methyl-2H-1,2,3-triazol-2-yl)-1,8-naphthyridin-4-yl)imidazo[1,2-b]pyridazin-7-yl)phenyl)methanamine

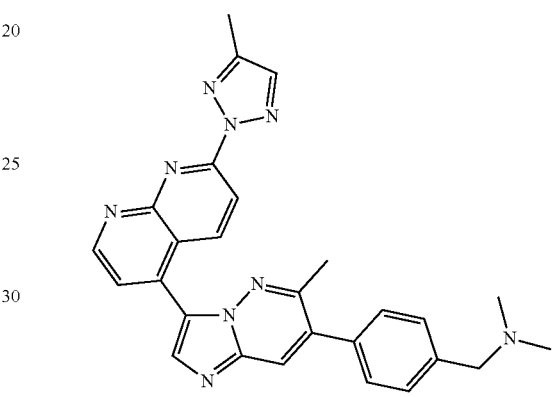

This compound was prepared according to the procedure described in Example 60, using N,N-dimethyl-1-(4-(4,4,5,5-tetramethyl-1,3,2-dioxaborolan-2-yl)phenyl)methanamine instead of 1-(4-(4,4,5,5-tetramethyl-1,3,2-dioxaborolan-2-yl)benzyl)pyrrolidine as the starting material. LCMS calculated for $C_{27}H_{26}N_9$(M+H)$^+$: m/z=476.2. found: 476.4.

Example 64. 4-(4-(6-Methyl-3-(7-(4-methyl-2H-1,2,3-triazol-2-yl)-1,8-naphthyridin-4-yl)imidazo[1,2-b]pyridazin-7-yl)benzyl)morpholine

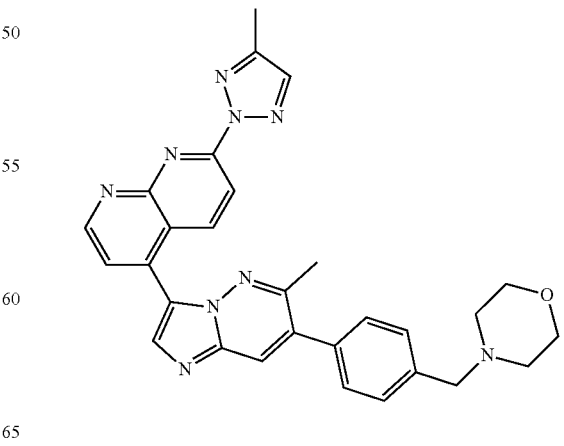

This compound was prepared according to the procedure described in Example 60, using 4-(4-(4,4,5,5-tetramethyl-1, 3,2-dioxaborolan-2-yl)benzyl)morpholine instead of 1-(4-(4,4,5,5-tetramethyl-1,3,2-dioxaborolan-2-yl)benzyl)pyrrolidine as the starting material. LCMS calculated for $C_{29}H_{28}N_9O$ (M+H)+: m/z=518.2. found: 518.2.

Example 65. N,N-dimethyl-1-(4-(6-methyl-3-(7-(4-methyl-2H-1,2,3-triazol-2-yl)-1,8-naphthyridin-4-yl)imidazo[1,2-b]pyridazin-7-yl)phenyl)methanamine

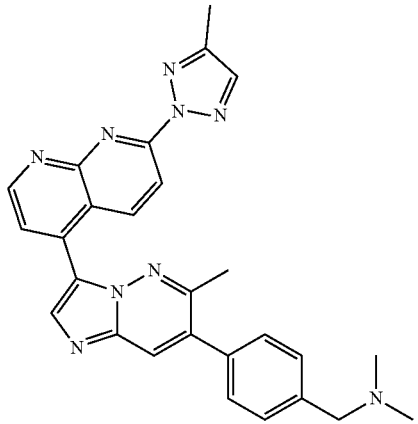 [SMILES: Cc1cnn(-c2ccc3c(-c4cnc5cc(-c6ccc(CN(C)C)cc6)c(C)nn45)ccnc3n2)n1]

This compound was prepared according to the procedure described in Example 60, using N,N-dimethyl-1-(4-(4,4,5,5-tetramethyl-1,3,2-dioxaborolan-2-yl)phenyl)methanamine instead of 1-(4-(4,4,5,5-tetramethyl-1,3,2-dioxaborolan-2-yl)benzyl)pyrrolidine as the starting material. LCMS calculated for $C_{27}H_{26}N_9$ (M+H)+: m/z=476.2. found: 476.2. ¹H NMR (TFA salt, 600 MHz, DMSO-d6) δ 9.84 (s, 1H), 9.29 (d, J=4.6 Hz, 1H), 8.70 (d, J=9.0 Hz, 1H), 8.32 (s, 1H), 8.30 (d, J=9.0 Hz, 1H), 8.20 (s, 1H), 8.14 (s, 1H), 8.07 (d, J=4.6 Hz, 1H), 7.70 (d, J=8.2 Hz, 2H), 7.66 (d, J=8.2 Hz, 2H), 4.39 (d, J=5.0 Hz, 2H), 2.81 (d, J=4.4 Hz, 6H), 2.47 (s, 3H), 2.42 (s, 3H)

Example 66. (S)-3-methyl-1-(4-(6-methyl-3-(7-(4-methyl-2H-1,2,3-triazol-2-yl)-1,8-naphthyridin-4-yl)imidazo[1,2-b]pyridazin-7-yl)benzyl)pyrrolidin-3-ol

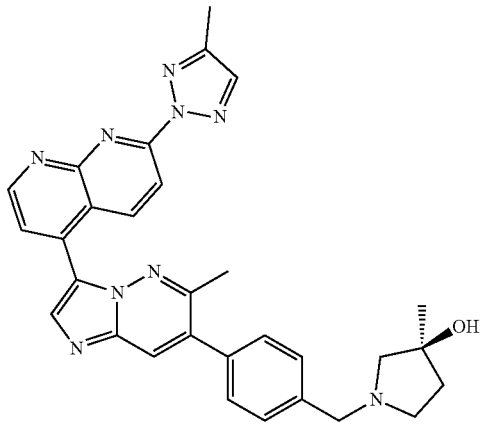 [SMILES: Cc1cnn(-c2ccc3c(-c4cnc5cc(-c6ccc(CN7CC[C@](C)(O)C7)cc6)c(C)nn45)ccnc3n2)n1]

Step 1: 3, (S)-3-methyl-1-(4-(4,4,5,5-tetramethyl-1,3,2-dioxaborolan-2-yl)benzyl)pyrrolidin-3-ol

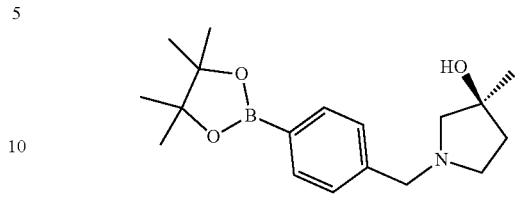

To a mixture of 2-(4-(bromomethyl)phenyl)-4,4,5,5-tetramethyl-1,3,2-dioxaborolane (115.6 mg, 0.389 mmol), $Cs_2CO_3$ (402.5 mg, 1.235 mmol) and (S)-3-methylpyrrolidin-3-ol (39.4 mg, 0.389 mmol) was added 1,4-Dioxane (2.50 ml). The mixture was heated to 80° C. for 2 h. After cooling to room temperature, the mixture was filtered. The filtrate was used directly in the next step without further purification.

Step 2: (S)-3-methyl-1-(4-(6-methyl-3-(7-(4-methyl-2H-1,2,3-triazol-2-yl)-1,8-naphthyridin-4-yl) imidazo[1,2-b]pyridazin-7-yl)benzyl)pyrrolidin-3-ol This compound was prepared according to the procedure described in Example 60, using (S)-3-methyl-1-(4-(4,4,5,5-tetramethyl-1,3,2-dioxaborolan-2-yl)benzyl)pyrrolidin-3-ol instead of 1-(4-(4,4,5,5-tetramethyl-1,3,2-dioxaborolan-2-yl)benzyl)pyrrolidine as the starting material. LCMS calculated for $C_{30}H_{30}N_9O$ (M+H)+: m/z=532.3. found: 532.4. ¹H NMR (TFA salt, 600 MHz, DMSO-d6 δ 10.38 (s, 1H), 9.29 (d, J=4.6 Hz, 1H), 8.70 (d, J=9.0 Hz, 1H), 8.34-8.28 (m, 2H), 8.20 (s, 1H), 8.14 (s, 1H), 8.07 (d, J=4.6 Hz, 1H), 7.74-7.63 (m, 4H), 4.55-4.47 (m, 2H), 4.39 (dd, J=12.8, 6.7 Hz, 1H), 3.69-3.55 (m, 1H), 3.49-3.30 (m, 2H), 3.22-3.07 (m, 2H), 2.47 (s, 3H), 2.42 (s, 3H), 2.19-1.84 (m, 2H), 1.37 (s, 3H).

Example 67. 1-(4-(6-methyl-3-(7-(4-methyl-2H-1,2,3-triazol-2-yl)-1,8-naphthyridin-4-yl)imidazo[1,2-b]pyridazin-7-yl)benzyl)piperidin-4-ol

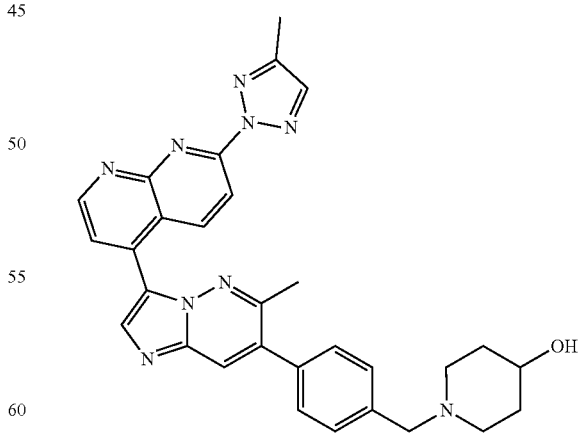

This compound was prepared according to the procedure described in Example 60, using 1-(4-(4,4,5,5-tetramethyl-1,3,2-dioxaborolan-2-yl)benzyl)piperidin-4-ol instead of 1-(4-(4,4,5,5-tetramethyl-1,3,2-dioxaborolan-2-yl)benzyl)pyrrolidine as the starting material. LCMS calculated for $C_{30}H_{30}N_9O$ (M+H)⁺: m/z=532.3. found: 532.3. ¹H NMR (TFA salt, 600 MHz, DMSO-d6) δ 9.47 (s, 1H), 9.29 (d, J=4.5 Hz, 1H), 8.69 (d, J=9.0 Hz, 1H), 8.35-8.27 (m, 2H), 8.20 (d, J=7.5 Hz, 1H), 8.14 (s, 1H) 8.06 (d, J=4.5 Hz, 1H), 7.77-7.69 (m, 3H), 7.66 (d, J=7.9 Hz, 1H), 4.43 (d, J=5.0 Hz, 1H), 4.38 (d, J=4.9 Hz, 1H), 3.97 (brs, 1H), 3.27-3.20 (m, 2H), 3.09-2.94 (m, 2H), 2.46 (s, 3H), 2.43 (s, 3H), 2.01 (d, J=12.6 Hz, 1H), 1.85-1.77 (m, 2H), 1.62-1.53 (m, 1H).

Example 68. 4-methyl-1-(4-(6-methyl-3-(7-(4-methyl-2H-1,2,3-triazol-2-yl)-1,8-naphthyridin-4-yl) imidazo[1,2-b]pyridazin-7-yl)benzyl)piperidin-4-ol

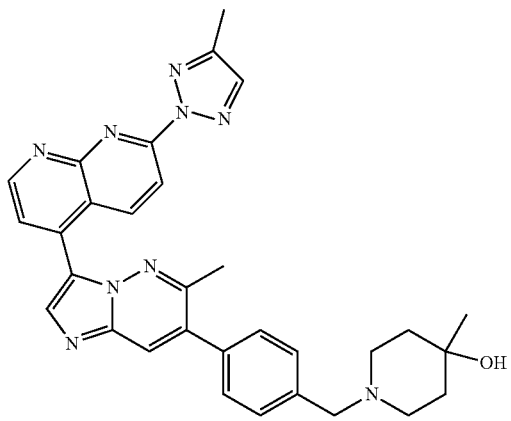 [SMILES: Cc1cnn(-c2ccc3c(-c4cnc5cc(-c6ccc(CN7CCC(C)(O)CC7)cc6)c(C)nn45)ccnc3n2)n1]

Step 1: 4-methyl-1-(4-(4,4,5,5-tetramethyl-1,3,2-dioxaborolan-2-yl)benzyl)piperidin-4-ol

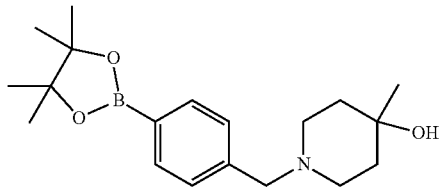 [SMILES: CC1(O)CCN(Cc2ccc(B3OC(C)(C)C(C)(C)O3)cc2)CC1]

To a 40 ml vial containing a stir bar was charged 2-(4-(bromomethyl)phenyl)-4,4,5,5-tetramethyl-1,3,2-dioxaborolane (500 mg, 1.684 mmol), 4-methylpiperidin-4-ol.HCl (AstaTech, 281 mg, 1.852 mmol) and cesium carbonate (549 mg, 1.684 mmol). The vial was sealed with a screw cap and flushed with $N_2$ three times. Then 8 ml acetonitrile was added. The resulting mixture was heated to 45° C. for 2 h. After cooling down to room temperature, 20 ml DCM and 5 ml methanol was added. The diluted solution was filtered through Celite and concentrated to give the crude product, which was directly used in the following step. LCMS calculated for $C_{19}H_{31}BNO_3$ (M+H)⁺: m/z=332.3. found: 332.3.

Step 2: 4-methyl-1-(4-(6-methyl-3-(7-(4-methyl-2H-1,2,3-triazol-2-yl)-1,8-naphthyridin-4-yl) imidazo[1,2-b]pyridazin-7-yl)benzyl)piperidin-4-ol This compound was prepared according to the procedure described in Example 60, using 4-methyl-1-(4-(4,4,5,5-te-tramethyl-1,3,2-dioxaborolan-2-yl)benzyl)piperidin-4-ol instead of 1-(4-(4,4,5,5-tetramethyl-1,3,2-dioxaborolan-2-yl)benzyl)pyrrolidine as the starting material. LCMS calculated for $C_{31}H_{32}N_9O$ (M+H)⁺: m/z=546.3. found: 546.4. ¹H NMR (TFA salt, 400 MHz, DMSO-d6) δ 9.54 (s, 1H), 9.29 (d, J=4.7 Hz, 1H), 8.71 (d, J=9.0 Hz, 1H), 8.34-8.28 (m, 2H), 8.21 (s, 1H), 8.14 (s, 1H), 8.08 (d, J=4.7 Hz, 1H), 7.70 (s, 4H), 4.43 (d, J=4.8 Hz, 2H), 3.39-3.13 (m, 4H), 2.46 (s, 3H), 2.43 (s, 3H), 1.81-1.64 (m, 4H), 1.20 (s, 3H).

Example 69. 3-methyl-1-(4-(6-methyl-3-(7-(4-methyl-2H-1,2,3-triazol-2-yl)-1,8-naphthyridin-4-yl) imidazo[1,2-b]pyridazin-7-yl)benzyl)azetidin-3-ol

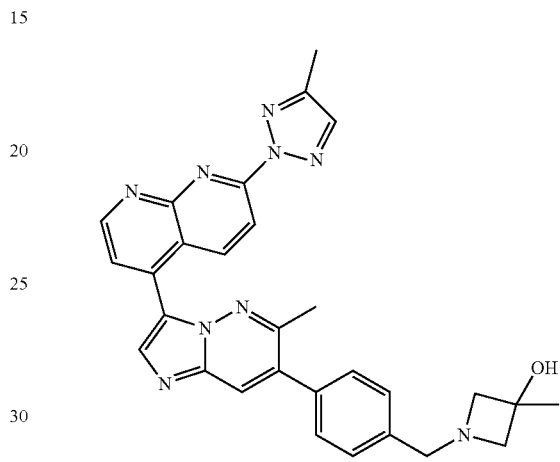

Step 1: 3-methyl-1-(4-(4,4,5,5-tetramethyl-1,3,2-dioxaborolan-2-yl)benzyl)azetidin-3-ol

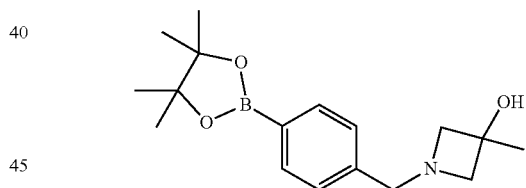

To a 40 ml vial containing a stir bar was charged 2-(4-(bromomethyl)phenyl)-4,4,5,5-tetramethyl-1,3,2-dioxaborolane (500 mg, 1.684 mmol), 3-methylazetidin-3-ol.HCl (AstaTech, 229 mg, 1.852 mmol) and cesium carbonate (549 mg, 1.684 mmol). The vial was sealed with a screw cap and flushed with $N_2$ three times. Then 8 ml acetonitrile was added. The resulting mixture was heated to 45° C. for 2 h. After cooling down to room temperature, 20 ml DCM and 5 ml methanol was added. The diluted solution was filtered through Celite and concentrated to give the crude product, which was directly used in the following step. LCMS calculated for $C_{17}H_{27}BNO_3$ (M+H)⁺: m/z=304.2. found: 304.3.

Step 2: 3-methyl-1-(4-(6-methyl-3-(7-(4-methyl-2H-1,2,3-triazol-2-yl)-1,8-naphthyridin-4-yl)imidazo[1,2-b]pyridazin-7-yl)benzyl)azetidin-3-ol This compound was prepared according to the procedure described in Example 60, using 3-methyl-1-(4-(4,4,5,5-tetramethyl-1,3,2-dioxaborolan-2-yl)benzyl)azetidin-3-ol instead of 1-(4-(4,4,5,5-tetramethyl-1,3,2-dioxaborolan-2-yl)benzyl)pyrrolidine as the starting material. LCMS calculated for $C_{29}H_{28}N_9O$ (M+H)⁺: m/z=518.2. found: 518.4.

Example 70. 2-(4-methyl-2H-1,2,3-triazol-2-yl)-5-(6-methyl-7-(4-((4-methylpiperazin-1-yl)methyl)phenyl)imidazo[1,2-b]pyridazin-3-yl)-1,8-naphthyridine

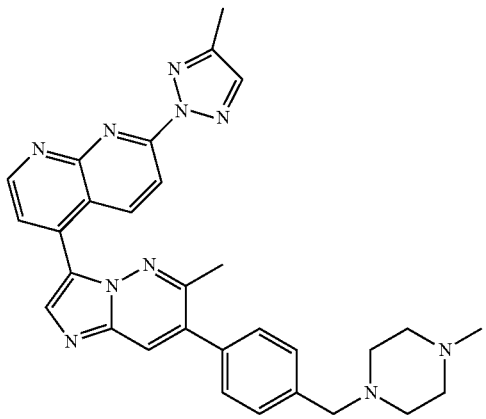 [SMILES: Cc1cnn(-c2ccc3c(-c4cnc5cc(-c6ccc(CN7CCN(C)CC7)cc6)c(C)nn45)ccnc3n2)n1]

This compound was prepared according to the procedure described in Example 60, using 1-methyl-4-(4-(4,4,5,5-tetramethyl-1,3,2-dioxaborolan-2-yl)benzyl)piperazine instead of 1-(4-(4,4,5,5-tetramethyl-1,3,2-dioxaborolan-2-yl)benzyl)pyrrolidine as the starting material. LCMS calculated for $C_{30}H_{31}N_{10}$ (M+H)⁺: m/z=531.3. found: 531.1. ¹H NMR (TFA salt, 600 MHz, DMSO-d6) δ 9.28 (d, J=4.6 Hz, 1H), 8.70 (d, J=9.0 Hz, 1H), 8.32-8.29 (m, 2H), 8.14 (d, J=5.9 Hz, 2H), 8.07 (d, J=4.6 Hz, 1H), 7.58 (d, J=8.0 Hz, 2H), 7.51 (d, J=7.9 Hz, 2H), 3.75-3.69 (m, 2H), 3.48-3.38 (m, 2H), 3.11-2.98 (m, 2H), 2.80 (s, 3H), 2.46 (s, 3H), 2.42 (s, 3H).

Example 71. 1-(4-(3-(7-(1-Ethyl-1H-imidazol-4-yl)-1,8-naphthyridin-4-yl)-6-methylimidazo[1,2-b]pyridazin-7-yl)benzyl)piperidin-4-ol

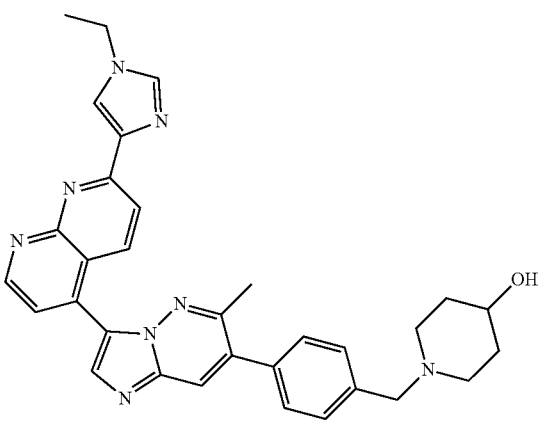 [SMILES: CCn1cnc(-c2ccc3c(-c4cnc5cc(-c6ccc(CN7CCC(O)CC7)cc6)c(C)nn45)ccnc3n2)c1]

This compound was prepared according to the procedure described in Example 52, using 1-(4-(4,4,5,5-tetramethyl-1,3,2-dioxaborolan-2-yl)benzyl)piperidin-4-ol instead of 1-(4-(4,4,5,5-tetramethyl-1,3,2-dioxaborolan-2-yl)benzyl)pyrrolidine as the starting material. LC-MS calculated for $C_{32}H_{33}N_8O$ (M+H)⁺: m/z=545.3. found 545.3.

Example 72. 1-(4-(3-(7-(1-Ethyl-1H-imidazol-4-yl)-1,8-naphthyridin-4-yl)-6-methylimidazo[1,2-b]pyridazin-7-yl)benzyl)-4-methylpiperidin-4-ol

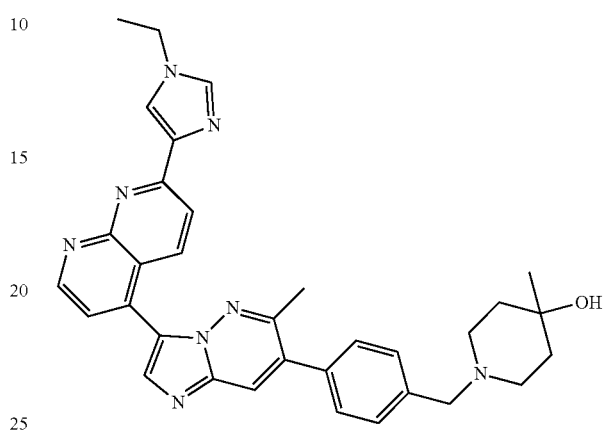

This compound was prepared according to the procedure described in Example 52, using 4-methyl-1-(4-(4,4,5,5-tetramethyl-1,3,2-dioxaborolan-2-yl)benzyl)piperidin-4-ol instead of 1-(4-(4,4,5,5-tetramethyl-1,3,2-dioxaborolan-2-yl)benzyl)pyrrolidine as the starting material. LC-MS calculated for $C_{33}H_{35}N_8O$ (M+H)⁺: m/z=559.3. found 559.3.

Example A. ALK2 HTRF Assay

ALK2 (aa 147-end) was obtained from BPS biosciences. The enzymatic assays were conducted in white 384-well polystyrene plates in a final volume of 8 μL. The inhibitors were serially diluted in DMSO and added to the plate wells prior to addition of the other reaction components. The assays were carried out at 25° C. in the assay buffer (50 mM HEPES, pH 7.0, 10% Glycerol, 0.01% Brij50, 10 mM $MgCl_2$, 1 mM EGTA, 5 mM DTT, and 0.01% BSA), containing 50 nM LANCE Ultra ULight™-DNA Topoisomerase 2-alpha peptide (Perkin Elmer TRF0130), and 3 μM ATP. The final concentration of DMSO in the assay was 1% and the enzyme concentration was 0.5 nM for ALK2. The reactions were allowed to proceed for 2 hr for ALK2 after which, the reaction was quenched by addition of EDTA at a final concentration of 20 mM along with 1.5 nM LANCE Ultra Europium-anti-phospho-DNA Topoisomerase 2-alpha (Thr1342) antibody (Perkin Elmer TRF0218). The reaction was incubated at 25° C. for 1 hr and read on a PHERAstar FS plate reader (BMG Labtech). $IC_{50}$ determination was performed by fitting percent control activity versus the log of the inhibitor concentration using the IDBS XLFit and GraphPad Prism 5.0 software.

Compounds of the present disclosure, as exemplified in Examples, showed the $IC_{50}$ values in the following ranges: +=$IC_{50}$≤1 nM; ++=1 nM<$IC_{50}$≤5 nM; +++=5 nM<$IC_{50}$≤100 nM, ++++=$IC_{50}$>100 nM.

TABLE 1

| Example # | ALK2 IC$_{50}$ (nM) |
|---|---|
| 1 | + |
| 2 | + |
| 3 | +++ |
| 4 | +++ |
| 5 | +++ |
| 6 | + |
| 7 | + |
| 8 | ++ |
| 9 | + |
| 10 | ++ |
| 11 | + |
| 12 | +++ |
| 13 | +++ |
| 14 | ++ |
| 15 | ++ |
| 16 | ++ |
| 17 | ++++ |
| 18 | ++ |
| 19 | ++ |
| 20 | ++ |
| 21 | +++ |
| 22 | + |
| 23 | +++ |
| 24 | +++ |
| 25 | ++ |
| 26 | +++ |
| 27 | + |
| 28 | +++ |
| 29 | + |
| 30 | +++ |
| 31 | ++++ |
| 32 | +++ |
| 33 | +++ |
| 34 | +++ |
| 35 | ++ |
| 36 | + |
| 37 | + |
| 38 | + |
| 39 | ++ |
| 40 | + |
| 41 | ++ |
| 42 | ++ |
| 43 | ++ |
| 44 | ++ |
| 45 | ++ |
| 46 | +++ |
| 47 | ++ |
| 48 | + |
| 49 | + |
| 50 | + |
| 51 | ++ |
| 52 | + |
| 53 | ++ |
| 54 | + |
| 55 | ++ |
| 56 | ++ |
| 57 | ++ |
| 58 | + |
| 59 | ++ |
| 60 | ++ |
| 61 | ++ |
| 62 | + |
| 63 | ++ |
| 64 | ++ |
| 65 | ++ |
| 66 | + |
| 67 | + |
| 68 | + |
| 69 | ++ |
| 70 | ++ |
| 71 | ++ |
| 72 | + |

Example B. ALK2 Cellular Assay

HeLa cells are cultured in MEM media with 10% FBS. Recombinant human BMP-7 is obtained from R&D Systems (cat #354-BP) and phospho SMAD1 (S463/S465) HTRF kit is purchased from Cisbio (63ADK062PEH). HeLa cells are plated in a 96 well flat-bottomed plate at 50,000 cells per well and incubated overnight. The next day, the media is removed and 50 μl fresh complete media is added. 5 μl compound is added to cells (3 μM final concentration at highest) and incubated for 60 min at 37° C. 200 ng/ml BMP-7 is added and incubated for 30 min at 37° C. After incubation, the media is removed, washed 2×PBS, and processed with an HTRF kit according to Cisbio HTRF kit instructions for measuring the Phospho SMAD1 (S463/S465). Finally, both the donor and acceptor are added into 384 well plates and incubated at room temperature overnight and the HTRF signal is measured via Pherastar next day.

Various modifications of the present disclosure, in addition to those described herein, will be apparent to those skilled in the art from the foregoing description. Such modifications are also intended to fall within the scope of the appended claims. Each reference, including without limitation all patent, patent applications, and publications, cited in the present application is incorporated herein by reference in its entirety.

What is claimed is:

1. A compound of Formula I:

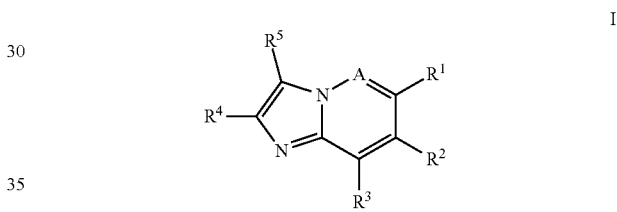

I or a pharmaceutically acceptable salt thereof, wherein:

$R^1$ is selected from $C_{1-6}$ alkyl, $C_{2-6}$ alkenyl, $C_{2-6}$ alkynyl, $C_{1-6}$ haloalkyl, CN, C(O)$R^b$, C(O)NR$^c$R$^d$, C(O)OR$^a$, C(=NR$^e$)R$^b$, C(=NOR$^a$)R$^b$, and C(=NR$^e$)NR$^c$R$^d$, wherein said $C_{1-6}$ alkyl, $C_{2-6}$ alkenyl and $C_{2-6}$ alkynyl are each optionally substituted with 1, 2, 3, or 4 substituents independently selected from $R^{10}$;

$R^2$ is selected from $C_{6-10}$ aryl and 5-10 membered heteroaryl; wherein the 5-10 membered heteroaryl has at least one ring-forming carbon atom and 1, 2, 3, or 4 ring-forming heteroatoms independently selected from N, O, and S; wherein the N and S are optionally oxidized; wherein a ring-forming carbon atom of the 5-10 membered heteroaryl is optionally substituted by oxo to form a carbonyl group; and wherein the $C_{6-10}$ aryl and 5-10 membered heteroaryl are each optionally substituted with 1, 2, 3, 4 or 5 substituents independently selected from $R^{20}$;

or two adjacent $R^{20}$ substituents on $R^2$, taken together with the atoms to which they are attached, form a fused 4-, 5-, 6- or 7-membered heterocycloalkyl ring, or a fused $C_{3-7}$ cycloalkyl ring; wherein the fused 4-, 5-, 6- or 7-membered heterocycloalkyl ring each has at least one ring-forming carbon atom and 1, 2, 3, or 4 ring-forming heteroatoms independently selected from N, O, and S; wherein a ring-forming carbon atom of each fused 4-, 5-, 6- or 7-membered heterocycloalkyl ring is optionally substituted by oxo to form a carbonyl group; and wherein the fused 4-, 5-, 6- or 7-membered heterocycloalkyl ring and fused $C_{3-7}$ cycloalkyl ring are each optionally substituted with 1, 2, 3 or 4 substituents independently selected from $R^{21}$;

$R^3$ is selected from H and $C_{1-6}$ alkyl;

$R^4$ is selected from H and $C_{1-6}$ alkyl;

$R^5$ is selected from $C_{6-10}$ aryl and 5-10 membered heteroaryl; wherein the 5-10 membered heteroaryl has at least one ring-forming carbon atom and 1, 2, 3, or 4 ring-forming heteroatoms independently selected from N, O, and S; wherein the N and S are optionally oxidized; wherein a ring-forming carbon atom of the 5-10 membered heteroaryl is optionally substituted by oxo to form a carbonyl group; and wherein the $C_{6-10}$ aryl and 5-10 membered heteroaryl are each optionally substituted with 1, 2, 3, 4 or 5 substituents independently selected from $R^{50}$;

or two adjacent $R^{50}$ substituents on $R^5$, taken together with the atoms to which they are attached, form a fused 4-, 5-, 6- or 7-membered heterocycloalkyl ring, or a fused $C_{3-7}$ cycloalkyl ring; wherein the fused 4-, 5-, 6- or 7-membered heterocycloalkyl ring each has at least one ring-forming carbon atom and 1, 2, 3, or 4 ring-forming heteroatoms independently selected from N, O, and S; wherein a ring-forming carbon atom of each fused 4-, 5-, 6- or 7-membered heterocycloalkyl ring is optionally substituted by oxo to form a carbonyl group; and wherein the fused 4-, 5-, 6- or 7-membered heterocycloalkyl ring and fused $C_{3-7}$ cycloalkyl ring are each optionally substituted with 1, 2, 3 or 4 substituents independently selected from $R^{51}$;

A is N;

each $R^{10}$ is independently selected from $C_{1-6}$ alkyl, $C_{2-6}$ alkenyl, $C_{2-6}$ alkynyl, $C_{1-6}$ haloalkyl, $C_{5-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NOR^{a1})R^{b1}$, $C(=NR^{e1})NR^{c1}R^{d1}$, $NR^{c1}C(=NR^{e1})NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, and $S(O)_2NR^{c1}R^{d1}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{11}$;

or two $R^{10}$ substituents taken together with the carbon atom to which they are attached form a spiro 4-7-membered heterocycloalkyl ring, or a spiro $C_{3-6}$ cycloalkyl ring; wherein each spiro 4-7-membered heterocycloalkyl ring has at least one ring-forming carbon atom and 1, 2 or 3, ring-forming heteroatoms independently selected from N, O, and S; wherein a ring-forming carbon atom of each spiro 4-7-membered heterocycloalkyl ring is optionally substituted by oxo to form a carbonyl group; and wherein the spiro 4-7-membered heterocycloalkyl ring and spiro $C_{3-6}$ cycloalkyl ring are each optionally substituted with 1, 2, 3 or 4 substituents independently selected from $R^{11}$;

each $R^{11}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a3}$, $SR^{a3}$, $C(O)R^{b3}$, $C(O)NR^{c3}R^{d3}$, $C(O)OR^{a3}$, $NR^{c3}R^{d3}$ $NR^{c3}C(O)R^{b3}$, $NR^{c3}C(O)OR^{a3}$, $NR^{c3}S(O)R^{b3}$, $NR^{c3}S(O)_2R^{b3}$, $NR^{c3}S(O)_2NR^{c3}R^{d3}$ $S(O)R^{b3}$, $S(O)NR^{c3}R^{d3}$, $S(O)_2R^{b3}$, and $S(O)_2NR^{c3}R^{d3}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{12}$;

each $R^{12}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, $C_{6-10}$ aryl, 5-10 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a5}$, $SR^{a5}$, $C(O)R^{b5}$, $C(O)NR^{c5}R^{d5}$, $C(O)OR^{a5}$, $NR^{c5}R^{d5}$ $NR^{c5}C(O)R^{b5}$ $NR^{c5}C(O)OR^{a5}$ $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2 NR^{c5}R^{d5}$; wherein said $C_{1-6}$ alkyl, $C_{2-6}$ alkenyl, $C_{2-6}$ alkynyl, $C_{3-6}$ cycloalkyl, $C_{6-10}$ aryl, 5-10 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, $C_{6-10}$ aryl-$C_{1-3}$ alkylene, and 5-10 membered heteroaryl-$C_{1-3}$ alkylene are each optionally substituted with 1, 2, 3, or 4 substituents independently selected from $R^g$;

each $R^{20}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NOR^{a2})R^{b2}$, $C(=NR^{e2})NR^{c2}R^{d2}$, $NR^{c2}C(=NR^{e2})NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$; wherein a ring-forming carbon atom of the 4-10 membered heterocycloalkyl is optionally substituted by oxo to form a carbonyl group; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{21}$;

each $R^{21}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a4}$, $SR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $NR^{c4}C(O)OR^{a4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2 NR^{c4}R^{d4}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{22}$;

each $R^{22}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, 5-6 membered heteroaryl-$C_{1-3}$ alkylene, halo, D, CN, $OR^{a6}$, $SR^{a6}$, $C(O)R^{b6}$, $C(O)NR^{c6}R^{d6}$, $C(O)OR^{a6}$, $NR^{c6}R^{d6}$, $NR^{c6}C(O)R^{b6}$, $NR^{c6}C(O)OR^{a6}$, $NR^{c6}S(O)R^{b6}$, $NR^{c6}S(O)_2R^{b6}$, $NR^{c6}S(O)_2NR^{c6}R^{d6}$, $S(O)R^{b6}$, $S(O)NR^{c6}R^{d6}$, $S(O)_2R^{b6}$, and $S(O)_2NR^{c6}R^{d6}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene are each optionally substituted with 1, 2, 3, or 4 substituents independently selected from $R^g$;

each $R^{50}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a9}$, $SR^{a9}$, $C(O)R^{b9}$, $C(O)NR^{c9}R^{d9}$, $C(O)OR^{a9}$, $OC(O)R^{b9}$, $OC(O)NR^{c9}R^{d9}$, $NR^{c9}R^{d9}$, $NR^{c9}C(O)R^{b9}$, $NR^{c9}C(O)OR^{a9}$, $NR^{c9}C(O)NR^{c9}R^{d9}$, $C(=NR^{e9})R^{b9}$, $C(=NOR^{a9})R^{b9}$, $C(=NR^{c9})NR^{c9}R^{d9}$, $NR^{c9}C(=NR^{e9})NR^{c9}R^{d9}$, $NR^{c9}S(O)R^{b9}$, $NR^{c9}S(O)_2R^{b9}$, $NR^{c9}S(O)_2NR^{c9}R^{d9}$, $S(O)R^{b9}$, $S(O)NR^{c9}R^{d9}$, $S(O)_2R^{b9}$, and $S(O)_2NR^{c9}R^{d9}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{51}$;

each $R^{51}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a10}$, $SR^{a10}$, $C(O)R^{b10}$, $C(O)NR^{c10}R^{d10}$, $C(O)OR^{a10}$, $NR^{c10}R^{d10}$, $NR^{c10}C(O)R^{b10}$, $NR^{c10}C(O)OR^{a10}$, $NR^{c10}S(O)R^{b10}$, $NR^{c10}S(O)_2R^{b10}$, $NR^{c10}S(O)_2NR^{c10}R^{d10}$, $S(O)R^{b10}$, $S(O)NR^{c10}R^{d10}$, $S(O)_2R^{b10}$, and $S(O)_2NR^{c10}R^{d10}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{52}$;

each $R^{52}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, 5-6 membered heteroaryl-$C_{1-3}$ alkylene, halo, D, CN, $OR^{a11}$, $SR^{a11}$, $C(O)R^{b11}$, $C(O)NR^{c11}R^{d11}$, $C(O)OR^{a11}$, $NR^{c11}R^{d11}$, $NR^{c11}C(O)R^{b11}$, $NR^{c11}C(O)OR^{a11}$, $NR^{c11}S(O)R^{b11}$, $NR^{c11}S(O)_2R^{b11}$, $NR^{c11}S(O)_2NR^{c11}R^{d11}$, $S(O)R^{b11}$, $S(O)NR^{c11}R^{d11}$, $S(O)_2R^{b11}$, and $S(O)_2NR^{c11}R^{d11}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene are each optionally substituted with 1, 2, 3, or 4 substituents independently selected from $R^g$;

each $R^a$, $R^c$, and $R^d$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene are each optionally substituted with 1, 2, 3, or 4 substituents independently selected from $R^{10}$;

or any $R^c$ and $R^d$ attached to the same N atom, together with the N atom to which they are attached, form a 4-10 membered heterocycloalkyl group optionally substituted with 1, 2, 3 or 4 substituents independently selected from $R^{10}$;

each $R^b$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene are each optionally substituted with 1, 2, 3, or 4 substituents independently selected from $R^{10}$;

each $R^e$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{a1}$, $R^{c1}$ and $R^{d1}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene are each optionally substituted with 1, 2, 3, or 4 substituents independently selected from $R^{11}$;

or any $R^{c1}$ and $R^{d1}$ attached to the same N atom, together with the N atom to which they are attached, form a 4-10 membered heterocycloalkyl group optionally substituted with 1, 2, 3 or 4 substituents independently selected from $R^{11}$;

each $R^{b1}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene are each optionally substituted with 1, 2, 3, or 4 substituents independently selected from $R^{11}$;

each $R^{e1}$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{a2}$, $R^{c2}$ and $R^{d2}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene are each optionally substituted with 1, 2, 3, or 4 substituents independently selected from $R^{21}$;

or any $R^{c2}$ and $R^{d2}$ attached to the same N atom, together with the N atom to which they are attached, form a 4-10 membered heterocycloalkyl group optionally substituted with 1, 2, 3 or 4 substituents independently selected from $R^{21}$;

each $R^{b2}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene are each optionally substituted with 1, 2, 3, or 4 substituents independently selected from $R^{21}$;

each $R^{e2}$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{a3}$, $R^{c3}$ and $R^{d3}$ is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene; wherein said $C_{1-6}$ alkyl $C_{2-6}$ alkenyl, $C_{2-6}$ alkynyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{13}$ alkylene are each optionally substituted with 1, 2, 3, or 4 substituents independently selected from $R^{12}$;

or any $R^{c3}$ and $R^{d3}$ attached to the same N atom, together with the N atom to which they are attached, form a 4-, 5-, 6- or 7-membered heterocycloalkyl group optionally substituted with 1, 2 or 3 substituents independently selected from $R^{12}$;

each $R^{b3}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene; wherein said $C_{1-6}$ alkyl $C_{2-6}$ alkenyl, $C_{2-6}$ alkynyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene are each optionally substituted with 1, 2, 3, or 4 substituents independently selected from $R^{12}$;

each $R^{a4}$, $R^{c4}$ and $R^{d4}$ is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene; wherein said $C_{1-6}$ alkyl $C_{2-6}$ alkenyl, $C_{2-6}$ alkynyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene are each optionally substituted with 1, 2, 3, or 4 substituents independently selected from $R^{22}$;

or any $R^{c4}$ and $R^{d4}$ attached to the same N atom, together with the N atom to which they are attached, form a 4-, 5-, 6- or 7-membered heterocycloalkyl group optionally substituted with 1, 2 or 3 substituents independently selected from $R^{22}$;

each $R^{b4}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene; wherein said $C_{1-6}$ alkyl $C_{2-6}$ alkenyl, $C_{2-6}$ alkynyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene are each optionally substituted with 1, 2, 3, or 4 substituents independently selected from $R^{22}$;

each $R^{a5}$, $R^{c5}$ and $R^{d5}$ is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

or any $R^{c5}$ and $R^{d5}$ attached to the same N atom, together with the N atom to which they are attached, form a 4-, 5-, 6- or 7-membered heterocycloalkyl group optionally substituted with 1, 2 or 3 substituents independently selected from $R^g$;

each $R^{b5}$ is independently selected from $C_{1-6}$ alkyl, $C_{2-6}$ alkenyl, $C_{2-6}$ alkynyl and $C_{1-6}$ haloalkyl; wherein said $C_{1-6}$ alkyl $C_{2-6}$ alkenyl and $C_{2-6}$ alkynyl are each optionally substituted with 1, 2, 3, or 4 substituents independently selected from $R^g$;

each $R^{a6}$, $R^{c6}$ and $R^{d6}$ is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

or any $R^{c6}$ and $R^{d6}$ attached to the same N atom, together with the N atom to which they are attached, form a 4-, 5-, 6- or 7-membered heterocycloalkyl group optionally substituted with 1, 2 or 3 substituents independently selected from $R^g$;

each $R^{b6}$ is independently selected from $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{a9}$, $R^{c9}$ and $R^{d9}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene are each optionally substituted with 1, 2, 3, or 4 substituents independently selected from $R^{51}$;

or any $R^{c9}$ and $R^{d9}$ attached to the same N atom, together with the N atom to which they are attached, form a 4-10 membered heterocycloalkyl group optionally substituted with 1, 2, 3 or 4 substituents independently selected from $R^{51}$;

each $R^{b9}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene are each optionally substituted with 1, 2, 3, or 4 substituents independently selected from $R^{51}$;

each $R^{e9}$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{a10}$, $R^{c10}$ and $R^{d10}$ is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene; wherein said $C_{1-6}$ alkyl $C_{2-6}$ alkenyl, $C_{2-6}$ alkynyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene are each optionally substituted with 1, 2, 3, or 4 substituents independently selected from $R^{52}$;

or any $R^{c10}$ and $R^{d10}$ attached to the same N atom, together with the N atom to which they are attached, form a 4-, 5-, 6- or 7-membered heterocycloalkyl group optionally substituted with 1, 2 or 3 substituents independently selected from $R^{52}$;

each $R^{b10}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene; wherein said $C_{1-6}$ alkyl $C_{2-6}$ alkenyl, $C_{2-6}$ alkynyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene are each optionally substituted with 1, 2, 3, or 4 substituents independently selected from $R^{52}$;

each $R^{a11}$, $R^{c11}$ and $R^{d11}$ is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

or any $R^{c11}$ and $R^{d11}$ attached to the same N atom, together with the N atom to which they are attached, form a 4-, 5-, 6- or 7-membered heterocycloalkyl group optionally substituted with 1, 2 or 3 substituents independently selected from $R^g$;

each $R^{b11}$ is independently selected from $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-6}$ haloalkyl, $C_{3-6}$ cycloalkyl, $C_{3-6}$ cycloalkyl-$C_{1-2}$ alkylene, $C_{1-6}$ alkoxy, $C_{1-6}$ haloalkoxy, $C_{1-3}$ alkoxy-$C_{1-3}$ alkyl, $C_{1-3}$ alkoxy-$C_{1-3}$ alkoxy, HO—$C_{1-3}$ alkoxy, HO—$C_{1-3}$ alkyl, cyano-$C_{1-3}$ alkyl, $H_2N$—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

2. The compound of claim 1, wherein $R^1$ is selected from $C_{1-6}$ alkyl, $C_{2-6}$ alkenyl, $C_{2-6}$ alkynyl, $C_{1-6}$ haloalkyl, CN, $C(O)R^b$, $C(O)NR^cR^d$, and $C(O)OR^a$; wherein said $C_{1-6}$ alkyl, $C_{2-6}$ alkenyl and $C_{2-6}$ alkynyl are each optionally substituted with 1, 2, 3, or 4 substituents independently selected from $R^{10}$.

3. The compound of claim 1, wherein $R^1$ is selected from $C_{1-6}$ alkyl, CN, C(O)NR$^c$R$^d$, C(O)R$^b$ and C(O)OR$^a$; wherein said $C_{1-6}$ alkyl is optionally substituted with 1, 2, 3, or 4 substituents independently selected from $R^{10}$.

4. The compound of claim 1, wherein $R^1$ is selected from methyl, methoxycarbonyl, carbamoyl, cyano, hydroxymethyl, methoxymethyl, N-(4-hydroxy-4-methylcyclohexyl)carbamoyl, and 4-ethoxycarbonyl-piperazin-1-ylcarbonyl.

5. The compound of claim 1, wherein each $R^{10}$ is selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, OR$^{a1}$, C(O)OR$^{a1}$, NR$^{c1}$R$^{d1}$, and S(O)$_2$NR$^{c1}$R$^{d1}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl are each optionally substituted with 1 or 2 substituents independently selected from $R^{11}$.

6. The compound of claim 1, wherein each $R^{10}$ is selected from $C_{1-6}$ alkyl, $C_{1-6}$ haloalkyl, halo, D, CN, OR$^{a1}$, C(O)R$^{b1}$, C(O)NR$^{c1}$R$^{d1}$, C(O)OR$^{a1}$, NR$^{c1}$R$^{d1}$, and S(O)$_2$NR$^{c1}$R$^{d1}$; wherein said $C_{1-6}$ alkyl is optionally substituted with 1, 2, 3, or 4 substituents independently selected from $R^{11}$.

7. The compound of claim 1, wherein each $R^{10}$ is selected from $C_{1-6}$ alkyl, OR$^{a1}$, and C(O)OR$^{a1}$; wherein said $C_{1-6}$ alkyl is optionally substituted with 1 or 2 substituents independently selected from $R^{11}$.

8. The compound of claim 1, wherein each $R^{10}$ is selected from methyl, OH, methoxy, and ethoxycarbonyl.

9. The compound of claim 1, wherein $R^2$ is 5-6 membered heteroaryl; wherein the 5-6 membered heteroaryl has at least one ring-forming carbon atom and 1, 2, 3, or 4 ring-forming heteroatoms independently selected from N, O, and S; wherein the N and S are optionally oxidized; wherein a ring-forming carbon atom of the 5-6 membered heteroaryl is optionally substituted by oxo to form a carbonyl group; and wherein the 5-6 membered heteroaryl is optionally substituted with 1, 2, 3, 4 or 5 substituents independently selected from $R^{20}$.

10. The compound of claim 1, wherein $R^2$ is selected from phenyl and pyrazolyl; wherein the phenyl and pyrazolyl are each optionally substituted with 1 or 2 substituents independently selected from $R^{20}$.

11. The compound of claim 1, wherein $R^2$ is phenyl, optionally substituted with 1, 2, 3, 4 or 5 substituents independently selected from $R^{20}$.

12. The compound of claim 1, wherein $R^2$ is pyrazole, optionally substituted with 1, 2, 3, or 4 substituents independently selected from $R^{20}$.

13. The compound of claim 1, wherein each $R^{20}$ is independently selected from $C_{1-6}$ alkyl, $C_{1-6}$ haloalkyl, $C_{3-6}$ cycloalkyl, 4-6 membered heterocycloalkyl, phenyl, 5-6 membered heteroaryl, $C_{3-6}$ cycloalkyl-$C_{1-3}$ alkylene, 4-6 membered heterocycloalkyl-$C_{1-3}$ alkylene, phenyl-$C_{1-3}$ alkylene, 5-6 membered heteroaryl-$C_{1-3}$ alkylene, halo, D, CN, OR$^{a2}$, C(O)R$^{b2}$, C(O)NR$^{c2}$R$^{d2}$, C(O)OR$^{a2}$, NR$^{c2}$R$^{d2}$, S(O)$_2$R$^{b2}$, and S(O)$_2$NR$^{c2}$R$^{d2}$; wherein a ring-forming carbon atom of the 4-6 membered heterocycloalkyl is optionally substituted by oxo to form a carbonyl group; wherein said $C_{1-6}$ alkyl, $C_{3-6}$ cycloalkyl, 4-6 membered heterocycloalkyl, phenyl, 5-6 membered heteroaryl, $C_{3-6}$ cycloalkyl-$C_{1-3}$ alkylene, 4-6 membered heterocycloalkyl-$C_{1-3}$ alkylene, phenyl-$C_{1-3}$ alkylene, and 5-6 membered heteroaryl-$C_{1-3}$ alkylene are each optionally substituted with 1, 2, 3, or 4 substituents independently selected from $R^{21}$.

14. The compound of claim 1, wherein each $R^{20}$ is independently selected from $C_{1-6}$ alkyl, $C_{3-6}$ cycloalkyl, 4-6 membered heterocycloalkyl, 4-6 membered heterocycloalkyl-$C_{1-3}$ alkylene, halo, NR$^{e2}$R$^{d2}$, and C(O)NR$^{c2}$R$^{d2}$, wherein a ring-forming carbon atom of the 4-6 membered heterocycloalkyl is optionally substituted by oxo to form a carbonyl group; wherein said $C_{1-6}$ alkyl, $C_{3-6}$ cycloalkyl, 4-6 membered heterocycloalkyl, and 4-6 membered heterocycloalkyl-$C_{1-3}$ alkylene are each optionally substituted with 1, 2, 3, or 4 substituents independently selected from $R^{21}$.

15. The compound of claim 1, wherein each $R^{21}$ is independently selected from $C_{1-6}$ alkyl, $C_{1-6}$ haloalkyl, $C_{3-6}$ cycloalkyl, 4-6 membered heterocycloalkyl, halo, D, CN, OR$^{a4}$, C(O)NR$^{c4}$R$^{d4}$ and NR$^{c4}$R$^{d4}$; wherein said $C_{1-6}$ alkyl, $C_{3-6}$ cycloalkyl, and 4-6 membered heterocycloalkyl, are each optionally substituted with 1, 2, 3, or 4 substituents independently selected from $R^{22}$.

16. The compound of claim 1, wherein each $R^{21}$ is independently selected from $C_{1-6}$ alkyl, $C_{3-6}$ cycloalkyl, 4-6 membered heterocycloalkyl, halo, OR$^{a4}$, and NR$^{c4}$R$^{d4}$; wherein said $C_{1-6}$ alkyl, $C_{3-6}$ cycloalkyl, and 4-6 membered heterocycloalkyl, are each optionally substituted with 1, 2, 3, or 4 substituents independently selected from $R^{22}$.

17. The compound of claim 1, wherein each $R^{22}$ is independently selected from $C_{1-6}$ alkyl, $C_{1-6}$ haloalkyl, halo, D, CN, OR$^{a6}$, and NR$^{c6}$R$^{d6}$; wherein said $C_{1-6}$ alkyl, is optionally substituted with 1, 2, 3, or 4 substituents independently selected from $R^g$.

18. The compound of claim 1, wherein each $R^{22}$ is independently selected from $C_{1-6}$ alkyl, halo and OR$^{a6}$; wherein said $C_{1-6}$ alkyl, is optionally substituted with 1, 2, 3, or 4 substituents independently selected from $R^g$.

19. The compound of claim 1, wherein $R^{22}$ is OH, F or methyl.

20. The compound of claim 1, wherein $R^{21}$ is selected from methyl, F, OH, dimethylamino, hydroxyethyl, piperazinyl, piperidinyl, methylpyrrolidinyl, azetidinyl, mopholino, 4-hydroxypiperidin-1-yl, 4-hydroxy-4-methylpiperidin-1-yl, 3-hydroxy-3-methylazetidin-1-yl, 4-methylpiperazin-1-yl, 3,3-difluoroazetidin-1-yl, 2-methylmorpholino, 2-(hydroxymethyl)morpholino, 3-hydroxy-3-methylpyrrolidin-1-yl, and pyrrolidin-1-yl.

21. The compound of claim 1, wherein $R^{20}$ is selected from fluoro, piperazin-1-yl, 4-(2-hydroxyethyl)piperazin-1-yl, 4-methyl-2-oxopiperazin-1-yl, 4-methylpiperazin-1-yl, piperazin-1-ylcarbonyl, 4-methylpiperazin-1-ylcarbonyl, (2-methylpyrrolidin-1-yl)methyl, piperidin-4-yl, tetrahydro-2H-pyran-4-yl, 4-hydroxycyclohexyl, piperidin-4-ylmethyl, (4-hydroxypiperidin-1-yl)methyl, (4-hydroxy-4-methylpiperidin-1-yl)methyl, (3-hydroxy-3-methylazetidin-1-yl)methyl, (4-methylpiperazin-1-yl)methyl, azetidin-1-ylmethyl, (3,3-difluoroazetidin-1-yl)methyl, methyl, ethyl, isopropyl, dimethylcarbamoyl, morpholinomethyl, (2-methylmorpholino)methyl, (2-(hydroxymethyl)morpholino)methyl, pyrrolidin-1-ylmethyl, (3-hydroxy-3-methylpyrrolidin-1-yl)methyl, and (dimethylamino)methyl.

22. The compound of claim 1, wherein $R^2$ is selected from 4-(piperazin-1-yl)phenyl, 4-(4-(2-hydroxyethyl)piperazin-1-yl)phenyl, 4-(4-methyl-2-oxopiperazin-1-yl)phenyl, 3-(4-methylpiperazin-1-yl)phenyl, 4-(4-methylpiperazin-1-ylcarbonyl)phenyl, 4-(piperazin-1-ylcarbonyl)phenyl, 3-fluoro-4-((2-methylpyrrolidin-1-yl)methyl)phenyl, 1-(tetrahydro-2H-pyran-4-yl)-1H-pyrazol-4-yl, (piperidin-4-ylmethyl)-1H-pyrazol-4-yl, (piperidin-4-yl)-1H-pyrazol-4-yl, 1-(4-hydroxycyclohexyl)-1H-pyrazol-4-yl, 4-(azetidin-1- ylmethyl)phenyl, 1-ethyl-1H-pyrazol-4-yl, 1-isopropyl-1H-pyrazol-4-yl, 4-(dimethylcarbamoyl)phenyl, 4-(pyrrolidin-1-ylmethyl)phenyl, 4-(morpholinomethyl)phenyl, 4-((3,3-difluoroazetidin-1-yl)methyl)phenyl, 4-((2-methylmorpholino)methyl)phenyl, 4-((2-(hydroxymethyl)morpholino)methyl)phenyl, 4-((3-hydroxy-3-methylpyrrolidin-1-yl)methyl)phenyl, 4-((4-hydroxypiperidin-1-yl)methyl)phenyl, 4-((4-hydroxy-4-methylpiperidin-1-yl)methyl)phenyl, 4-((3-hydroxy-3-methylazetidin-1-yl)methyl)phenyl, 4-((4-methylpiperazin-1-yl)methyl)phenyl, 4-((4-hydroxypiperidin-1-yl)methyl)phenyl and 4-((dimethylamino)methyl)phenyl.

23. The compound of claim 1, wherein $R^5$ is $C_{6-10}$ aryl, optionally substituted with 1, 2, 3, 4 or 5 substituents independently selected from $R^{50}$.

24. The compound of claim 1, wherein $R^5$ is a 5-10 membered heteroaryl; wherein the 5-10 membered heteroaryl has at least one ring-forming carbon atom and 1, 2, 3, or 4 ring-forming heteroatoms independently selected from N, O, and S; wherein the N and S are optionally oxidized; wherein a ring-forming carbon atom of the 5-10 membered heteroaryl is optionally substituted by oxo to form a carbonyl group; and wherein the 5-10 membered heteroaryl is optionally substituted with 1, 2, 3, 4 or 5 substituents independently selected from $R^{50}$.

25. The compound of claim 1, wherein $R^5$ is selected from quinolinyl, naphthyridinyl, pyridinyl, and phenyl, wherein the quinolinyl, naphthyridinyl, pyridinyl, and phenyl are each optionally substituted with 1, 2, or 3 substituents independently selected from $R^{50}$.

26. The compound of claim 1, wherein each $R^{50}$ is independently selected from $C_{1-6}$ alkyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $OR^{a9}$, $C(O)R^{b9}$, $C(O)NR^{c9}R^{d9}$, $C(O)OR^{a9}$, $NR^{c9}R^{d9}$, $S(O)_2R^{b9}$, and $S(O)_2NR^{c9}R^{d9}$; wherein said $C_{1-6}$ alkyl, $C_{3-10}$ cycloalkyl, 4-10 membered heterocycloalkyl, $C_{6-10}$ aryl, and 5-10 membered heteroaryl, are each optionally substituted with 1, 2, 3, or 4 substituents independently selected from $R^{51}$; and wherein a ring-forming carbon atom of said 4-10 membered heterocycloalkyl is optionally oxidized to form a carbonyl group.

27. The compound of claim 1, wherein each $R^{50}$ is independently selected from $C_{1-6}$ alkyl, 4-10 membered heterocycloalkyl, 5-10 membered heteroaryl, halo, CN, C(O)Rb, $C(O)NR^{c9}R^{d9}$, and $NR^{c9}R^{d9}$; wherein said $C_{1-6}$ alkyl, 4-10 membered heterocycloalkyl, and 5-10 membered heteroaryl, are each optionally substituted with 1, 2 or 3 substituents independently selected from $R^{51}$; and wherein a ring-forming carbon atom of said 4-10 membered heterocycloalkyl is optionally oxidized to form a carbonyl group.

28. The compound of claim 1, wherein each $R^{50}$ is independently selected from fluoro, hydroxyethyl, cyano, carbamoyl, methylcarbamoyl, pyridinyl, morpholino, morpholinomethyl, pyrazolyl, 6-oxaspiro[3.4]octanyl, pyridinylamino, benzyl, piperazinyl, piperazin-1-ylcarbonyl, pyrimidinyl, pyrazinyl, (2-hydroxyethyl)carbamoyl, hexahydropyrrolo[1,2-a]pyrazinyl, 2,5-diazabicyclo[2.2.1]heptanyl, triazolyl, imidazolyl, and pyrazinyl, wherein the methylcarbamoyl, pyridinyl, morpholino, morpholinomethyl, pyrazolyl, 6-oxaspiro[3.4]octanyl, pyridinylamino, benzyl, piperazinyl, piperazin-1-ylcarbonyl, pyrimidinyl, pyrazinyl, (2-hydroxyethyl)carbamoyl, hexahydropyrrolo[1,2-a]pyrazinyl, 2,5-diazabicyclo[2.2.1]heptanyl, triazolyl, imidazolyl, and pyrazinyl are each optionally substituted with 1, 2, 3, or 4 substituents independently selected from $R^{51}$; or two adjacent $R^{50}$ substituents, taken together with the atoms to which they are attached, to form a fused 5- or 6-membered heterocycloalkyl ring; wherein the fused 5- or 6-membered heterocycloalkyl ring each has at least one ring-forming carbon atom and 1, 2, 3, or 4 ring-forming heteroatoms independently selected from N, O, and S; wherein a ring-forming carbon atom of each fused 5- or 6-membered heterocycloalkyl ring is optionally substituted by oxo to form a carbonyl group; and wherein the fused 5- or 6-membered heterocycloalkyl ring is optionally substituted with 1, 2, 3 or 4 substituents independently selected from $R^{51}$.

29. The compound of claim 1, wherein $R^5$ is substituted with at least two adjacent $R^{50}$ substituents, taken together with the atoms to which they are attached, to form a fused 5- or 6-membered heterocycloalkyl ring; wherein the fused 5- or 6-membered heterocycloalkyl ring each has at least one ring-forming carbon atom and 1, 2, 3, or 4 ring-forming heteroatoms independently selected from N, O, and S; wherein a ring-forming carbon atom of each fused 5- or 6-membered heterocycloalkyl ring is optionally substituted by oxo to form a carbonyl group; and wherein the fused 5- or 6-membered heterocycloalkyl ring is optionally substituted with 1, 2, 3 or 4 substituents independently selected from $R^{51}$.

30. The compound of claim 1, wherein each $R^{51}$ is independently selected from $C_{1-6}$ alkyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $OR^{a10}$, $C(O)R^{b10}$, $C(O)NR^{c10}R^{d10}$, $C(O)OR^{a10}$, $NR^{c10}R^{d10}$, $S(O)_2R^{b10}$, and $S(O)_2NR^{c10}R^{d10}$; wherein said $C_{1-6}$ alkyl, $C_{3-10}$ cycloalkyl, 4-10 membered heterocycloalkyl, $C_{6-10}$ aryl, and 5-10 membered heteroaryl, are each optionally substituted with 1, 2, 3, or 4 substituents independently selected from $R^{52}$.

31. The compound of claim 1, wherein each $R^{51}$ is independently selected from $C_{1-6}$ alkyl, 4-10 membered heterocycloalkyl, $C_{6-10}$ aryl, $OR^{a10}$, and $C(O)R^{b10}$; wherein said $C_{1-6}$ alkyl, 4-10 membered heterocycloalkyl, and $C_{6-10}$ aryl are each optionally substituted with 1, 2, 3, or 4 substituents independently selected from $R^{52}$.

32. The compound of claim 1, wherein each $R^{52}$ is independently selected from $C_{1-6}$ alkyl, $C_{1-6}$ haloalkyl, halo, D, CN, $OR^{a11}$, and $NR^{c11}R^{d11}$.

33. The compound of claim 1, wherein each $R^{52}$ is independently selected from halo, and $OR^{a11}$.

34. The compound of claim 1, wherein each $R^{51}$ is selected from methyl, OH, hydroxymethyl, hydroxyethyl, acetyl, 4-morpholino, 4-methylpiperazin-1-yl, pyridin-3-yl, 3,5-difluorophenyl, and pyridin-4-yl-carbonyl.

35. The compound of claim 1, wherein $R^{50}$ is independently selected from fluoro, hydroxyethyl, cyano, carbamoyl, methylcarbamoyl, pyridin-4-yl, 3-hydroxymethylpyridin-4-yl, 4-morpholino, 4-morpholinomethyl, 1-methyl-1H-pyrazol-3-yl, 6-oxaspiro[3.4]octan-2-yl, pyridin-3-ylamino, (3,5-difluorophenyl)(hydroxyl)methyl, 4-acetylpiperazin-1-yl, 4-methylpiperazin-1-ylcarbonyl, (2-hydroxyethyl)carbamoyl, 6-oxohexahydropyrrolo[1,2-a]pyrazin-2(1H)-yl, 5-acetyl-2,5-diazabicyclo[2.2.1]heptan-2-yl, pyridin-2-yl, pyrazin-2-yl, pyrimidin-2-yl, 1-methyl-1H-pyrazol-3-yl, 5-methyl-1H-pyrazol-3-yl, 1-methyl-1H-pyrazol-4-yl, 1-methyl-1H-imidazol-4-yl, 1-ethyl-1H-imidazol-4-yl, and 4-methyl-2H-1,2,3-triazol-2-yl.

36. The compound of claim 1, wherein $R^5$ is substituted with at least two adjacent $R^{50}$ substituents, taken together with the atoms to which they are attached, to form a fused heterocycloalkyl ring selected from:

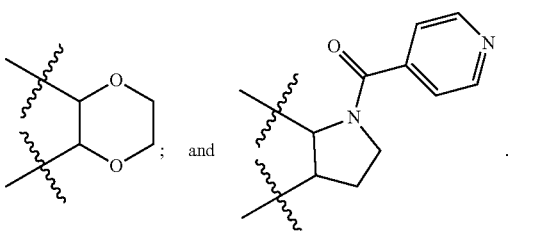 [SMILES: *C1OCCOC1* ; *C1CCN(C(=O)c2ccncc2)C1*] ; and 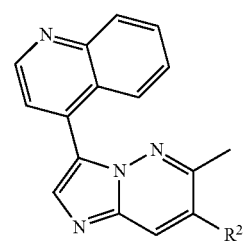

37. The compound of claim 1, wherein $R^5$ is selected from 1,8-naphthyridin-4-yl, quinolin-4-yl, 7-(hydroxymethyl)quinolin-4-yl, 7-(pyridin-4-yl)quinolin-4-yl, 7-(2-(hydroxymethyl)pyridin-4-yl)quinolin-4-yl, 7-morpholinoquinolin-4-yl, 7-(1-methyl-1H-pyrazol-3-yl)quinolin-4-yl, 7-(6-oxa-2-azaspiro[3.4]octan-2-yl)quinolin-4-yl, 7-(methylcarbamoyl)quinolin-4-yl, 7-(pyridin-3-ylamino)quinolin-4-yl, 7-((3,5-difluorophenyl)(hydroxy)methyl)quinolin-4-yl, 7-(4-acetylpiperazin-1-yl)quinolin-4-yl, 7-(4-methylpiperazin-1-ylcarbonyl)quinolin-4-yl, 7-(morpholinomethyl)quinolin-4-yl, 7-((2-hydroxyethyl)carbamoyl)quinolin-4-yl, 7-cyanoquinolin-4-yl, 7-(6-oxohexahydropyrrolo[1,2-a]pyrazin-2(1H)-yl)quinolin-4-yl, 7-(5-acetyl-2,5-diazabicyclo[2.2.1]heptan-2-yl)quinolin-4-yl, 8-cyanoquinolin-5-yl, 2,3-dihydro-[1,4]dioxino[2,3-b]pyridin-8-yl, 1-isonicotinoyl-2,3-dihydro-1H-pyrrolo[2,3-b]pyridin-4-yl, 4-carbamoyl-3-fluorophenyl, 7-(pyridin-2-yl)-1,8-naphthyridin-4-yl, 7-(pyrimidin-2-yl)-1,8-naphthyridin-4-yl, 7-(pyrazin-2-yl)-1,8-naphthyridin-4-yl, 7-(1-methyl-1H-pyrazol-3-yl)-1,8-naphthyridin-4-yl, 7-(5-methyl-1H-pyrazol-3-yl)-1,8-naphthyridin-4-yl, 7-(1-methyl-1H-pyrazol-4-yl)-1,8-naphthyridin-4-yl, 7-(1-methyl-1H-imidazol-4-yl)-1,8-naphthyridin-4-yl, 7-(1-ethyl-1H-imidazol-4-yl)-1,8-naphthyridin-4-yl, and 7-(4-methyl-2H-1,2,3-triazol-2-yl)-1,8-naphthyridin-4-yl.

38. The compound of claim 1, wherein the compound is a compound of Formula II:

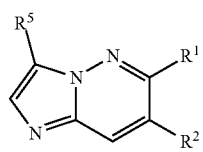

II or a pharmaceutically acceptable salt thereof.

39. The compound of claim 1, wherein the compound is a compound of Formula III:

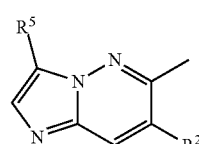

III or a pharmaceutically acceptable salt thereof.

40. The compound of claim 1, wherein the compound is a compound of Formula IVa or Formula IVb:

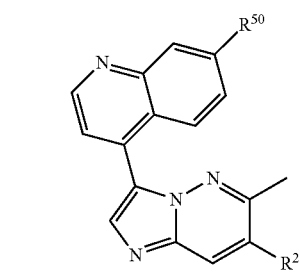

IVa

IVb or a pharmaceutically acceptable salt thereof.

41. The compound of claim 1, wherein the compound is a compound of Formula Va, Formula Vb or Formula Vc:

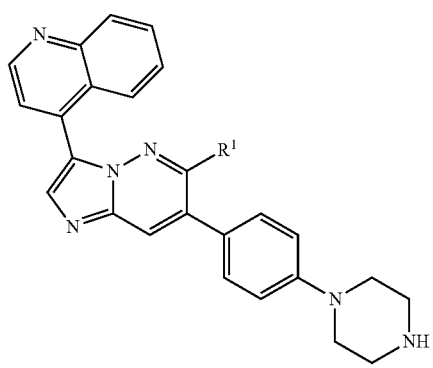

Va

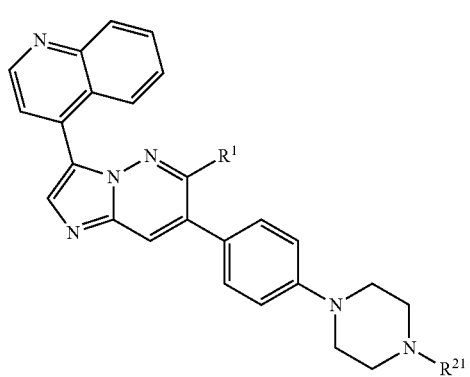

Vb

-continued

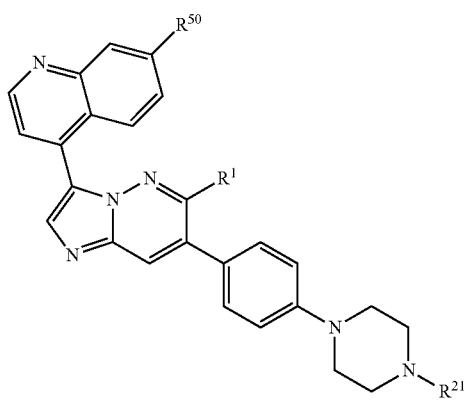

Vc or a pharmaceutically acceptable salt thereof.

42. The compound of claim 1, wherein the compound is a compound of Formula VIa or Formula VIb:

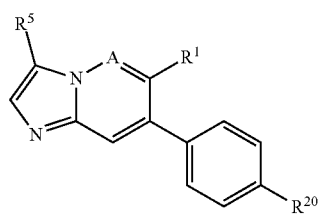

VIa

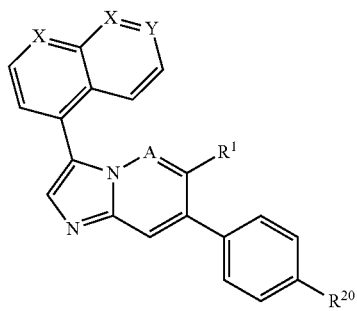

VIb or a pharmaceutically acceptable salt thereof.

43. The compound of claim 1, wherein the compound is a compound of Formula VIIa, Formula VIIb, Formula VIIc or Formula VIId:

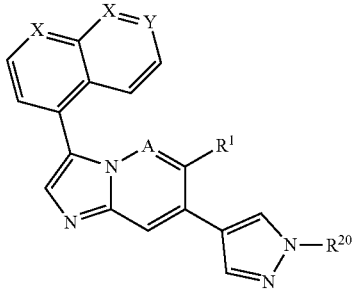

VIIa

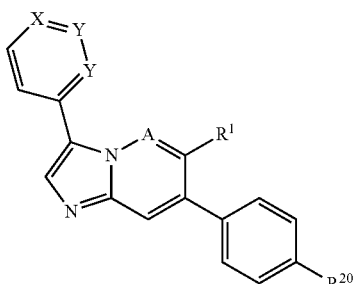

VIIb

VIIc

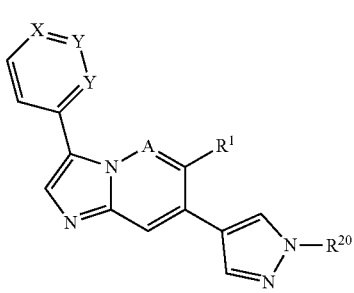

VIId or a pharmaceutically acceptable salt thereof, wherein:
each X is independently selected from CH, N and $CR^{50}$; and
each Y is independently selected from CH and $CR^{50}$.

44. The compound of claim 1, wherein:
$R^1$ is selected from $C_{1-6}$ alkyl, $C_{1-6}$ haloalkyl, CN, C(O)$R^b$, C(O)$NR^cR^d$, and C(O)$OR^a$; wherein said $C_{1-6}$ alkyl, is optionally substituted with 1, 2, 3, or 4 substituents independently selected from $R^{10}$;

$R^2$ is selected from $C_{6-10}$ aryl and 5-10 membered heteroaryl; wherein the 5-10 membered heteroaryl has at least one ring-forming carbon atom and 1, 2, 3, or 4 ring-forming heteroatoms independently selected from N, O, and S; wherein the N and S are optionally oxidized; wherein a ring-forming carbon atom of the 5-10 membered heteroaryl is optionally substituted by oxo to form a carbonyl group; and wherein the $C_{6-10}$ aryl and 5-10 membered heteroaryl are each optionally substituted with 1, 2, 3, 4 or 5 substituents independently selected from $R^{20}$;

$R^3$ is selected from H and $C_{1-6}$ alkyl;
$R^4$ is selected from H and $C_{1-6}$ alkyl;
$R^5$ is selected from $C_{6-10}$ aryl and 5-10 membered heteroaryl; wherein the 5-10 membered heteroaryl has at least one ring-forming carbon atom and 1, 2, 3, or 4 ring-forming heteroatoms independently selected from N, O, and S; wherein the N and S are optionally oxidized; wherein a ring-forming carbon atom of the 5-10 membered heteroaryl is optionally substituted by oxo to form a carbonyl group; and wherein the $C_{6-10}$ aryl and 5-10 membered heteroaryl are each optionally substituted with 1, 2, 3, 4 or 5 substituents independently selected from $R^{50}$;

or two adjacent $R^{50}$ substituents on $R^5$, taken together with the atoms to which they are attached, form a fused 4-, 5-, 6- or 7-membered heterocycloalkyl ring, or a fused $C_{3-7}$ cycloalkyl ring; wherein the fused 4-, 5-, 6- or 7-membered heterocycloalkyl ring each has at least one ring-forming carbon atom and 1, 2, 3, or 4 ring-forming heteroatoms independently selected from N, O, and S; wherein a ring-forming carbon atom of each fused 4-, 5-, 6- or 7-membered heterocycloalkyl ring is optionally substituted by oxo to form a carbonyl group; and wherein the fused 4-, 5-, 6- or 7-membered heterocycloalkyl ring and fused $C_{3-7}$ cycloalkyl ring are each optionally substituted with 1, 2, 3 or 4 substituents independently selected from $R^{51}$;

A is N;

each $R^{10}$ is independently selected from $C_{1-6}$ alkyl, $C_{1-6}$ haloalkyl, halo, D, CN, $OR^{a1}$, $C(O)R^{b1}$, $C(O)NR^{c1}R^{d1}$, $C(O)OR^{a1}$, $NR^{c1}R^{d1}$, and $S(O)_2NR^{c1}R^{d1}$; wherein said $C_{1-6}$ alkyl is optionally substituted with 1, 2, 3, or 4 substituents independently selected from $R^{11}$;

each $R^{20}$ is independently selected from $C_{1-6}$ alkyl, $C_{1-6}$ haloalkyl, $C_{3-6}$ cycloalkyl, 4-6 membered heterocycloalkyl, phenyl, 5-6 membered heteroaryl, $C_{3-6}$ cycloalkyl-$C_{1-3}$ alkylene, 4-6 membered heterocycloalkyl-$C_{1-3}$ alkylene, phenyl-$C_{1-3}$ alkylene, 5-6 membered heteroaryl-$C_{1-3}$ alkylene, halo, D, CN, $OR^{a2}$, $C(O)R^{b2}$, $C(O)NR^{c2}R^{d2}$, $C(O)OR^{a2}$, $NR^{c2}R^{d2}$, $S(O)_2R^{b2}$, and $S(O)_2NR^{c2}R^{d2}$; wherein a ring-forming carbon atom of the 4-6 membered heterocycloalkyl is optionally substituted by oxo to form a carbonyl group; wherein said $C_{1-6}$ alkyl, $C_{3-6}$ cycloalkyl, 4-6 membered heterocycloalkyl, phenyl, 5-6 membered heteroaryl, $C_{3-6}$ cycloalkyl-$C_{1-3}$ alkylene, 4-6 membered heterocycloalkyl-$C_{1-3}$ alkylene, phenyl-$C_{1-3}$ alkylene, and 5-6 membered heteroaryl-$C_{1-3}$ alkylene are each optionally substituted with 1, 2, 3, or 4 substituents independently selected from $R^{21}$;

each $R^{21}$ is independently selected from $C_{1-6}$ alkyl, $C_{1-6}$ haloalkyl, $C_{3-6}$ cycloalkyl, 4-6 membered heterocycloalkyl, halo, D, CN, $OR^{a4}$, $C(O)NR^{c4}R^{d4}$ and $NR^{c4}R^{d4}$; wherein said $C_{1-6}$ alkyl, $C_{3-6}$ cycloalkyl, and 4-6 membered heterocycloalkyl, are each optionally substituted with 1, 2, 3, or 4 substituents independently selected from $R^{22}$;

each $R^{22}$ is independently selected from $C_{1-6}$ alkyl, $C_{1-6}$ haloalkyl, halo, D, CN, $OR^{a6}$, and $NR^{c6}R^{d6}$; wherein said $C_{1-6}$ alkyl, is optionally substituted with 1, 2, 3, or 4 substituents independently selected from $R^g$;

each $R^{50}$ is independently selected from $C_{1-6}$ alkyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $OR^{a9}$, $C(O)R^{b9}$, $C(O)NR^{c9}R^{d9}$, $C(O)OR^{a9}$, $NR^{c9}R^{d9}$ $S(O)_2R^{b9}$, and $S(O)_2NR^{c9}R^{d9}$; wherein said $C_{1-6}$ alkyl, $C_{3-10}$ cycloalkyl, 4-10 membered heterocycloalkyl, $C_{6-10}$ aryl, and 5-10 membered heteroaryl, are each optionally substituted with 1, 2, 3, or 4 substituents independently selected from $R^{51}$;

each $R^{51}$ is independently selected from $C_{1-6}$ alkyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $OR^{a10}$, $C(O)R^{b10}$, $C(O)NR^{c10}R^{d10}$, $C(O)OR^{a10}$, $NR^{c10}R^{d10}$, $S(O)_2R^{b10}$, and $S(O)_2NR^{c10}R^{d10}$; wherein said $C_{1-6}$ alkyl, $C_{3-10}$ cycloalkyl, 4-10 membered heterocycloalkyl, $C_{6-10}$ aryl, and 5-10 membered heteroaryl, are each optionally substituted with 1, 2, 3, or 4 substituents independently selected from $R^{52}$;

each $R^{52}$ is independently selected from $C_{1-6}$ alkyl, $C_{1-6}$ haloalkyl, halo, D, CN, $OR^{a11}$, and $NR^{c11}R^{d11}$;

each $R^a$, $R^c$, and $R^d$ is independently selected from H, $C_{1-6}$ alkyl, $C_{1-6}$ haloalkyl, $C_{3-10}$ cycloalkyl, and 4-10 membered heterocycloalkyl; wherein said $C_{1-6}$ alkyl, $C_{3-10}$ cycloalkyl, and 4-10 membered heterocycloalkyl, are each optionally substituted with 1, 2, 3, or 4 substituents independently selected from $R^{10}$;

or any $R^c$ and $R^d$ attached to the same N atom, together with the N atom to which they are attached, form a 4-10 membered heterocycloalkyl group optionally substituted with 1, 2, 3 or 4 substituents independently selected from $R^{10}$;

each $R^b$ is independently selected from $C_{1-6}$ alkyl, $C_{1-6}$ haloalkyl, and 4-10 membered heterocycloalkyl, wherein the 4-10 membered heterocycloalkyl is optionally substituted with 1, 2, 3, or 4 substituents independently selected from $R^{10}$;

each $R^{a1}$, $R^{c1}$ and $R^{d1}$ is independently selected from H and $C_{1-6}$ alkyl;

each $R^{b1}$ is independently selected from $C_{1-6}$ alkyl, and $C_{1-6}$ haloalkyl;

each $R^{a2}$, $R^{c2}$ and $R^{d2}$ is independently selected from H, $C_{1-6}$ alkyl, and $C_{1-6}$ haloalkyl;

or any $R^{c2}$ and $R^{d2}$ attached to the same N atom, together with the N atom to which they are attached, form a 4-10 membered heterocycloalkyl group optionally substituted with 1, 2, 3 or 4 substituents independently selected from $R^{21}$;

each $R^{b2}$ is independently selected from $C_{1-6}$ alkyl, and $C_{1-6}$ haloalkyl;

each $R^{a4}$, $R^{c4}$ and $R^{d4}$ is independently selected from H and $C_{1-6}$ alkyl;

each $R^{b4}$ is independently selected from $C_{1-6}$ alkyl, and $C_{1-6}$ haloalkyl;

each $R^{a6}$, $R^{c6}$ and $R^{d6}$ is independently selected from H and $C_{1-6}$ alkyl;

each $R^{a9}$, $R^{c9}$ and $R^{d9}$ is independently selected from H, $C_{1-6}$ alkyl, $C_{1-6}$ haloalkyl, 4-10 membered heterocycloalkyl, and 5-10 membered heteroaryl; wherein said $C_{1-6}$ alkyl, 4-10 membered heterocycloalkyl, and 5-10 membered heteroaryl, are each optionally substituted with 1, 2, 3, or 4 substituents independently selected from $R^{51}$;

or any $R^{c9}$ and $R^{d9}$ attached to the same N atom, together with the N atom to which they are attached, form a 4-10 membered heterocycloalkyl group optionally substituted with 1, 2, 3 or 4 substituents independently selected from $R^{51}$;

each $R^{b9}$ is independently selected from $C_{1-6}$ alkyl, and $C_{1-6}$ haloalkyl;

each $R^{a10}$, $R^{c10}$ and $R^{d10}$ is independently selected from H and $C_{1-6}$ alkyl;

each $R^{b10}$ is independently selected from $C_{1-6}$ alkyl, $C_{1-6}$ haloalkyl, 5-6 membered heteroaryl, and 4-7 membered heterocycloalkyl; wherein said $C_{1-6}$ alkyl 5-6 membered heteroaryl, and 4-7 membered heterocycloalkyl, are each optionally substituted with 1, 2, 3, or 4 substituents independently selected from $R^{52}$; and each $R^{a22}$, $R^{c11}$ and $R^{d11}$ is independently selected from H and $C_{1-6}$ alkyl; and each $R^g$ is independently selected from OH, CN, halo, $C_{1-6}$ alkyl, $C_{1-6}$ haloalkyl, $C_{1-6}$ alkoxy, $C_{1-6}$ haloalkoxy, amino, $C_{1-6}$ alkylamino and di($C_{1-6}$ alkyl)amino.

45. The compound of claim 1, wherein:

$R^1$ is selected from $C_{1-6}$ alkyl, CN, $C(O)NR^cR^d$, $C(O)R^b$ and $C(O)OR^a$; wherein said $C_{1-6}$ alkyl, is optionally substituted with 1, 2, 3, or 4 substituents independently selected from $R^{10}$;

$R^2$ is selected from phenyl and 5-6 membered heteroaryl; wherein the 5-6 membered heteroaryl has at least one ring-forming carbon atom and 1, 2, 3, or 4 ring-forming heteroatoms independently selected from N, O, and S; wherein the N and S are optionally oxidized; wherein a ring-forming carbon atom of the 5-6 membered heteroaryl is optionally substituted by oxo to form a carbonyl group; and wherein the phenyl and 5-6 membered heteroaryl are each optionally substituted with 1, 2, 3, 4 or 5 substituents independently selected from $R^{20}$;

$R^3$ is H;

$R^4$ is H;

$R^5$ is selected from $C_{6-10}$ aryl and 5-10 membered heteroaryl; wherein the 5-10 membered heteroaryl has at least one ring-forming carbon atom and 1, 2, 3, or 4 ring-forming heteroatoms independently selected from N, O, and S; wherein the N and S are optionally oxidized; wherein a ring-forming carbon atom of the 5-10 membered heteroaryl is optionally substituted by oxo to form a carbonyl group; and wherein the $C_{6-10}$ aryl and 5-10 membered heteroaryl are each optionally substituted with 1, 2, 3, 4 or 5 substituents independently selected from $R^{50}$;

or two adjacent $R^{50}$ substituents on $R^5$, taken together with the atoms to which they are attached, form a fused 4-, 5-, 6- or 7-membered heterocycloalkyl ring; wherein the fused 4-, 5-, 6- or 7-membered heterocycloalkyl ring each has at least one ring-forming carbon atom and 1, 2, 3, or 4 ring-forming heteroatoms independently selected from N, O, and S; wherein a ring-forming carbon atom of each fused 4-, 5-, 6- or 7-membered heterocycloalkyl ring is optionally substituted by oxo to form a carbonyl group; and wherein the fused 4-, 5-, 6- or 7-membered heterocycloalkyl ring and fused $C_{3-7}$ cycloalkyl ring are each optionally substituted with 1, 2, 3 or 4 substituents independently selected from $R^{51}$;

A is N;

each $R^{10}$ is independently selected from $C_{1-6}$ alkyl, $OR^{a1}$, and $C(O)OR^{a1}$; wherein said $C_{1-6}$ alkyl is optionally substituted with 1, 2, 3, or 4 substituents independently selected from $R^{11}$;

each $R^{20}$ is independently selected from $C_{1-6}$ alkyl, $C_{3-6}$ cycloalkyl, 4-6 membered heterocycloalkyl, 4-6 membered heterocycloalkyl-$C_{1-3}$ alkylene, halo, $NR^{c2}R^{d2}$, and $C(O)NR^{c2}R^{d2}$, wherein a ring-forming carbon atom of the 4-6 membered heterocycloalkyl is optionally substituted by oxo to form a carbonyl group; wherein said $C_{1-6}$ alkyl, $C_{3-6}$ cycloalkyl, 4-6 membered heterocycloalkyl and 4-6 membered heterocycloalkyl-$C_{1-3}$ alkylene are each optionally substituted with 1, 2, 3, or 4 substituents independently selected from $R^{21}$;

each $R^{21}$ is independently selected from $C_{1-6}$ alkyl, $C_{3-6}$ cycloalkyl, 4-6 membered heterocycloalkyl, halo, $OR^{a4}$, and $NR^{c4}R^{d4}$; wherein said $C_{1-6}$ alkyl, $C_{3-6}$ cycloalkyl, and 4-6 membered heterocycloalkyl, are each optionally substituted with 1, 2, 3, or 4 substituents independently selected from $R^{22}$;

each $R^{22}$ is independently selected from $C_{1-6}$ alkyl, halo, and OH;

each $R^{50}$ is independently selected from $C_{1-6}$ alkyl, 4-10 membered heterocycloalkyl, 5-10 membered heteroaryl, halo, CN, $C(O)NR^{c9}R^{d9}$, and $NR^{c9}R^{d9}$; wherein said $C_{1-6}$ alkyl, 4-10 membered heterocycloalkyl, and 5-10 membered heteroaryl, are each optionally substituted with 1, 2, 3, or 4 substituents independently selected from $R^{51}$;

each $R^{51}$ is independently selected from $C_{1-6}$ alkyl, 4-10 membered heterocycloalkyl, $C_{6-10}$ aryl, OH, and $C(O)R^{b10}$; wherein said $C_{1-6}$ alkyl, 4-10 membered heterocycloalkyl, and $C_{6-10}$ aryl, are each optionally substituted with 1, 2, 3, or 4 substituents independently selected from $R^{52}$;

each $R^{52}$ is independently selected from halo, and OH;

each $R^a$, $R^c$, and $R^d$ is independently selected from H, $C_{1-6}$ alkyl, and $C_{3-10}$ cycloalkyl; wherein said $C_{1-6}$ alkyl, and $C_{3-10}$ cycloalkyl, are each optionally substituted with 1, 2, 3, or 4 substituents independently selected from $R^{10}$;

or any $R^c$ and $R^d$ attached to the same N atom, together with the N atom to which they are attached, form a 4-10 membered heterocycloalkyl group optionally substituted with 1, 2, 3 or 4 substituents independently selected from $R^{10}$;

each $R^b$ is independently selected from $C_{1-6}$ alkyl, $C_{1-6}$ haloalkyl, and 4-10 membered heterocycloalkyl, wherein the 4-10 membered heterocycloalkyl is optionally substituted with 1, 2, 3, or 4 substituents independently selected from $R^{10}$;

each $R^{a1}$ is independently selected from H and $C_{1-6}$ alkyl;

each $R^{a2}$, $R^{c2}$ and $R^{d2}$ is independently selected from H, $C_{1-6}$ alkyl, and $C_{1-6}$ haloalkyl;

or any $R^{c2}$ and $R^{d2}$ attached to the same N atom, together with the N atom to which they are attached, form a 4-10 membered heterocycloalkyl group optionally substituted with 1, 2, 3 or 4 substituents independently selected from $R^{21}$;

each $R^{a4}$, $R^{c4}$ and $R^{d4}$ is independently selected from H, $C_{1-6}$ alkyl, and $C_{1-6}$ haloalkyl;

or any $R^{c4}$ and $R^{d4}$ attached to the same N atom, together with the N atom to which they are attached, form a 4-10 membered heterocycloalkyl group optionally substituted with 1, 2, 3 or 4 substituents independently selected from $R^{21}$;

each $R^{c9}$ and $R^{d9}$ is independently selected from H, $C_{1-6}$ alkyl, and 5-10 membered heteroaryl; wherein said $C_{1-6}$ alkyl, and 5-10 membered heteroaryl, are each optionally substituted with 1, 2, 3, or 4 substituents independently selected from $R^{51}$;

or any $R^{c9}$ and $R^{d9}$ attached to the same N atom, together with the N atom to which they are attached, form a 4-10 membered heterocycloalkyl group optionally substituted with 1, 2, 3 or 4 substituents independently selected from $R^{51}$;

each $R^{b10}$ is independently selected from $C_{1-6}$ alkyl, and 5-6 membered heteroaryl; wherein said $C_{1-6}$ alkyl, and 5-6 membered heteroaryl, are each optionally substituted with 1, 2, 3, or 4 substituents independently selected from $R^{52}$.

46. The compound of claim 1, wherein the compound is
4-(6-Methyl-7-(4-(piperazin-1-yl)phenyl)imidazo[1,2-b]pyridazin-3-yl)quinolone;
methyl 7-(4-(piperazin-1-yl)phenyl)-3-(quinolin-4-yl)imidazo[1,2-b]pyridazine-6-carboxylate;
N-((1R,4R)-4-Hydroxy-4-methylcyclohexyl)-7-(4-(piperazin-1-yl)phenyl)-3-(quinolin-4-yl)imidazo[1,2-b]pyridazine-6-carboxamide;

ethyl 4-(7-(4-(piperazin-1-yl)phenyl)-3-(quinolin-4-yl)imidazo[1,2-b]pyridazine-6-carbonyl)piperazine-1-carboxylate;

7-(4-(Piperazin-1-yl)phenyl)-3-(quinolin-4-yl)imidazo[1,2-b]pyridazine-6-carboxamide;

7-(4-(piperazin-1-yl)phenyl)-3-(quinolin-4-yl)imidazo[1,2-b]pyridazine-6-carbonitrile;

(7-(4-(Piperazin-1-yl)phenyl)-3-(quinolin-4-yl)imidazo[1,2-b]pyridazin-6-yl)methanol;

4-(6-(Methoxymethyl)-7-(4-(piperazin-1-yl)phenyl)imidazo[1,2-b]pyridazin-3-yl)quinolone;

4-(6-Methyl-7-(1-(piperidin-4-ylmethyl)-1H-pyrazol-4-yl)imidazo[1,2-b]pyridazin-3-yl)-7-(pyridin-4-yl)quinolone;

(trans)-4-(4-(6-Methyl-3-(7-(pyridin-4-yl)quinolin-4-yl)imidazo[1,2-b]pyridazin-7-yl)-1H-pyrazol-1-yl)cyclohexan-1-ol;

2-(4-(4-(6-Methyl-3-(7-(pyridin-4-yl)quinolin-4-yl)imidazo[1,2-b]pyridazin-7-yl)phenyl)piperazin-1-yl)ethan-1-ol;

4-Methyl-1-(4-(6-methyl-3-(7-(pyridin-4-yl)quinolin-4-yl)imidazo[1,2-b]pyridazin-7-yl)phenyl)piperazin-2-one;

4-(6-Methyl-7-(3-(4-methylpiperazin-1-yl)phenyl)imidazo[1,2-b]pyridazin-3-yl)-7-(pyridin-4-yl)quinolone;

(4-(6-Methyl-3-(7-(pyridin-4-yl)quinolin-4-yl)imidazo[1,2-b]pyridazin-7-yl)phenyl)(4-methylpiperazin-1-yl)methanone;

(R)-4-(7-(3-fluoro-4-((2-methylpyrrolidin-1-yl)methyl)phenyl)-6-methylimidazo[1,2-b]pyridazin-3-yl)-7-(pyridin-4-yl)quinolone;

N-methyl-4-(6-methyl-7-(4-(piperazin-1-yl)phenyl)imidazo[1,2-b]pyridazin-3-yl)quinoline-7-carboxamide;

(4-(6-methyl-7-(4-(piperazin-1-yl)phenyl)imidazo[1,2-b]pyridazin-3-yl)quinolin-7-yl)(4-methylpiperazin-1-yl)methanone;

7-(1-methyl-1H-pyrazol-3-yl)-4-(6-methyl-7-(4-(piperazin-1-yl)phenyl)imidazo[1,2-b]pyridazin-3-yl)quinolone;

(4-(4-(6-methyl-7-(4-(piperazin-1-yl)phenyl)imidazo[1,2-b]pyridazin-3-yl)quinolin-7-yl)pyridin-2-yl)methanol;

4-(4-(6-methyl-7-(4-(piperazin-1-yl)phenyl)imidazo[1,2-b]pyridazin-3-yl)quinolin-7-yl)morpholine;

2-(4-(6-methyl-7-(4-(piperazin-1-yl)phenyl)imidazo[1,2-b]pyridazin-3-yl)quinolin-7-yl)-6-oxa-2-azaspiro[3.4]octane;

4-(6-methyl-7-(4-(piperazin-1-yl)phenyl)imidazo[1,2-b]pyridazin-3-yl)-N-(pyridin-3-yl)quinolin-7-amine;

1-(4-(4-(6-methyl-7-(4-(piperazin-1-yl)phenyl)imidazo[1,2-b]pyridazin-3-yl)quinolin-7-yl)piperazin-1-yl)ethan-1-one;

4-((4-(6-methyl-7-(4-(piperazin-1-yl)phenyl)imidazo[1,2-b]pyridazin-3-yl)quinolin-7-yl)methyl)morpholine;

(3,5-difluorophenyl)(4-(6-methyl-7-(4-(piperazin-1-yl)phenyl)imidazo[1,2-b]pyridazin-3-yl)quinolin-7-yl)methanol;

(4-(6-methyl-7-(4-(piperazin-1-yl)phenyl)imidazo[1,2-b]pyridazin-3-yl)quinolin-7-yl)methanol;

4-(6-methyl-7-(4-(piperazin-1-yl)phenyl)imidazo[1,2-b]pyridazin-3-yl)-1,8-naphthyridine;

5-(6-methyl-7-(4-(piperazin-1-yl)phenyl)imidazo[1,2-b]pyridazin-3-yl)quinoline-8-carbonitrile;

8-(6-methyl-7-(4-(piperazin-1-yl)phenyl)imidazo[1,2-b]pyridazin-3-yl)-2,3-dihydro-[1,4]dioxino[2,3-b]pyridine;

4-(6-methyl-7-(4-(piperazin-1-yl)phenyl)imidazo[1,2-b]pyridazin-3-yl)quinoline-7-carbonitrile;

N-(2-hydroxyethyl)-4-(6-methyl-7-(4-(piperazin-1-yl)phenyl)imidazo[1,2-b]pyridazin-3-yl)quinoline-8-carboxamide;

(4-(6-methyl-7-(1-(tetrahydro-2H-pyran-4-yl)-1H-pyrazol-4-yl)imidazo[1,2-b]pyridazin-3-yl)-2,3-dihydro-1H-pyrrolo[2,3-b]pyridin-1-yl)(pyridin-4-yl)methanone;

1-((1S,4S)-5-(4-(7-(1-((1R,4R)-4-hydroxycyclohexyl)-1H-pyrazol-4-yl)-6-methylimidazo[1,2-b]pyridazin-3-yl)quinolin-7-yl)-2,5-diazabicyclo[2.2.1]heptan-2-yl)ethan-1-one;

2-(4-(7-(1-((1R,4R)-4-hydroxycyclohexyl)-1H-pyrazol-4-yl)-6-methylimidazo[1,2-b]pyridazin-3-yl)quinolin-7-yl)hexahydropyrrolo[1,2-a]pyrazin-6(2H)-one;

4-(6-methyl-7-(1-(piperidin-4-yl)-1H-pyrazol-4-yl)imidazo[1,2-a]pyridin-3-yl)quinolone; or 2-fluoro-4-(6-methyl-7-(1-(piperidin-4-yl)-1H-pyrazol-4-yl)imidazo[1,2-a]pyridin-3-yl)benzamide;

or a pharmaceutically acceptable salt thereof.

47. The compound of claim 1, wherein the compound is (1R,4R)-4-(4-(6-Methyl-3-(7-(pyridin-2-yl)-1,8-naphthyridin-4-yl)imidazo[1,2-b]pyridazin-7-yl)-1H-pyrazol-1-yl)cyclohexan-1-ol;

5-(7-(4-(Azetidin-1-ylmethyl)phenyl)-6-methylimidazo[1,2-b]pyridazin-3-yl)-2-(pyridin-2-yl)-1,8-naphthyridine;

5-(7-(1-Ethyl-1H-pyrazol-4-yl)-6-methylimidazo[1,2-b]pyridazin-3-yl)-2-(pyridin-2-yl)-1,8-naphthyridine;

5-(7-(1-Isopropyl-1H-pyrazol-4-yl)-6-methylimidazo[1,2-b]pyridazin-3-yl)-2-(pyrimidin-2-yl)-1,8-naphthyridine;

(1R,4R)-4-(4-(6-Methyl-3-(7-(pyrazin-2-yl)-1,8-naphthyridin-4-yl)imidazo[1,2-b]pyridazin-7-yl)-1H-pyrazol-1-yl)cyclohexan-1-ol;

5-(7-(4-(Azetidin-1-ylmethyl)phenyl)-6-methylimidazo[1,2-b]pyridazin-3-yl)-2-(pyrazin-2-yl)-1,8-naphthyridine;

5-(7-(1-Isopropyl-1H-pyrazol-4-yl)-6-methylimidazo[1,2-b]pyridazin-3-yl)-2-(pyrazin-2-yl)-1,8-naphthyridine;

5-(6-Methyl-7-(1-(tetrahydro-2H-pyran-4-yl)-1H-pyrazol-4-yl)imidazo[1,2-b]pyridazin-3-yl)-2-(pyrazin-2-yl)-1,8-naphthyridine;

5-(7-(1-Isopropyl-1H-pyrazol-4-yl)-6-methylimidazo[1,2-b]pyridazin-3-yl)-2-(1-methyl-1H-pyrazol-3-yl)-1,8-naphthyridine;

5-(7-(4-(Azetidin-1-ylmethyl)phenyl)-6-methylimidazo[1,2-b]pyridazin-3-yl)-2-(1-methyl-1H-pyrazol-3-yl)-1,8-naphthyridine;

N,N-dimethyl-4-(6-methyl-3-(7-(1-methyl-1H-pyrazol-3-yl)-1,8-naphthyridin-4-yl)imidazo[1,2-b]pyridazin-7-yl)benzamide;

5-(7-(4-(Azetidin-1-ylmethyl)phenyl)-6-methylimidazo[1,2-b]pyridazin-3-yl)-2-(5-methyl-1H-pyrazol-3-yl)-1,8-naphthyridine;

4-(4-(6-methyl-3-(7-(5-methyl-1H-pyrazol-3-yl)-1,8-naphthyridin-4-yl)imidazo[1,2-b]pyridazin-7-yl)benzyl)morpholine;

5-(7-(1-Isopropyl-1H-pyrazol-4-yl)-6-methylimidazo[1,2-b]pyridazin-3-yl)-2-(5-methyl-1H-pyrazol-3-yl)-1,8-naphthyridine;

5-(7-(1-Isopropyl-1H-pyrazol-4-yl)-6-methylimidazo[1,2-b]pyridazin-3-yl)-2-(1-methyl-1H-pyrazol-4-yl)-1,8-naphthyridine;

2-(1-Ethyl-1H-imidazol-4-yl)-5-(6-methyl-7-(4-(pyrrolidin-1-ylmethyl)phenyl)imidazo[1,2-b]pyridazin-3-yl)-1,8-naphthyridine;

4-(4-(3-(7-(1-Ethyl-1H-imidazol-4-yl)-1,8-naphthyridin-4-yl)-6-methylimidazo[1,2-b]pyridazin-7-yl)benzyl)morpholine;

1-(4-(3-(7-(1-Ethyl-1H-imidazol-4-yl)-1,8-naphthyridin-4-yl)-6-methylimidazo[1,2-b]pyridazin-7-yl)phenyl)-N,N-dimethylmethanamine;

2-(1-Ethyl-1H-imidazol-4-yl)-5-(7-(1-isopropyl-1H-pyrazol-4-yl)-6-methylimidazo[1,2-b]pyridazin-3-yl)-1,8-naphthyridine;

5-(7-(4-(Azetidin-1-ylmethyl)phenyl)-6-methylimidazo[1,2-b]pyridazin-3-yl)-2-(1-ethyl-1H-imidazol-4-yl)-1,8-naphthyridine;

5-(7-(4-((3,3-Difluoroazetidin-1-yl)methyl)phenyl)-6-methylimidazo[1,2-b]pyridazin-3-yl)-2-(1-ethyl-1H-imidazol-4-yl)-1,8-naphthyridine;

(S)-4-(4-(3-(7-(i-ethyl-1H-imidazol-4-yl)-1,8-naphthyridin-4-yl)-6-methylimidazo[1,2-b]pyridazin-7-yl)benzyl)-2-methylmorpholine;

(S)-(4-(4-(3-(7-(i-ethyl-1H-imidazol-4-yl)-1,8-naphthyridin-4-yl)-6-methylimidazo[1,2-b]pyridazin-7-yl)benzyl)morpholin-2-yl)methanol;

2-(4-Methyl-2H-1,2,3-triazol-2-yl)-5-(6-methyl-7-(4-(pyrrolidin-1-ylmethyl)phenyl)imidazo[1,2-b]pyridazin-3-yl)-1,8-naphthyridine;

5-(7-(1-Isopropyl-1H-pyrazol-4-yl)-6-methylimidazo[1,2-b]pyridazin-3-yl)-2-(4-methyl-2H-1,2,3-triazol-2-yl)-1,8-naphthyridine;

2-(4-Methyl-2H-1,2,3-triazol-2-yl)-5-(6-methyl-7-(1-(tetrahydro-2H-pyran-4-yl)-1H-pyrazol-4-yl)imidazo[1,2-b]pyridazin-3-yl)-1,8-naphthyridine;

N,N-dimethyl-1-(4-(6-methyl-3-(7-(4-methyl-2H-1,2,3-triazol-2-yl)-1,8-naphthyridin-4-yl)imidazo[1,2-b]pyridazin-7-yl)phenyl)methanamine;

4-(4-(6-Methyl-3-(7-(4-methyl-2H-1,2,3-triazol-2-yl)-1,8-naphthyridin-4-yl)imidazo[1,2-b]pyridazin-7-yl)benzyl)morpholine;

N,N-dimethyl-1-(4-(6-methyl-3-(7-(4-methyl-2H-1,2,3-triazol-2-yl)-1,8-naphthyridin-4-yl)imidazo[1,2-b]pyridazin-7-yl)phenyl)methanamine;

(S)-3-methyl-1-(4-(6-methyl-3-(7-(4-methyl-2H-1,2,3-triazol-2-yl)-1,8-naphthyridin-4-yl)imidazo[1,2-b]pyridazin-7-yl)benzyl)pyrrolidin-3-ol; or 1-(4-(6-methyl-3-(7-(4-methyl-2H-1,2,3-triazol-2-yl)-1,8-naphthyridin-4-yl)imidazo[1,2-b]pyridazin-7-yl)benzyl)piperidin-4-ol;

or a pharmaceutically acceptable salt thereof.

48. The compound of claim 1, wherein the compound is
4-methyl-1-(4-(6-methyl-3-(7-(4-methyl-2H-1,2,3-triazol-2-yl)-1,8-naphthyridin-4-yl)imidazo[1,2-b]pyridazin-7-yl)benzyl)piperidin-4-ol;

3-methyl-1-(4-(6-methyl-3-(7-(4-methyl-2H-1,2,3-triazol-2-yl)-1,8-naphthyridin-4-yl)imidazo[1,2-b]pyridazin-7-yl)benzyl)azetidin-3-ol;

2-(4-methyl-2H-1,2,3-triazol-2-yl)-5-(6-methyl-7-(4-((4-methylpiperazin-1-yl)methyl)phenyl)imidazo[1,2-b]pyridazin-3-yl)-1,8-naphthyridine;

1-(4-(3-(7-(1-ethyl-1H-imidazol-4-yl)-1,8-naphthyridin-4-yl)-6-methylimidazo[1,2-b]pyridazin-7-yl)benzyl)piperidin-4-ol; or 1-(4-(3-(7-(1-ethyl-1H-imidazol-4-yl)-1,8-naphthyridin-4-yl)-6-methylimidazo[1,2-b]pyridazin-7-yl)benzyl)-4-methylpiperidin-4-ol;

or a pharmaceutically acceptable salt thereof.

49. A pharmaceutical composition comprising a compound of claim 1, or a pharmaceutically acceptable salt thereof, and at least one pharmaceutically acceptable carrier or excipient.

50. A method of inhibiting ALK2 activity, wherein said method comprises administering to a patient a compound of claim 1, or a pharmaceutically acceptable salt thereof.

51. A method of treating a disease or disorder associated with inhibition of ALK2 interaction, wherein said method comprises administering to a patient in need thereof a therapeutically effective amount of a compound of claim 1, or a pharmaceutically acceptable salt thereof.

52. A method of treating a cancer in a patient, wherein said method comprises administering to the patient a therapeutically effective amount of a compound of claim 1, or a pharmaceutically acceptable salt thereof.

53. A method of treating myeloproliferative diseases in a patient, wherein said method comprises administering to the patient a therapeutically effective amount of a compound of claim 1, or a pharmaceutically acceptable salt thereof, and ruxolitinib, or a pharmaceutically acceptable salt thereof.

54. The compound of claim 1, wherein the compound is 3-methyl-1-(4-(6-methyl-3-(7-(4-methyl-2H-1,2,3-triazol-2-yl)-1,8-naphthyridin-4-yl)imidazo[1,2-b]pyridazin-7-yl)benzyl)azetidin-3-ol.

55. A pharmaceutical composition comprising a compound of claim 54, or a pharmaceutically acceptable salt thereof, and at least one pharmaceutically acceptable carrier or excipient.

56. The compound of claim 1, wherein the compound is 1-(4-(6-methyl-3-(7-(4-methyl-2H-1,2,3-triazol-2-yl)-1,8-naphthyridin-4-yl)imidazo[1,2-b]pyridazin-7-yl)benzyl)piperidin-4-ol.

57. A pharmaceutical composition comprising a compound of claim 56, or a pharmaceutically acceptable salt thereof, and at least one pharmaceutically acceptable carrier or excipient.

58. The compound of claim 1, wherein the compound is (S)-4-(4-(3-(7-(1-ethyl-1H-imidazol-4-yl)-1,8-naphthyridin-4-yl)-6-methylimidazo[1,2-b]pyridazin-7-yl)benzyl)-2-methylmorpholine.

59. A pharmaceutical composition comprising a compound of claim 58, or a pharmaceutically acceptable salt thereof, and at least one pharmaceutically acceptable carrier or excipient.

60. The compound of claim 1, wherein $R^3$ is H.

61. The compound of claim 1, wherein $R^4$ is H.

* * * * *